(12) United States Patent
Boyce et al.

(10) Patent No.: US 7,625,909 B2
(45) Date of Patent: Dec. 1, 2009

(54) SUBSTITUTED QUINAZOLINONE COMPOUNDS

(75) Inventors: Rustum S. Boyce, San Francisco, CA (US); Natalia Aurrecoechea, Oakland, CA (US); Daniel Chu, Santa Clara, CA (US); Aaron Smith, Union City, CA (US); Christopher R. Conlee, Morrisville, NC (US); Brian D. Thompson, Chapel Hill, NC (US); Judith de Armas Kuntz, Raleigh, NC (US); David L. Musso, Raleigh, NC (US); Kevin K. Barvian, Morrisville, NC (US); Stephen A. Thomson, Durham, NC (US); William R. Swain, Durham, NC (US); Kien S. Du, Durham, NC (US); Brian A. Chauder, Raleigh, NC (US); Jason D. Speake, Cary, NC (US); Michael J. Bishop, Chapel Hill, NC (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/850,967

(22) Filed: May 21, 2004

(65) Prior Publication Data

US 2005/0059662 A1 Mar. 17, 2005

Related U.S. Application Data

(60) Provisional application No. 60/473,317, filed on May 23, 2003, provisional application No. 60/523,336, filed on Nov. 19, 2003, provisional application No. 60/524,492, filed on Nov. 24, 2003.

(51) Int. Cl.
```
A61K 31/517    (2006.01)
A61K 31/519    (2006.01)
A61P 5/50      (2006.01)
C07D 239/88    (2006.01)
C07D 239/95    (2006.01)
C07D 471/04    (2006.01)
C07D 487/04    (2006.01)
```
(52) U.S. Cl. .............................. 514/266.2; 514/266.31; 544/284; 544/286; 544/287
(58) Field of Classification Search .............. 514/266.2, 514/266.31, 261.1, 262.1, 264.1; 544/284, 544/286, 287, 254, 256, 257, 279, 285
See application file for complete search history.

(56) References Cited

U.S. PATENT DOCUMENTS

| | | |
|---|---|---|
| 3,177,218 A | 4/1965 | Brown |
| 4,128,643 A | 12/1978 | Merkel et al. |
| 4,211,867 A | 7/1980 | Rasmussen |
| 4,287,341 A | 9/1981 | Hess et al. |
| 4,496,571 A | 1/1985 | Yellin et al. |

(Continued)

FOREIGN PATENT DOCUMENTS

DE 31 08 322 12/1981

(Continued)

OTHER PUBLICATIONS

Wagner, J. G. "Intrasubject Variation in Elimination Half-Lives of Drugs . . . " Journal of Pharmacokinetics and Biopharmaceutics, 1973, vol. 1, No. 2, pp. 165-173.*

(Continued)

*Primary Examiner*—James O Wilson
*Assistant Examiner*—Tamthom N Truong
(74) *Attorney, Agent, or Firm*—Vinit Kathardekar; Joseph Meara

(57) ABSTRACT

A variety of small molecule, guanidine-containing molecules capable of acting as MC4-R agonists are provided. The compounds are useful in treating MC4-R mediated diseases when administered to subjects. The compounds have the structure IA, IB, and IC where the values of the variables are defined herein.

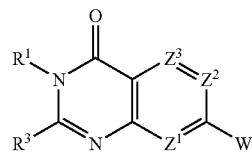

IA

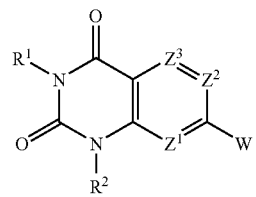

IB

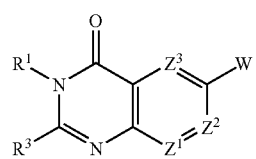

IC

21 Claims, No Drawings

U.S. PATENT DOCUMENTS

| | | | |
|---|---|---|---|
| 4,626,537 A | 12/1986 | Dave et al. | |
| 4,732,916 A | 3/1988 | Satoh et al. | |
| 4,748,165 A | 5/1988 | Jones et al. | |
| 4,874,864 A | 10/1989 | Schnur et al. | |
| 4,948,891 A | 8/1990 | Schnur et al. | |
| 4,948,901 A | 8/1990 | Schnur et al. | |
| 5,086,057 A | 2/1992 | Sasagawa | |
| 5,124,328 A | 6/1992 | Fisher et al. | |
| 5,352,704 A | 10/1994 | Okuyama et al. | |
| 5,362,902 A | 11/1994 | Bamish et al. | |
| 5,547,966 A | 8/1996 | Atwal et al. | |
| 5,637,439 A | 6/1997 | Kaneko et al. | |
| 5,731,408 A | 3/1998 | Hadley et al. | |
| 5,750,573 A | 5/1998 | Bianchi et al. | |
| 5,885,985 A | 3/1999 | Macdonald et al. | |
| 5,889,025 A | 3/1999 | Lohray et al. | |
| 5,952,381 A | 9/1999 | Chen et al. | |
| 5,962,530 A | 10/1999 | Engel et al. | |
| 6,020,349 A | 2/2000 | Ankerson et al. | |
| 6,030,985 A | 2/2000 | Gentile et al. | |
| 6,054,556 A | 4/2000 | Huby et al. | |
| 6,060,589 A | 5/2000 | Stark et al. | |
| 6,127,343 A | 10/2000 | Andersen et al. | |
| 6,180,603 B1 | 1/2001 | Frey, II | |
| 6,225,331 B1 | 5/2001 | Cupps et al. | |
| 6,297,233 B1 | 10/2001 | Stein et al. | |
| 6,313,093 B1 | 11/2001 | Frey, II | |
| 6,391,878 B2 | 5/2002 | Cupps et al. | |
| 6,638,927 B2 | 10/2003 | Renhowe et al. | |
| 6,716,840 B2 | 4/2004 | Chu et al. | |
| 6,995,269 B2 | 2/2006 | Renhowe et al. | |
| 7,034,033 B2 | 4/2006 | Boyce et al. | |
| 7,368,453 B2 * | 5/2008 | Boyce et al. | 514/266.2 |
| 2003/0195187 A1 | 10/2003 | Boyce et al. | |
| 2003/0207814 A1 | 11/2003 | Boyce et al. | |
| 2003/0229025 A1 | 12/2003 | Xiao et al. | |
| 2004/0019049 A1 | 1/2004 | Boyce et al. | |
| 2006/0235019 A1 * | 10/2006 | Boyce et al. | 514/243 |

FOREIGN PATENT DOCUMENTS

| | | |
|---|---|---|
| EP | 0343894 | 11/1989 |
| WO | WO 96/24580 | 8/1996 |
| WO | WO 97/19911 | 6/1997 |
| WO | WO 97/41119 | 11/1997 |
| WO | WO 98/07420 | 2/1998 |
| WO | WO 98/23596 | 6/1998 |
| WO | WO 99/64002 | 12/1999 |
| WO | WO 00/03973 | 1/2000 |
| WO | WO 00/17191 | 3/2000 |
| WO | WO 00/74679 | 12/2000 |
| WO | WO 01/04103 | 1/2001 |
| WO | WO 01/10842 | 2/2001 |
| WO | WO 01/55106 | 8/2001 |
| WO | WO 01/55107 | 8/2001 |
| WO | WO 01/55109 | 8/2001 |
| WO | WO 01/70337 | 9/2001 |
| WO | WO 01/70708 | 9/2001 |
| WO | WO 02/18327 | 3/2002 |
| WO | WO 02/062776 | 8/2002 |
| WO | WO 02/081443 | 10/2002 |
| WO | WO 03/072056 | 9/2003 |
| WO | WO 03/099818 | 12/2003 |
| WO | WO 2005/051391 | 6/2005 |

OTHER PUBLICATIONS

Julia, M. et al., "Amidines and guanidines related to congocidine. III. Urea and trazene diamidines," *Bull. Soc. Chim. Fr.*, No. 1, pp. 376-382, 1968, published by Masson Editeur, Paris, France.

Mountjoy, K. G. et al., "The Cloning of a Family of Genes That Encode the Melanocortin Receptors," *Science*, vol. 257, pp. 1248-1251, Aug. 28, 1992.

Lu, D. et al., "Agouti protein is an antagonist of the melanocyte-stimulating-hormone receptor," *Nature*, vol. 371, pp. 799-802, Oct. 27, 1994.

Huszar, D. et al., "Targeted Disruption of the Melanocortin-4 Receptor Results in Obesity in Mice," *Cell*, vol. 88, pp. 131-141, Jan. 10, 1997, published by Cell Press.

Ollmann, M. M. et al., "Antagonism of Central melanocortin Receptors in Vitro and in Vivo by Agouti-Related Protein," *Science*, vol. 278, pp. 135-138, Oct. 3, 1997.

Kiefer, L.L. et al., "Mutations in the Carboxyl Terminus of the Agouti Protein Decrease Agouti Inhibition of Ligand Binding to the Melanocortin Receptors," *Biochemistry*, vol. 36, pp. 2084-2090, 1997, published by American Chemical Society.

Fong, T. M. et al., "ART (Protein Product of Agouti-Related Transcript) as an Antagonist of MC-3 and MC-4 Receptors," *Biochemical and Biophysical Res. Comm.*, vol. 237, pp. 629-631, 1997, published by Academic Press.

Asagarasu, A. et al., "Synthesis of Dipeptide-Type Human Immunodeficiency Virus (HIV) Protease Inhibitors with a Binding Unit to GP120," *Chem. Pharm. Bull.*, vol. 46, No. 5, pp. 867-870, 1998, published by Pharmaceutical Society of Japan.

Rossi, M. et al., "A C-terminal fragment of Agouti-related protein increases feeding and antagonizes the effect of alpha-melanocyte stimulating hormone in vivo," *Endocrinology*, vol. 139, No. 10, pp. 4428-4431, 1998. published by The Endocrine Society.

Hadley, M. E. et al., "The Proopiomelanocortin System," *Ann. N. Y. Acad. Sci.*, 885:1, pp. 1-21, 1999.

Smolnik, R. et al., "Brain Potentials and Attention after Acute and Subchronic Intranasal Administration of ACTH 4-10 and Desacetyl-α-MSH in Humans," *Neuroendocrinology*, vol. 70, pp. 63-72, 1999, published by S. Karger AG, Basel.

Fehm, H. L. et al., "The Melanocortin Melanocyte-Stimulating Hormone/Adrenocorticotropin$_{4-10}$ Decreases Body Fat in Humans," *J. Clin. Endocrinology & Metabolism*, vol. 86, No. 3, pp. 1144-1148, 2001, published by the Endocrine Society.

Smith, R. A. et al., "Discovery and Parallel Synthesis of a New Class of Cathepsin K Inhibitors," *Bioorganic & Medicinal Chemistry Letters*, vol. 11, pp. 2951-2954, 2001, published by Elsevier Science Ltd.

Shadiak, A. M. et al. "Intranasal Delivery of a Melanocortin for the Treatment of Sexual Dysfunction," Presentation at Fifth International Conference Exploring the Rapidly Developing Area of Nasal Drug Delivery, Mar. 21 and 22, Le Meridien Hotel, Piccadilly, London, United Kingdom., 2002.

Runti, C.; DeNardo, M.; Ulian F., "Fusaric Acid Derivatives and Analogues as Possible Antihypertensive Drugs," Il Farmaco Edizione Scientifica, vol. 36(4), pp. 260-268(1981), published in Italy by the Society of Italian Pharmaceutical Science. This is an English-language document.

Wolff, M. E., "Burger's Medicinal Chemistry and Drug Discovery 5$^{th}$ Edition," pp. 975-977 (1995), M. E. Wolff (ed.); published by John Wiley & Sons (New York, NY).

Banker, G. S. et al., "Modern Pharmaceutics, 3$^{rd}$ Edition," pp. 596 and 451 (1996), G. S. Banker and C. T. Rhodes (eds.); published by Marcel Dekker, Inc. (New York, NY).

West, A. R., "Solid State Chemistry and Its Applications," pp. 358 and 365 (1988), A. R. West (ed.); published by John Wiley & Sons (New York, NY).

Goodfellow, V. S. et al., "The Melanocortin System and its Role in Obesity and Cachexia," *Current Top. Med. Chem.*, vol. 3, No. 8, pp. 855-883 (2003); published by Bentham Science Publishers Ltd. (San Francisco, CA).

Fisher, S. L. et al., Int. J. Obes. Relat. Metab. Disord. Suppl. 1, pp. 54-48 (Feb. 1999); published by the American Dietetic Association (Chicago, IL).

Dörwald, F. Zaragoza, Side Reactions in Organic Synthesis: A Guide to Successful Synthesis Design, Weinheim: Wiley-VCH Verlag GmbH & Co. KGaA, 2005, Preface.

Examination Report for EP 03738964.0 dated Aug. 5, 2008.

Examination Report for EP 03738964.0 dated Jan. 31, 2008.

Jordan, V. C., Nature Reviews: Drug Discovery, 2, pp. 205-213, 2003.

Supplementary European Search Report for Application No. 04811698.2 dated Oct. 7, 2008.
Supplementary European Search Report for EP 03738964.0 dated Jul. 25, 2006.
Vippagunta et al., "Crystalline solids," *Advanced Drug Delivery Reviews*, 48, pp. 3-26, 2001.
Examination Report for EP 04776069.9 dated Mar. 25, 2008.
International Preliminary Examination Report for PCT/US03/16442 dated Feb. 17, 2004.
International Preliminary Report on Patentability and Written Opinion for PCT/US2004/039020 dated May 22, 2006.
International Preliminary Report on Patentability for PCT/US2004/015959 dated Sep. 8, 2005.
International Search Report for PCT/US03/16442 dated Oct. 9, 2003.
International Search Report for PCT/US2004/015959 dated Oct. 22, 2004.
International Search Report for PCT/US2004/039020 dated Apr. 19, 2005.
Supplementary European Search Report for Application No. 04811698.2 dated Oct. 7, 2008.
Supplementary European Search Report for EP 03738964.0 dated Jul. 25, 2006.
Vippagunta et al., "Crystalline solids," *Advanced Drug Delivery Reviews*, 48, pp. 3-26, 2001.

* cited by examiner

SUBSTITUTED QUINAZOLINONE COMPOUNDS

CROSS-REFERENCES TO RELATED APPLICATIONS

This application claims priority to U.S. Provisional Application No. 60/473,317 filed May 23, 2003, U.S. Provisional Application No. 60/523,336 filed Nov. 19, 2003, and U.S. Provisional Application No. 60/524,492 filed Nov. 24, 2003, the entire disclosures of which are incorporated herein by reference and for all purposes as if fully set forth herein.

FIELD OF THE INVENTION

This invention relates to melanocortin-4 receptor (MC4-R) agonists and methods of their preparation. More specifically, the invention relates to quinazolinone compounds that exhibit reduced bioaccumulation properties when administered to a subject.

BACKGROUND OF THE INVENTION

Melanocortins are peptide products resulting from post-translational processing of pro-opiomelanocortin and are known to have a broad array of physiological activities. The natural melanocortins include the different types of melanocyte stimulating hormone ($\alpha$-MSH, $\beta$-MSH, $\gamma$-MSH) and ACTH. Of these, $\alpha$-MSH and ACTH are considered to be the main endogenous melanocortins.

The melanocortins mediate their effects through melanocortin receptors (MC-Rs), a subfamily of G-protein coupled receptors. There are at least five different receptor subtypes (MC1-R to MC5-R). MC1-R mediates pigmentation of the hair and skin. MC2-R mediates the effects of ACTH on steroidogenesis in the adrenal gland. MC3-R and MC4-R are predominantly expressed in the brain. MC5-R is considered to have a role in the exocrine gland system.

The melanocortin-4 receptor (MC4-R) is a seven-transmembrane receptor. MC4-R may participate in modulating the flow of visual and sensory information, coordinate aspects of somatomotor control, and/or participate in the modulation of autonomic outflow to the heart. K. G. Mountjoy et al., *Science*, 257:1248-125 (1992). Significantly, inactivation of this receptor by gene targeting has resulted in mice that develop a maturity onset obesity syndrome associated with hyperphagia, hyperinsulinemia, and hyperglycemia. D. Husznar et al., *Cell*, 88(1): 131-41 (1997). MC4-R has also been implicated in other disease states including erectile disorders, cardiovascular disorders, neuronal injuries or disorders, inflammation, fever, cognitive disorders, and sexual behavior disorders. M. E. Hadley and C. Haskell-Luevano, *The Proopiomelanocortin system, Ann. N.Y. Acad. Sci.*, 885:1 (1999).

Furthermore, observations in connection with endogenous MC4-R antagonists indicate that MC4-R is implicated in endogenous energy regulation. For example, an agouti protein is normally expressed in the skin and is an antagonist of the cutaneous MC receptor involved in pigmentation, MC1-R. M. M. Ollmann et al., *Science*, 278:135-138 (1997). However, overexpression of agouti protein in mice leads to a yellow coat color due to antagonism of MC1-R and increased food intake and body weight due to antagonism of MC4-R. L. L. Kiefer et al., *Biochemistry*, 36: 2084-2090 (1997); D. S. Lu et al., *Nature*, 371:799-802 (1994). Agouti related protein (AGRP), an agouti protein homologue, antagonizes MC4-R but not MC1-R. T. M. Fong et al., *Biochem. Biophys. Res. Commun.* 237:629-631 (1997). Administration of AGRP in mice increases food intake and causes obesity but does not alter pigmentation. M. Rossi et al., *Endocrinology*, 139:4428-4431 (1998). Together, this research indicates that MC4-R participates in energy regulation, and therefore, identifies this receptor as a target for a rational drug design for the treatment of obesity.

In connection with MC4-R and its uncovered role in the etiology of obesity and food intake, the prior art includes reports of compounds and compositions that act as agonists or antagonists of MC4-R. As examples, U.S. Pat. No. 6,060,589 describes polypeptides that are capable of modulating signaling activity of melanocortin receptors. Also, U.S. Pat. Nos. 6,054,556 and 5,731,408 describe families of agonists and antagonists for MC4-R receptors that are lactam heptapeptides having a cyclic structure. WO 01/10842 discloses MC4-R binding compounds having a multitude of structures and methods of using such compounds to treat MC4-R associated disorders. Some of the compounds described include amidino- and guanidino-containing arenes and heteroarenes.

Various other classes of compounds have been disclosed as having MC4-R agonist activity. For example, WO 01/70708 and WO 00/74679 disclose MC4-R agonists that are piperidine compounds and derivatives, while WO 01/70337 and WO 99/64002 disclose MC-R agonists that are spiropiperidine derivatives. Other known melanocortin receptor agonists include aromatic amine compounds containing amino acid residues, particularly tryptophan residues, as disclosed in WO 01/55106. Similar agonists are disclosed in WO 01/055107 which comprise aromatic amine compounds containing tertiary amide or tertiary amine groups. Finally, WO 01/055109 discloses melanocortin receptor agonists comprising aromatic amines which are generally bisamides separated by a nitrogen-containing alkyl linker.

Guanidine-containing compounds having a variety of biological activities are also known in the prior art. For example, U.S. Pat. No. 4,732,916 issued to Satoh et al. discloses guanidine compounds useful as antiulcer agents; U.S. Pat. No. 4,874,864, U.S. Pat. No. 4,949,891, and U.S. Pat. No. 4,948,901 issued to Schnur et al. and EP 0343 894 disclose guanidino compounds useful as protease inhibitors and as anti-plasmin and anti-thrombin agents; and U.S. Pat. No. 5,352,704 issued to Okuyama et al. discloses a guanidino compound useful as an antiviral agent. Guanidine-containing compounds are also disclosed in other references. For example, U.S. Pat. No. 6,030,985 issued to Gentile et al. discloses guanidine compounds useful for treating and preventing conditions in which inhibition of nitric oxide synthetase is beneficial such as stroke, schizophrenia, anxiety, and pain. U.S. Pat. No. 5,952,381 issued to Chen et al. discloses certain guanidine compounds for use in selectively inhibiting or antagonizing $\alpha_v\beta_3$ integrins.

Various 5-, 6-, and 7-membered fully saturated 1-azacarbocyclic-2-ylidene derivatives of guanidine are disclosed as having anti-secretory and hypoglycemic activities by U.S. Pat. No. 4,211,867 issued to Rasmussen. Such compounds are also taught as useful for the treatment of cardiovascular disease. Other guanidine derivatives are disclosed by U.S. Pat. No. 5,885,985 issued to Macdonald et al. as useful in therapy to treat inflammation. Various guanidinobenzamide compounds are disclosed in WO 02/18327. The guanidinobenzamides are disclosed as useful for treating obesity and type II diabetes.

The synthesis of various quinazolinone compounds is set forth in U.S. patent application Ser. No. 10/444,495, published on Jan. 29, 2004 as US 2004/0019049, international application number PCT/US03/16442, published on Dec. 4, 2003 as WO 03/099818, and U.S. Provisional Application Nos. 60/382,762, 60/441,019, 60/473,317, 60/523,336, and 60/524,492 each of which is hereby incorporated by reference in its entirety and for all purposes as if fully set forth herein.

Despite the recent disclosure of various compounds that exhibit MC4-R agonist activity, a need remains for new compounds and pharmaceutical compositions that may be used to treat MC4-R mediated diseases and disease states. A need also remains for compounds that exhibit desirable pharmacological properties such as compounds that have reduced bioaccumulation properties in subjects to which they are administered.

SUMMARY OF THE INVENTION

The instant invention provides potent and specific agonists of MC4-R that are small molecules. Thus, there has been provided, in accordance with one aspect of the invention, compounds of formula IA, IB, or IC:

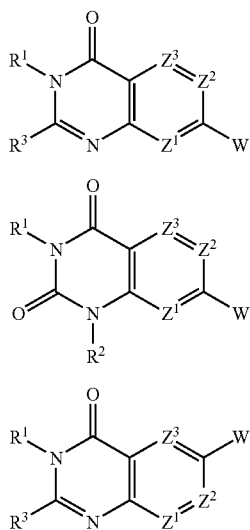

wherein
$Z^1$ is selected from the group consisting of $CR^4$ and N;
$Z^2$ is selected from the group consisting of $CR^5$ and N;
$Z^3$ is selected from the group consisting of $CR^6$ and N;
$R^1$ is selected from the group consisting of substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;
$R^2$ is selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups;
$R^3$ is selected from the group consisting of H, and substituted and unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, and alkyl groups;
$R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

W is a group of formula IIA or IIB;

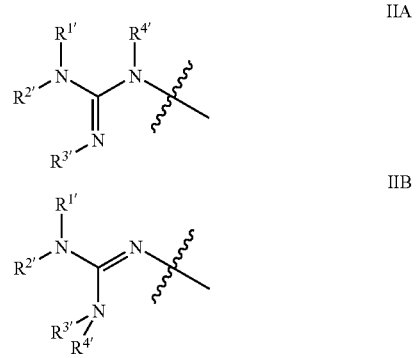

$R^{1'}$ is selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl groups, and heterocyclylalkyl groups;

$R^{2'}$ is selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl groups, and heterocyclylalkyl groups; wherein at least one of $R^{1'}$ and $R^{2'}$ is a substituted or unsubstituted heterocyclylalkyl group;

$R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups; and $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups.

In accordance with a second aspect of the invention, the invention provides compounds of formula IA, IB, or IC in which:

$Z^1$ is selected from the group consisting of $CR^4$ and N;
$Z^2$ is selected from the group consisting of $CR^5$ and N;
$Z^3$ is selected from the group consisting of $CR^6$ and N;
$R^1$ is selected from the group consisting of substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;
$R^2$ is selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups;
$R^3$ is selected from the group consisting of H, and substituted and unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, and alkyl groups;
$R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

W is a group of formula IIA or IIB;

wherein, $R^{1'}$ and $R^{2'}$, together with the nitrogen to which they are bound, join together to form a heterocyclic ring substituted with at least one group selected from the group consisting of substituted and unsubstituted arylalkyl, —C(=O)-alkyl, -alkyl-C(=O)—O-alkyl, —C(=O)—O-alkyl, —C(=O)—NH$_2$, —C(=O)—NH(alkyl), —C(=O)—N(alkyl)$_2$, dialkylaminoalkyl, alkylaminoalkyl, aminoalkyl, aryl, heteroaryl, heterocyclyl, heteroarylalkyl, heterocyclylalkyl, and alkylthioalkyl groups;

$R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups; and $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups.

Compounds provided by the invention further include prodrugs of the compound of formula IA, IB, and IC, pharmaceutically acceptable salts thereof, stereoisomers thereof, tautomers thereof, hydrates thereof, or solvates thereof.

In some embodiments, the invention provides compounds of formula IA, IB, and IC in which W is a group of formula IIA. In some such embodiments, the compound has the formula IA.

The invention further provides compounds of formula IA, IB, and IC in which at least one of $R^{1'}$ and $R^{2'}$ is a pyrrolidinylalkyl group such as, but not limited to, a pyrrolidinylmethyl or pyrrolidinylethyl group.

The invention further provides compounds of formula IA and IC in which $R^3$ is H.

The invention further provides compounds of formula IA, IB, and IC in which $Z^1$ is a $CR^4$ group, $Z^2$ is a $CR^5$ group, and $Z^3$ is a $CR^6$ group. In some such embodiments, at least one of $R^4$, $R^5$, or $R^6$ is a F.

The invention further provides compounds of formula IA, IB, and IC in which at least one of $Z^1$, $Z^2$, or $Z^3$ is N. In some such embodiments, $Z^1$ is N. In other such embodiments, $Z^2$ is N.

The invention further provides compounds of formula IA, IB, and IC in which $R^{3'}$ is selected from the group consisting of substituted and unsubstituted cycloalkyl, polycyclic cycloalkyl, alkenyl, alkyl, and aryl groups. In other embodiments of compounds of formula IA, IB, and IC, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of compounds of formula IA, IB, and IC, $R^3$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl (polycyclic cycloalkyl), fluoromethyl(polycyclic cycloalkyl), and fluoro(polycyclic cycloalkyl) groups.

The invention further provides compounds of formula IA, IB, and IC in which $R^1$ is a 2,4-disubstituted phenylethyl group. In still other embodiments of compounds of formula IA, IB, and IC, $R^1$ is selected from the group consisting of 2,4-dihalophenylethyl, and 2,4-dialkylphenylethyl groups. In still other embodiments of compounds of formula IA, IB, and IC, $R^1$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl groups, (2-pyridyl)ethyl, (3-pyridyl)ethyl, (4-pyridyl)ethyl, (pyridyl)(hydroxymethyl) ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl) ethyl, substituted and unsubstituted (aryl)(heterocyclyloxymethyl)ethyl, substituted and unsubstituted (heteroaryl) (alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In still other embodiments of compounds of formula IA, IB, and IC, $R^1$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, indolylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, and (phenyl)(hydroxymethyl)ethyl groups.

In some embodiments where $R^{1'}$ and $R^{2'}$, together with the nitrogen to which they are bound, join together to form a heterocyclic ring, the heterocyclic ring is a substituted piperazine and in other such embodiments, the heterocyclic ring is a piperidine ring. In some such embodiments, the piperazine or piperidine ring is substituted with a group selected from a phenylalkyl group, a substituted or unsubstituted phenyl group, an -alkyl-$SCH_3$ group, an indolylalkyl group, a morpholinylalkyl group, a pyridyl group, a piperidinyl group, or a tetrahydrofuranylalkyl group.

In still further embodiments, the invention provides compounds of formula IA, IB and IC in which $R^1$ is a substituted or unsubstituted alkenyl group such as a substituted or unsubstituted allyl group or a substituted or unsubstituted vinyl group.

The invention further provides compounds of formula IB in which $R^2$ is H.

In still further embodiments, the invention provides compounds of formula IA and IC in which $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

In accordance with another aspect, the invention provides compounds of formula VA, VB, and mixtures thereof.

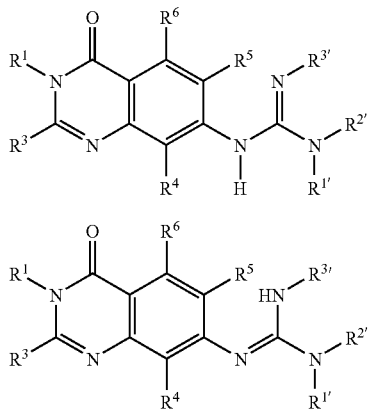

where
$R^1$ is selected from substituted or unsubstituted arylalkyl, heteroarylalkyl, aryl, heteroaryl, heterocyclyl, cycloalkyl, heterocyclylalkyl, cycloalkylalkyl, alkenyl, alkynyl, or alkyl groups;
$R^3$ is selected from substituted or unsubstituted aryl, heteroaryl, heterocyclyl, cycloalkyl, heterocyclylalkyl, or cyloalkylamino groups;
$R^4$, $R^5$, and $R^6$ are independently selected from H, Cl, I, F, Br, OH, $NH_2$, CN, $NO_2$, and substituted and unsubstituted alkoxy, and alkyl groups;
$R^{1'}$ and $R^{2'}$, together with the nitrogen to which they are bound, form a substituted or unsubstituted heterocyclyl group; and $R^{3'}$ is selected from substituted or unsubstituted cycloalkyl groups.

In another aspect, the invention provides compounds of formula VIA, VIB, and mixtures thereof.

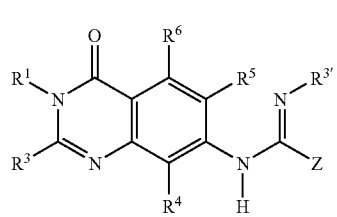

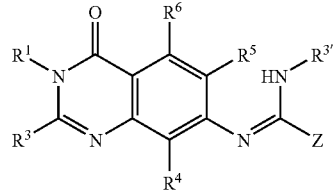

where
$R^1$ is selected from substituted or unsubstituted arylalkyl, heteroarylalkyl, aryl, heteroaryl, heterocyclyl, cycloalkyl, heterocyclylalkyl, cycloalkylalkyl, alkenyl, alkynyl, or alkyl groups;
$R^3$ is selected from H or substituted or unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, or alkyl groups;
$R^4$, $R^5$, and $R^6$ are independently selected from H, Cl, I, F, Br, OH, $NH_2$, CN, $NO_2$, and substituted and unsubstituted alkoxy, and alkyl groups;
$R^{3'}$ is selected from H or substituted or unsubstituted aryl, alkyl, alkenyl, alkynyl, cycloalkyl, heteroaryl, heterocyclyl, heterocyclylalkyl, arylalkyl, heteroarylalkyl, or cycloalkylalkyl groups; and
Z is selected from a piperazinone of formula

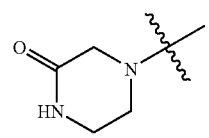

which may be additionally substituted.

In another aspect, the invention provides compounds of formula VIIA, VIIB, and mixtures thereof,

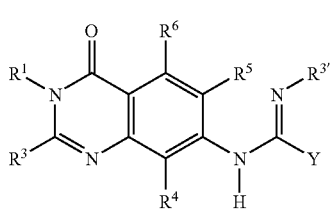

-continued

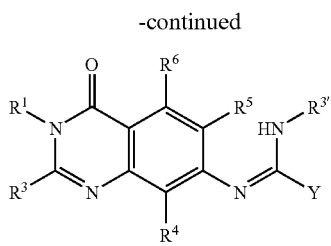

VIIB

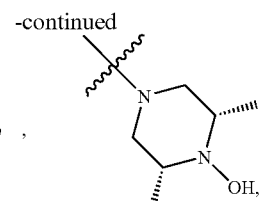

wherein $R^1$ is selected from substituted or unsubstituted arylalkyl, heteroarylalkyl, aryl, heteroaryl, heterocyclyl, cycloalkyl, heterocyclylalkyl, cycloalkylalkyl, alkenyl, alkynyl, or alkyl groups;

$R^3$ is selected from H or substituted or unsubstituted arylalkyl, heteroarylalkyl, alkoxy, alkylamino, dialkylamino, aryl, heteroaryl, heterocyclyl, cycloalkyl, aminocycloalkyl, heterocyclylalkyl, cycloalkylalkyl, alkenyl, alkynyl, or alkyl groups;

$R^4$, $R^5$, and $R^6$ are independently selected from H, Cl, I, F, Br, OH, $NH_2$, CN, $NO_2$, and substituted and unsubstituted alkoxy, and alkyl groups;

$R^{3'}$ is selected from H or substituted or unsubstituted aryl, alkyl, alkenyl, alkynyl, cycloalkyl, heteroaryl, heterocyclyl, heterocyclylalkyl, arylalkyl, heteroarylalkyl, or cycloalkylalkyl groups;

Y is selected from a moiety of formula

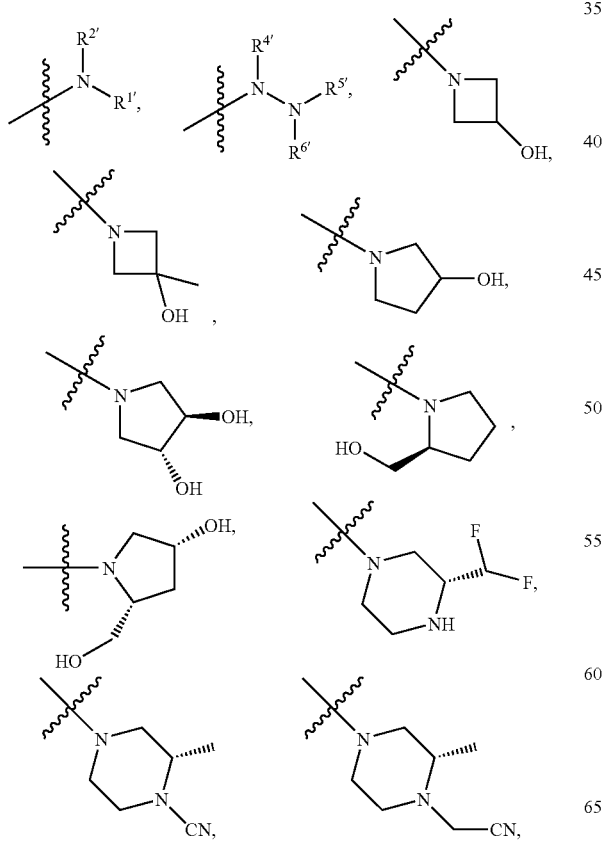

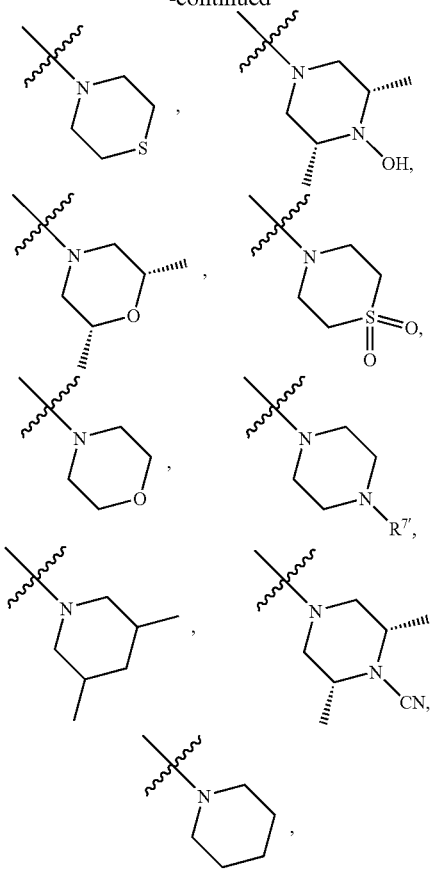

wherein $R^{1'}$ is selected from substituted or unsubstituted alkyl groups;

$R^{2'}$, $R^{4'}$, $R^{5'}$ are independently selected from H or substituted or unsubstituted alkyl groups;

$R^{6'}$ is selected from substituted or unsubstituted alkyl groups; or $R^{5'}$ and $R^{6'}$ together with the nitrogen to which they are bound form a heterocyclyl or heteroaryl group; and $R^{7'}$ is selected from CN, or substituted or unsubstituted alkyl, aryl, or arylalkyl groups.

Compounds provided by the invention further include prodrugs of the compound of formula VA, VB, VIA, VIB, VIIA, and VIIB, pharmaceutically acceptable salts thereof, stereoisomers thereof, tautomers thereof, hydrates thereof, or solvates thereof.

The invention further provides compounds of formula VA, VB, VIA, VIB, VIIA, and VIIB in which $R^4$, $R^5$, and $R^6$ are all H.

The invention further provides compounds of formula VA, VB, VIA, VIB, VIIA, and VIIB in which $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, 3,3,5-trimethylcyclohexyl, 4-t-butylcyclohexyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups.

The invention further provides compounds of formula VA, VB, VIA, VIB, VIIA, and VIIB in which $R^{3'}$ is a substituted or unsubstituted polycyclic cycloalkyl group. In some such embodiments, $R^{3'}$ is a substituted or unsubstituted polycyclic cycloalkyl group having the formula II

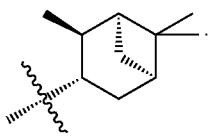

VIII

The invention further provides compounds of formula VA, VB, VIA, VIB, VIIA, and VIIB in which $R^1$ is a substituted or unsubstituted arylalkyl group such as a substituted or unsubstituted phenylethyl group. In some such embodiments, $R^1$ is a substituted phenylethyl group such as a 4-substituted phenylethyl group or a 2,4-disubstituted phenylethyl group. In some embodiments, $R^1$ is selected from phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-fluorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, indolylethyl, 4-hydroxyphenylethyl, 3,4-dimethoxyphenylethyl, 2-chloro-4-iodophenylethyl, 2-fluoro-4-methylphenylethyl, 4-chloro-2-fluorophenylethyl, 4-bromo-2-fluorophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, and (phenyl)(hydroxymethyl)ethyl groups. In still other embodiments, $R^1$ is selected from a 2-fluoro-4-methoxyphenylethyl group, a 2-chloro-4-methoxyphenylethyl, 4-fluorophenylethyl, a 4-chlorophenylethyl, a 4-chloro-2-fluorophenylethyl, a 2,4-dichlorophenylethyl, a 4-bromophenylethyl, or a 4-bromo-2-fluorophenylethyl group.

The invention further provides compounds of formula VA, VB, VIA, VIB, VIIA, and VIIB in which $R^3$ is selected from substituted or unsubstituted heterocyclyl groups or substituted or unsubstituted heteroaryl groups. In some embodiments, $R^3$ is selected from substituted or unsubstituted pyridinyl, piperidinyl, piperazinyl, morpholinyl, thiomorpholinyl, tetrahydrofuranyl, furanyl, pyrrolidinyl, pyrrolyl, thiophenyl, tetrahydrothiophenyl, pyranyl, tetrahydropyranyl, tetrahydrothiopyranyl, pyrazinyl, thiazolyl, pyrimidinyl, quinuclidinyl, indolyl, imidazolyl, triazolyl, tetrazolyl, or pyridazinyl groups. In some such embodiments, $R^3$ is selected from heteroaryl or heterocyclyl groups of formula

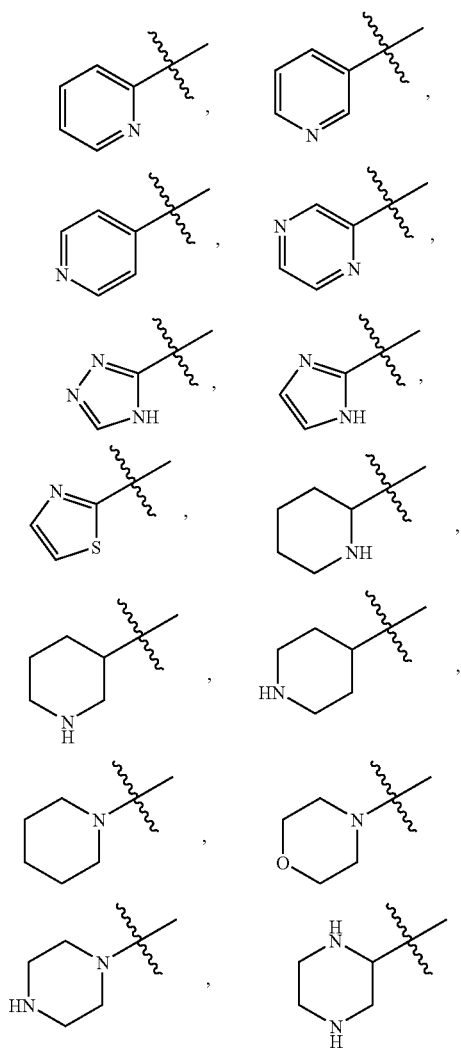

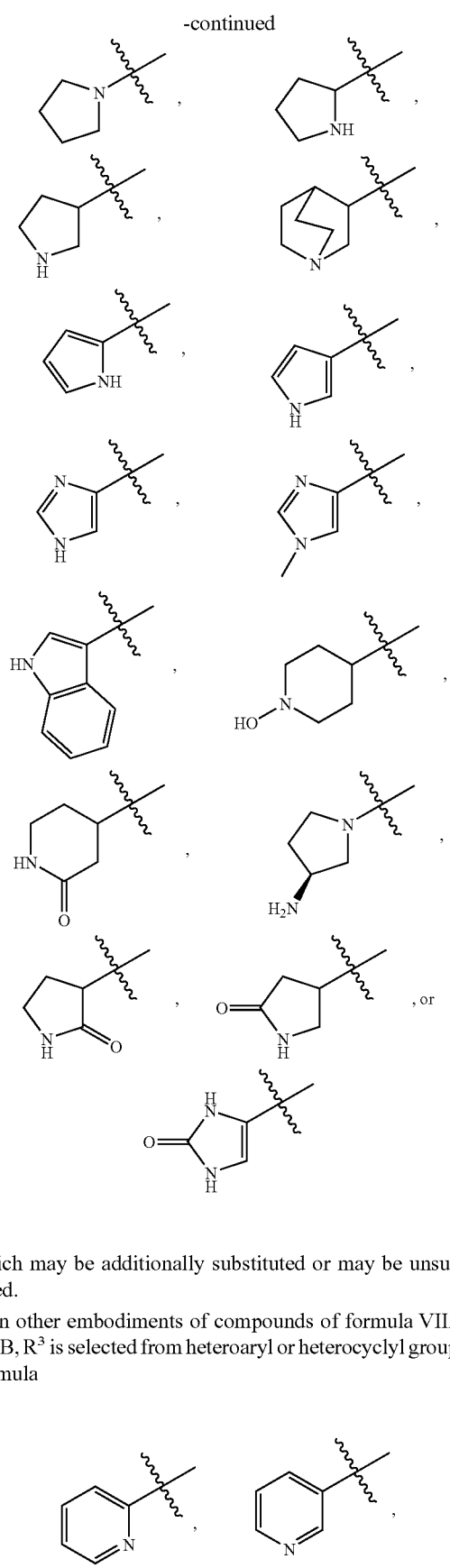
which may be additionally substituted or may be unsubstituted.
In other embodiments of compounds of formula VIIA or VIIB, $R^3$ is selected from heteroaryl or heterocyclyl groups of formula
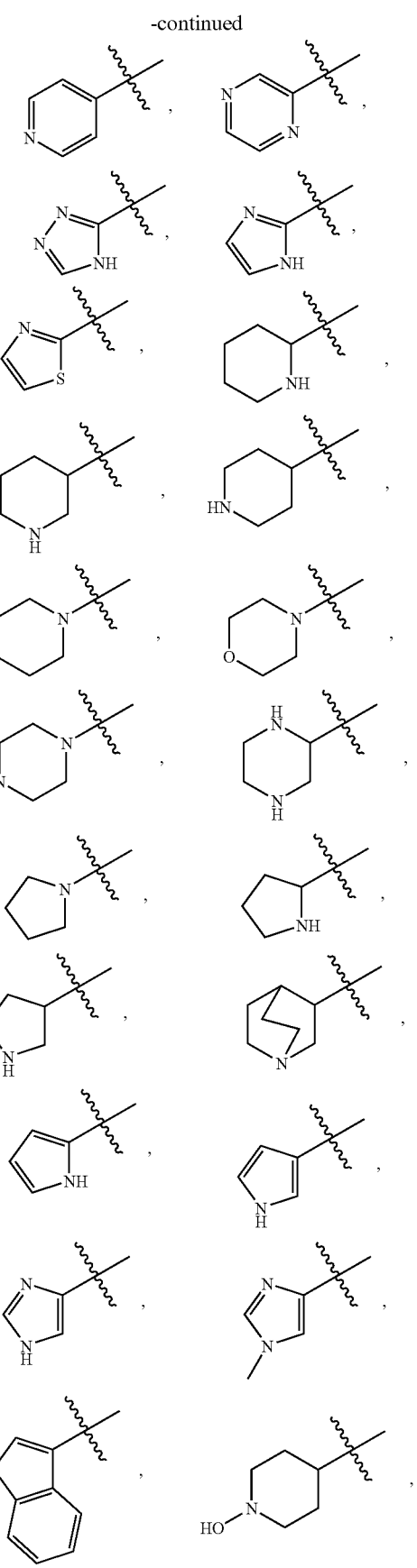

-continued

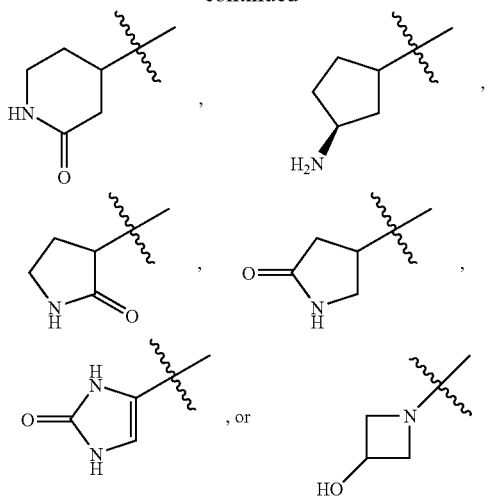

which may be additionally substituted or may be unsubstituted.

The invention further provides compounds of formula VA, VB, VIA, and VIB in which $R^3$ is selected from substituted or unsubstituted aryl or cycloalkyl groups. For example, in some embodiments, $R^3$ is selected from aryl or cycloalkyl groups of formula

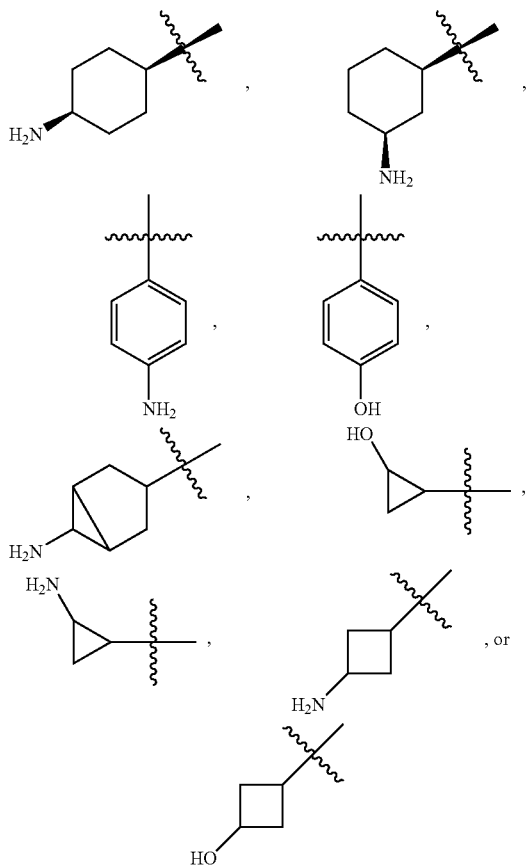

which may be additionally substituted or may be unsubstituted.

The invention further provides compounds of formula VIIA and VIIB in which $R^3$ is selected from substituted or unsubstituted aryl, cycloalkyl, or aminocycloalkyl groups. For example, in some embodiments, $R^3$ is selected from aryl, cycloalkyl, or aminocycloalkyl groups of formula

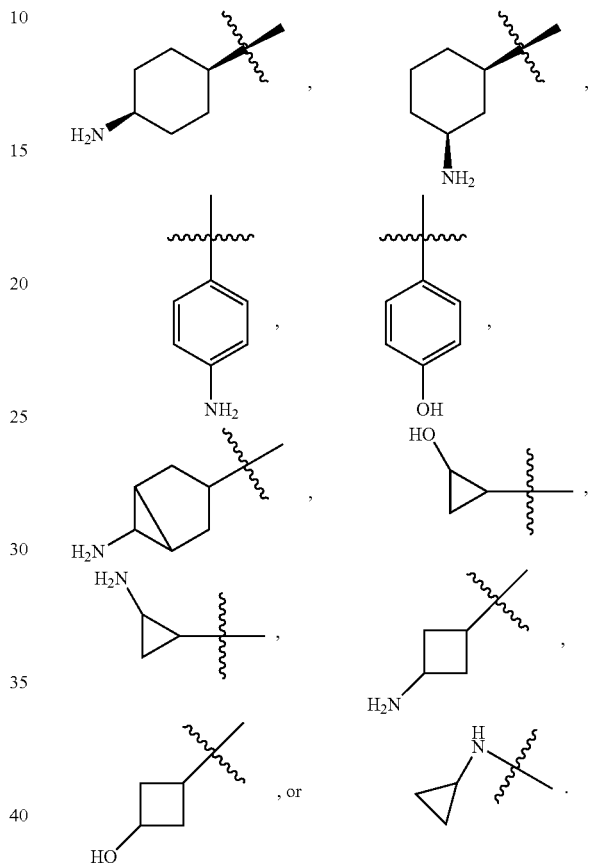

which may be additionally substituted or may be unsubstituted.

The invention further provides compounds of formula VA, VB, VIA, VIB, VIIA, and VIIB in which $R^3$ is selected from substituted or unsubstituted heterocyclylalkyl, or cycloalkylamino groups. For example, in some embodiments, $R^3$ is selected from a group such as a substituted or unsubstituted cyclopropylamino group; a substituted or unsubstituted piperazinylalkyl group such as a piperazinylmethyl group or an N-methylpiperazinylmethyl group; or a piperidinylalkyl group such as a piperidinylmethyl group or a piperidinylethyl group.

The invention further provides compounds of formula VA and VB in which $R^{1'}$ and $R^{2'}$, together with the nitrogen to which they are bound, form a substituted or unsubstituted piperazinyl group. In some such embodiments, $R^{1'}$ and $R^{2'}$, together with the nitrogen to which they are bound, form a piperazinyl group that is substituted with at least one group selected from, fluoromethyl, difluoromethyl, or trifluoromethyl groups. In other embodiments, $R^{1'}$ and $R^{2'}$, together with the nitrogen to which they are bound, form a piperazinyl group substituted with at least one carbonyl group such that the piperazinyl group is a piperazinone that may be additionally substituted. In some such embodiments, $R^{1'}$ and $R^{2'}$, together with the nitrogen to which they are bound form a piperazinone of formula

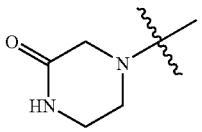

which may be additionally substituted. In some embodiments of compounds of formula IA and IB, $R^{1'}$ and $R^{2'}$, together with the nitrogen to which they are bound form a piperazinone having the following formula and in some embodiments of compounds of formula VIA and VIB, Z is a piperazinone having the following formula

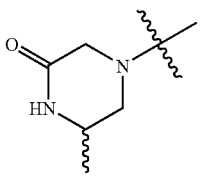

In some such embodiments, $R^{1'}$ and $R^{2'}$, together with the nitrogen to which they are bound form a piperazinone having the following formula or Z is a piperazinone having the following formula

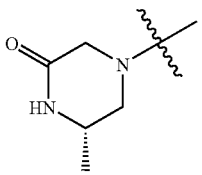

The invention further provides compounds of formula VA and VB in which $R^{1'}$ and $R^{2'}$, together with the nitrogen to which they are bound, form a piperazinyl group of formula

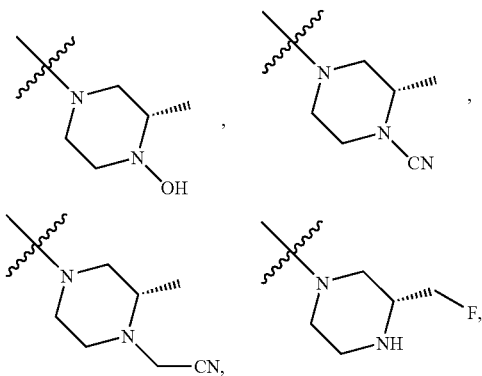

-continued

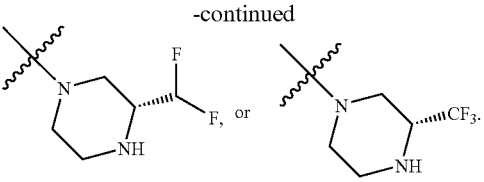

In some embodiments, the invention provides compounds in which the $t_{1/2}$ value for the compound is less than 35, 30, 25, 20, 15, 10, or 5 hours in a tissue with high blood perfusion such as brain, liver, kidney, and heart. In some such embodiments, the $t_{1/2}$ is less than or about 4 hours and in some embodiments is less than or about 3 hours in a subject to which the compound(s) have been administered.

There has also been provided, in accordance with another aspect of the invention, a composition such as a pharmaceutical formulation or medicament comprising a compound according to the instant invention and a pharmaceutically acceptable carrier. The invention further provides the use of the compounds of the invention in preparing a medicament or pharmaceutical formulation for use in treating an MC4-R mediated disease. In some embodiments, such a disease is obesity or type II diabetes.

There has also been provided, in accordance with another aspect of the invention, a method of treating an MC4-R mediated disease, comprising administering to a subject in need thereof, a compound or composition of the instant invention. In some such embodiments, the compounds of the invention exhibit reduced bioaccumulation in the tissue and plasma of the subject.

In one embodiment, a disease to be treated by those methods of the instant invention is obesity or type II diabetes.

In one embodiment, a compound or composition of the invention is intranasally administered.

In one embodiment, a compound or composition of the invention is administered to a human subject.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

The instant invention relates to novel classes of small molecule melanocortin-4 receptor (MC4-R) agonists. These compounds can be formulated into compositions and are useful in activating MC4-R, or in the treatment of MC4-R-mediated diseases, such as obesity, type II diabetes, erectile dysfunction, polycystic ovary disease, complications resulting from or associated with obesity and diabetes, and Syndrome X.

The following definitions are used throughout this specification.

Alkyl groups include straight chain and branched alkyl groups having from 1 to about 8 carbon atoms. Examples of straight chain alkyl groups include methyl, ethyl, propyl, butyl, pentyl, hexyl, heptyl, and octyl groups. Examples of branched alkyl groups, include, but are not limited to, isopropyl, sec-butyl, t-butyl, and isopentyl groups. Representative substituted alkyl groups may be substituted one or more times with, for example, amino, thio, alkoxy, or halo groups such as F, Cl, Br, and I groups.

Cycloalkyl groups are cyclic alkyl groups such as, but not limited to, cyclopropyl, cyclobutyl, cyclopentyl, cyclohexyl, cycloheptyl, and cyclooctyl groups. Cycloalkyl groups also includes rings that are substituted with straight or branched chain alkyl groups as defined above, and further include cycloalkyl groups that are substituted with other rings including fused rings such as, but not limited to, decalinyl, tetrahydronaphthyl, and indanyl. Cycloalkyl groups also include polycyclic cycloalkyl groups such as, but not limited to, norbornyl, adamantyl, bornyl, camphenyl, isocamphenyl, and carenyl groups. Representative substituted cycloalkyl groups may be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which may be substituted with, for example, alkyl, alkoxy, amino, thio, cyano, or halo groups.

Alkenyl groups are straight chain, branched or cyclic lower alkyl groups having 2 to about 8 carbon atoms, and further including at least one double bond, as exemplified, for instance, by vinyl, propenyl, 2-butenyl, 3-butenyl, isobutenyl, cyclohexenyl, cyclopentenyl, cyclohexadienyl, butadienyl, pentadienyl, and hexadienyl groups among others.

Alkynyl groups are straight chain or branched lower alkyl groups having 2 to about 8 carbon atoms, and further including at least one triple bond, as exemplified by groups, including, but not limited to, ethynyl, propynyl, and butynyl groups.

Aryl groups are cyclic aromatic hydrocarbons that do not contain heteroatoms. Thus aryl groups include, but are not limited to, phenyl, azulene, heptalene, biphenylene, indacene, fluorene, phenanthrene, triphenylene, pyrene, naphthacene, chrysene, biphenyl, anthracenyl, and naphthenyl groups. Although the phrase "aryl groups" includes groups containing fused rings, such as fused aromatic-aliphatic ring systems, it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or benzyl groups, which may be substituted with groups including, but not limited to, amino, alkoxy, alkyl, cyano, or halo.

Cycloalkylalkyl groups are alkyl groups as defined above in which a hydrogen or carbon bond of an alkyl group is replaced with a bond to a cycloalkyl group as defined above.

Arylalkyl groups are alkyl groups as defined above in which a hydrogen or carbon bond of an alkyl group is replaced with a bond to an aryl group as defined above.

Heterocyclyl groups are nonaromatic ring compounds containing 3 or more ring members, of which, one or more is a heteroatom such as, but not limited to, N, O, and S. The phrase "heterocyclyl group" includes fused ring species including those comprising fused aromatic and nonaromatic groups. The phrase also includes polycyclic ring systems containing a heteroatom such as, but not limited to, quinuclidyl. However, the phrase does not include heterocyclyl groups that have other groups, such as alkyl or halo groups, bonded to one of the ring members. Rather, these are referred to as "substituted heterocyclyl groups". Heterocyclyl groups include, but are not limited to, piperazino, morpholino, thiomorpholino, pyrrolidino, piperidino and homopiperazino groups. Representative substituted heterocyclyl groups may be mono-substituted or substituted more than once, such as, but not limited to, morpholino or piperazino groups, which are 2-, 3-, 4-, 5-, or 6-substituted, or disubstituted with groups including, but not limited to, amino, alkoxy, alkyl, cyano, or halo.

Heteroaryl groups are aromatic ring compounds containing 3 or more ring members, of which, one or more is a heteroatom such as, but not limited to, N, O, and S. Heteroaryl groups include, but are not limited to, groups such as furan, thiophene, pyrrole, isopyrrole, diazole, imidazole, isoimidazole, triazole, dithiole, oxathiole, isoxazole, oxazole, thiazole, isothiazole, oxadiazole, oxatriazole, dioxazole, oxathiazole, pyran, dioxin, pyridine, pyrimidine, pyridazine, pyrazine, triazine, oxazine, isoxazine, oxathiazine, azepin, oxepin, thiepin, diazepine, benzofuran, and isobenzofuran. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with groups including, but not limited to, amino, alkoxy, alkyl, cyano, or halo.

Heterocyclylalkyl groups are alkyl groups as defined above in which a hydrogen or carbon bond of an alkyl group is replaced with a bond to a heterocyclyl group as defined above.

Heteroarylalkyl groups are alkyl groups as defined above in which a hydrogen or carbon bond of an alkyl group is replaced with a bond to a heteroaryl group as defined above.

Aminocarbonyl groups are groups of the formula RR'NC(O)—, wherein R or R' may be the same or different, and each is independently selected from H, or substituted or unsubstituted alkyl, cycloalkyl, aryl, heterocyclyl or heteroaryl groups, as defined above.

In general, "substituted" refers to a group as defined above in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles.

Substituted cycloalkyl, substituted aryl, substituted heterocyclyl and substituted heteroaryl also include rings and fused ring systems in which a bond to a hydrogen atom is replaced with a bond to a carbon atom. Therefore, substituted cycloalkyl, substituted aryl, substituted heterocyclyl and substituted heteroaryl groups may also be substituted with alkyl groups as defined above.

Pharmaceutically acceptable salts include a salt with an inorganic base, organic base, inorganic acid, organic acid, or basic or acidic amino acid. As salts of inorganic bases, the invention includes, for example, alkali metals such as sodium or potassium, alkali earth metals such as calcium and magnesium or aluminum, and ammonia. As salts of organic bases, the invention includes, for example, trimethylamine, triethylamine, pyridine, picoline, ethanolamine, diethanolamine, triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, lactic acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

Prodrugs, as used in the context of the instant invention, includes those derivatives of the instant compounds which undergo in vivo metabolic biotransformation, by enzymatic or nonenzymatic processes, such as hydrolysis, to form a compound of the invention. Prodrugs can be employed to improve pharmaceutical or biological properties, as for example solubility, melting point, stability and related physicochemical properties, absorption, pharmacodynamics and other delivery-related properties.

The instant invention provides potent and specific agonists of MC4-R that are small molecules. In accordance with one aspect of the invention, the invention provides a first and second group compounds of formula IA, IB, and IC. Compounds of the invention further include prodrugs of compounds of formula IA, IB, and IC, pharmaceutically acceptable salts thereof, stereoisomers thereof, tautomers thereof, hydrates thereof, or solvates thereof.

Compounds of formula IA, IB, and IC have the following structure.

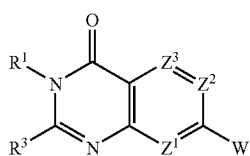

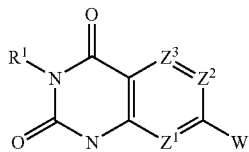

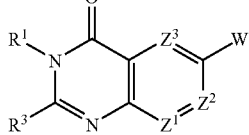

In the first and second groups of compounds of formula IA, IB, and IC, $Z^1$ is selected from the group consisting of $CR^4$ and N. In some embodiments of the compounds of formula IA, IB, and IC, $Z^1$ is a $CR^4$ group whereas in other embodiments, $Z^1$ is a N.

In the first and second groups of compounds of formula IA, IB, and IC, $Z^2$ is selected from the group consisting of $CR^5$ and N. In some embodiments of the compounds of formula IA, IB, and IC, $Z^2$ is a $CR^5$ group whereas in other embodiments, $Z^2$ is a N.

In the first and second groups of compounds of formula IA, IB, and IC, $Z^3$ is selected from the group consisting of $CR^6$ and N. In some embodiments of the compounds of formula IA, IB, and IC, $Z^3$ is a $CR^6$ group whereas in other embodiments, $Z^3$ is a N.

In some embodiments of the first and second groups of compounds of formula IA, IB, and IC, $Z^1$ is a $CR^4$ group, $Z^2$ is a $CR^5$ group, and $Z^3$ is a $CR^6$ group. Thus, in some embodiments of compounds of formula IA, IB, and IC, the ring that includes $Z^1$, $Z^2$, and $Z^3$ may be a carbocyclic aromatic ring. In some embodiments of compounds of formula IA, IB, and IC, where $Z^1$ is a $CR^4$ group, $Z^2$ is a $CR^5$ group, and $Z^3$ is a $CR^6$ group, at least one of $R^4$, $R^5$, or $R^6$ is a halogen such as Cl or F. In other such embodiments, at least one of $R^4$, $R^5$, or $R^6$ is a F.

In some embodiments of the first and second groups of compounds of formula IA, IB, and IC, at least one of $Z^1$, $Z^2$, or $Z^3$ is a N.

In the first and second groups of compounds of formula IA, IB, and IC, $R^1$ is selected from the group consisting of substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups. In some embodiments of the compounds of formula IA, IB, and IC, $R^1$ is a substituted phenethyl group such as a 2,4-disubstituted phenylethyl group or a 4-substituted phenylethyl group. In other embodiments of the compounds of formula IA, IB, and IC, $R^1$ is selected from 2,4-dihalophenylethyl and 2,4-dialkylphenylethyl groups. In still other embodiments of the compounds of formula IA, IB, and IC, $R^1$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro- 4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In other embodiments, $R^1$ is selected from phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, indolylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, or (phenyl)(hydroxymethyl)ethyl groups.

In some embodiments of the first and second groups of compounds of formula IA, IB and IC, $R^1$ is a substituted or unsubstituted alkenyl group such as a substituted or unsubstituted allyl group or a substituted or unsubstituted vinyl group.

In the first and second groups of compounds of formula IB, $R^2$ is selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups. In some embodiments of the compounds of formula IB, $R^2$ is H.

In the first and second groups of compounds of formula IA and IC, $R^3$ is selected from the group consisting of H, and substituted and unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, and alkyl groups. In some embodiments of the compounds of formula IA and IC, $R^3$ is H. In still further embodiments, the invention provides compounds of formula IA and IC in which $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

In the first and second groups of compounds of formula IA, IB, and IC, $R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups. In some embodiments of compounds of formula IA, IB, and IC, $R^4$, $R^5$, and $R^6$ are selected from H or a halogen such as Cl or F. In other embodiments of compounds of formula IA, IB, and IC, at least one of $R^4$, $R^5$, or $R^6$ is a F whereas in other embodiments of compounds of formula IA, IB, and IC, $R^4$, $R^5$, and $R^6$ are all H.

In the first and second groups of compounds of formula IA, IB, and IC, W is a group of formula IIA or IIB having the following structure.

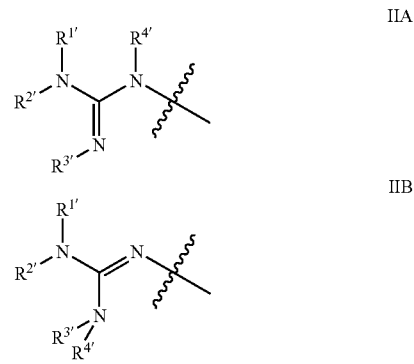

In the first group of compounds of formula IA, IB, and IC, $R^{1'}$ is selected from H, or substituted and unsubstituted alkyl, alkenyl, alkynyl, cycloalkyl, aryl, heteroaryl, heterocyclyl, arylalkyl, heteroarylalkyl, cycloalkylalkyl, or heterocyclylalkyl groups and $R^{2'}$ is selected from H, or substituted and unsubstituted alkyl, alkenyl, alkynyl, cycloalkyl, aryl, heteroaryl, heterocyclyl, arylalkyl, heteroarylalkyl, cycloalkylalkyl, and heterocyclylalkyl groups. In some such embodiments, at least one of $R^{1'}$ and $R^{2'}$ is a heterocyclylalkyl group such as, but not limited to, a substituted or unsubstituted pyrrolidinylmethyl or pyrrolidinylethyl group. In some such embodiments, the compounds has the formula IA or IC and W is a group of formula IIA.

In the second group of compounds of formula IA, IB, and IC, $R^{1'}$ and $R^{2'}$, together with the nitrogen to which they are bound, join together to form a heterocyclic ring. The heterocyclic ring is substituted with at least one group selected from the group consisting of substituted and unsubstituted arylalkyl, —C(=O)-alkyl, -alkyl-C(=O)—O-alkyl, —C(=O)—O-alkyl, —C(=O)—$NH_2$, —C(=O)—NH(alkyl), —C(=O)—N(alkyl)$_2$, dialkylaminoalkyl, alkylaminoalkyl, aminoalkyl, aryl, heteroaryl, heterocyclyl, heteroarylalkyl, heterocyclylalkyl, and alkylthioalkyl groups. In some such embodiments, the heterocyclic ring is a substituted piperazine and in other such embodiments, the heterocyclic ring is a piperidine ring. In some such embodiments, the piperazine or piperidine ring is substituted with a group selected from the group consisting of a phenylalkyl group, a substituted or unsubstituted phenyl group, an -alkyl-$SCH_3$ group, an indolylalkyl group, a morpholinylalkyl group, a pyridyl group, a piperidinyl group, and a tetrahydrofuranylalkyl group.

In the first and second groups of compounds of formula IA, IB, and IC, $R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups. In one embodiment of compounds of formula IA, IB, and IC, $R^{3'}$ is selected from the group consisting of substituted and unsubstituted cycloalkyl, polycyclic cycloalkyl, alkenyl, alkyl, and aryl groups. In still other embodiments of compounds of formula IA, IB, and IC, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of compounds of formula IA, IB, and IC, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups. By way of nonlimiting example, suitable $R^{3'}$ cycloalkyl, cyclohexyl, and polycyclic cycloalkyl groups that include fluorine, include, but are not limited to, the following structures:

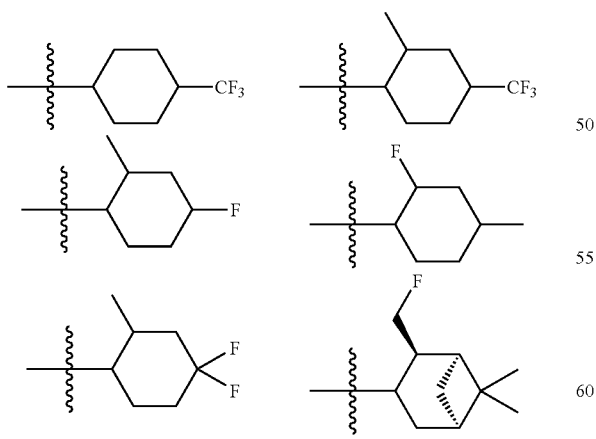

In the first and second groups of compounds of formula IA, IB, and IC, $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups. In one embodiment of compounds of formula IA, IB, and IC, $R^{4'}$ is H.

In one embodiment of the first and second groups of compounds of formula IA, the compounds of formula IA are selected from the group consisting of compounds having the formula IIIA, IIIB, IIIC, IIID, IIIE, IIIF, and IIIG such as shown below where $R^1$, W, $R^{1'}$, $R^{2'}$, $R^{3'}$, and $R^{4'}$ have the same values as those described above with respect to the compounds and various embodiments of formula IA, IB, and IC.

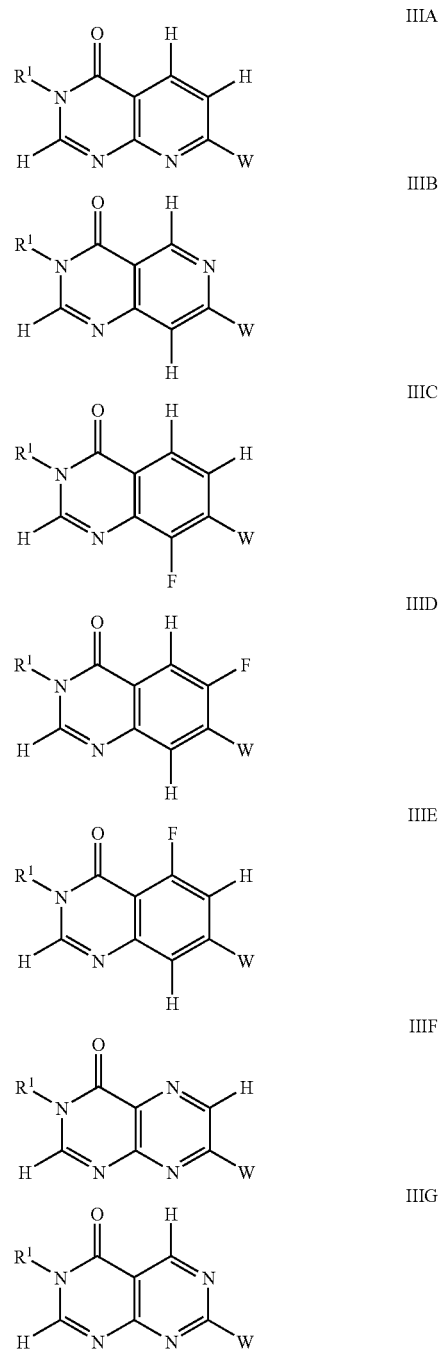

In an embodiment of the first and second groups of compounds of formula IB, the compounds of formula IB are selected from the group consisting of compounds having the formula IVA and IVB such as shown below where $R^1$, W, $R^{1'}$, $R^{2'}$, $R^{3'}$, and $R^{4'}$ have the same values as those described above with respect to the compounds of formula IA, IB, and IC.

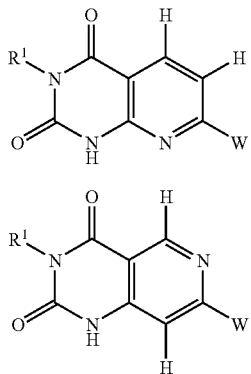

The instant invention provides a third and fourth group of compounds that are potent and specific agonists of MC4-R that are small molecules. Thus, in accordance with one aspect of the invention, the invention provides a third and fourth group of compounds of formula IA and IC. Compounds of the invention further include prodrugs of compounds of formula IA and IC, pharmaceutically acceptable salts thereof, stereoisomers thereof, tautomers thereof, hydrates thereof, or solvates thereof.

Compounds of formula IA and IC have the following structure.

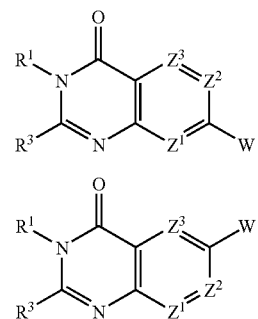

In the third and fourth groups of compounds of formula IA and IC, $Z^1$ is selected from the group consisting of $CR^4$ and N. In some embodiments of the second compounds of formula IA and IC, $Z^1$ is a $CR^4$ group whereas in other embodiments, $Z^1$ is a N.

In the third and fourth groups of compounds of formula IA and IC, $Z^2$ is selected from the group consisting of $CR^5$ and N. In some embodiments of the second group of compounds of formula IA and IC, $Z^2$ is a $CR^5$ group whereas in other embodiments, $Z^2$ is a N.

In the third and fourth groups of compounds of formula IA and IC, $Z^3$ is selected from the group consisting of $CR^6$ and N. In some embodiments, $Z^3$ is a $CR^6$ group whereas in other embodiments, $Z^3$ is a N.

In some embodiments of the third and fourth groups of compounds of formula IA and IC, $Z^1$ is a $CR^4$ group, $Z^2$ is a $CR^5$ group, and $Z^3$ is a $CR^6$ group. Thus, in some embodiments the ring that includes $Z^1$, $Z^2$, and $Z^3$ may be a carbocyclic aromatic ring. In some embodiments of the third and fourth groups of compounds of formula IA and IC, where $Z^1$ is a $CR^4$ group, $Z^2$ is a $CR^5$ group, and $Z^3$ is a $CR^6$ group, at least one of $R^4$, $R^5$, or $R^6$ is a halogen such as Cl or F. In other such embodiments, at least one of $R^4$, $R^5$, or $R^6$ is a F.

In some embodiments of the third and fourth groups of compounds of formula IA and IC, at least one of $Z^1$, $Z^2$, or $Z^3$ is a N.

In the third and fourth groups of compounds of formula IA and IC, $R^1$ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups. In some embodiments of the third and fourth groups of compounds of formula IA and IC, $R^1$ is a 2,4-disubstituted phenylethyl group. In other embodiments, $R^1$ is selected from 2,4-dihalophenylethyl and 2,4-dialkylphenylethyl groups. In still other embodiments, $R^1$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In other embodiments, $R^1$ is a H or is an alkyl group having from one to eight carbon atoms. In some such embodiments, $R^1$ is H whereas in other such embodiments, $R^1$ is a methyl, ethyl, or propyl group. In some such embodiments, $R^1$ is a methyl group.

In still further embodiments, the invention provides compounds of formula IA and IC in which $R^1$ is a substituted or unsubstituted alkenyl group such as a substituted or unsubstituted allyl group or a substituted or unsubstituted vinyl group.

In the third and fourth groups of compounds of formula IA and IC, $R^3$ is selected from the group consisting of substituted and unsubstituted arylalkyl, heteroarylalkyl, alkoxy, alkoxyalkyl, aryloxyalkyl, alkylamino, dialkylamino, aryl, heteroaryl, heterocyclyl, cycloalkyl, heterocyclylalkyl, cycloalkylalkyl, alkenyl, alkynyl, alkyl groups, and —C(=NH)-heterocyclyl groups, and groups of formula -L$R^7$. In some embodiments of the third and fourth groups of compounds of formula IA and IC, $R^3$ is a 2,4-disubstituted phenylethyl group. In other embodiments, $R^3$ is selected from 2,4-dihalophenylethyl and 2,4-dialkylphenylethyl groups. In still other embodiments, $R^3$ is selected from the group that includes phenylethyl, 2,4-dichlorophenylethyl, 4-methoxyphenylethyl, 4phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments of the third and fourth groups of compounds, $R^3$ has any of the values described in this paragraph, and $R^1$ is H or is a substituted or unsubstituted alkyl group. In some such embodiments, $R^1$ is H.

In some aspects of the invention of compounds of the third and fourth groups of compounds of potent and specific agonists of MC4-R, the invention further provides compounds of formula IA and IC in which $R^3$ is a substituted or unsubstituted alkyl group such as a substituted or unsubstituted aryloxyalkyl group or a substituted or unsubstituted heteroaryloxyalkyl group. In some such embodiments, $R^3$ is a substituted or unsubstituted aryloxymethyl group. In some such embodiments, $R^3$ is selected from the group consisting of —$CH_2$—O-aryl groups where the aryl group is substituted with one or more halogen group such as with one or more Cl or F. In some such embodiments, the aryl group is additionally substituted with an alkoxy group such as a methoxy or ethoxy group. In some embodiments of the third and fourth groups of compounds of formula IA and IC, $R^3$ is a —$CH_2$—O-aryl group where the aryl group is selected from the group consisting of 2,4-difluorophenyl, 4-fluorophenyl, 2-fluorophenyl, 2-fluoro-4-methoxyphenyl, 2,4-dichlorophenyl, 4-chlorophenyl, 2-chlorophenyl, and 2-chloro-4-methoxyphenyl groups. In other embodiments, $R^3$ is a heterocyclylalkyl group. In some other embodiments of compounds of formula IA and IC, $R^3$ is a substituted or unsubstituted arylalkoxyalkyl group or a heteroarylalkoxyalkyl group.

In some aspects of the invention of compounds of the third and fourth groups of compounds of potent and specific agonists of MC4-R, the invention further provides compounds of formula IA and IC in which $R^3$ is a substituted or unsubstituted heterocyclylalkyl group. In some such embodiments, $R^3$ is a substituted or unsubstituted heterocyclylmethyl group. In some such embodiments, the heterocyclyl group is selected from the group consisting of substituted and unsubstituted 1H-tetrazole, piperazine, piperidine, imidazole, and morpholine groups. In some such embodiments, $R^3$ is a —$CH_2$-heterocyclyl group where the heterocyclyl group is a 1H-tetrazole, an imidazole, an N-methylpiperazine, a 4-hydroxypiperidine, a 3-hydroxypiperidine, or a morpholine. In still other embodiments of the third and fourth groups of compounds of formula IA and IC, $R^3$ is a heterocyclyl group. In some embodiments of the third and fourth groups of compounds of formula IA and IC, $R^3$ is a substituted or unsubstituted piperazinyl group such as an N-methylpiperazinyl group, is a substituted or unsubstituted pyridine group, is a substituted or unsubstituted tetrazole group, is a substituted or unsubstituted cycloalkyl group such as a 4-methylcyclohexyl group, or is a substituted or unsubstituted phenyl group. In yet other embodiments, $R^3$ is an alkoxyalkyl group such as a methoxyalkyl group or an ethoxyalkyl group. In some such embodiments, $R^3$ is a an alkoxyalkyl group such as an alkoxymethyl group such as a methoxymethyl group.

In some other embodiments of the third and fourth groups of compounds of formula IA and IC, $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

In some embodiments of the third and fourth groups of compounds of formula IA and IC, $R^1$ is an arylalkyl group such as those described above for $R^3$. In some such embodiments, $R^1$ is a substituted or unsubstituted phenylethyl group and $R^3$ is an alkyl group such as a methyl group. In other embodiments, $R^1$ is an alkyl group such as a methyl group and $R^3$ is selected from substituted aryloxyalkyl groups, phenylaminoalkyl groups or groups of -$LR^7$ where $R^7$ is a group formula IIC.

In the third and fourth groups of compounds of formula IA and IC, $R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups. In some embodiments of the third and fourth groups of compounds of formula IA and IC, $R^4$, $R^5$, and $R^6$ are selected from H or a halogen such as Cl or F. In other embodiments of the third and fourth groups of compounds of formula IA and IC, at least one of $R^4$, $R^5$, or $R^6$ is a F whereas in other embodiments of the third and fourth groups of compounds of formula IA and IC, $R^4$, $R^5$, and $R^6$ are all H.

In the third and fourth groups of compounds of formula IA and IC, W is a group of formula IIA or IIB having the following structure.

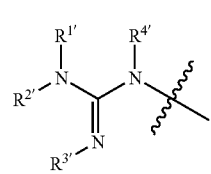

IIA

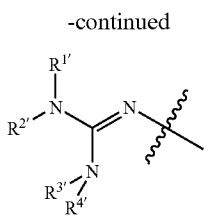

In the third group of compounds of formula IA and IC, $R^{1'}$ is selected from H, or substituted and unsubstituted alkyl, alkenyl, alkynyl, cycloalkyl, aryl, heteroaryl, heterocyclyl, arylalkyl, heteroarylalkyl, cycloalkylalkyl, or heterocyclylalkyl groups and $R^{2'}$ is selected from H, or substituted and unsubstituted alkyl, alkenyl, alkynyl, cycloalkyl, aryl, heteroaryl, heterocyclyl, arylalkyl, heteroarylalkyl, cycloalkylalkyl, and heterocyclylalkyl groups. In some such embodiments, at least one of $R^{1'}$ and $R^{2'}$ is a heterocyclylalkyl group such as, but not limited to, a substituted or unsubstituted pyrrolidinylmethyl or pyrrolidinylethyl group. In some such embodiments, W is a group of formula IIA.

In the fourth group of compounds of formula IA and IC, $R^{1'}$ and $R^{2'}$, together with the nitrogen to which they are bound, join together to form a heterocyclic ring. The heterocyclic ring is substituted with at least one group selected from the group consisting of substituted and unsubstituted arylalkyl, —C(=O)-alkyl, -alkyl—C(=O)—O-alkyl, —C(=O)—O-alkyl, —C(=O)—NH$_2$, —C(=O)—NH(alkyl), —C(=O)—N(alkyl)$_2$, dialkylaminoalkyl, alkylaminoalkyl, aminoalkyl, aryl, heteroaryl, heterocyclyl, heteroarylalkyl, heterocyclylalkyl, and alkylthioalkyl groups. In some such embodiments, the heterocyclic ring is a substituted piperazine and in other such embodiments, the heterocyclic ring is a piperidine ring. In some such embodiments, the piperazine or piperidine ring is substituted with a group selected from the group consisting of a phenylalkyl group, a substituted or unsubstituted phenyl group, an -alkyl-SCH$_3$ group, an indolylalkyl group, a morpholinylalkyl group, a pyridyl group, a piperidinyl group, and a tetrahydrofuranylalkyl group.

In the third and fourth groups of compounds of formula IA and IC, $R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups. In one embodiment, $R^{3'}$ is selected from the group consisting of substituted and unsubstituted cycloalkyl, polycyclic cycloalkyl, alkenyl, alkyl, and aryl groups. In still other embodiments, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,5-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocyclohexyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl (polycyclic cycloalkyl), fluoromethyl(polycyclic cycloalkyl), and fluoro(polycyclic cycloalkyl) groups.

In the third and fourth groups of compounds of formula IA and IC, $R^{4'}$ is selected from H, or substituted and unsubstituted alkyl, alkenyl, alkynyl, cycloalkyl, heterocyclylalkyl, cycloalkylalkyl, aryl, heteroaryl, heterocyclyl, arylalkyl, or heteroarylalkyl groups. In one embodiment, $R^{4'}$ is H.

In the third and fourth groups of compounds of formula IA and IC, L is selected from the group consisting of a covalent bond, —CH$_2$—, —O—, —S—, and —NH—.

In the third and fourth groups of compounds of formula IA and IC, $R^7$ is selected from the group consisting of substituted and unsubstituted arylaminoalkyl, aryl, and aryloxyalkyl groups or is selected from a group of formula IIC;

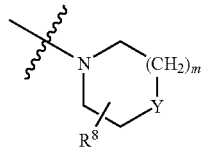

In the third and fourth groups of compounds of formula IA and IC, Y is selected from the group consisting of CH$_2$, O, S, and NR$^9$ where R$^9$. In some embodiments, Y is an NR$^9$ group and in some such embodiments, m is 1. In some such embodiments, R$^9$ is an alkyl group such as a methyl group or is a H.

In the third and fourth groups of compounds of formula IA and IC, $R^8$ is selected from the group consisting of H, a halogen, hydroxyl, carboxylic acid, and substituted or unsubstituted alkyl, amino, alkylamino, dialkylamino, alkylaminoalkyl, heterocyclyl, alkoxy, carbonyl, and aminocarbonyl groups.

In the third and fourth groups of compounds of formula IA and IC, m is an integer selected from the group consisting of 0, 1, and 2. In some embodiments, m is 1.

The instant invention provides a fifth and a sixth group of compounds that are potent and specific agonists of MC4-R that are small molecules. Thus, in accordance with one aspect of the invention, the invention provides a fifth and a sixth group of compounds of formula ID. Compounds of the invention further include prodrugs of compounds of formula ID, pharmaceutically acceptable salts thereof, stereoisomers thereof, tautomers thereof, hydrates thereof, or solvates thereof.

Compounds of formula ID have the following structure.

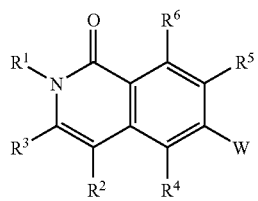

In some embodiments of the fifth and sixth group of compounds of formula ID, at least one of $R^4$, $R^5$, or $R^6$ is a halogen such as Cl or F. In other such embodiments, at least one of $R^4$, $R^5$, or $R^6$ is a F.

In the fifth and sixth groups of compounds of formula ID, $R^1$ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups. In some embodiments, $R^1$ is a 2,4-disubstituted phenylethyl group. In other embodiments, $R^1$ is selected from 2,4-dihalophenylethyl and 2,4-dialkylphenylethyl groups. In still other embodiments, $R^1$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments of the fifth and sixth groups of compounds, $R^1$ is a H or is an alkyl group having from one to eight carbon atoms. In some such embodiments, $R^1$ is H whereas in other such embodiments, $R^1$ is a methyl, ethyl, or propyl group. In some such embodiments, $R^1$ is a methyl group.

In still further embodiments, the invention provides compounds of formula ID in which $R^1$ is a substituted or unsubstituted alkenyl group such as a substituted or unsubstituted allyl group or a substituted or unsubstituted vinyl group.

In the fifth and sixth groups of compounds of formula ID, $R^2$ and $R^3$ are independently selected from the group consisting of substituted and unsubstituted arylalkyl, heteroarylalkyl, alkoxy, alkoxyalkyl, aryloxyalkyl, alkylamino, dialkylamino, aryl, heteroaryl, heterocyclyl, cycloalkyl, heterocyclylalkyl, cycloalkylalkyl, alkenyl, alkynyl, alkyl groups, and —C(=NH)-heterocyclyl groups, and groups of formula -L$R^7$. In some embodiments of the fifth and sixth groups of compounds of formula ID, $R^2$ is —H or a substituted or unsubstituted alkyl group. In some embodiments, $R^3$ is a 2,4-disubstituted phenylethyl group. In other embodiments, $R^3$ is selected from 2,4-dihalophenylethyl and 2,4-dialkylphenylethyl groups. In still other embodiments, $R^3$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl) ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments of the fifth and sixth groups of compounds, $R^3$ has any of the values described in this paragraph, and $R^1$ or $R^2$ is H or is a substituted or unsubstituted alkyl group. In some such embodiments, $R^1$ is H. In other such embodiments, $R^2$ is H.

In some aspects of the invention of compounds of the fifth and sixth groups of potent and specific agonists of MC4-R, the invention further provides compounds of formula ID in which $R^3$ is a substituted or unsubstituted alkyl group such as a substituted or unsubstituted aryloxyalkyl group or a substituted or unsubstituted heteroaryloxyalkyl group. In some such embodiments, $R^3$ is a substituted or unsubstituted aryloxymethyl group. In some other such embodiments, $R^3$ is selected from the group consisting of —CH$_2$—O-aryl groups where the aryl group is substituted with one or more halogen group such as with one or more Cl or F. In some such embodiments, the aryl group is additionally substituted with an alkoxy group such as a methoxy or ethoxy group. In some embodiments of the fifth and sixth groups of compounds of formula ID, $R^3$ is a —CH$_2$—O-aryl group where the aryl group is selected from the group consisting of 2,4-difluorophenyl, 4-fluorophenyl, 2-fluorophenyl, 2-fluoro-4-methoxyphenyl, 2,4-dichlorophenyl, 4-chlorophenyl, 2-chlorophenyl, and 2-chloro-4-methoxyphenyl groups. In other embodiments, $R^3$ is a heterocyclylalkyl group. In some other embodiments, $R^3$ is a substituted or unsubstituted arylalkoxyalkyl group or a heteroarylalkoxyalkyl group.

In some aspects of the invention of compounds of the fifth and sixth groups of potent and specific agonists of MC4-R, the invention further provides compounds of formula ID in which $R^3$ is a substituted or unsubstituted heterocyclylalkyl group. In some such embodiments, $R^3$ is a substituted or unsubstituted heterocyclylmethyl group. In still other such embodiments, the heterocyclyl group is selected from the group consisting of substituted and unsubstituted 1H-tetrazole, piperazine, piperidine, imidazole, and morpholine groups. In some such embodiments, $R^3$ is a —$CH_2$-heterocyclyl group where the heterocyclyl group is a 1H-tetrazole, an imidazole, an N-methylpiperazine, a 4-hydroxypiperidine, a 3-hydroxypiperidine, or a morpholine. In still other embodiments of the fifth and sixth groups of compounds of formula ID, $R^3$ is a heterocyclyl group. In some embodiments, $R^3$ is a substituted or unsubstituted piperazinyl group such as an N-methylpiperazinyl group, is a substituted or unsubstituted pyridine group, is a substituted or unsubstituted tetrazole group, is a substituted or unsubstituted cycloalkyl group such as a 4-methylcyclohexyl group, or is a substituted or unsubstituted phenyl group. In yet other embodiments, $R^3$ is an alkoxyalkyl group such as a methoxyalkyl group or an ethoxyalkyl group. In some embodiments, $R^3$ is a an alkoxyalkyl group such as an alkoxymethyl group such as a methoxymethyl group.

In some other embodiments of the fifth and sixth groups of compounds of formula ID, $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

In some embodiments of the fifth and sixth groups of compounds of formula ID, $R^1$ is an arylalkyl group such as those described above for $R^3$. In some such embodiments, $R^1$ is a substituted or unsubstituted phenylethyl group and $R^3$ is an alkyl group such as a methyl group. In other embodiments of the fifth and sixth groups of compounds, $R^1$ is an alkyl group such as a methyl group and $R^3$ is selected from substituted aryloxyalkyl groups, phenylaminoalkyl groups or groups of -$LR^7$ where $R^7$ is a group formula IIC.

In the fifth and sixth groups of compounds of formula ID, $R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups. In some embodiments of the fifth and sixth groups of compounds of formula ID, $R^4$, $R^5$, and $R^6$ are selected from H or a halogen such as Cl or F. In other embodiments of the fifth and sixth groups of compounds of formula ID, at least one of $R^4$, $R^5$, or $R^6$ is a F whereas in other embodiments, $R^4$, $R^5$, and $R^6$ are all H.

In the fifth and sixth groups of compounds of formula ID, W is a group of formula IIA or IIB having the following structure.

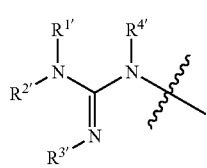

IIA

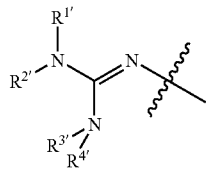

IIB

In the fifth group of compounds of formula ID, $R^{1'}$ is selected from H, or substituted and unsubstituted alkyl, alkenyl, alkynyl, cycloalkyl, aryl, heteroaryl, heterocyclyl, arylalkyl, heteroarylalkyl, cycloalkylalkyl, or heterocyclylalkyl groups and $R^{2'}$ is selected from H, or substituted and unsubstituted alkyl, alkenyl, alkynyl, cycloalkyl, aryl, heteroaryl, heterocyclyl, arylalkyl, heteroarylalkyl, cycloalkylalkyl, and heterocyclylalkyl groups. In some such embodiments, at least one of $R^{1'}$ and $R^{2'}$ is a heterocyclylalkyl group such as, but not limited to, a substituted or unsubstituted pyrrolidinylmethyl or pyrrolidinylethyl group. In some such embodiments, W is a group of formula IIA.

In the sixth group of compounds of formula ID, $R^{1'}$ and $R^{2'}$ together with the nitrogen to which they are bound, join together to form a heterocyclic ring. The heterocyclic ring is substituted with at least one group selected from the group consisting of substituted and unsubstituted arylalkyl, —C(=O)-alkyl, -alkyl—C(=O)—O-alkyl, —C(=O)—O-alkyl, —C(=O)—$NH_2$, —C(=O)—NH(alkyl), —C(=O)—N(alkyl)$_2$, dialkylaminoalkyl, alkylaminoalkyl, aminoalkyl, aryl, heteroaryl, heterocyclyl, heteroarylalkyl, heterocyclylalkyl, and alkylthioalkyl groups. In some such embodiments, the heterocyclic ring is a substituted piperazine and in other such embodiments, the heterocyclic ring is a piperidine ring. In some such embodiments, the piperazine or piperidine ring is substituted with a group selected from the group consisting of a phenylalkyl group, a substituted or unsubstituted phenyl group, an -alkyl-$SCH_3$ group, an indolylalkyl group, a morpholinylalkyl group, a pyridyl group, a piperidinyl group, and a tetrahydrofuranylalkyl group.

In the fifth and sixth groups of compounds of formula ID, $R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups. In one embodiment, $R^{3'}$ is selected from the group consisting of substituted and unsubstituted cycloalkyl, polycyclic cycloalkyl, alkenyl, alkyl, and aryl groups. In still other embodiments, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments, R$^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl (polycyclic cycloalkyl), fluoromethyl(polycyclic cycloalkyl), and fluoro(polycyclic cycloalkyl) groups. By way of nonlimiting example, suitable R$^{3'}$ cycloalkyl, cyclohexyl, and polycyclic cycloalkyl groups that include fluorine, include, but are not limited to, the structures set forth above with respect to the first group of compounds of formula IA, IB, and IC In the fifth and sixth groups of compounds of formula ID, R$^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups. In one embodiment of the fifth and sixth groups of compounds of formula ID, R$^{4'}$ is H.

In the fifth and sixth groups of compounds of formula ID, L is selected from the group consisting of a covalent bond, —CH$_2$—, —O—, —S—, and —NH—.

In the fifth and sixth groups of compounds of formula ID, R$^7$ is selected from the group consisting of substituted and unsubstituted arylaminoalkyl, aryl, and aryloxyalkyl groups or is selected from a group of formula IIC;

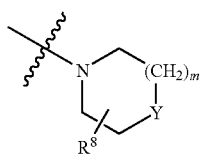

IIC

In the fifth and sixth groups of compounds of formula ID, Y is selected from the group consisting of CH$_2$, O, S, and NR$^9$ where R$^9$. In some embodiments, Y is an NR$^9$ group and in some such embodiments, m is 1. In some such embodiments, R$^9$ is an alkyl group such as a methyl group or is a H.

In the fifth and sixth groups of compounds of formula ID, R$^8$ is selected from the group consisting of H, a halogen, hydroxyl, carboxylic acid, and substituted or unsubstituted alkyl, amino, alkylamino, dialkylamino, alkylaminoalkyl, heterocyclyl, alkoxy, carbonyl, and aminocarbonyl groups.

In the fifth and sixth groups of compounds of formula ID, m is an integer selected from the group consisting of 0, 1, and 2. In some embodiments, m is 1.

The instant invention provides a seventh and an eighth group of compounds that are potent and specific agonists of MC4-R that are small molecules. Thus, in accordance with one aspect of the invention, the invention provides a seventh and an eighth group of compounds of formula IE. Compounds of the invention further include prodrugs of compounds of formula IE, pharmaceutically acceptable salts thereof, stereoisomers thereof, tautomers thereof, hydrates thereof, or solvates thereof.

Compounds of formula IE have the following structure.

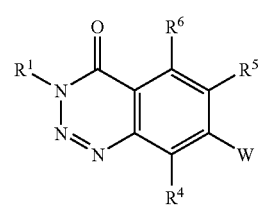

IE

In some embodiments of the seventh and eighth groups of compounds of formula IE, at least one of R$^4$, R$^5$, or R$^6$ is a halogen such as Cl or F. In other such embodiments, at least one of R$^4$, R$^5$, or R$^6$ is a F.

In the seventh and eighth groups of compounds of formula IE, R$^1$ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups. In some embodiments, R$^1$ is a 2,4-disubstituted phenylethyl group. In other embodiments, R$^1$ is selected from 2,4-dihalophenylethyl and 2,4-dialkylphenylethyl groups. In still other embodiments of the seventh and eighth groups of compounds of formula IE, R$^1$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl) ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments, R$^1$ is a H or is an alkyl group having from one to eight carbon atoms. In some such embodiments, R$^1$ is H whereas in other such embodiments, R$^1$ is a methyl, ethyl, or propyl group. In some such embodiments, R$^1$ is a methyl group.

In still further embodiments of the seventh and eighth groups, the invention provides compounds of formula IE in which R$^1$ is a substituted or unsubstituted alkenyl group such as a substituted or unsubstituted allyl group or a substituted or unsubstituted vinyl group.

In the seventh and eighth groups of compounds of formula IE, $R^1$ is H or is a substituted or unsubstituted alkyl group. In some such embodiments, $R^1$ is H.

In the seventh and eighth groups of compounds of formula IE, $R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups. In some embodiments, $R^4$, $R^5$, and $R^6$ are selected from H or a halogen such as Cl or F. In other embodiments, at least one of $R^4$, $R^5$, or $R^6$ is a F whereas in other embodiments, $R^4$, $R^5$, and $R^6$ are all H.

In the seventh and eighth groups of compounds of formula IE, W is a group of formula IIA or IIB having the following structure.

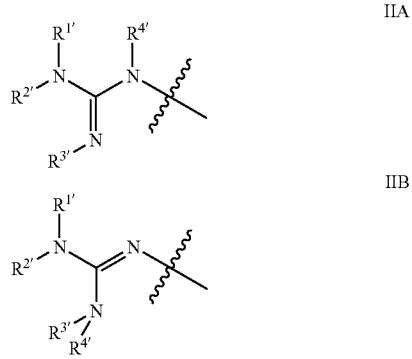

In the seventh group of compounds of formula IE, $R^{1'}$ is selected from H, or substituted and unsubstituted alkyl, alkenyl, alkynyl, cycloalkyl, aryl, heteroaryl, heterocyclyl, arylalkyl, heteroarylalkyl, cycloalkylalkyl, or heterocyclylalkyl groups and $R^{2'}$ is selected from H, or substituted and unsubstituted alkyl, alkenyl, alkynyl, cycloalkyl, aryl, heteroaryl, heterocyclyl, arylalkyl, heteroarylalkyl, cycloalkylalkyl, and heterocyclylalkyl groups. In some such embodiments, at least one of $R^{1'}$ and $R^{2'}$ is a heterocyclylalkyl group such as, but not limited to, a substituted or unsubstituted pyrrolidinylmethyl or pyrrolidinylethyl group. In some such embodiments, W is a group of formula IIA.

In the eighth group of compounds of formula IE, $R^{1'}$ and $R^{2'}$, together with the nitrogen to which they are bound, join together to form a heterocyclic ring. The heterocyclic ring is substituted with at least one group selected from the group consisting of substituted and unsubstituted arylalkyl, —C(=O)-alkyl, -alkyl-C(=O)—O-alkyl, —C(=O)—O-alkyl, —C(=O)—$NH_2$, —C(=O)—NH(alkyl), —C(=O)—N(alkyl)$_2$, dialkylaminoalkyl, alkylaminoalkyl, aminoalkyl, aryl, heteroaryl, heterocyclyl, heteroarylalkyl, heterocyclylalkyl, and alkylthioalkyl groups. In some such embodiments, the heterocyclic ring is a substituted piperazine and in other such embodiments, the heterocyclic ring is a piperidine ring. In some such embodiments, the piperazine or piperidine ring is substituted with a group selected from the group consisting of a phenylalkyl group, a substituted or unsubstituted phenyl group, an -alkyl-$SCH_3$ group, an indolylalkyl group, a morpholinylalkyl group, a pyridyl group, a piperidinyl group, and a tetrahydrofuranylalkyl group.

In the seventh and eighth groups of compounds of formula IE, $R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups. In one embodiment of the seventh and eighth groups of compounds of formula IE, $R^{3'}$ is selected from the group consisting of substituted and unsubstituted cycloalkyl, polycyclic cycloalkyl, alkenyl, alkyl, and aryl groups. In still other embodiments, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of the seventh and eighth groups of compounds of formula IE, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl (polycyclic cycloalkyl), fluoromethyl(polycyclic cycloalkyl), and fluoro(polycyclic cycloalkyl) groups. By way of nonlimiting example, suitable $R^{3'}$ cycloalkyl, cyclohexyl, and polycyclic cycloalkyl groups that include fluorine, include, but are not limited to, the structures set forth above with respect to the first group of compounds of formula IA, IB, and IC.

In the seventh and eighth groups of compounds of formula IE, $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups. In one embodiment, $R^{4'}$ is H.

In some embodiments of any of the compounds of the invention which includes a W group of formula IIA or IIB where $R^{1'}$ and $R^{2'}$ join together with the nitrogen to which they are bound to form a heterocyclic group, the heterocyclic group is substituted with a —CN group, an —OH group, a —$CF_3$ group, a —$CH_2F$ group, a —$CHF_2$ group, a —$CH_2CN$ group, a —$CH_2OH$ group, a —$CH_2O$-alkyl group, or a cycloalkyl group such as a cyclopropyl group. In some such compounds, the heterocyclic compound is a piperidine or a piperazine. In some such compounds, $R^{1'}$ and $R^{2'}$ join together with the nitrogen to which they are bound to form a piperazine in which the N atom in the piperazine ring which is not part of the guanidine group is substituted with a —C≡N group, an —OH group, a —CH₂CN group, or a cycloalkyl group. In some compounds in which $R^{1'}$ and $R^{2'}$ join together with the nitrogen to which they are bound to form a heterocyclic ring, the heterocycle is a bicyclic structure that includes a spirocenter such that the heterocyclic ring is part of a spirocyclic structure. In some compounds in which $R^{1'}$ and $R^{2'}$ join together with the nitrogen to which they are bound to form a heterocyclic ring, the heterocyclic ring is substituted such that a ring carbon atom of the heterocyclic ring is a carbonyl carbon or the carbon of the heterocyclic ring is replaced with a sulfur that is bonded to one or more oxygen atoms. For example, in some embodiments $R^{1'}$ and $R^{2'}$ join together with the nitrogen to which they are bound to form a piperazine ring in which one of the ring carbon atoms is a carbonyl carbon atom such that the piperazine compound is a lactam which may be further substituted, for example, with an alkyl group such as a methyl group.

The instant invention provides potent and specific agonists of MC4-R that are small molecules and may exhibit reduced bioaccumulation properties when administered to animal subjects. In accordance with one aspect of the invention, the invention provides compounds of formula VA and VB. Compounds provided by the invention further include prodrugs of the compound of formula VA and VB, pharmaceutically acceptable salts thereof, stereoisomers thereof, tautomers thereof, hydrates thereof, and solvates thereof. Compounds of formula VA or VB have the following structures:

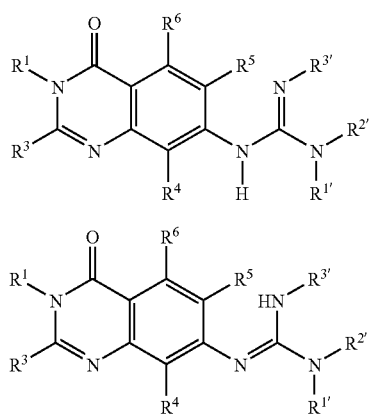

In compounds of formula VA and VB, $R^1$ is selected from substituted or unsubstituted arylalkyl, heteroarylalkyl, aryl, heteroaryl, heterocyclyl, cycloalkyl, heterocyclylalkyl, cycloalkylalkyl, alkenyl, alkynyl, or alkyl groups. In some embodiments, $R^1$ is a substituted or unsubstituted arylalkyl group such as a substituted or unsubstituted phenylethyl group. In some such embodiments, $R^1$ is a substituted phenylethyl group such as a 4-substituted phenylethyl group or a 2,4-disubstituted phenylethyl group such as 4-halophenylethyl, 2-halo-4-alkoxyphenylethyl, and 2,4-dihalophenylethyl groups. In some embodiments, $R^1$ is selected from phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-fluorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, indolylethyl, 4-hydroxyphenylethyl, 3,4-dimethoxyphenylethyl, 2-chloro-4-iodophenylethyl, 2-fluoro-4-methylphenylethyl, 4-chloro-2-fluorophenylethyl, 4-bromo-2-fluorophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, and (phenyl)(hydroxymethyl)ethyl groups. In still other embodiments, $R^1$ is selected from a 2-fluoro-4-methoxyphenylethyl group, a 2-chloro-4-methoxyphenylethyl, 4-fluorophenylethyl, a 4-chlorophenylethyl, a 4-chloro-2-fluorophenylethyl, a 2,4-dichlorophenylethyl, a 4-bromophenylethyl, or a 4-bromo-2-fluorophenylethyl group. In still other embodiments, $R^1$ is selected from phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups.

In compounds of formula VA and VB, $R^3$ is selected from substituted or unsubstituted aryl, heteroaryl, heterocyclyl, cycloalkyl, heterocyclylalkyl, or cyloalkylamino groups. Compounds of formula VA and VB with $R^3$ values such as those set forth above have been found to exhibit reduced bioaccumulation properties as evidenced by lower $t_{1/2}$ blood plasma values in test subjects to which the compounds have been administered. Generally, such compounds also provide improved plasma $C_{max}$ values and may also provide improved brain $C_{max}$ values. In some embodiments, $R^3$ is selected from substituted or unsubstituted heterocyclyl groups or substituted or unsubstituted heteroaryl groups. In other embodiments, $R^3$ is selected from substituted or unsubstituted pyridinyl, piperidinyl, piperazinyl, morpholinyl, thiomorpholinyl, tetrahydrofuranyl, furanyl, pyrrolidinyl, pyrrolyl, thiophenyl, tetrahydrothiophenyl, pyranyl, tetrahydropyranyl, tetrahydrothiopyranyl, pyrazinyl, thiazolyl, pyrimidinyl, quinuclidinyl, indolyl, imidazolyl, triazolyl, tetrazolyl, or pyridazinyl groups. In some such embodiments, $R^3$ is selected from heteroaryl or heterocyclyl group of formula

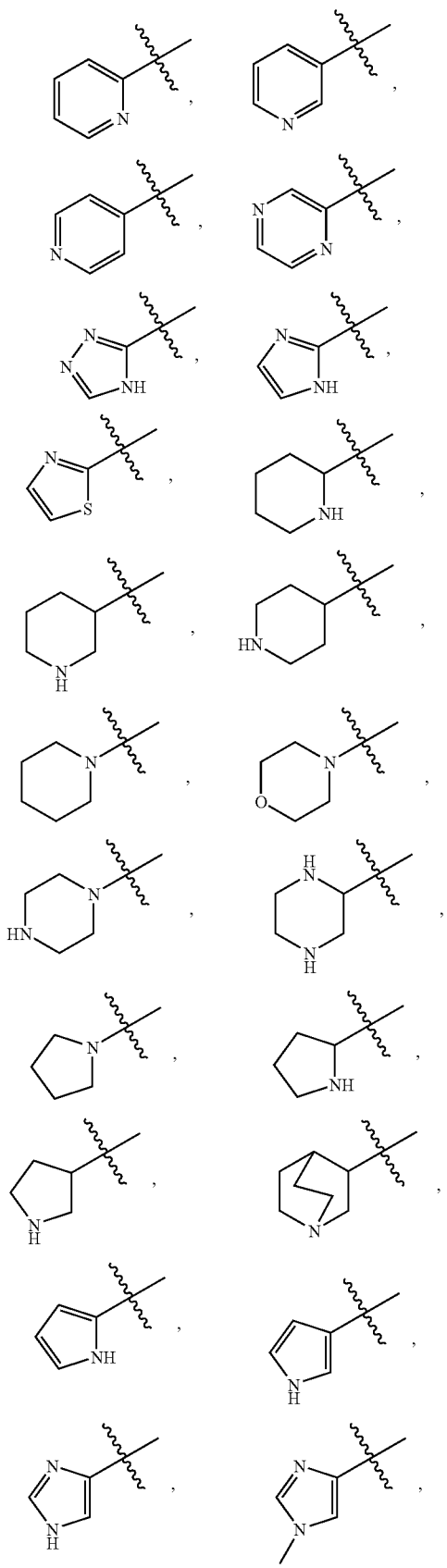

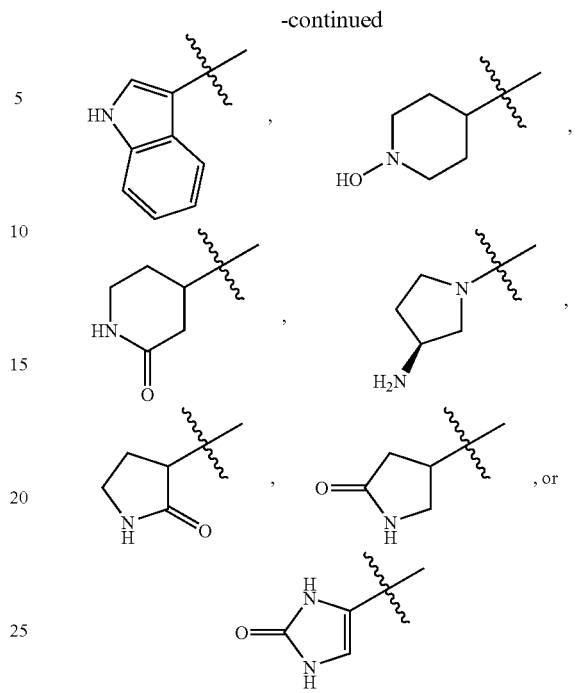

which may be additionally substituted or may be unsubstituted. In some embodiments, the invention provides compounds of formula VA and VB in which $R^3$ is selected from substituted or unsubstituted heterocyclylalkyl, or cycloalkylamino groups. For example, in some embodiments, $R^3$ is selected from a group such as a substituted or unsubstituted cyclopropylamino group; a substituted or unsubstituted piperazinylalkyl group such as a piperazinylmethyl group or an N-methylpiperazinylmethyl group; or a piperidinylalkyl group such as a piperidinylmethyl group or a piperidinylethyl group. In some embodiments, $R^3$ may be selected from a substituted or unsubstituted aryl or cycloalkyl group. Examples include compounds of the following formula which may be additionally substituted.

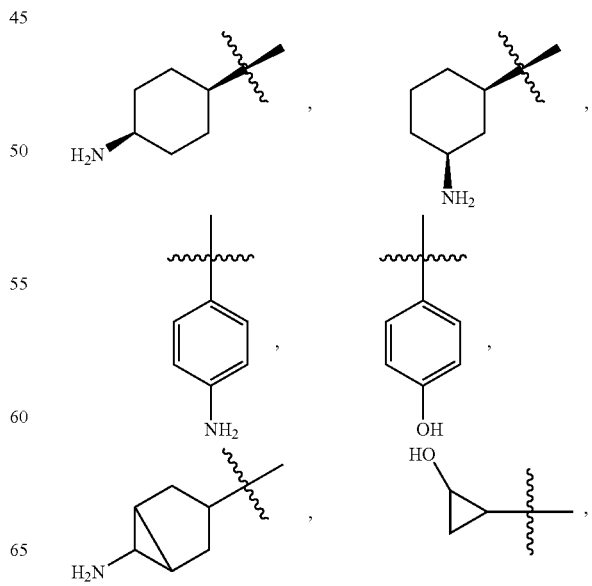

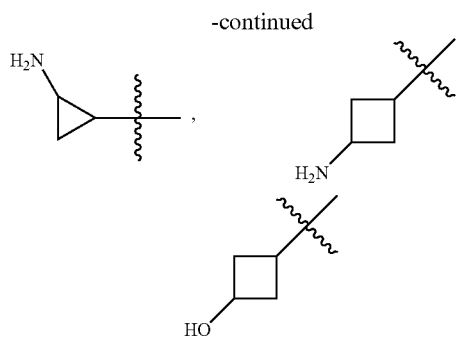

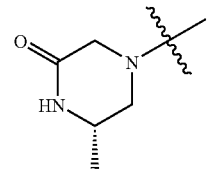

In compounds of formula VA and VB, $R^4$, $R^5$, and $R^6$ are independently selected from H, Cl, I, F, Br, OH, $NH_2$, CN, $NO_2$, and substituted and unsubstituted alkoxy, and alkyl groups. In some embodiments, each of $R^4$, $R^5$, and $R^6$ are H.

In compounds of formula VA and VB, $R^{1'}$ and $R^{2'}$, together with the nitrogen to which they are bound, form a substituted or unsubstituted heterocyclyl group. In some embodiments, $R^{1'}$ and $R^{2'}$, together with the nitrogen to which they are bound, form a substituted or unsubstituted saturated heterocyclyl group such as, but not limited to, a piperazinyl group, a piperidinyl group, or the like. In some such embodiments, $R^{1'}$ and $R^{2'}$ together with the nitrogen to which they are bound, form a substituted or unsubstituted piperazinyl group. In some such embodiments, $R^{1'}$ and $R^{2'}$, together with the nitrogen to which they are bound, form a piperazinyl group that is substituted with at least one group selected from, fluoromethyl, difluoromethyl, or trifluoromethyl groups. In other embodiments, $R^{1'}$ and $R^{2'}$, together with the nitrogen to which they are bound, form a piperazinyl group substituted with at least one carbonyl group such that the piperazinyl group is a piperazinone that may be additionally substituted. In some such embodiments, $R^{1'}$ and $R^{2'}$, together with the nitrogen to which they are bound form a piperazinone of formula

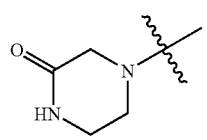

which may be additionally substituted. In some such embodiments, $R^{1'}$ and $R^{2'}$, together with the nitrogen to which they are bound form a piperazinone of formula

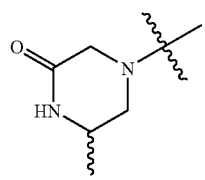

In some such embodiments, $R^{1'}$ and $R^{2'}$, together with the nitrogen to which they are bound form a piperazinone of formula

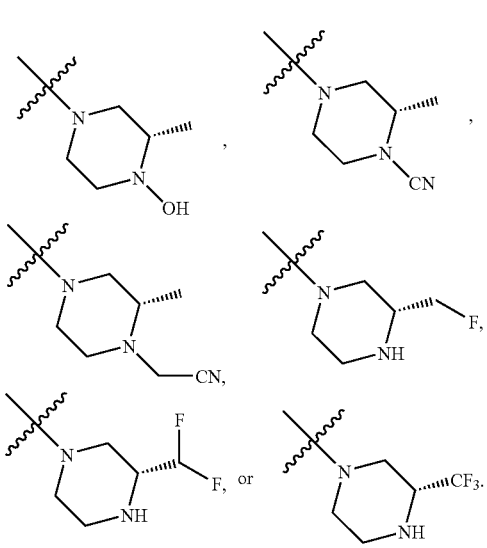

In some embodiments, the invention provides compounds of formula VA and VB in which $R^{1'}$ and $R^{2'}$, together with the nitrogen to which they are bound, form a piperazinyl group of formula Compounds of formula VA and VB with $R^{1'}$ and $R^{2'}$ values such as those set forth above have been found to exhibit reduced bioaccumulation properties as evidenced by lower $t_{1/2}$ blood plasma values in test subjects to which the compounds have been administered. Generally, such compounds also provide improved plasma $C_{max}$ values and may also provide improved brain $C_{max}$ values and intracerebroventricular (icv) efficacy. Significant reductions in FI (food intake) at 16 hours and 30 mpK (mg/kg) were also observed in some subjects for some compounds of formula VA and VB. Compounds in which $R^{1'}$ and $R^{2'}$ join together with the nitrogen to which they are bound to form a piperazine, particularly a piperazine with reduced basicity at the distal NH group have been found particularly suitable as possessing reduced bioaccumulation properties. Examples of such compounds are set forth in the various embodiments described above. Compounds of formula VA and VB in which $R^{1'}$ and $R^{2'}$ join to form a piperazine substituted with a monofluoroalkyl, a difluoroalkyl, and/or a trifluoroalkyl group, or a piperazinone such as an alkylpiperazinone, are just some examples of compounds which exhibit reduced bioaccumulation properties while possessing excellent efficacy.

In compounds of formula VA and VB, $R^{3'}$ is selected from substituted or unsubstituted cycloalkyl groups. In some embodiments, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, 3,3,5-trimethylcyclohexyl, 4-t-butylcyclohexyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups. In some embodiments, $R^{3'}$ is a substituted or unsubstituted polycyclic cycloalkyl group. In some such embodiments, $R^{3'}$ is a substituted or unsubstituted polycyclic cycloalkyl group having the formula III

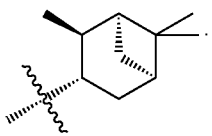
VIII

In some embodiments, compounds of formula VA and VB are selected from any of the following compounds:

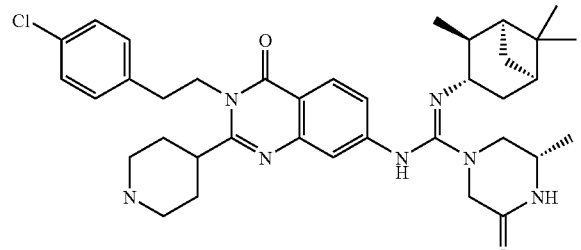

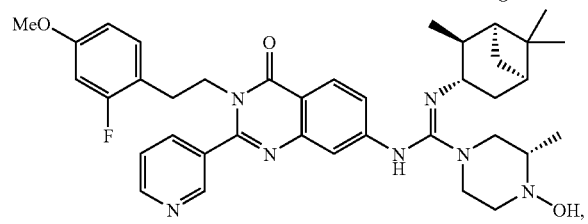

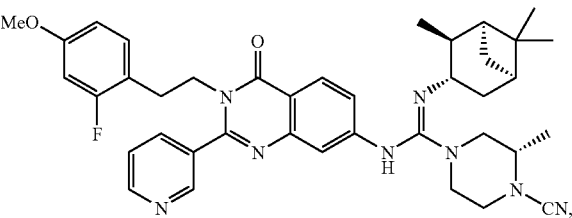

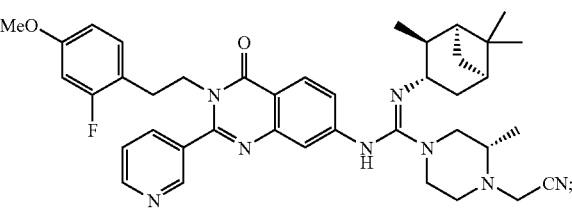

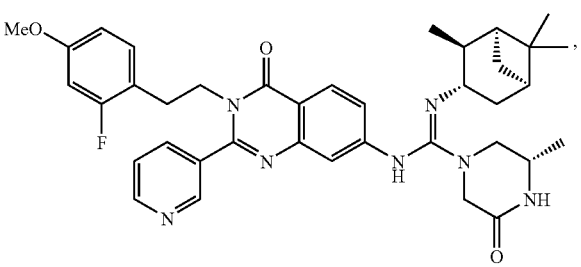

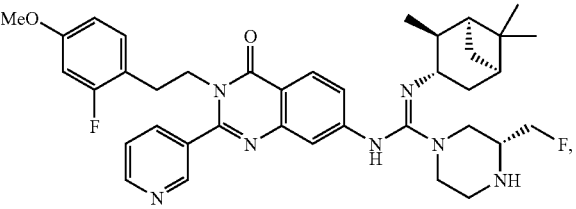

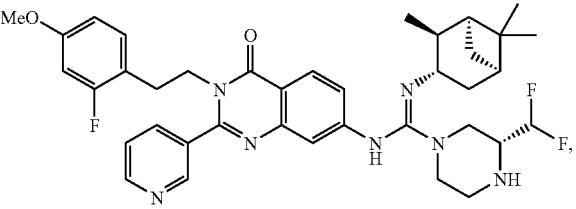

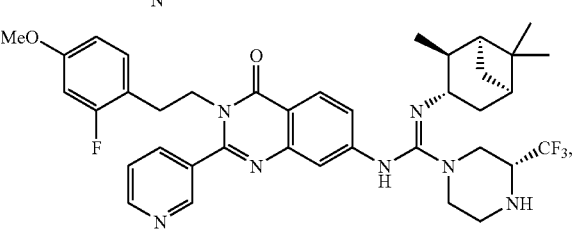

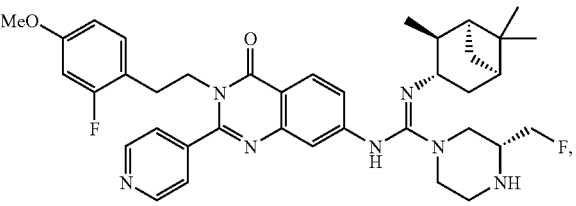

-continued

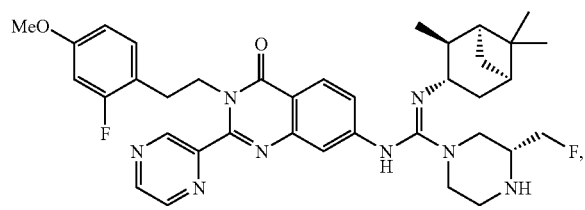

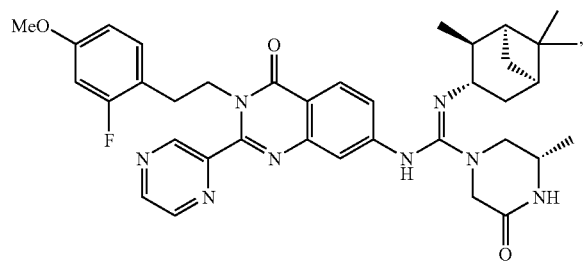

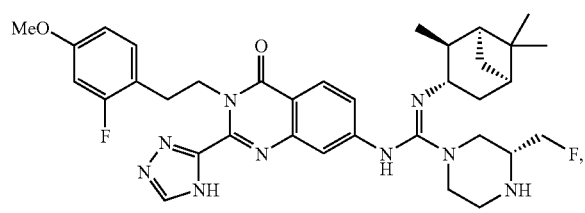

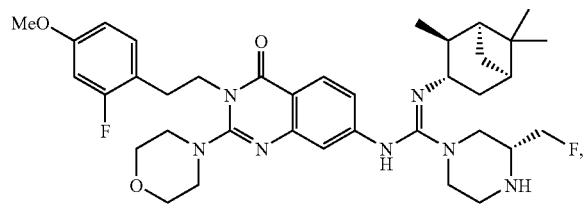

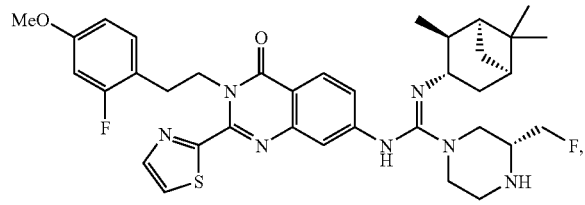

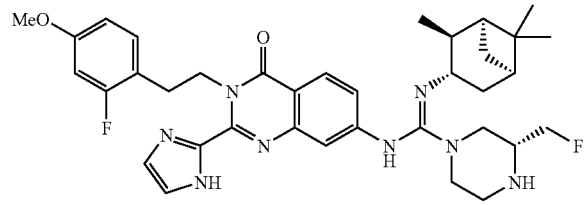

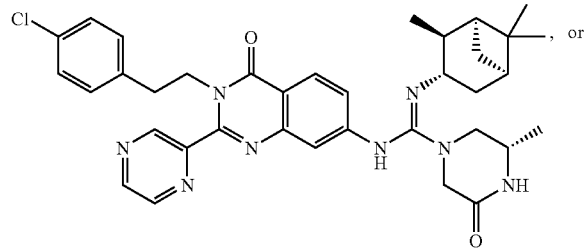

-continued

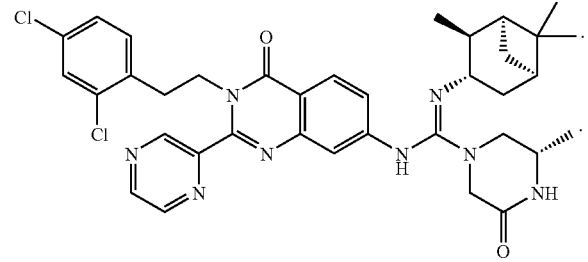

As described, the instant invention provides potent and specific agonists of MC4-R that are small molecules and may exhibit reduced bioaccumulation properties when administered to animal subjects. In accordance with one aspect of the invention, the invention provides compounds of formula VIA and VIB. Compounds provided by the invention further include prodrugs of the compound of formula VIA and VIB, pharmaceutically acceptable salts thereof, stereoisomers thereof, tautomers thereof, hydrates thereof, and solvates thereof. Compounds of formula VIA and VIB have the following structures:

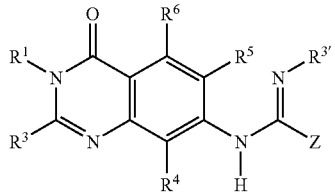

VIA

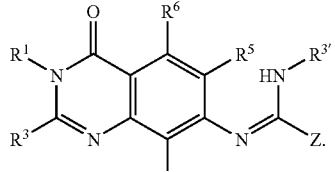

VIB

In compounds of formula VIA and VIB, $R^1$ is selected from substituted or unsubstituted arylalkyl, heteroarylalkyl, aryl, heteroaryl, heterocyclyl, cycloalkyl, heterocyclylalkyl, cycloalkylalkyl, alkenyl, alkynyl, or alkyl groups. In some embodiments, $R^1$ is a substituted or unsubstituted arylalkyl group such as a substituted or unsubstituted phenylethyl group. In some such embodiments, $R^1$ is a substituted phenylethyl group such as a 4-substituted phenylethyl group or a 2,4-disubstituted phenylethyl group such as 4-halophenylethyl, 2-halo-4-alkoxyphenylethyl, and 2,4-dihalophenylethyl groups. In some embodiments, $R^1$ is selected from phenylethyl, 2,4-dichlorophenylethyl, 4-methoxyphenylethyl, 4phenoxyphenylethyl, 4-bromophenylethyl, 4-methylphenylethyl, 4-chlorophenylethyl, 4-fluorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, indolylethyl, 4-hydroxyphenylethyl, 3,4-dimethoxyphenylethyl, 2-chloro-4-iodophenylethyl, 2-fluoro-4-methylphenylethyl, 4-chloro-2-fluorophenylethyl, 4-bromo-2-fluorophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, and (phenyl)(hydroxymethyl)ethyl groups. In still other embodiments, $R^1$ is selected from a 2-fluoro-4-methoxyphenylethyl group, a 2-chloro-4-methoxyphenylethyl, 4-fluorophenylethyl, a 4-chlorophenylethyl, a 4-chloro-2-fluorophenylethyl, a 2,4-dichlorophenylethyl, a 4-bromophenylethyl, or a 4-bromo-2-fluorophenylethyl group. In still other embodiments, $R^1$ is selected from phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl) ethyl, substituted and unsubstituted (aryl)(aryloxymethyl) ethyl, substituted and unsubstituted (aryl)(arylalkoxymethyl) ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl) ethyl, and substituted and unsubstituted (heteroaryl)(heterocyclyloxymethyl)ethyl groups.

In compounds of formula VIA and VIB, $R^3$ is selected from H or substituted or unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, or alkyl groups. Compounds of formula VIA and VIB with $R^3$ values such as those set forth above have been found to exhibit reduced bioaccumulation properties as evidenced by lower $t_{1/2}$ blood plasma values in test subjects to which the compounds have been administered. Generally, such compounds also provide improved plasma $C_{max}$ values and may also provide improved brain $C_{max}$ values. In some embodiments, $R^3$ is selected from substituted or unsubstituted heterocyclyl groups or substituted or unsubstituted heteroaryl groups. In other embodiments, $R^3$ is selected from substituted or unsubstituted pyridinyl, piperidinyl, piperazinyl, morpholinyl, thiomorpholinyl, tetrahydrofuranyl, furanyl, pyrrolidinyl, pyrrolyl, thiophenyl, tetrahydrothiophenyl, pyranyl, tetrahydropyranyl, tetrahydrothiopyranyl, pyrazinyl, thiazolyl, pyrimidinyl, quinuclidinyl, indolyl, imidazolyl, triazolyl, tetrazolyl, or pyridazinyl groups. In some such embodiments, $R^3$ is selected from heteroaryl or heterocyclyl group of formula

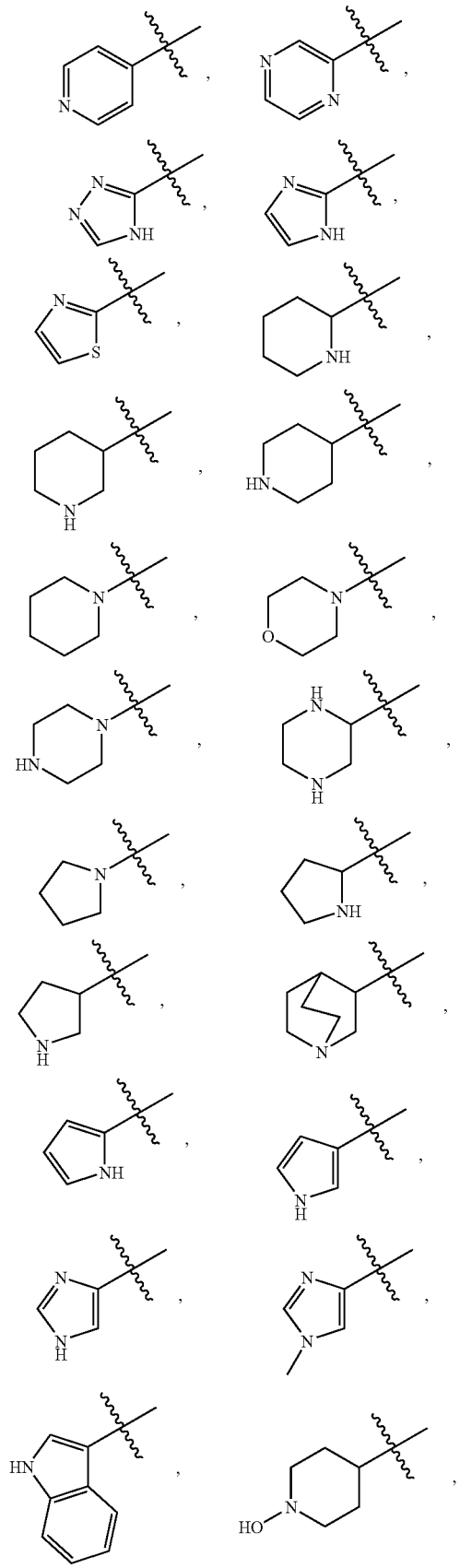

-continued

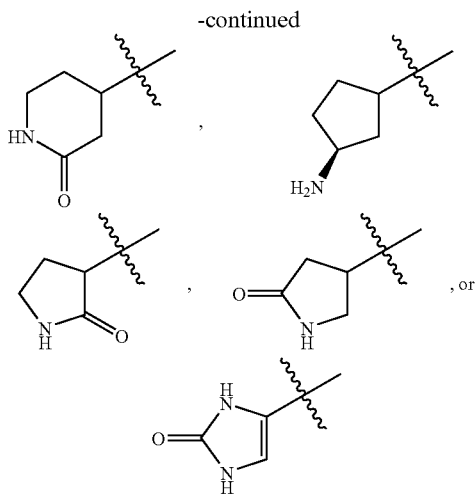

which may be additionally substituted or may be unsubstituted. In some embodiments, the invention provides compounds of formula VIA and VIB in which $R^3$ is selected from substituted or unsubstituted heterocyclylalkyl, or cycloalkylamino groups. For example, in some embodiments, $R^3$ is selected from a group such as a substituted or unsubstituted cyclopropylamino group; a substituted or unsubstituted piperazinylalkyl group such as a piperazinylmethyl group or an N-methylpiperazinylmethyl group; or a piperidinylalkyl group such as a piperidinylmethyl group or a piperidinylethyl group. In some embodiments, $R^3$ may be selected from a substituted or unsubstituted aryl or cycloalkyl group. Examples include compounds of the following formula which may be additionally substituted.

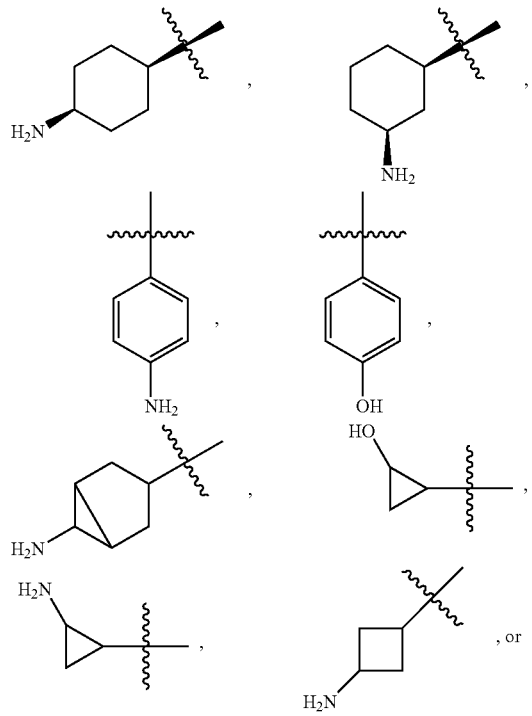

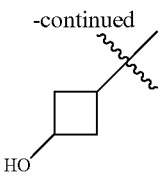

In compounds of formula VIA and VIB, $R^4$, $R^5$, and $R^6$ are independently selected from H, Cl, I, F, Br, OH, $NH_2$, CN, $NO_2$, and substituted and unsubstituted alkoxy, and alkyl groups. In some embodiments, each of $R^4$, $R^5$, and $R^6$ are H.

In compounds of formula VIA and VIB, Z is a piperazinone of formula

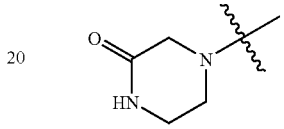

which may be additionally substituted. In some embodiments, Z is a piperazinone of formula

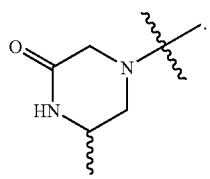

In some such embodiments, Z is a piperazinone of formula

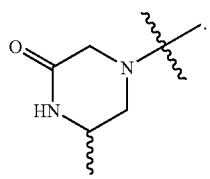

Compounds of formula VIA and VIB with Z values such as those set forth above have been found to exhibit reduced bioaccumulation properties as evidenced by lower $t_{1/2}$ blood plasma values in test subjects to which the compounds have been administered. Generally, such compounds also provide improved plasma $C_{max}$ values and may also provide improved brain $C_{max}$ values and intracerebroventricular (icv) efficacy. Significant reductions in FI (food intake) at 16 hours and 30 mpK (mg/kg) were also observed in some subjects for some compounds of formula VIA and VIB. Compounds of formula VIA and VIB have been found particularly suitable as possessing reduced bioaccumulation properties. Examples of such compounds are set forth in the various embodiments described above.

In compounds of formula VIA and VIB, $R^{3'}$ is selected from H or substituted or unsubstituted aryl, alkyl, alkenyl, alkynyl, cycloalkyl, heteroaryl, heterocyclyl, heterocyclylalkyl, arylalkyl, heteroarylalkyl, or cycloalkylalkyl groups. In some embodiments, $R^{3'}$ is selected from substituted or unsubstituted cycloalkyl groups. In some embodiments, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, 3,3,5-trimethylcyclohexyl, 4-t-butylcyclohexyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups. In some embodiments, $R^{3'}$ is a substituted or unsubstituted polycyclic cycloalkyl group. In some such embodiments, $R^{3'}$ is a substituted or unsubstituted polycyclic cycloalkyl group having the formula VIII

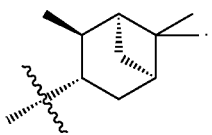

VIII

In accordance with one aspect of the invention, there is provided any of the compounds of Examples 113-390, tautomers thereof, salts thereof, mixtures thereof, or pharmaceutical formulations comprising the compounds, tautomers, salts, or mixtures thereof. In some such embodiments, the invention provides any of the compounds of Examples 113-343. In some such embodiments, the invention provides any of the compounds of Examples 113-215. In other such embodiments, the invention provides any of the compounds of Examples 216-343. In other such embodiments, the invention provides any of the compounds of Examples 344-390.

In accordance with another aspect of the invention, there are provided compounds of formula VIIA and VIIB. Compounds provided by the invention further include prodrugs of the compound of formula VIIA and VIIB, pharmaceutically acceptable salts thereof, stereoisomers thereof, tautomers thereof, hydrates thereof, and solvates thereof. Compounds of formula VIIA and VIIB have the following structures:

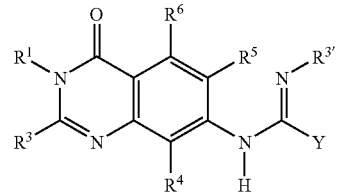

VIIA

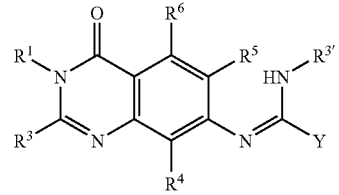

VIIB

In compounds of formula VIIA and VIIB, $R^1$ is selected from substituted or unsubstituted arylalkyl, heteroarylalkyl, aryl, heteroaryl, heterocyclyl, cycloalkyl, heterocyclylalkyl, cycloalkylalkyl, alkenyl, alkynyl, or alkyl groups. In some embodiments, $R^1$ is a substituted or unsubstituted arylalkyl group such as a substituted or unsubstituted phenylethyl group. In some such embodiments, $R^1$ is a substituted phenylethyl group such as a 4-substituted phenylethyl group or a 2,4-disubstituted phenylethyl group such as 4-halophenylethyl, 2-halo-4-alkoxyphenylethyl, and 2,4-dihalophenylethyl groups. In some embodiments, $R^1$ is selected from phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-fluorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, indolylethyl, 4-hydroxyphenylethyl, 3,4-dimethoxyphenylethyl, 2-chloro-4-iodophenylethyl, 2-fluoro-4-methylphenylethyl, 4-chloro-2-fluorophenylethyl, 4-bromo-2-fluorophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl) ethyl, and (phenyl)(hydroxymethyl)ethyl groups. In still other embodiments, $R^1$ is selected from a 2-fluoro-4-methoxyphenylethyl group, a 2-fluoro-4-methylphenylethyl group, a 2-chloro-4-methoxyphenylethyl, 4-fluorophenylethyl, a 4-chlorophenylethyl, a 4-chloro-2-fluorophenylethyl, a 2,4-dichlorophenylethyl, a 4-bromophenylethyl, or a 4-bromo-2-fluorophenylethyl group. In still other embodiments, $R^1$ is selected from phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl,2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl) ethyl, (3-pyridyl)ethyl, (4-pyridyl)ethyl, (pyridyl) (hydroxymethyl)ethyl, (phenyl)(hydroxymethyl)ethyl, substituted and unsubstituted (heteroaryl)(hydroxymethyl) ethyl, substituted and unsubstituted (aryl)(hydroxymethyl) ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl) ethyl, and substituted and unsubstituted (heteroaryl)(heterocyclyloxymethyl)ethyl groups.

In compounds of formula VIIA and VIIB, $R^3$ is selected from H or substituted or unsubstituted arylalkyl, heteroarylalkyl, alkoxy, alkylamino, dialkylamino, aryl, heteroaryl, heterocyclyl, cycloalkyl, aminocycloalkyl, heterocyclylalkyl, cycloalkylalkyl, alkenyl, alkynyl, or alkyl groups. Compounds of formula VIIA and VIIB with $R^3$ values such as those set forth above have been found to exhibit reduced bioaccumulation properties as evidenced by lower $t_{1/2}$ blood plasma values in test subjects to which the compounds have been administered. Generally, such compounds also provide improved plasma $C_{max}$ values and may also provide improved brain $C_{max}$ values. In some embodiments, $R^3$ is selected from substituted or unsubstituted heterocyclyl groups or substituted or unsubstituted heteroaryl groups. In other embodiments, $R^3$ is selected from substituted or unsubstituted pyridinyl, piperidinyl, piperazinyl, morpholinyl, thiomorpholinyl, tetrahydrofuranyl, furanyl, pyrrolidinyl, pyrrolyl, thiophenyl, tetrahydrothiophenyl, pyranyl, tetrahydropyranyl, tetrahydrothiopyranyl, pyrazinyl, thiazolyl, pyrimidinyl, quinuclidinyl, indolyl, imidazolyl, triazolyl, tetrazolyl, or pyridazinyl groups. In some such embodiments, $R^3$ is selected from heteroaryl or heterocyclyl group of formula

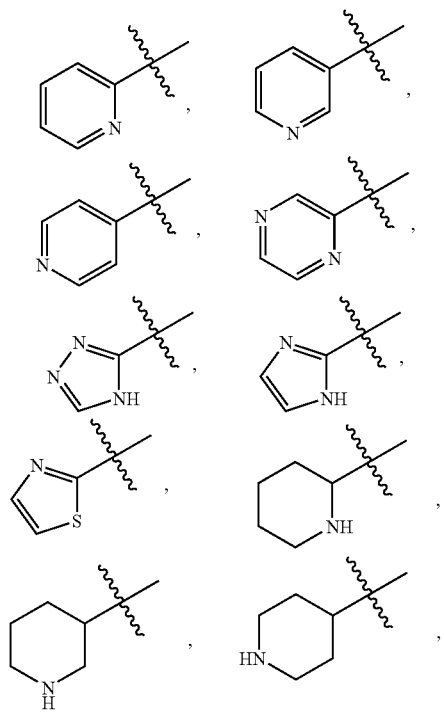

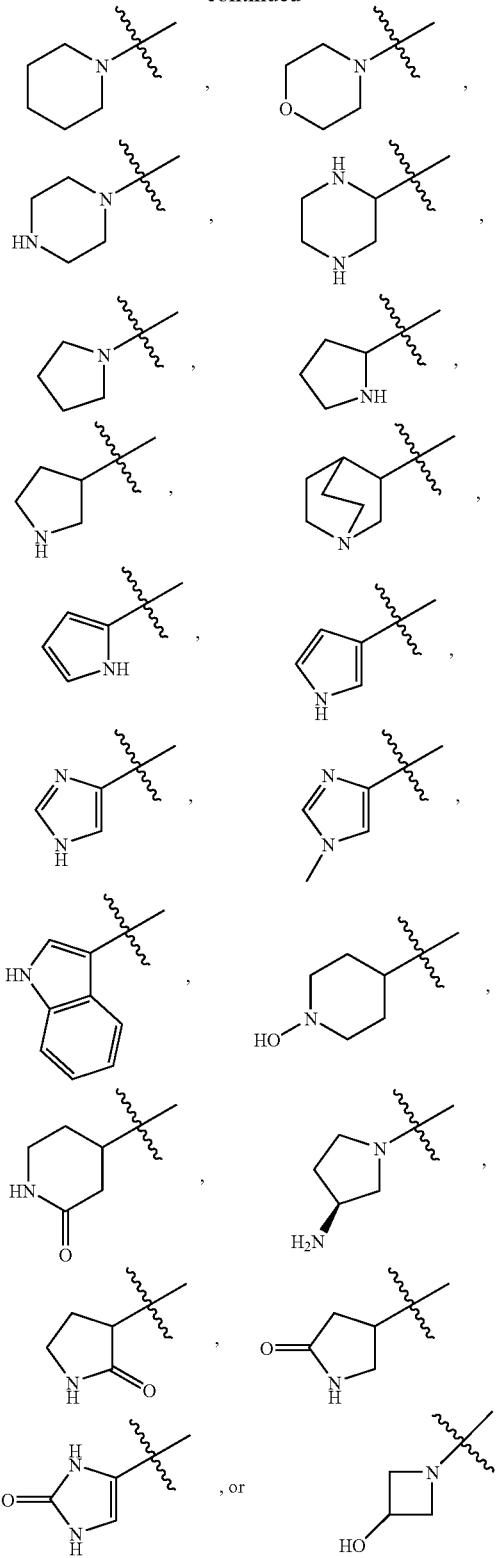

which may be additionally substituted or may be unsubstituted. In some embodiments, the invention provides compounds of formula VIIA and VIIB in which $R^3$ is selected from substituted or unsubstituted heterocyclylalkyl, or cycloalkylamino groups. For example, in some embodiments, $R^3$ is selected from a group such as a substituted or unsubstituted cyclopropylamino group; a substituted or unsubstituted piperazinylalkyl group such as a piperazinylmethyl group or an N-methylpiperazinylmethyl group; or a piperidinylalkyl group such as a piperidinylmethyl group or a piperidinylethyl group. In some embodiments, $R^3$ may be selected from a substituted or unsubstituted aryl, cycloalkyl, or aminocycloalkyl group. Examples include compounds of the following formula which may be additionally substituted.

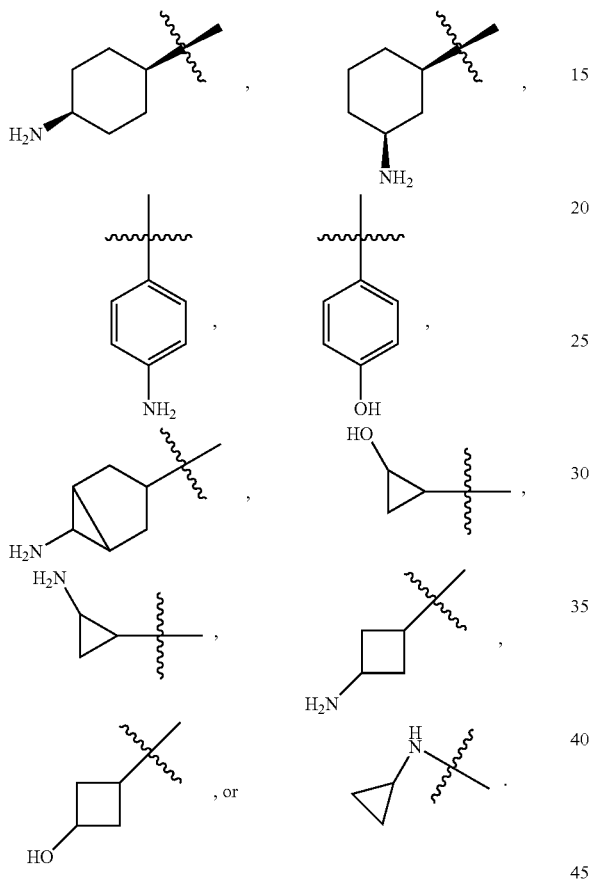

In compounds of formula VIIA and VIIB, $R^4$, $R^5$, and $R^6$ are independently selected from H, Cl, I, F, Br, OH, $NH_2$, CN, $NO_2$, and substituted and unsubstituted alkoxy, and alkyl groups. In some embodiments, each of $R^4$, $R^5$, and $R^6$ are H.

In compounds of formula VIIA and VIIB, Y is selected from a moiety of formula

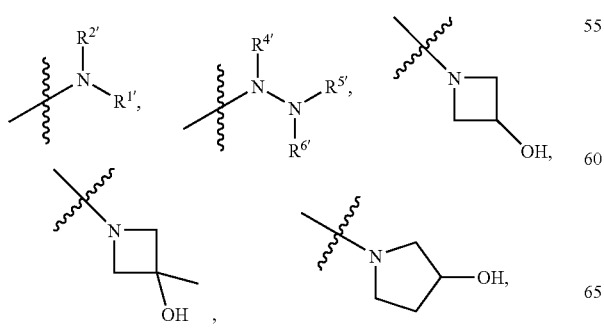

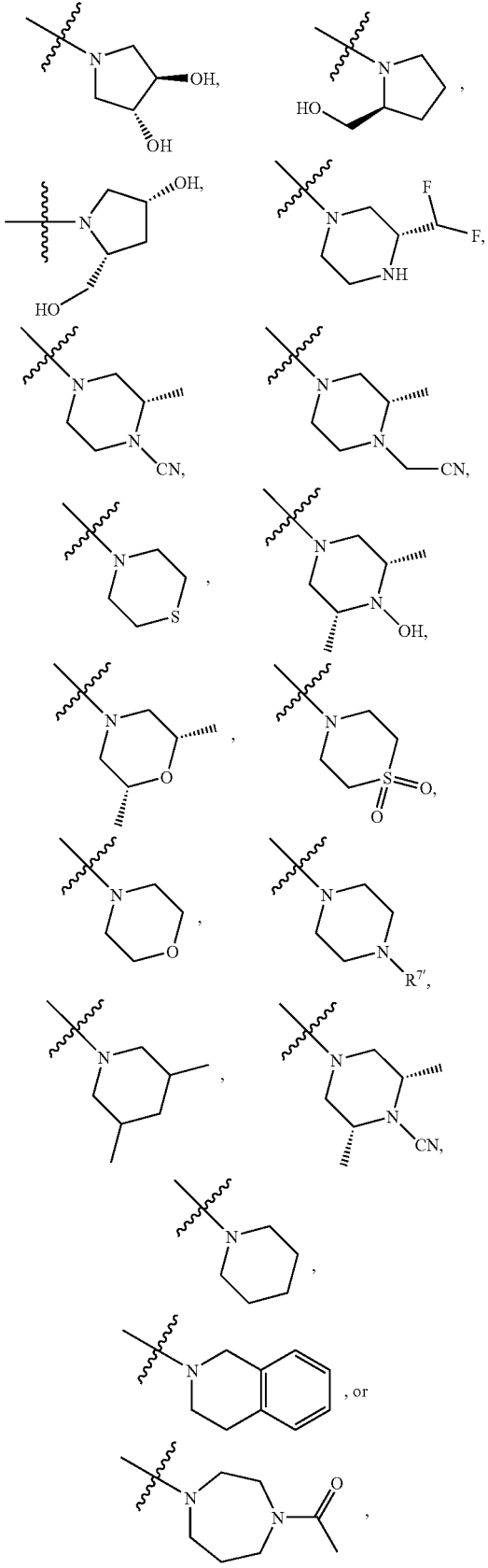

in which $R^{1'}$ is selected from substituted or unsubstituted alkyl groups; $R^{2'}$, $R^{4'}$, $R^{5'}$ are independently selected from H or substituted or unsubstituted alkyl groups; $R^{6'}$ is selected from substituted or unsubstituted alkyl groups; or $R^{5'}$ and $R^{6'}$ together with the nitrogen to which they are bound form a heterocyclyl or heteroaryl group; and $R^{7'}$ is selected from CN, or substituted or unsubstituted alkyl, aryl, or arylalkyl groups.

In some embodiments, Y is selected from a moiety of formula

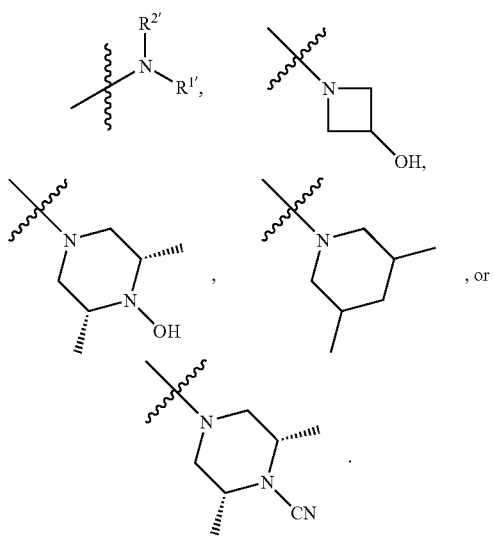

In other embodiments, Y is selected from

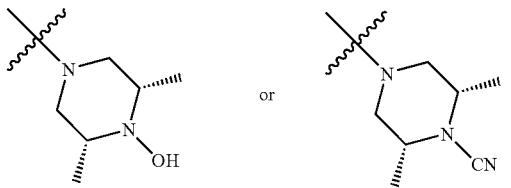

Compounds of formula VIIA and VIIB with Y values such as those set forth above have been found to exhibit reduced bioaccumulation properties as evidenced by lower $t_{1/2}$ blood plasma values in test subjects to which the compounds have been administered. Generally, such compounds also provide improved plasma $C_{max}$ values and may also provide improved brain $C_{max}$ values and intracerebroventricular (icv) efficacy. Significant reductions in FI (food intake) at 16 hours and 30 mpK (mg/kg) were also observed in some subjects for some compounds of formula VIIA and VIIB. Compounds of formula VIIA and VIIB have been found particularly suitable as possessing reduced bioaccumulation properties. Examples of such compounds are set forth in the various embodiments described above.

In compounds of formula VIIA and VIIB, $R^{3'}$ is selected from H or substituted or unsubstituted aryl, alkyl, alkenyl, alkynyl, cycloalkyl, heteroaryl, heterocyclyl, heterocyclylalkyl, arylalkyl, heteroarylalkyl, or cycloalkylalkyl groups. In some embodiments, $R^{3'}$ is selected from substituted or unsubstituted cycloalkyl groups. In some embodiments, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, 3,3,5-trimethylcyclohexyl, 4-t-butylcyclohexyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups. In some embodiments, $R^{3'}$ is a substituted or unsubstituted polycyclic cycloalkyl group. In some such embodiments, $R^{3'}$ is a substituted or unsubstituted polycyclic cycloalkyl group having the formula VIII

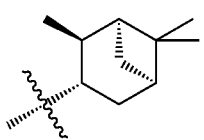

VIII

Compounds of formula VA, VB, VIA, VIB, VIIA, and VIIB may exhibit reduced bioaccumulation properties in animal subjects to which they are administered. Such subjects may include human and non-human animal subjects. Examples of mammalian subjects include, but are not limited to, rodents such as mice and rats, bovines, equines, canines, felines, rabbits, guinea pigs, porcines, primates such as humans and monkeys, and the like. In some embodiments, the invention provides compounds in which the $t_{1/2}$ value for the compound is less than 35, 30, 25, 20, 15, 10, or 5 hours in a tissue with high blood perfusion such as brain, liver, kidney, and heart. In some such embodiments, the $t_{1/2}$ value for the compound is less than 4 hours and in some embodiments is less than or about 3 hours in a tissue of a subject to which the compound has been administered.

The invention also includes tautomers of the compounds, prodrugs, pharmaceutically acceptable salts of the compounds or tautomers, stereoisomers, hydrates, and solvates thereof.

One or more compounds of the invention may be included in pharmaceutical formulations or medicaments. Such compositions include at least one compound of the invention and a pharmaceutically acceptable carrier, but may also include mixtures of compounds of the invention. The compounds of the invention may thus be used to prepare medicaments and pharmaceutical formulations for use in treating an MC4-R mediated disease such as, but not limited to, obesity, type II diabetes, erectile dysfunction, polycystic ovary disease, and Syndrome X. In some embodiments, the MC4-R mediated disease is obesity or type II diabetes.

Methods for treating MC4-R mediated diseases include administering to a subject in need thereof, a compound or composition of the instant invention. In some such embodiments, the compounds of the invention exhibit reduced bioaccumulation in the tissues such as in the brain or blood plasma of a subject. Administration of the compounds and compositions of the invention may be accomplished using various methods such as those described herein. In one embodiment, the compound or composition is administered intranasally. In some such embodiments, the compound or composition is intranasally administered to a human.

The instant compounds may exist as one or more stereoisomers. The various stereoisomers include enantiomers, diastereomers, atropisomers and geometric isomers. In some cases, one stereoisomer may be more active and/or may exhibit beneficial effects in comparison to other stereoisomer(s) or when separated from the other stereoisomer(s). However, it is well within the skill of the ordinary artisan to separate,. and/or to selectively prepare said stereoisomers. Accordingly, "stereoisomers" of the instant invention necessarily includes mixtures of stereoisomers, individual stereoisomers, or optically active forms.

The instant invention also provides for compositions which may be prepared by mixing one or more compounds of the instant invention, or pharmaceutically acceptable salts or tautomers thereof, with pharmaceutically acceptable carriers, excipients, binders, diluents or the like, to treat or ameliorate a variety of disorders. Examples of such disorders include, but are not limited to obesity, erectile disorders, cardiovascular disorders, neuronal injuries or disorders, inflammation, fever, cognitive disorders, sexual behavior disorders. A therapeutically effective dose further refers to that amount of one or more compounds of the instant invention sufficient to result in amelioration of symptoms of the disorder. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, a thickeners, buffers, a sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00/33813, WO 91/97947, U.S. Pat. No. 6,180,603, and U.S. Pat. No. 5,624,898. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

A therapeutically effective dose refers to that amount of the compound that results in amelioration of symptoms. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant invention. A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The present invention also provides methods of enhancing MC4-R activity in a human or non-human animal. The method comprises administering an effective amount of a compound, or composition, of the instant invention to said mammal or non-human animal. Effective amounts of the compounds of the instant invention include those amounts that activate MC4-R which are detectable, for example, by an assay described below in the illustrative Examples, or any other assay known by those skilled in the art that a detect signal transduction, in a biochemical pathway, through activation of G-protein coupled receptors, for example, by measuring an elevated cAMP level as compared to a control model. Accordingly, "activating" means the ability of a compound to initiate a detectable signal. Effective amounts may also include those amounts which alleviate symptoms of a MC4-R disorder treatable by activating MC4-R.

An MC4-R disorder, or MC4-R-mediated disease, which may be treated by those methods provided, include any biological disorder or disease in which MC4-R is implicated, or which inhibition of MC4-R potentiates a biochemical pathway that is defective in the disorder or disease state. Examples of such diseases are obesity, erectile disorders, cardiovascular disorders, neuronal injuries or disorders, inflammation, fever, cognitive disorders, type II diabetes, polycystic ovary disease, Syndrome X, complications from obesity and diabetes, and sexual behavior disorders. In a preferred embodiment, the instant invention provides compounds, compositions, and methods effective for reducing energy intake and body weight; reducing serum insulin and glucose levels; alleviating insulin resistance; and reducing serum levels of free fatty acids. Accordingly, the instant invention is particularly effective in treating those disorders or diseases associated with obesity or type II diabetes.

"Treating" within the context of the instant invention, therefore, means an alleviation of symptoms associated with a disorder or disease, or halt of further progression or worsening of those symptoms, or prevention or prophylaxis of the disease or disorder. For example, within the context of obesity, successful treatment may include an alleviation of symptoms or halting the progression of the disease, as measured by reduction in body weight, or a reduction in amount of food or energy intake. In this same vein, successful treatment of type I or type II diabetes may include an alleviation of symptoms or halting the progression of the disease, as measured by a decrease in serum glucose or insulin levels in, for example, hyperinsulinemic or hyperglycemic patients.

Scheme 1a illustrates a general synthetic route that may be used to synthesize various guanidinyl-substituted quinazolinone compounds. As shown in Scheme 1a, nitro and amino quinazolinone compounds such as (d) and (e) may be readily converted into a plethora of guanidinyl quinazolinones by converting the amino functionality to an isothiocyanate functionality such as possessed by compound (f). This may be accomplished reacting the amine group with thiophosgene. Isothiocyanate compounds such as (f) may then be readily converted into a thiourea such as compound (g) by reaction with a suitable amine compound such as (1S,2S,3S,5R)-(+)-isopinocampheylamine. Preparation of the desired guanidinylamine such as compound (h) may then be accomplished by reacting the thiourea with a compound such as 1-[3-(dimethylamino)-propyl]-3-ethylcarbodiimide hydrochloride and then with a suitable amine such as cis-2,6-dimethylpiperazine, (S)-2-(fluoromethyl)piperazine, or the like. Various fluorine-substituted compounds may be prepared using the methodology shown in Scheme 1a using an appropriately substituted 4-nitroanthranilic acid. Other compounds may be prepared by using 5-nitroanthranilic acid in place of 4-nitroanthranilic acid.

shown in Scheme 1b, conversion of compound (d) to (e) may be accomplished by initially adding trimethylphosphine to form a reactive iminophosphorane intermediate, adding a

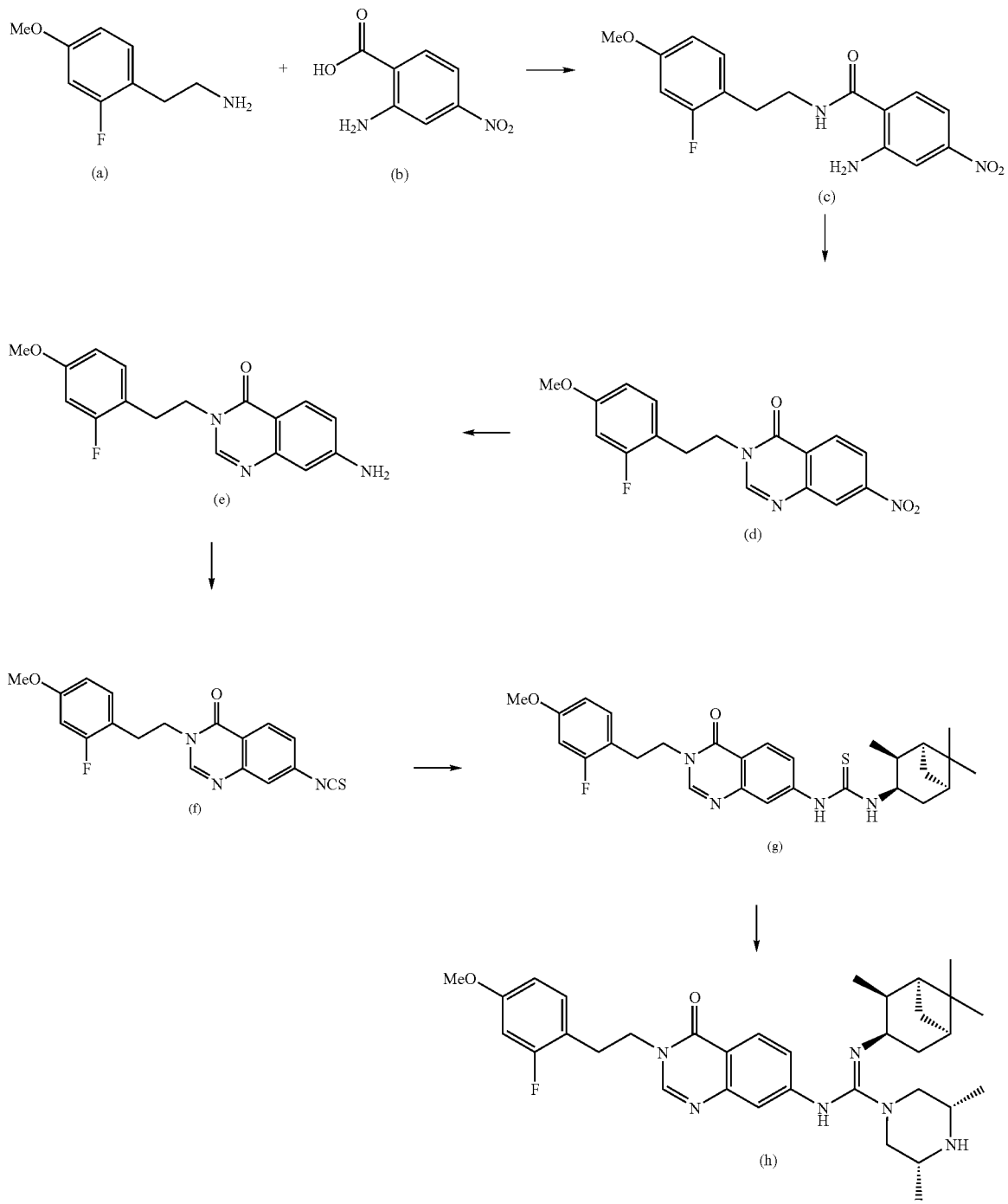

Scheme 1b illustrates another generally applicable method that may be employed to synthesize a large number of guanidinyl-substituted quinazolinones and heterocyclic derivatives of such compounds where a carbon of the benzene ring of the quinazolinone is replaced with a nitrogen atom. As substituted isocyanate such as a cycloalkyl isocyanate for example, a polycyclic isocyanate to produce a carbodiimide, and finally forming (e) by addition of and reaction with an amine such as, but not limited to a substituted piperazine.

SCHEME 1b

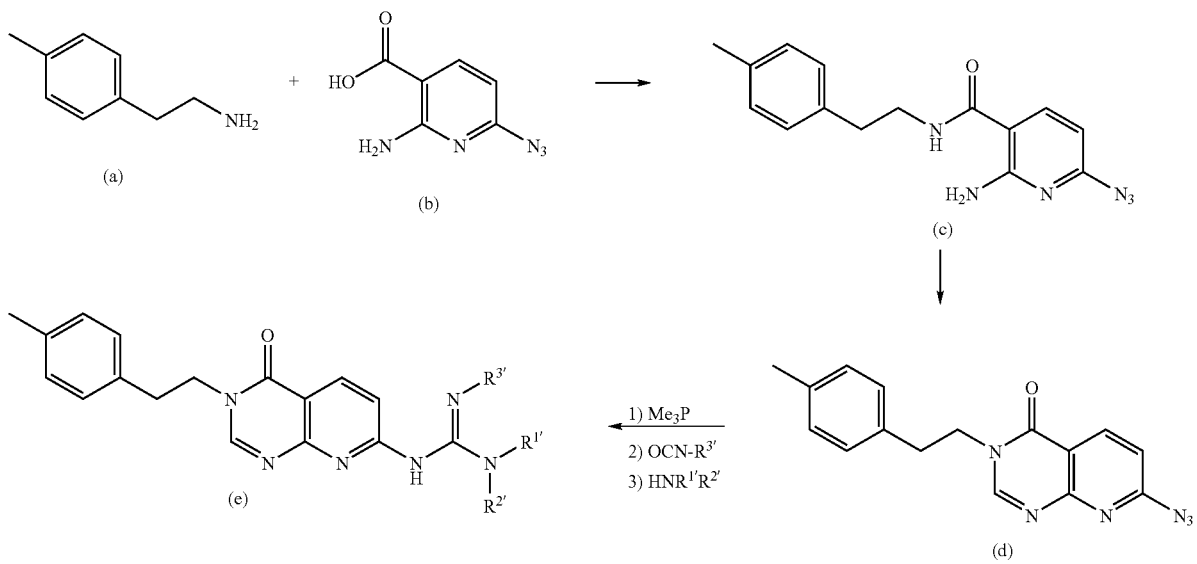

Scheme 2a illustrates another general procedure that may be used to prepare a wide variety of guanidinyl-substituted quinazolinone compounds.

Scheme 2a

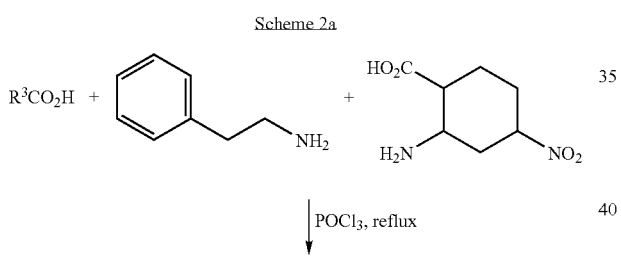

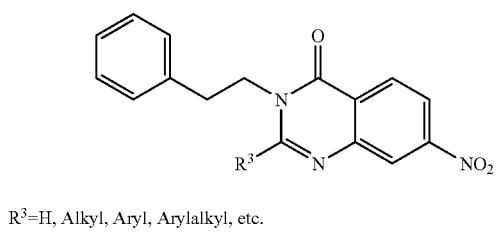

R³=H, Alkyl, Aryl, Arylalkyl, etc.

Scheme 2b shows yet another alternative route that may be used to prepare various compounds of formula IA, IB, IIIA, IIIB, IVA, and IVB.

Scheme 2b

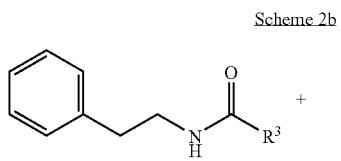

-continued

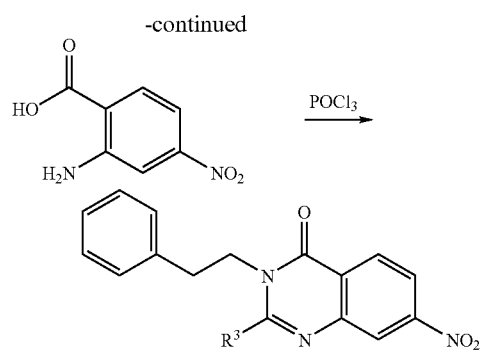

Still another route that may be used to prepare various compounds of the invention is depicted in Scheme 2c.

SCHEME 2c

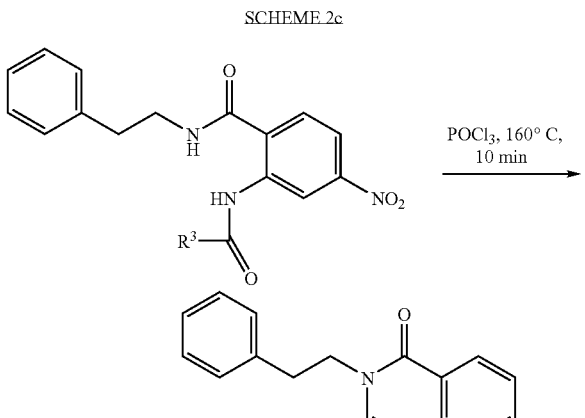

The invention provides various methods for synthesizing compounds of formula IA and IC, various intermediate compounds, and salts of the compounds and intermediate compounds. For example, a method for producing a compound having the formula IXA is provided where $R^1$, $R^3$, $Z^1$, $Z^2$, $Z^3$, $R^4$, $R^5$, and $R^6$ have any of the values described above with respect to compounds of formula IA and embodiments of compounds of formula IA, and $Y^1$ is selected from the group consisting of $NO_2$, a protected amine group, a halogen such as Cl, F, Br, or I, an —NCS, and an $N_3$ group. In some embodiments of the method, $R^1$ is a substituted or unsubstituted arylalkyl group. In some embodiments of the method, $R^3$ is H. In some embodiments, $Y^1$ is selected from a F, $NO_2$, or an $N_3$ group. In some embodiments of the method, $R^1$ is a substituted or unsubstituted arylalkyl group, $R^3$ is H, and $Y^1$ is selected from a F, $NO_2$, or an $N_3$ group. In some such embodiments, $Z^1$, $Z^2$, and $Z^3$ are each carbon atoms and $R^4$, $R^5$, and $R^6$ are each H. Compounds of formula IXA may be readily converted into compounds of formula IA as shown in Scheme 1a and the procedures set forth herein. Typically a compound of formula IXA where $Y^1$ is a —NCS is reacted with a first amine and then is reacted with a second amine as described in Procedure 1a. Any of the amines defined by the $R^{1'}$, $R^{2'}$, and $R^{3'}$ of compounds of formula IA may be used. The versatility of this procedure allows a wide range of compounds of formula IA to be prepared where W is a guanidine group prepared from compounds of formula IXA where $Y^1$ is a —NCS group. Another procedure that may be used to prepare compounds of formula IA from compounds of formula IXA where $Y^1$ is an $N_3$ group is shown in Scheme 1b where nitrogen compounds with any of the $R^{1'}$, $R^{2'}$, and $R^{3'}$ groups of compounds of formula IA may be used.

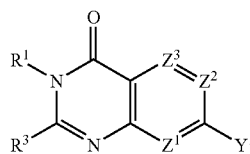

IXA

A method for preparing a compound of formula IXA typically includes cyclizing a compound of formula IXB by reacting it with an electrophilic carbon bearing an $R^3$ group such as a trialkyl orthoformate such as triethyl orthoformate, trimethyl orthoformate or the like where the $R^3$ is a H; Gold's Reagent; a substituted or unsubstituted alkanoyl halide such as acetyl chloride where $R^3$ is a methyl group; a substituted or unsubstituted alkanoic acid in the presence of an acid halide producing agent such as thionyl chloride, $POCl_3$, various phosphorous halides, and the like (e.g. an alkanoic acid of formula $R^3CO_2H$ in combination with $POCl_3$); a benzoyl chloride or an analogous heteroaryl acid chloride compound; or a substituted or unsubstituted benzoic acid or analogous heteroaryl carboxylic acid compound and an acid halide producing agent. The reaction provides the compound of formula IXA. Compounds of formula IXB have the following formula.

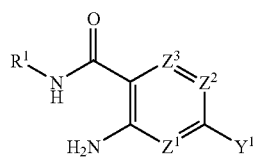

IXB

In compounds of formula IXB, the variables may have any of the same values as described above with respect to compounds of formula IXA. The method of forming a compound of formula IXA may include reacting a compound of formula IXC with an amine of formula $R^1$—$NH_2$ to produce the compound of formula IXB using standard amide-forming procedures and where $R^1$ has any of the values of the compounds of formula IXA and IXB and the variables in the compound of IXC have the values of compounds of formula IXA and IXB and $Y^2$ is a hydroxyl group or is an equivalent thereof. Compounds of formula IXC have the following formula.

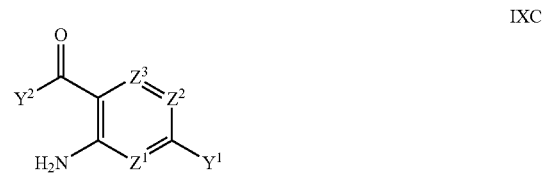

IXC

An alternative method for synthesizing compounds of formula IA is shown in Scheme 2a. Such a method generally includes reacting a compound of formula IXC with an amine of formula $R^1$—$NH_2$ and an electrophilic carbon bearing an $R^3$ group such as a carboxylic acid of formula $R^3$—$CO_2H$. Compounds of formula IA may further be prepared according to the procedure in Scheme 2b by reacting a compound of formula IXC with an amide of formula $R^1$—N(H)—C(=O)—$R^3$ in the presence of $POCl_3$ or an analogous compound.

Compounds of formula IE may be prepared from compounds of formula IXB where $Y^1$ is a $NO_2$ group by reacting the compound with $NaNO_2$ as described in Method 6 to produce the analogs of compounds of formula IXA which may then be converted to the compounds of formula IE from the compounds where $Y^1$ is an —$N_3$ group or is an —NCS group.

Compounds of formula IB may be produced from compounds of formula IXB by reacting the compound of formula IXB with phosgene or an equivalent thereof as described in Step 2 of Example 2 and subsequent conversion to the guanidine compounds from the $N_3$ or —NCS compounds using the standard procedures. Finally, compounds of formula ID may be prepared using the procedures described in Method 7 (Steps 1 and 2) using the fragments with the variables described above with respect to compounds of formula ID.

As noted above, the invention also provides methods for synthesizing compounds of formula IC, various intermediate compounds, and salts of the compounds and intermediate compounds. For example, a method for producing a compound having the formula XA is provided where $R^1$, $R^3$, $Z^1$, $Z^2$, $Z^3$, $R^4$, $R^5$, and $R^6$ have any of the values described above with respect to compounds of formula IC and embodiments of compounds of formula IC, and $Y^1$ is selected from the group consisting of $NO_2$, a protected amine group, a halogen such as Cl, F, Br, or I, an —NCS, and an $N_3$ group. In some embodiments of the method, $R^1$ is a substituted or unsubstituted arylalkyl group. In some embodiments of the method, $R^3$ is H. In some embodiments, $Y^1$ is selected from a F, $NO_2$, or an $N_3$ group. In some embodiments of the method, $R^1$ is a substituted or unsubstituted arylalkyl group, $R^3$ is H, and $Y^1$ is selected from a F, $NO_2$, or an $N_3$ group. In some such embodiments, $Z^1$, $Z^2$, and $Z^3$ are each carbon atoms and $R^4$, $R^5$, and $R^6$ are each H. Compounds of formula XA may be readily converted into compounds of formula IC as shown in Scheme 1a and the procedures set forth herein. Typically a compound of formula XA where $Y^1$ is a —NCS is reacted with a first amine and then is reacted with a second amine as described in Procedure 1a. Any of the amines defined by the $R^{1'}$, $R^{2'}$, and $R^{3'}$ of compounds of formula IC may be used. The versatility of this procedure allows a wide range of compounds of formula IC to be prepared where W is a guanidine group prepared from compounds of formula XA where $Y^1$ is a —NCS group. Another procedure that may be used to prepare compounds of formula IC from compounds of formula XA where $Y^1$ is an $N_3$ group is shown in Scheme 1b where nitrogen compounds with any of the $R^{1'}$, $R^{2'}$, and $R^{3'}$ groups of compounds of formula IC may be used.

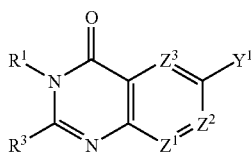

XA

A method for preparing a compound of formula XA typically includes cyclizing a compound of formula XB by reacting it with an electrophilic carbon bearing an $R^3$ group such as a trialkyl orthoformate such as triethyl orthoformate, trimethyl orthoformate or the like where the $R^3$ is a H; Gold's Reagent; a substituted or unsubstituted alkanoyl halide such as acetyl chloride where $R^3$ is a methyl group; a substituted or unsubstituted alkanoic acid in the presence of an acid halide producing agent such as thionyl chloride, $POCl_3$, various phosphorous halides, and the like (e.g. an alkanoic acid of formula $R^3CO_2H$ in combination with $POCl_3$); a benzoyl chloride or an analogous heteroaryl acid chloride compound; or a substituted or unsubstituted benzoic acid or analogous heteroaryl carboxylic acid compound and an acid halide producing agent. The reaction provides the compound of formula XA. Compounds of formula XB have the following formula.

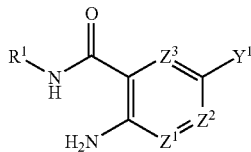

XB

In compounds of formula XB, the variable may have any of the same values as described above with respect to compounds of formula XA. The method of forming a compound of formula XA may include reacting a compound of formula XC with an amine of formula $R^1$—$NH_2$ to produce the compound of formula XB using standard amide-forming procedures and where $R^1$ has any of the values of the compounds of formula XA and XB and the variables in the compound of XC have the values of compounds of formula XA and XB and $Y^2$ is a hydroxyl group or is an equivalent thereof. Compounds of formula XC have the following formula.

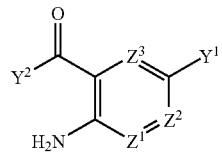

XC

An alternative method for synthesizing compounds of formula IC is shown for analogous compounds of formula IA in Scheme 2a. Such a method generally includes reacting a compound of formula XC with an amine of formula $R^1$—$NH_2$ and an electrophilic carbon bearing an $R^3$ group such as a carboxylic acid of formula $R^3$—$CO_2H$. Compounds of formula IC may further be prepared according to a procedure analogous to that shown in Scheme 2b by reacting a compound of formula XC with an amide of formula $R^1$—N(H)—C(=O)—$R^3$ in the presence of $POCl_3$ or an analogous compound.

The present invention, thus generally described, will be understood more readily by reference to the following examples, which are provided by way of illustration and are not intended to be limiting of the present invention.

EXAMPLES

The following abbreviations and terms are used throughout the Examples:

| | |
|---|---|
| Boc: | t-Butyl carbamate protecting group |
| Celite ®: | Diatomaceous earth filter agent |
| DAST: | (Dimethylamino)sulfur trifluoride |
| DCM: | Dichloromethane |
| DIBAL: | Diisobutylaluminum hydride |
| DIEA: | N,N-Diisoproylethylamine |
| DMF: | N,N-Dimethylformamide |
| DMSO: | Dimethylsulfoxide |
| EDCI: | 1-(3-Dimethylaminopropyl)-3-ethylcarbodiimide hydrochloride |
| EtOAc: | Ethyl acetate |
| EtOH: | Ethanol |
| Gold's Reagent: | (Dimethylaminomethyleneaminomethylene)dimethyl ammonium chloride |
| HOBt: | Hydroxybenzotriazole |
| HPLC: | High perfomance liquid chromatography |
| HCl: | Hydrochloric acid |
| HBTU: | O-Benzotriazol-1-yl-N,N,N',N'-tetramethyluronium hexafluorophosphate |
| KOH: | Potassium hydroxide |
| LC: | Liquid Chromatography |
| MS: | Mass Spectroscopy |
| MeOH: | Methanol |
| mL: | Milliliter |
| NMO: | N-Morpholine oxide |
| NMP: | 1-Methyl-2-pyrrolidinone |
| NMR: | Nuclear magnetic resonance spectroscopy |
| TFA: | Trifluoroacetic acid |
| THF: | Tetrahydrofuran |

Syntheses of 6-Methylpiperazin-2-One

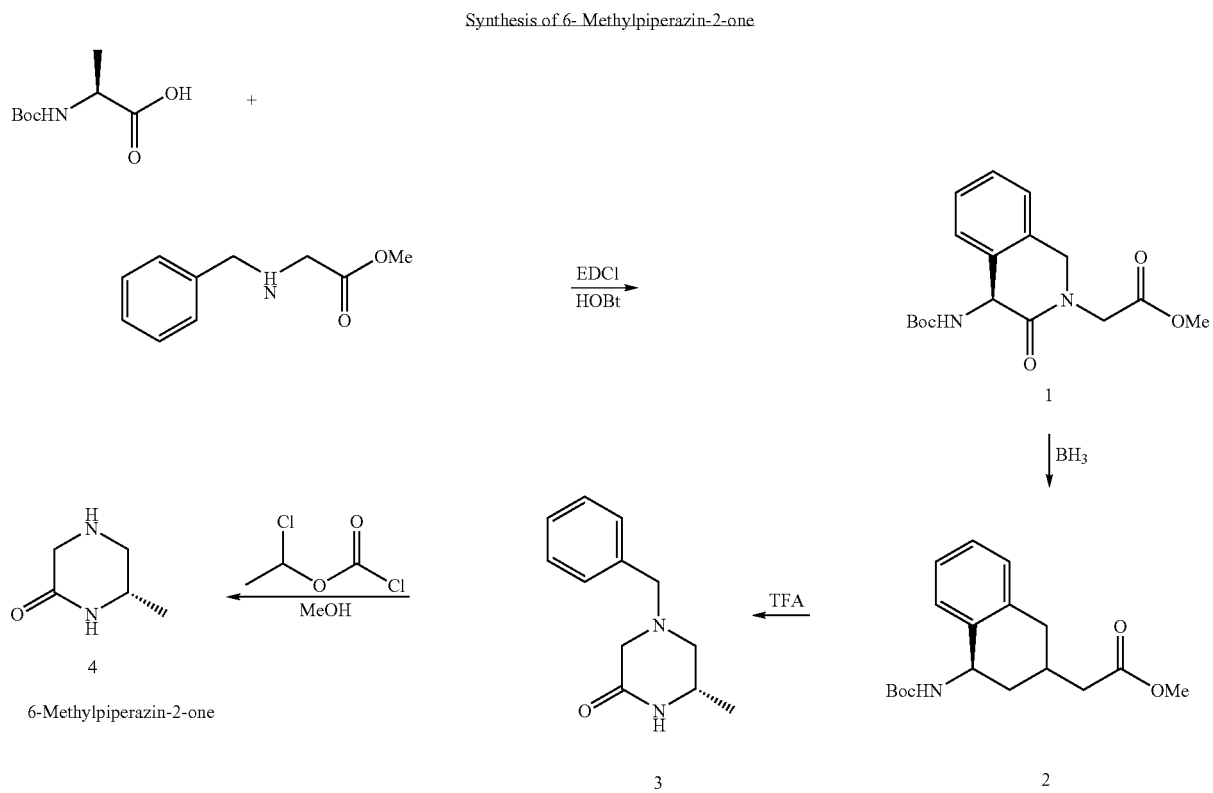

Step 1: Synthesis of N-Boc-alanine-N'-benzyl glycine methyl ester (1)

To a stirred solution of N-Boc-L-alanine (1 equivalent) and N-benzyl glycine methyl ester (1 equivalent) in dichloromethane was added TEA (1 equivalent) and HOBt (1 equivalent), followed by EDCl (1 equivalent). The solution was allowed to stir at room temperature under $N_2$ for 48 hours. The reaction was diluted with 10% HCl, and the organic layer was separated and dried over $MgSO_4$. Crude product was chromatographed on silica (30% EtOAc/hexanes) giving the desired product (1) as a clear oil (75%).

Step 2. Synthesis of [benzyl-(2-tertbutoxycarbonylamino-propyl)-amino]-acetic acid methyl ester (2)

To a stirred solution of $BH_3$ in THF (1 M, 2 equivalents), was added dropwise a solution of dipeptide (1) in THF. The reaction was then maintained at room temperature for 24 hours and then diluted with methylene chloride, washed with $NaHCO_3$, and dried over $MgSO_4$. Crude product was chromatographed on silica eluting with 20% EtOAc/hexanes giving the desired product (2) a colorless oil (40%).

Step 3. Synthesis of 1-benzyl-5-(S)-methyl-3-oxo-piperazine (3)

Ester (2) was stirred in a 50:50 solution of $TFA:CH_2Cl_2$ for 1 hour. The solvent was then removed, and the residue was redissolved in methylene chloride and washed with a saturated solution of $Na_2CO_3$. The organic layer was then separated and dried over $MgSO_4$ giving desired piperazine compound (3) as a white solid (87%).

Step 4. Synthesis of 6-(S)-methylpiperazin-2-one (4)

To a dichloroethane solution of 3 at room temperature was added 3 equivalents of chloroethylchloroformate and Hunig's base (3 equivalents). The solution was stirred overnight, and the reaction was then directly loaded onto a silica gel column and chromatographed eluting with EtOAc/hexanes (4:6). The isolated carbamate intermediate was dissolved in methanol and heated at reflux for 2 hours. Removal of methanol provided the desired piperazin-2-one (4) as an off white solid (yield was not optimized, but was approximately 60% for the 2 steps). 6(S)-methyl piperazin-2-one compounds of the invention were made according to the following methods by EDC activation of the thiourea intermediate to the carbodiimide followed by coupling with 6(S)-methyl piperazin-2-one.

Synthesis of 6-(S)-methylpiperazin-2-one guanidine Compounds

6(S)-Methyl piperazin-2-one guanidine compounds of the invention were prepared according to the methods described herein by EDC activation of the thiourea intermediate to provide the carbodiimide followed by coupling with 6(S)-Methyl piperazin-2-one.

Synthesis of 2-(R)-Fluoromethylpiperazine and 2-(R)-Difluoromethylpiperazine
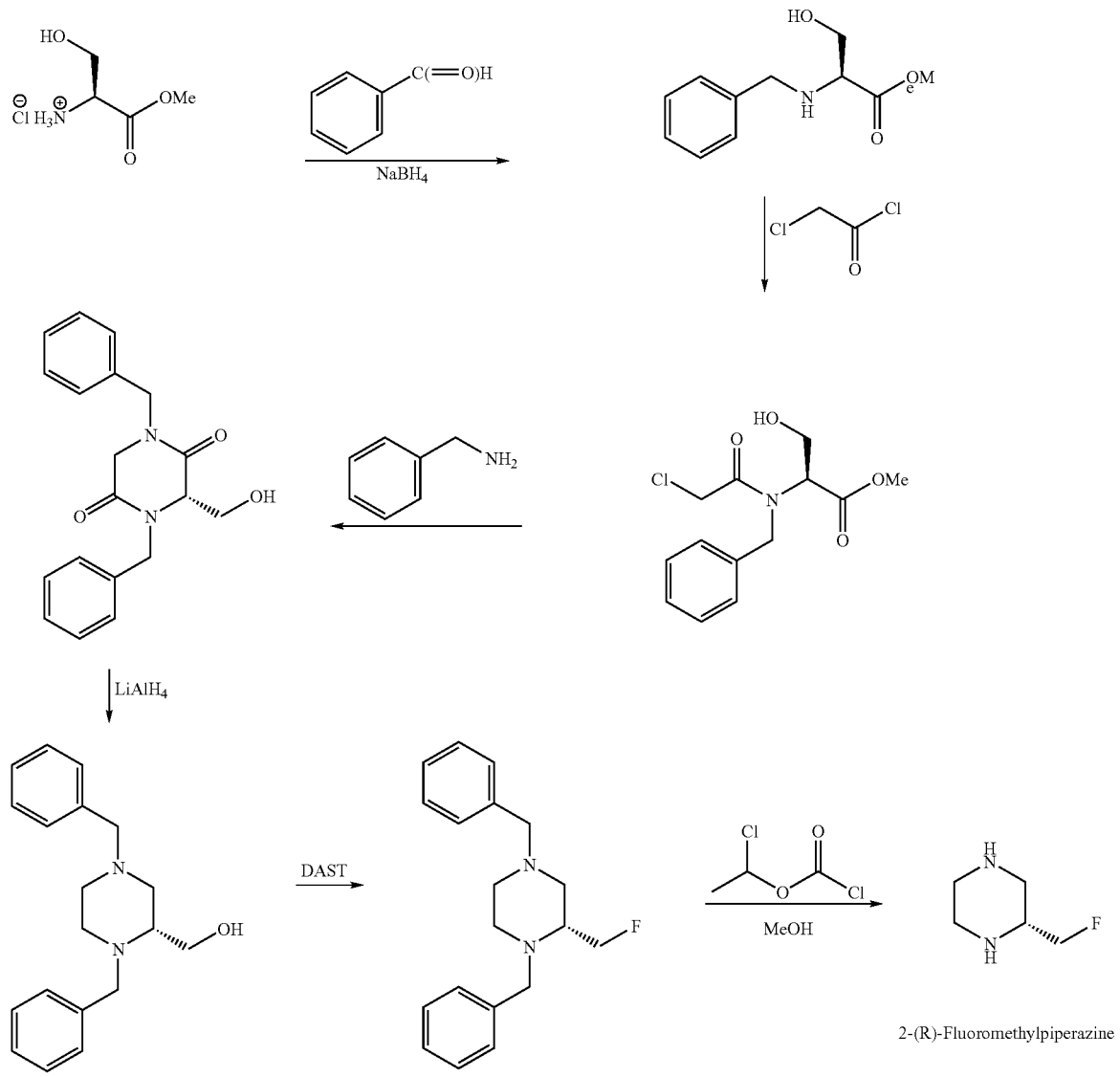
Synthesis of 2-(R)-Fluoromethylpiperazine
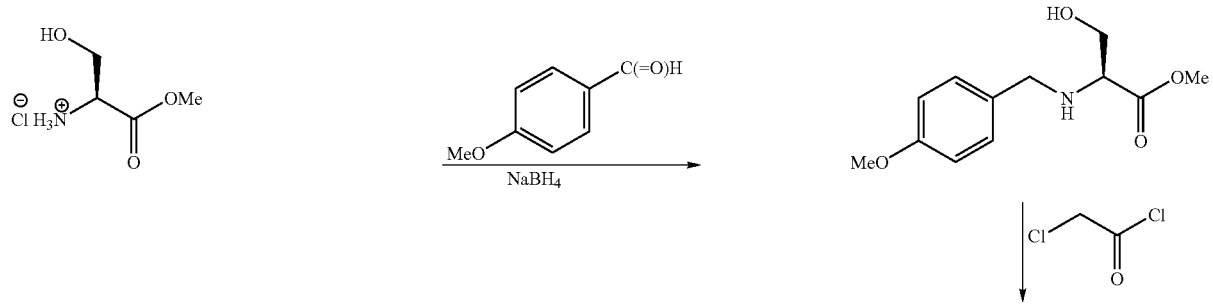
Synthesis of 2-(R)-Difluoromethylpiperazine -continued

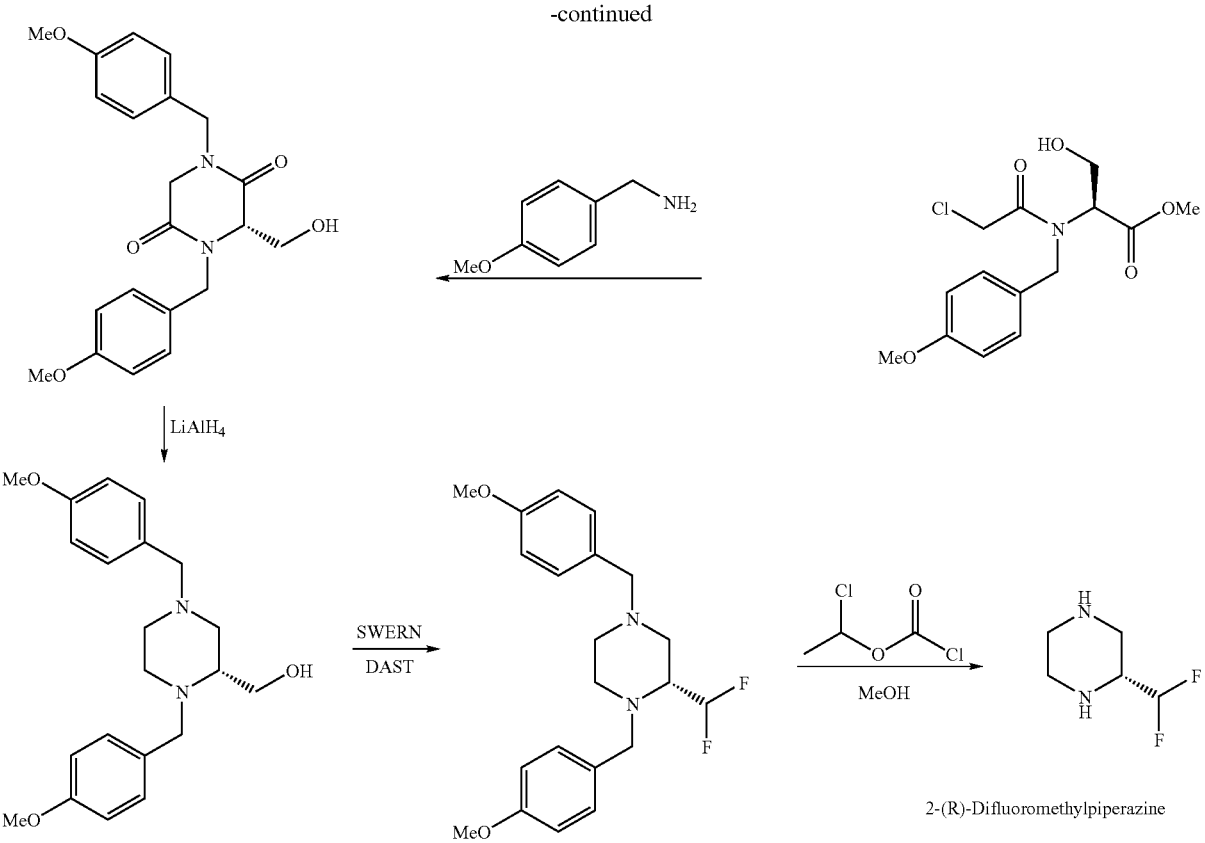

2-(R)-Difluoromethylpiperazine

Step 1. Synthesis of N-benzyl serine methyl ester

To a stirred solution of serine methyl ester hydrochloride (3.0 g, 19.28 mmol) and triethylamine (2.7 mL, 19.28 mmol) in methylene chloride (30 mL) was added benzaldehyde (1 equivalent), followed by 2 g anhydrous $MgSO_4$. The mixture was stirred at room temperature in a sealed flask for 20 hours, and then the solids were filtered away, and the filtrate was evaporated. The residue was redissolved in methanol (50 mL), and sodium borohydride (1 equivalent) was carefully added. The mixture was stirred for 30 minutes, was diluted with methylene chloride, was washed with $NaHCO_3$, and was then dried over magnesium sulfate. The desired title product was obtained as a yellow oil and was used crude. N-4-methoxybenzyl serine methyl ester was made in a similar fashion using anisaldehyde in place of benzaldehyde.

Step 2. Synthesis of N-benzyl-N-chloroacetyl serine methyl ester

To an ice cooled solution of the crude benzyl amino acid prepared as described in Step 1 and triethylamine (1 equivalent) in methylene chloride (30 mL) was added chloroacetyl chloride (1 equivalent) dropwise. After 1 hour, the reaction was washed with 10% HCl, and the organic layer was separated and dried over sodium sulfate. Crude product was chromatographed on silica gel eluting with 60% EtOAc/hexanes (Rf=0.3) giving the desired title compound as a colorless oil (67%).

Step 3. Synthesis of di-N-benzyl cyclo serine glycine

The chloride prepared in Step 2 was dissolved in acetonitrile, and benzyl amine was added (3 equivalents). The solution was heated at reflux for 20 hours, during which time a solid formed in the flask. The reaction was cooled, and the solvent was removed. The residue was dissolved in methylene chloride, was washed with 10% HCl, and was dried over $MgSO_4$. Crude product was passed through a silica gel plug (100% EtOAc, Rf=0.5) giving a white solid (80%). Di-N-4-methoxybenzyl cyclo serine glycine was made in a similar fashion using p-methoxybenzyl amine and the p-methoxybenzyl derivative of the starting material.

Step 4. Synthesis of 1,4-dibenzyl-2-(R)-piperazinemethanol

To an ice cooled mixture of $LiAlH_4$ (10 equivalents) in anhydrous THF under $N_2$ was added the cyclic dipeptide produced in Step 3 in THF dropwise. The resulting grey mixture was heated to reflux for 16 hours. The reaction was carefully quenched with $H_2O$, NaOH, $H_2O$ (1:1:3), and the resulting white mixture was filtered through celite. The filtrate was dried over $MgSO_4$ and concentrated, giving the desired product as a colorless oil (93%).

Step 5. Synthesis of 1,4-dibenzyl-2-(R)-fluoromethylpiperazine

To an ice cooled solution of DAST (2 equivalents) in methylene chloride under N₂ was added the alcohol prepared in Step 4 in methylene chloride dropwise. The yellow solution was stirred at 0° C. to room temperature for 20 hours. The reaction was diluted with NaHCO₃, and the organic layer was separated and dried over sodium sulfate. The crude product was chromatographed on silica gel eluting with 10-50% EtOAc/hexanes giving the desired title compound as a yellow oil (40%).

Step 6 Synthesis of 2-(R)-fluoromethylpiperazine 1,4-Dibenzylfluoromethylpiperazine from Step 5 was dissolved in dichloroethane, and α-chloroethyl chloroformate (3 equivalents) was added. The resulting solution was heated to reflux for 16 hours. The reaction was directly loaded onto a silica gel column and chromatographed eluting with 10-20% EtOAc/hexanes. The intermediate dicarbamate was isolated as a clear oil. The intermediate dicarbamate oil was dissolved in methanol and heated at reflux for 2 hours. The solvent was then thoroughly removed giving the desired deprotected piperazine as a white solid (90% for 2 steps).

Synthesis of 1,4-di-p-methoxybenzyl-2-(R)-piperazine-carboxaldehyde 1,4-di-p-methoxybenzyl-2-(R)-difluoromethylpiperazine To a dry flask containing a solution of oxalyl chloride in methylene chloride (2.0 M, 1.2 equivalents) at −78° C. was added DMSO (2.4 equivalents) dropwise under a stream of nitrogen. After stirring for 15 minutes, a solution of 1,4-di-p-methoxybenzyl-2-(R)-piperazinemethanol (1 equivalent) in methylene chloride was added dropwise, and the resulting solution was stirred for 1 hour. TEA (5 equivalents) was added, and the mixture was added to NaHCO₃(aq), separated, and dried over MgSO₄. After filtering, the filtrate was cooled to −78° C., and DAST was added dropwise (1.2 equivalents). The resulting orange solution was stirred for 12 hours. The reaction was then diluted with aqueous sodium bicarbonate, and the organic layer was separated and chromatographed in silica (10% EtOAc/hexanes) giving the desired title difluoro compound as a light brown oil (33%). Deprotection of the difluoride was carried out in the same manner as described in Step 6 using α-chloroethyl chloroformate giving a white solid (85%).

Synthesis of 2-(R)-Fluoromethylpiperazine and 2-(R)-Difluoromethylpiperazine Guanidine Compounds 2-(R)-Fluoromethylpiperazine and 2-(R)-difluoromethylpiperazine guanidine compounds of the invention were prepared according to the methods described herein by EDC activation of the thiourea intermediate to provide the carbodiimide followed by coupling with 2-(R)-fluoromethylpiperazine or 2-(R)-difluoromethylpiperazine.

Syntheses of (6S)-6-Methylpiperazin-2-One)

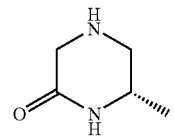

Step 1. Synthesis of S-ethyl(2R)-2-{[(benzyloxy)carbonyl]-amino}propanethioate

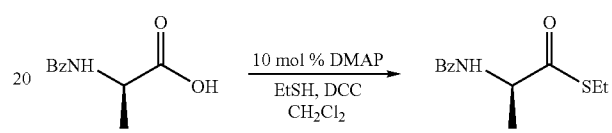

A 250 mL round bottom flask was charged with benzyloxycarbonyl-L alanine (15.0 g, 67.2 mmol) and 67.2 mL of dichloromethane. To this mixture was added DMAP (0.82 g, 6.72 mmol) and chilled EtSH (0° C., 5.46 mL, 73.9 mmol) followed by the addition of DCC (15.2 g, 73.9 mmol) in one portion. The addition of the DCC is highly exothermic so the reaction will bubble upon addition, and the reaction should be kept well vented. The resulting mixture was stirred for 30 minutes at 22° C. The resulting white solid was then removed by vacuum filtration, and the filtrate was concentrated. Silica Gel chromatography using hexanes with polarization to 8:1 hexanes/ethyl acetate afforded 93% yield (18.0g, 62.5 mmol) of the desired product as a colorless oil.

Step 2. Synthesis of Benzyl(1R)-1-methyl-2-oxoethylcarbamate

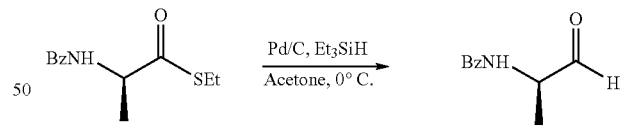

To a stirred solution containing S-ethyl (2R)-2-{[(benzyloxy)carbonyl]amino}-propanethioate (18.9 g, 62.5 mmol), wet 10% Pd/C (1.89 g), and acetone (347 mL) at 0° C. was added triethylsilane (29.9 mL, 187.5 mmol). The resulting mixture was stirred for 30 minutes at 0° C. and then filtered through celite using ethyl acetate to wash the celite thoroughly. The filtrate was concentrated and partitioned between acetonitrile (500 mL) and hexanes (150 mL). The layers were separated, and the acetonitrile phase was washed once with hexane (150 mL) and then concentrated to provide the desired product (59.4 mmol, 95%) which was used in the next step without further purification.

Step 3. Synthesis of Methyl N-((2R)-2-{[(benzyloxy)carbonyl]-amino}propyl)glycinate

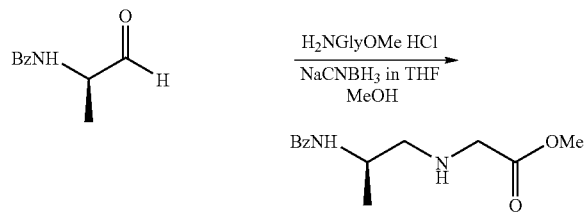

A 1000 mL round bottom flask was charged with benzyl (1R)-1-methyl-2-oxoethylcarbamate (59.4 mmol) and 347 mL of anhydrous methanol. The resulting mixture was cooled to 0° C. and glycine methyl ester hydrochloride (29.3 g, 237.6 mmol) was added. After 10 minutes, 1.0 M NaCNBH$_4$ in THF (95 mL, 95.0 mmol) was added and the reaction was allowed to warm to 22° C. overnight. The reaction mixture was then concentrated, redissolved in diethyl ether (200 mL) and placed in a separatory funnel. The organic phase was washed with saturated NaHCO$_3$ (200 mL) and separated. The basic aqueous layer was washed twice with diethyl ether (2×200 mL), and the combined organic layers were washed with brine (2×200 mL), dried with Na$_2$SO$_4$ and concentrated. Silica gel chromatography using 2:1 hexanes/ethyl acetate with gradual polarization to 1:1 hexanes/ethyl acetate provided the desired product as a clear oil in 75% yield (12.5 g, 44.6 mmol).

Step 4. Synthesis of (6S)-6-Methylpiperazin-2-one)

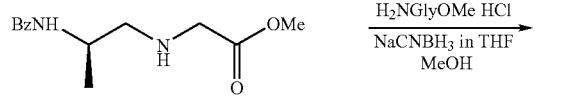

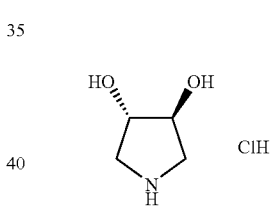

To a solution of methyl N-((2R)-2-{[(benzyloxy)carbonyl]-amino}propyl)glycinate (12.5 g, 44.6 mmol) in anhydrous methanol (446 mL) under an atmosphere of N$_2$ was added 10% Pd/C (1.25 g). The flask was then placed on a Buchi hydrogenator and purged three times with N$_2$ followed by 3 times with H$_2$. The reaction was allowed to stir under hydrogen (2.2 L, 98.12 mmol) until no more hydrogen was consumed. Once complete (24 hours), the reaction mixture was poured through Celite and the filtrate was concentrated. Ethyl acetate (5-10 mL) was added causing a white solid to crash out. This white solid was dried and collected to provide the desired product in 95% yield (4.8 g, 42.37 mmol). (The filtrate can be concentrated and more of the product can be crashed out by addition of ethyl acetate. If any starting material remains, it will be in the filtrate.

Synthesis of (3R,4R)-3,4-Pyrrolidinediol Hydrochloride

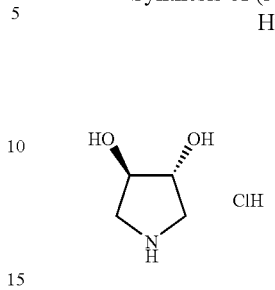

(3R,4R)-1-(Phenylmethyl)-3,4-pyrrolidinediol (250 mg, 1.30 mmol) was dissolved in ethyl acetate and added to a suspension of 10% Pd on carbon in ethyl acetate. The mixture was hydrogenated on a Parr hydrogenator at 57 PSI for 12 hours. The reaction was then filtered through Celite to remove catalyst. Excess 4N HCl in dioxane was added and then concentrated give the title compound as a brown oil which was used without further purification.

Synthesis of (3S,4S)-3,4-Pyrrolidinediol Hydrochloride (3S,4S)-1-(Phenylmethyl)-3,4-pyrrolidinediol was converted to the title compound using the procedure described above for the synthesis of (3R,4R)-3,4-pyrrolidinediol hydrochloride.

Synthesis of Thiomorpholine 1,1-Dioxide Hydrochloride

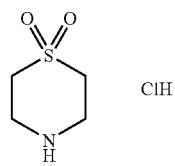

4-(Phenylmethyl)thiomorpholine 1,1-dioxide was converted to the title compound using the procedure described above for the synthesis of (3R,4R)-3,4-pyrrolidinediol hydrochloride.

Synthesis of
(3R,5R)-5-(Hydroxymethyl)-3-Pyrrolidinol
Trifluoroacetate (SALT)

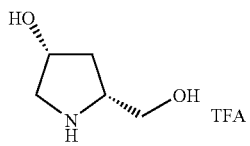

Step 1. Synthesis of 1-(1,1-Dimethylethyl)2-methyl (2R,4R)-4-hydroxy-1,2-pyrrolidinedicarboxylate

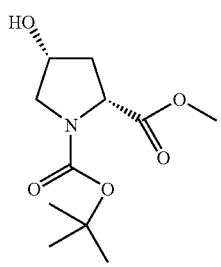

Trimethylsilyl diazomethane (3.89 mmol) was slowly added to an ice cooled solution of (4R)-1-{[(1,1-dimethylethyl)oxy]carbonyl}4-hydroxy-D-proline (0.75 g, 3.25 mmol), 60 mL toluene and 20 mL of methanol. The reaction was stirred for 2 hours on the ice bath, was warmed to room temperature, and was concentrated to give 0.89 g of the title compound as a clear yellow oil. $^1$H NMR (400 MHz, DMSO-D6) δ ppm 1.4 (m, 9H), 1.8 (dt, J=12.8, 4.9 Hz, 1H), 2.4 (m, 1H), 3.1 (m, 1H), 3.5 (dd, J=10.8, 5.7 Hz, 1H), 3.6 (s, 3H), 4.2 (m, 2H).

Step 2. Synthesis of 1,1-Dimethylethyl(2R,4R)-4-hydroxy-2-(hydroxymethyl)-1-pyrrolidinecarboxylate

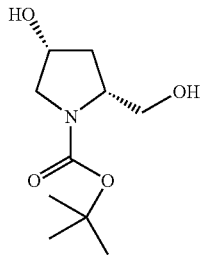

LiBH$_4$ (6.46 mmol as a solution in THF) was added to an ice cooled solution of (1,1-dimethylethyl)2-methyl (2R,4R)-4-hydroxy-1,2-pyrrolidinedicarboxylate (0.36 g, 1.47 mmol) in THF. The reaction was heated at 70° C. for 48 hours. The reaction was quenched with isopropanol and then saturated NaHCO$_3$. The mixture was diluted with water and extracted twice with ethyl acetate. The organic layers were washed with 1N NaOH, dried over MgSO$_4$ and concentrated to give 0.185 g of the title compound. $^1$H NMR (400 MHz, DMSO-D6) δ ppm 1.4 (m, 9H), 1.8 (m, 1H), 2.0 (m, 1H), 3.0 (m, 1H), 3.4 (m, 1H), 3.5 (m, 2H), 3.7 (m, 1H), 4.1 (m, 1H), 4.9 (dd, J=5.3, 5.3 Hz, 1H), 5.1 (m, 1H).

Step 3. Synthesis of
(3R,5R)-5-(Hydroxymethyl)-3-pyrrolidinol
trifluoroacetate (salt)

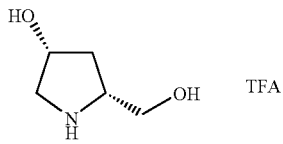

1,1-Dimethylethyl(2R,4R)-4-hydroxy-2-(hydroxymethyl)-1-pyrrolidinecarboxylate (0.185 g, 0.852 mmol) was stirred in a 1:1 solution of methylene chloride:TFA for 14 hours. The reaction was concentrated, and the crude material was used without further purification. $^1$H NMR (400 MHz, DMSO-D6) δ ppm 1.5 (m, 1H), 2.2 (m, 4H), 3.0 (m, 1H), 3.1 (m, 1H), 3.6 (m, 3H), 4.3 (m, 1H), 5.3 (s, br, 2H), 8.6 (s, br, 1H), 9.2 (s, br, 1H).

Synthesis of
Cis-2,6-Dimethyl-Piperazine-1-Carbonitrile
Hydrochloride

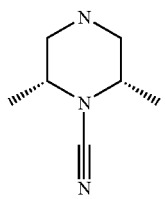

Step 1. Synthesis of
4-Cyano-cis-3,5-dimethylpiperazine-1-carboxylic
acid tert-butyl ester

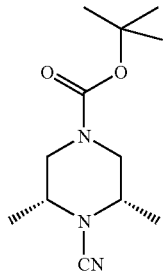

4.00 g of cis-3,5-dimethylpiperazine-1-carboxylic acid tert-butyl ester (prepared according to the method E. Jon Jacobson et. al. J. Med. Chemistry. 1999, Vol. 42, 1123-144)

in 91 mL of dichloromethane was treated with sodium bicarbonate (4.7 g) followed by addition of cyanogen bromide (7.5 mL). The reaction mixture was heated at reflux overnight, was filtered, and was purified by column chromatography (0 to 50% ethyl acetate/hexanes) to afford 3.9 g of the title compound as a white solid. $^1$H NMR (CDCl$_3$, 300 MHz) δ ppm 1.33 (d, 6H, J=6.5 Hz), 1.44 (s, 9H), 2.54 (m, 2H), 3.09 (m, 2H), 4.09 (m, 2H); $^{13}$C NMR (CDCl$_3$, 75 MHz) 16.70 (2C), 28.54 (3C), 53.86 (4C), 80.86, 114.10, 154.22.

Step 2. Synthesis of
cis-2,6-Dimethyl-piperazine-1-carbonitrile
hydrochloride

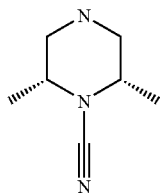

4-Cyano-cis-3,5-dimethylpiperazine-1-carboxylic acid tert-butyl ester (1.0 g) in 10 mL THF was treated with 4.0 N HCl/dioxane (25 mL), stirred for five hours and concentrated to provide 1.1 g of the title compound. $^1$H NMR (DMSO-D6, 300 MHz) δ ppm 1.24 (d, 6H, J=6.6 Hz), 2.65 (q, 2H, J=11.1 Hz), 3.27 (d, 2H, J=12.2 Hz), 3.63 (m, 2H); $^{13}$C (DMSO, 75 MHz) 16.73 (2C), 46.81 (2C), 50.80 (2C), 104.20.

Synthesis of Cis-2,6-Dimethyl-Piperazin-1-Ol Hydrochloride

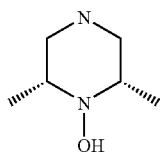

Step 1. Synthesis of cis-3,5-Dimethyl-4-(3-oxo-butyl)-piperazine-1-carboxylic acid tert-butyl ester

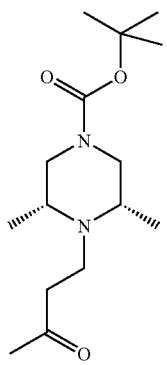

Cis-3,5-dimethylpiperazine-1-carboxylic acid tert-butyl ester (3.00 g; prepared according to the method E. Jon Jacobson et. al.: J. Med. Chemistry. 1999, Vol. 42, 1123-144) in 47 mL chloroform was treated with methylvinylketone (1.7 mL) at room temperature and heated at reflux for two days. The reaction was then concentrated, diluted with THF and heated at reflux for 1 day before purifying by column chromatography (0 to 10% MeOH/DCM) to afford 0.865 g of the title compound as a clear, colorless oil. $^1$H NMR (CDCl$_3$, 300 MHz) δ ppm 1.08 (d, 2H, J=6.07 Hz), 1.47 (s, 9H), 2.17 (s, 3H), 2.52 (m, 6H), 3.10 (m, 2H), 2.86 (bs, 2H); $^{13}$C NMR (CDCl$_3$, 75 MHz) 17.6 (2C), 28.62 (5C), 30.8, 37.34, 42.46, 53.57 (4C), 79.85, 154.49, 208.29.

Step 1. Synthesis of cis-2,6-Dimethyl-piperazin-1-ol hydrochloride

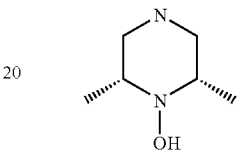

Cis-3,5-Dimethyl-4-(3-oxo-butyl)-piperazine-1-carboxylic acid tert-butyl ester (1.00 g) in chloroform (40 mL) was treated with m-chloroperbenzoic acid (77%, 0.97 g) at 0° C. The solution was allowed to warm to room temperature and stirred overnight. The reaction mixture was then cooled to 0° C., filtered to remove precipitates, washed with saturated aqueous sodium bicarbonate, filtered through a plug of silica gel and concentrated. The residue was taken up in a 1:1 mixture of DCM and MeOH and treated with an excess of 4.0 M HCl/dioxane. The reaction mixture was stirred overnight and then purified by column chromatography (0 to 10% MeOH:DCM) to yield 50 mg of the title compound. ESMS (0.41 minutes, (M+1) 131.13, Method E).

Synthesis of 3-Methyl-Azetin-3-Ol Hydrochloride

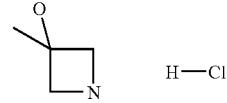

Step 1. Synthesis of 1-benzhydryl-azetidin-3-ol

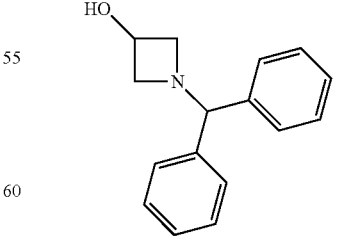

A solution of 1-(diphenylmethyl)-3-(methanesulphonyloxy) azetidine (1.0 g) in. THF (17 mL) was treated with 3.0 M methylmagnesium bromide (1.2 mL) in diethyl ether at 0° C. The reaction was stirred for 1.5 hours at 0° C. and then quenched with saturated aqueous sodium bicarbonate, filtered through Celite, and concentrated. The residue was then take up in methylene chloride and washed with saturated aqueous sodium bicarbonate, followed by brine. The organic layer was dried over magnesium sulfate, filtered, concentrated and purified by column chromatography (0 to 60% EtOAc/hexanes) to provide 640 mg of the title compounds as a clear, yellow oil. ESMS: 240.19 (M+1), 1.22 minutes, Method D.

Step 2. Synthesis of 1-Benzhydryl-azetidin-3-one

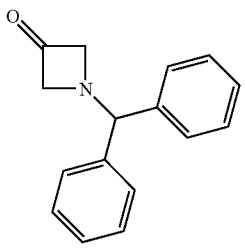

To a solution of 1-benzhydryl-azetidin-3-ol (640 mg) in methylene chloride (6.0 mL) was added 4 Å molecular sieves. The reaction vessel was purged with nitrogen followed by addition of NMO (800 mg) and then TPAP (42 mg). The reaction was stirred over night and then filtered through a plug of silica to yield 335 mg of the title compound as a clear, colorless oil. $^1$H NMR (CDCl$_3$, 300 MHz) δ ppm 4.03 (s, 4H), 4.61 (s, 1H), 7.25 (m, 2H), 7.32 (m, 4H), 7.50 (m, 4H).

Step 3. Synthesis of 1-Benzhydryl-3-methyl-azetidin-3-ol

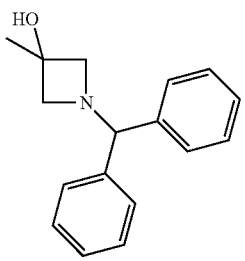

1-Benzhydryl-azetidin-3-one (335 mg) in diethyl ether (6.0 mL) was treated with 3.0 M methylmagnesium bromide in diethyl ether (0.52 mL) at 0° C., stirred for 10 minutes and quenched with saturated aqueous sodium bicarbonate. The solution was then extracted with methylene chloride (×3), and the combined organics were dried over magnesium sulfate, and concentrated to provide 363 mg of the title compound as a clear, colorless oil. $^1$H NMR (CDCl$_3$, 300 MHz) δ ppm 1.53 (s, 3H), 1.96 (s, 1H), 1.96 (d, 2H, J=8.42 Hz), 3.19 (d, 2H, J=8.42 Hz), 4.34 (s, 1H), 7.17 (m, 2H), 7.26 (m, 2H), 7.31 (m, 2H), 7.40 (m, 4H).

Step 4. Synthesis of 3-Methyl-azetin-3-ol hydrochloride

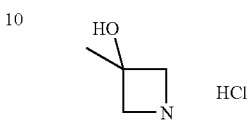

A suspension of 1-benzhydryl-3-methyl-azetidin-3-ol (363 mg) in MeOH (10 mL) was treated with 4.0 N HCl/dioxane (1.0 mL) followed by an excess of palladium hydroxide on carbon (wet, Degusa type). The solution was then reacted with hydrogen on a Parr hydrogenator over night at 45 psi. The reaction mixture was then filtered through Celite, concentrated, diluted to a known concentration and used without further purification.

Synthesis of Piperidin-4-One O-Methyl-Oxime Hydrochloride

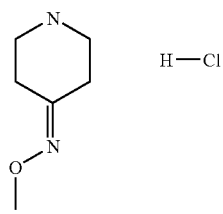

Step 1. Synthesis of 4-Methoxyimino-piperidine-1-carboxylic acid tert-butyl ester

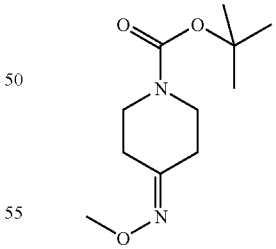

A solution of tert-butyl 4-oxo-1-piperidinecarboxylate (2.0 g) and methoxylamine hydrochloride (2.93 g) in THF (66 mL) was treated with sodium bicarbonate (2.95 g) dissolved in water (20 mL). The biphasic mixture was stirred vigorously for 10 minutes, diluted with water, and extracted with ethyl acetate (×3). The combined extracts were dried over magnesium sulfate, filtered and concentrated to afford 2.12 g of the title compound, which was used without further purification. $^1$H NMR (CDCl$_3$, 300 MHz) δ ppm 1.49 (s, 9H), 2.34 (t, 2H, J=6.07 Hz), 2.57 (t, 2H, J=6.07 Hz), 3.51 (t, 2H, J=6.07 Hz), 3.56 (t, 2H, J=6.07 Hz), 3.85 (s, 3H).

Step 2. Synthesis of Piperidin-4-one O-methyl-oxime hydrochloride

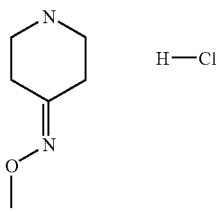

4-Methoxyimino-piperidine-1-carboxylic acid tert-butyl ester in MeOH (10 mL) was treated with 4.0 M HCl/dioxane (1.0 mL) and stirred at room temperature over night. The solution was concentrated to yield 213 mg of the title compound without further purification. $^1$H NMR (DMSO, 300 MHz) δ ppm 2.47 (t, 2H, J=6.62 Hz), 2.68 (t, 2H, J=6.07 Hz), 3.17 (m, 4H), 3.77 (s, 3H), 9.08 (bs, 1H).

Synthesis of 4-Methyl-Piperidin-4-Ol Hydrochloride

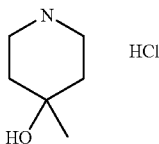

A solution of tert-butyl 4-oxo-1-piperidinecarboxylate (500 mg) in THF (6 mL) at 0° C. was treated with 3.0 M methylmagnesium bromide/diethyl ether (0.80 mL). The solution was allowed to warm to room temperature and stirred for 48 hours. The reaction was quenched with sodium bicarbonate, diluted with saturated Rochele's Salt, and extracted with methylene chloride (×3). The combined organics were filtered through Celite, concentrated, and purified by column chromatography (0 to 40% EtOAc/hexanes). The impure residue was then taken up in MeOH (5 mL) and treated with 4.0 M HCl/dioxane (4 mL), stirred for 30 minutes and concentrated to provide the crude title compound.

Synthesis of Ethyl (3S)-3-Hydroxy-L-Prolinate Hydrochloride

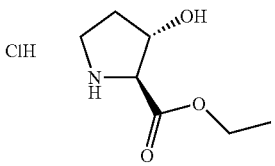

Acetyl chloride (10.8 mL, 153 mmol) was slowly added to ice cold 100% Ethanol (100 mL). (3S)-3-hydroxy-L-proline (5 g, 38.2 mmol) was added and heated at 100° C. for 16 hours. The ester was concentrated to a solid and used without purification. $^1$H NMR (400 MHz, DMSO-D6) δ ppm 1.2 (t, J=8.1 Hz, 3H), 1.9 (m, 2H), 3.3 (m, 2H), 4.1 (m, 1H), 4.2 (q, J=7.1 Hz, 2H) 4.4 (m, 1H), 9.0 (s, 1H), 10.4 (s, 1H).

Synthesis of [(2S,3S)-3-Methyl-2-Pyrrolidinyl]Methanol Hydrochloride

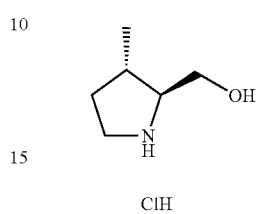

Step 1. Synthesis of Ethyl(3S)-3-methyl-L-prolinate

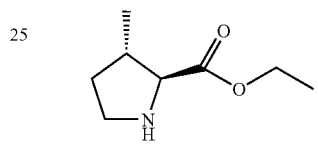

The title compound was prepared from (3S)-3-methyl-L-proline, using the methods used to prepare ethyl(3S)-3-hydroxy-L-prolinate hydrochloride. $^1$H NMR (400 MHz, DMSO-D6) δ ppm 1.1 (d, J=6.8 Hz, 3H) 1.2 (t, J=6.8 Hz, 3H), 1.6 (m, 1H), 2.1 (m, 1H), 2.3 (m, 1H), 3.2 (m, 2H), 3.8 (m, 1H), 4.2 (m, 2H), 4.7 (m, 1H), 9.0(s, 1H), 10.4 (s, 1H).

Step 2. Synthesis of 1-(1,1-Dimethylethyl)2-ethyl (2S,3S)-3-methyl-1,2-pyrrolidinedicarboxylate

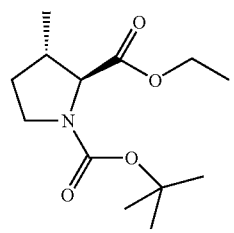

Ethyl(3S)-3-methyl-L-prolinate (0.837 g, 4.32 mmol), bis (1,1-dimethylethyl)dicarbonate (0.942 g, 4.32 mmol), and triethylamine (1.5 mL, 10.8 mmol) were heated in an approximately 2:1 mixture of THF and ethanol at 75° C. for 16 hours. The reaction was allowed to cool to room temperature, then diluted with water. The crude mixture was extracted 2× with ethyl acetate. The organic layers were washed with 1N NaOH, dried over MgSO$_4$, and concentrated under reduce pressure to give the title compound (855 mg, 3.3 mmol) as a clear oil. $^1$H NMR (400 MHz, DMSO-D6) δ ppm 1.1 (d, J=6.8 Hz, 3H), 1.2 (m, 3H), 1.3 (m, 9H), 1.5 (m, 1H), 1.9 (m, 1H), 2.2 (m, 1H), 3.2 (m, 1H), 3.4 (m, 1H), 3.6 (m, 1H), 4.1 (m, 2H).

Step 3. Synthesis of 1,1-Dimethylethyl(2S,3S)-2-(hydroxymethyl)-3-methyl-1-pyrrolidinecarboxylate

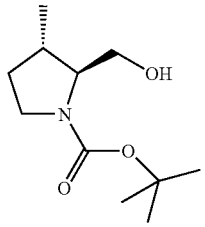

Lithium borohydride (6.6 mmol, 3.31 mL of a 2M in THF solution) was added dropwise to an ice cold THF solution of 1-(1,1-dimethylethyl)2-ethyl(2S,3S)-3-methyl-1,2-pyrrolidinedicarboxylate (850 mg, 3.3 mmol) and methanol (0.133 mL, 3.3 mmol). The reaction was warmed to room temperature and then stirred for 4 hours. The reaction was quenched with i-propanol then with saturated NaHCO$_3$. The reaction mixture was extracted 3× with ethyl acetate. The organic layers were dried over MgSO$_4$ and concentrated under reduced pressure to give the title compound, which was used without further purification. $^1$H NMR (400 MHz, DMSO-D6) δ ppm 0.9 (t, J=7.0 Hz, 3H), 1.3 (m, 9H), 1.9 (m, 1H), 2.2 (m, 1H), 3.1 (m, 2H), 3.3 (m, 2H), 3.5 (m, 1H), 4.7 (m, 1H).

Step 4. Synthesis of [(2S,3S)-3-Methyl-2-pyrrolidinyl]methanol hydrochloride

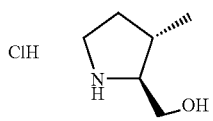

The crude 1,1-dimethylethyl(2S,3S)-2-(hydroxymethyl)-3-methyl-1-pyrrolidinecarboxylate from step 3 was dissolved in a 1:1 mixture of methylene chloride:methanol. Excess 4N HCl in dioxane was added, and the reaction stirred at room temperature for 1 hour, concentrated under reduced pressure, and then used in the final step (see Scheme 1a (g) to (h)). $^1$H NMR (400 MHz, DMSO-D6) δ ppm 1.1 (d, J=6.2 Hz, 3H), 1.5 (m, 1H), 2.1 (m, 2H), 3.1 (m, 1H), 3.3 (m, 1H), 3.4 (m, 1H), 4.5 (dd, J=12.1, 8.1 Hz, 1H), 4.7 (dd, J=12.3, 3.1 Hz, 1H).

Synthesis of Ethyl (3S)-3-Hydroxy-L-Prolinate Hydrochloride

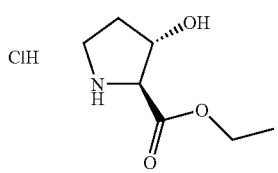

Acetyl chloride (10.8 mL, 153 mmol) was slowly added to ice cold 100% Ethanol (100 mL). (3S)-3-hydroxy-L-proline (5 g, 38.2 mmol) was added and heated at 100° C. for 16 hours. The ester was concentrated to a solid and used without purification. $^1$H NMR (400 MHz, DMSO-D6) δ ppm 1.2 (t, J=8.1 Hz, 3H), 1.9 (m, 2H), 3.3 (m, 2H), 4.1 (m, 1H), 4.2 (q, J=7.1 Hz, 2H) 4.4 (m, 1H), 9.0 (s, 1H), 10.4 (s, 1H).

Synthesis of (2R,3S)-2-Methyl-3-Pyrrolidinol Hydrochloride

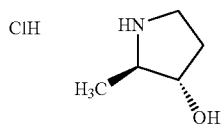

Step 1. Synthesis of 1-(1,1-Dimethylethyl)2-ethyl (2S,3S)-3-hydroxy-1,2-pyrrolidinedicarboxylate

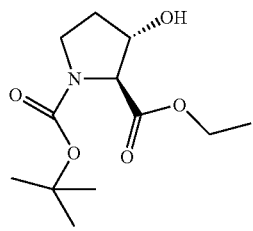

The title compound was prepared from ethyl(3S)-3-hydroxy-L-prolinate using the methods used to prepare 1-(1,1-dimethylethyl) 2-ethyl (2S,3S)-3-methyl-1,2-pyrrolidinedicarboxylate. $^1$H NMR (400 MHz, DMSO-D6) δ ppm 1.2 (m, 3H), 1.3 (m, 9H), 1.7 (m, 1H), 1.9 (m, 1H), 3.3 (m, 2H), 4.1 (m, 4H), 5.5 (s, 1H).

Step 2. Synthesis of 1-(1,1-Dimethylethyl)2-ethyl (2S,3S)-3-{[(1,1-dimethylethyl)(dimethyl)silyl]oxy}-1,2-pyrrolidinedicarboxylate

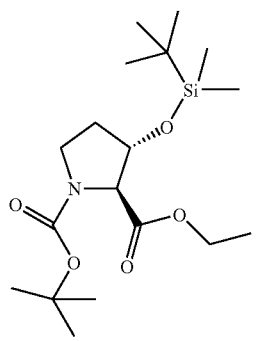

1-(1,1-dimethylethyl)2-ethyl(2S,3S)-3-hydroxy-1,2-pyrrolidinedicarboxylate (8.98 g, 34.7 mmol), imidazole (2.36 g, 34.7 mmol), dimethylaminopyridine (50 mg, catalytic) and chloro(1,1-dimethylethyl)dimethylsilane (4.96 g, 32.9 mmol) were stirred at room temperature for 16 hours. The reaction was diluted with water and 1N HCl to make the mixture acidic. The mixture was extracted three times with methylene chloride. The organic layer was washed with 1M HCl, dried over MgSO₄ to give the title compound as a clear brown oil (10.88 g, 29.1 mmol). ¹H NMR (400 MHz, DMSO-D6) δ ppm 0.0 (m, 6H), 0.8 (m, 9H), 1.2 (m, 3H), 1.3 (m, 9H), 1.7 (m, 1H), 1.9 (m, 1H), 3.4 (m, 2H), 3.9 (m, 1H), 4.1 (m, 2H), 4.4 (m, 1H). ES+=374.30.

Step 3. Synthesis of 1,1-Dimethylethyl(2R,3S)-3-{[(1,1-dimethylethyl)(dimethyl)silyl]oxy}-2-(hydroxymethyl)-1-pyrrolidinecarboxylate

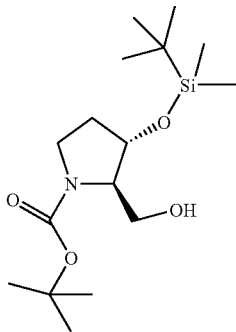

The title compound was prepared from 1-(1,1-dimethylethyl) 2-ethyl(2S,3S)-3-{[(1,1-dimethylethyl)(dimethyl)silyl]oxy}-1,2-pyrrolidinedicarboxylate using the methods used for preparation of 1,1-dimethylethyl(2S,3S)-2-(hydroxymethyl)-3-methyl-1-pyrrolidinecarboxylate. ¹H NMR (400 MHz, DMSO-D6) δ ppm −0.0 (m, 6H), 0.8 (m, 9H), 1.0 (m, 1H), 1.4 (m, 9H), 1.6 (m, 1H), 3.1 (m, 1H), 3.2 (m, 2H), 3.5 (m, 2H), 4.3 (m, 1H), 4.8 (m, 1H).

Step 4. Synthesis of 1,1-Dimethylethyl(2R,3S)-3-{[(1,1-dimethylethyl)(dimethyl)silyl]oxy}-2-{[(methylsulfonyl)oxy]methyl}-1-pyrrolidinecarboxylate

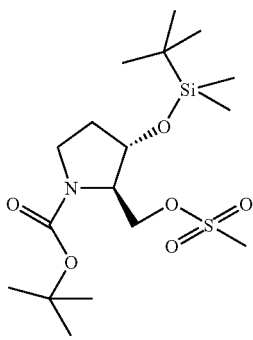

Methanesulfonyl chloride (3.85 mL, 39.29 mmol) was added to an ice cold methylene chloride solution of 1,1-dimethylethyl(2R,3S)-3-{[(1,1-dimethylethyl)(dimethyl)silyl]oxy-}2-(hydroxymethyl)-1-pyrrolidinecarboxylate (6.05 g, 26.19 mmol) and triethylamine (7.28 mL, 52.38 mmol). The reaction was warmed to room temperature, stirred for 16 hours then concentrated under reduced pressure. The crude material was dissolved in ethyl acetate and washed with saturated NaHCO₃, dried over MgSO₄ and concentrated under reduced pressure. The crude material was purified by silica gel column chromatography to give the title compound as a yellow oil. (4.69 g, 11.4 mmol). ¹H NMR (400 MHz, DMSO-D6) δ ppm 0.1 (s, 6H), 0.8 (s, 9H), 1.4 (m, 9H), 1.7 (m, 1H), 2.0 (m, 1H), 3.2 (s, 3H), 3.3 (m, 2H), 3.7 (m, 1H), 4.0 (m, 1H), 4.2 (m, 1H), 4.3 (m, 1H). ES+=410.16.

Step 5. Synthesis of 1,1-Dimethylethyl(2R,3S)-3-{[(1,1-dimethylethyl)(dimethyl)silyl]oxy}-2-methyl-1-pyrrolidinecarboxylate

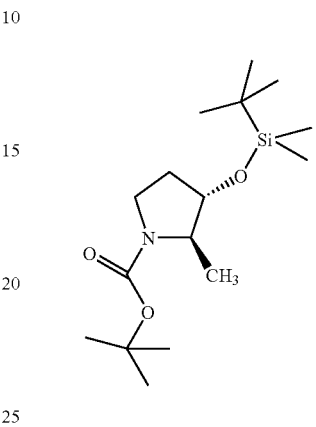

Superhydride (45.8 mL, 1M, 45.8 mmol) was added dropwise to an ice cold solution of 1,1-dimethylethyl(2R,3S)-3-{[(1,1-dimethylethyl)(dimethyl)silyl]oxy}-2-{[(methylsulfonyl)oxy]methyl}-1-pyrrolidinecarboxylate (4.69 g, 11.47 mmol) in THF. The reaction was warmed to room temperature and stirred for 16 hours. The reaction was quenched with i-propanol until gas evolution ceased. The reaction was diluted with saturated NaHCO₃ then extracted with ethyl acetate, dried over MgSO₄ and concentrated under reduced pressure. The crude material was purified by silica gel column chromatography to yield the title compound (2.69 g, 8.5 mmol). ¹H NMR (400 MHz, DMSO-D6) δ ppm 0.0 (s, 6H), 0.8 (s, 9H), 1.0 (m, 3H), 1.4 (s, 9H), 1.6 (m, 1H), 2.0 (m, 1H), 3.3 (m, 2H), 3.5 (m, 1H), 4.0 (m, 1H). ES+=316.22.

Step 6. Synthesis of 1,1-Dimethylethyl(2R,3S)-3-hydroxy-2-methyl-1-pyrrolidinecarboxylate

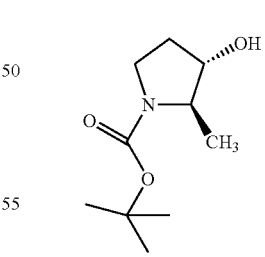

Tetrabutyl ammonium fluoride (16.7 mL, 1N in THF, 16.73 mmol) was added to a solution of 1,1-dimethylethyl(2R,3S)-3-{[(1,1-dimethylethyl)(dimethyl)silyl]oxy}-2-methyl-1-pyrrolidinecarboxylate in THF and stirred for 16 hours at room temperature. The reaction mixture was concentrated under reduced pressure and purified by silica gel column chromatography to yield the title compound (1.55 g, 7.8 mmol). ¹H NMR (400 MHz, DMSO-D6) δ ppm 1.0 (m, 3H), 1.4 (s, 9H), 1.6 (m, 1H), 1.9 (m, 1H), 3.3 (m, 2H), 3.5 (m, 1H), 3.8 (m, 1H), 4.9 (s, 1H). ES+=202.15.

Step 7. Synthesis of (2R,3S)-2-Methyl-3-pyrrolidinol hydrochloride

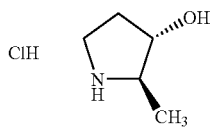

The title compound was prepared from 1,1-dimethylethyl (2R,3S)-3-hydroxy-2-methyl-1-pyrrolidinecarboxylate using the methods used for preparation of [(2S,3S)-3-methyl-2-pyrrolidinyl]methanol hydrochloride. $^1$H NMR (400 MHz, DMSO-D6) δ ppm 1.2 (d, J=7.0 Hz, 3H), 1.7 (m, 1H), 2.1 (m, 1H), 3.2 (m, 2H), 3.3 (m, 1H), 3.9 (m, 1H), 5.5 (m, 1H), 9.0 (s, 1H), 9.4 (m, 1H). ES+=101.82.

Synthesis of (2R,3S)-2-(Hydroxymethyl)-3-Pyrrolidinol Hydrochloride

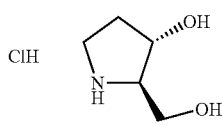

Step 1. Synthesis of 1,1-Dimethylethyl(2R,3S)-3-hydroxy-2-(hydroxymethyl)-1-pyrrolidinecarboxylate

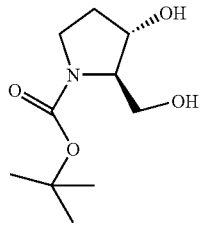

The title compound was prepared from 1-(1,1-dimethylethyl) 2-ethyl(2S,3S)-3-hydroxy-1,2-pyrrolidinedicarboxylate using the methods used to prepare 1,1-dimethylethyl(2S,3S)-2-(hydroxymethyl)-3-methyl-1-pyrrolidinecarboxylate. $^1$H NMR (400 MHz, DMSO-D6) δ ppm 1.4 (s, 9H), 1.6 (m, 1H), 1.9 (m, 1H), 3.1 (m, 1H), 3.2 (m, 2H), 3.4 (m, 2H), 4.1 (m, 1H). ES+=218.24, 117.97 (-Boc).

Step 2. Synthesis of (2R,3S)-2-(Hydroxymethyl)-3-pyrrolidinol hydrochloride

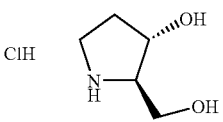

The title compound was prepared from 1,1-dimethylethyl (2R, 3S)-3-hydroxy-2-(hydroxymethyl)-1-pyrrolidinecarboxylate using the methods used to prepare [(2S,3S)-3-methyl-2-pyrrolidinyl]methanol hydrochloride. $^1$H NMR (400 MHz, DMSO-D6) δ ppm 1.8 (m, 1H), 2.0 (m, 1H), 2.5 (m, 2H), 3.2 (m, 2H), 3.3 (m, 1H), 3.5 (m, 1H), 3.6 (m, 1H), 4.1 (m, 1H), 8.7 (s, 1H), 9.5 (m, 1H). ES+=117.97.

Synthesis of N-3-Azetidinylmethanesulfonamide

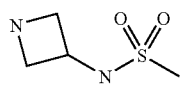

Step 1. Synthesis of N-[1-(diphenylmethyl)-3-azetidinyl]methanesulfonamide

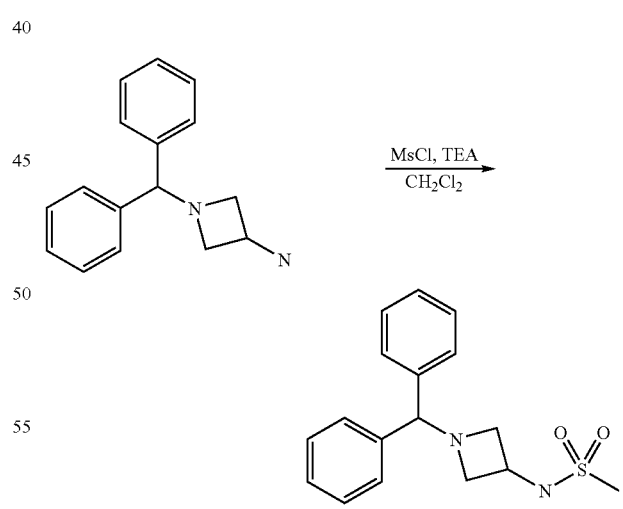

A solution of 1-(diphenylmethyl)-3-azetidinamine (synthesized according to the methods of Arimoto et. al., J. of Antibiotics 39 (9), 1243-56, 1986) (197 mg, 0.83 mmol) in dichloromethane (10 mL) was treated with excess triethylamine at 0° C. followed by methanesulfonyl chloride (71 μL, 0.91 mmol). The reaction was stirred for 30 minutes and then concentrated and purified on silica gel (0-10% methanol/dichloromethane) to provide 185 mg of the desired product as a white solid. LC/MS: M+H 317.19 at 0.31 minutes, Method D.

Step 2. Synthesis of N-3-azetidinylmethanesulfonamide

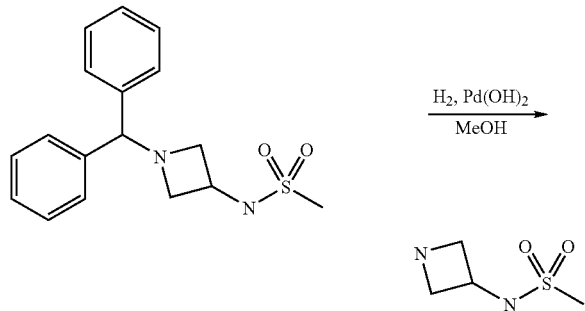

A solution of N-[1-(diphenylmethyl)-3-azetidinyl]-methanesulfonamide (185 mg, 0.585 mmol) in MeOH (10 mL) was treated with 1 mL of 4.0 N HCl/dioxane and then reacted overnight with hydrogen gas at 50 psi. The reaction mixture was then filtered through a pad of Celite and used without further purification.

Synthesis of (4E)-3-Methyl-4-Piperidinone-O-Methyloxime

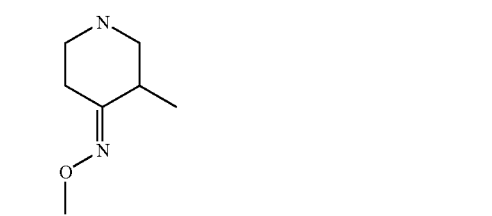

Step 1. Synthesis of 1,1-Dimethylethyl 3-methyl-4-oxo-1-piperidinecarboxylate

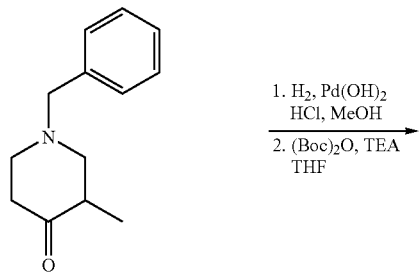

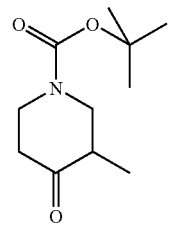

A solution of 3-methyl-1-(phenylmethyl)-4-piperidinone (1.5 g, 7.4 mmol) in methanol (10 mL) was treated with 4.0 N HCl/dioxane (2.2 mL), followed by palladium hydroxide. The mixture was then reacted overnight with hydrogen gas at 50 psi. The reaction was then filtered through Celite, concentrated, and then taken up in THF (20 mL). The crude reaction mixture was then treated with triethylamine (2.3 mL), followed by di-tert-butyl dicarbonate (1.9 g, 8.9 mmol). The reaction was stirred for two hours, concentrated, taken up in dichloromethane and washed with saturated aqueous ammonium hydroxide, followed by brine. The organic layer was dried over magnesium sulfate and purified by column chromatography to provide 734 mg of 1,1-dimethylethyl 3-methyl-4-oxo-1-piperidinecarboxylate as a white solid. $^1$H NMR (400 MHz, CDCl$_3$) δ ppm 1.0 (d, J=6.69, 3H), 1.5 (s, 9H), 2.4 (m, 2H), 2.5 (m, 1H), 2.8 (m, 1H), 3.2 (m, 1H), 4.2 (m, 2H).

Step 2. Synthesis of 1,1-Dimethylethyl(4E)-3-methyl-4-[(methyloxy)imino]-1-piperidinecarboxylate

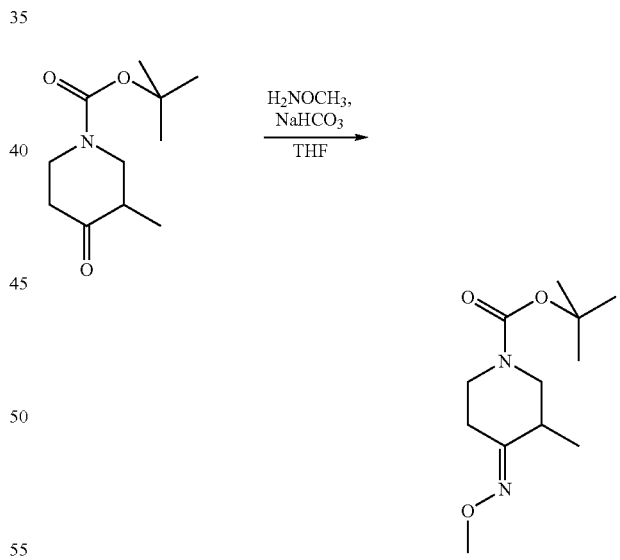

A solution of 1,1-dimethylethyl 3-methyl-4-oxo-1-piperidinecarboxylate (367 mg, 1.72 mmol) in THF (10 mL) was treated with methylhydroxylamine hydrochloride (503 mg, 6.02 mmol) followed by a solution of sodium hydrogencarbonate (506 mg, 6.02 mmol) in water (3 mL). The reaction was stirred vigorously overnight. The reaction was then filtered, diluted with water, and extracted with dichloromethane. The crude material was purified by column chromatography (0-10% ethyl acetate/hexanes) to provide 197 mg of the desired product as a white solid. $^1$H NMR (400 MHz, CDCl$_3$) δ ppm 1.1 (d, J=6.8 Hz, 3H), 1.5 (s, 9H), 2.5 (m, 1H), 2.6 (m, 2H), 3.5 (m, 4H), 3.8 (s, 3H).

Step 3. Synthesis of (4E)-3-methyl-4-piperidinone O-methyloxime

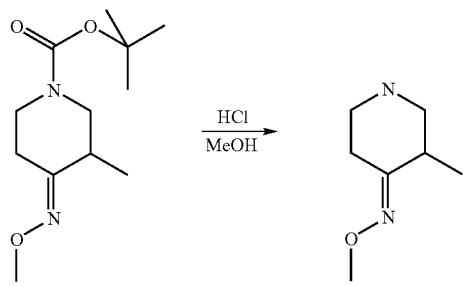

1,1-Dimethylethyl(4E)-3-methyl-4-[(methyloxy)imino]-1-piperidinecarboxylate (197 mg) was dissolved in methanol, treated with 4.0 N HCl/dioxane (4 mL) and stirred overnight. The reaction was then concentrated to provide the product as a white solid (170 mg). The crude material was used without further purification.

Synthesis of 4,4-Dimethylcyclohexanone

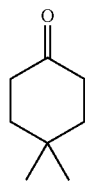

The title compound was synthesized using the following literature procedure which is hereby incorporated by reference and for all purposes as if fully set forth in its entirety. Liu, Hsing-Jang; Browne, Eric N. C. and Chew, Sew Yeu. Can. J. Chem. 66, 2345-2347 (1988).

Synthesis of (4,4-Dimethylcyclohexyl)Amine

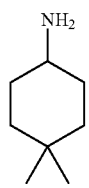

The title compound was synthesized using the following literature procedure which is hereby incorporated by reference and for all purposes as if fully set forth in its entirety. Faller, A., MacPherson, D. T., Ner, P. H., Stanway, S. J. and Trouw, L. S. WO04/5913A1 (2003).

Synthesis of N-{3-(2-[2-Fluoro-4-(Methyloxy)Phenyl]Ethyl}-4-OXO-3,4-Dihydro-7-Quinazolinyl)-N'-[(1S,2S,3S,5R)-2,6,6-Trimethylbicyclo[3.1.1]Hept-3-YL]Carbodiimide Carbodiimide A

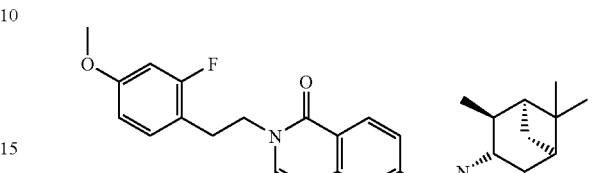

N-(3-{2-[2-fluoro-4-(methyloxy)phenyl]ethyl}4-oxo-3, 4-dihydro-7-quinazolinyl)-N'-[(1S,2S,3S,5R)-2,6,6-trimethylbicyclo[3.1.1]hept-3-yl]thiourea was gently stirred with Argonaut PS-Carbodiimide (1.5 eq) for 15 hours in THF. The resin was filtered off and the solution of carbodiimide A was diluted to a known volume to give a solution of known molarity.

Synthesis of N-{3-[2-(2,4-Dichlorophenyl)Ethyl]-4-OXO-3,4-Dihydro-7-Quinazolinyl}-N'-[(1S,2S,3S,5R)-2,6,6-Trimethylbicyclo[3.1.1]Hept-3-YL]Carbodiimide Carbodiimide B

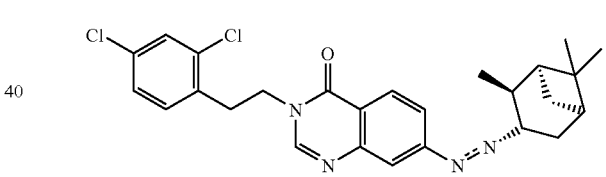

N-{3-[2-(2,4-dichlorophenyl)ethyl]-4-oxo-3,4-dihydro-7-quinazolinyl}-N'-[(1S,2S,3S,5R)-2,6,6-trimethylbicyclo[3.1.1]hept-3-yl]thiourea was gently stirred with Argonaut PS-Carbodiimide (1.5 eq) for 15 hours in THF. The resin was filtered off and the solution of carbodiimide B was diluted to a known volume to give a solution of known molarity.

Synthesis of 2-Chloro-3-[2-(2,4-Dichlorophenyl)Ethyl]-7-Nitro-4(3H)-Quinazolinone

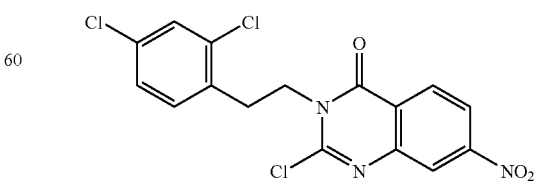

Step 1. Synthesis of 2-Amino-N-[2-(2,4-dichlorophenyl)ethyl]-4-nitrobenzamide

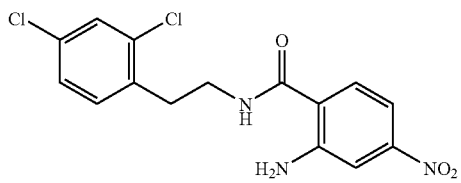

To a stirred solution of 4-nitro-isatoic anhydride (10.0 g, 0.048 mol) in CH$_2$Cl$_2$ (100 mL) was added 2,4-dichlorophenethylamine (10.08 g, 0.053 mol) followed by DMF (10 mL). The reaction mixture was stirred at room temperature for 30 min. The resulting mixture was then dissolved in 1.0 L CH$_2$Cl$_2$ and washed with 1.0 M NaOH. The combined organic layers were concentrated under reduced pressure and purified by silica gel flash chromatography (0-100% EtOAc/hexanes eluent) to give the product (16.5 g, 97% yield) as a yellow solid. HPLC retention time: 3.04 min; Method A; LRMS (ESI) m/z 354 (M+1).

Step 2. Synthesis of 3-[2-(2,4-Dichlorophenyl)ethyl]-7-nitro-2,4(1H,3H)-quinazolinedione

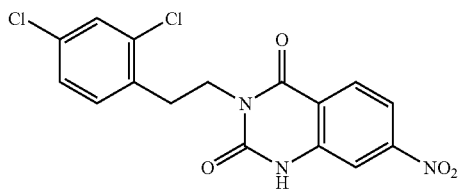

To a stirred solution of 2-amino-N-[2-(2,4-dichlorophenyl)ethyl]-4-nitrobenzamide (1.0 g, 2.82 mmol) in toluene (30 mL) was added a 1.9 M solution of phosgene in toluene (4.5 mL, 8.5 mmol). The reaction mixture was heated to 60° C. and stirred for 4 hours. The solvent was removed under reduced pressure and CH$_2$Cl$_2$ was added to the residue. The precipitate was collected via vacuum filtration and washed with CH$_2$Cl$_2$ to give the product (0.92 g, 86% yield) as a white solid. HPLC retention time: 3.28 min; Method A; LRMS (ESI) m/z 378 (M−1).

Step 3. Synthesis of 2-Chloro-3-[2-(2,4-dichlorophenyl)ethyl]-7-nitro-4(3H)-quinazolinone

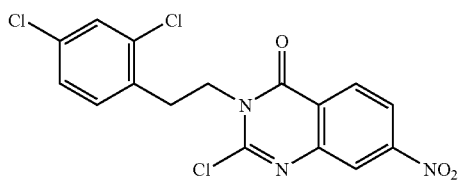

3-[2-(2,4-Dichlorophenyl)ethyl]-7-nitro-2,4(1H, 3H)-quinazolinedione (2.0 g, 5.26 mmol) and PCl$_5$ (1.2 g, 5.79 mmol) were added to a flask containing POCl$_3$ (20 mL) and the resulting solution was refluxed with stirring for 6 hours. The reaction was allowed to cool to RT and stirred overnight at this temp. The POCl$_3$ was removed under reduced pressure and CH$_2$Cl$_2$ was added to the residue. The unreacted starting material was removed via vacuum filtration and the product was purified by silica gel flash chromatography (100% CH$_2$Cl$_2$ eluent) to give the product (0.96 g, 46% yield) as a white solid. $^1$H NMR (DMSO-D6) 400 MHz δ ppm 8.35-8.25 (m, 3H), 7.58 (d, J=2.2 Hz, 1H), 7.41-7.34 (m, 2H), 4.41 (t, J=7.5 Hz, 2H), 3.15 (t, J=7.5 Hz, 2H) ppm.

Synthesis of 3-Amino-N-{3-[2-(4-Fluorophenyl)Ethyl]-4-OXO-3,4-Dihydro-7-Quinazolinyl}-N'-[(1S,2S,3S,5R)-2,6,6-Trimethylbicyclo[3.1.1]Hept-3-YL]-1-Azetidinecarboximidamide

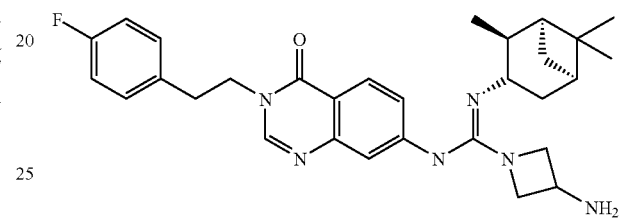

Step 1. Synthesis of 1-Dimethylethyl [1-(diphenylmethyl)-3-azetidinyl]carbamate

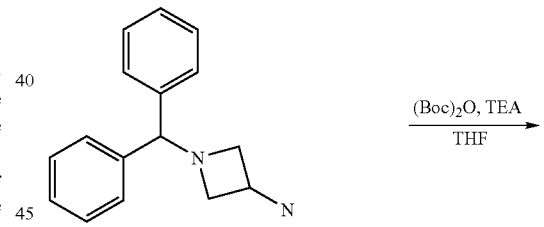

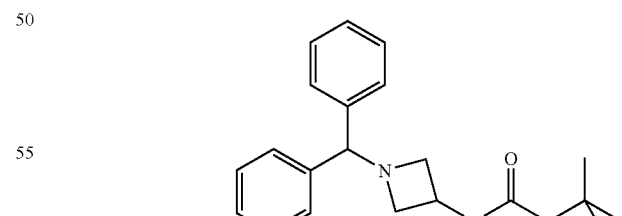

To a solution of 1-(diphenylmethyl)-3-azetidinamine (232 mg, 0.97 mmol) in THF (6 mL) at 0° C. was added a solution di-tert-butyl dicarbonate (255 mg, 1.17 mmol) in THF (4 mL). The reaction was warmed to room temperature and dichloromethane (4 mL) was added to bring the slurry into solution. The reaction was stirred overnight, concentrated and then purified by column chromatography (0-30% ethyl acetate/hexanes) to afford 211 mg of the desired product as a white solid. LC/MS: M+H 339.19 at 1.20 minutes, Method D.

Step 2. Synthesis of 1,1-Dimethylethyl 3-azetidinylcarbamate

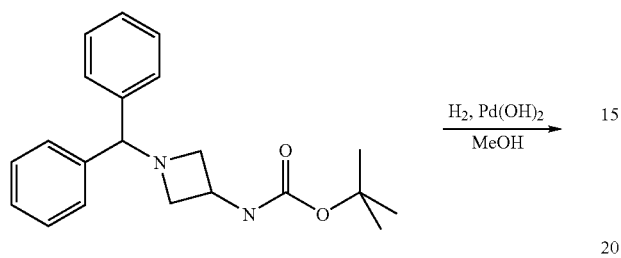

A solution of 1,1-dimethylethyl [1-(diphenylmethyl)-3-azetidinyl]carbamate in MeOH (10 mL) was treated with of 4.0 N HCl/dioxane (1 mL) and then reacted overnight with hydrogen gas at 50 psi. The reaction mixture was then filtered through a pad of Celite, concentrated and the crude residue was used without further purification.

Step 3. Synthesis of 3-Amino-N-{3-[2-(4-fluorophenyl)ethyl]-4-oxo-3,4-dihydro-7-quinazolinyl}-N'-[(1S,2S,3S,5R)-2,6,6-trimethylbicyclo[3.1.1]hept-3-yl]-1-azetidinecarboximidamide 1,1-dimethylethyl [1-((Z)-({3-[2-(4-fluorophenyl)ethyl]-4-oxo-3,4-dihydro-7-quinazolinyl}amino){[(1S,2S,3S,5R)-2,6,6-trimethylbicyclo[3.1.1]hept-3-yl]imino}methyl)-3-azetidinyl]carbamate (synthesized using 1,1-dimethylethyl 3-azetidinylcarbamate by the methods described previously) was treated with 4.0 N HCl/dioxane (4 mL) and stirred overnight. The reaction was then purified by preparatory HPLC to provide 3-amino-N-{3-[2-(4-fluorophenyl)ethyl]-4-oxo-3,4-dihydro-7-quinazolinyl}-N'-[(1S,2S,3S,5R)-2,6,6-trimethylbicyclo[3.1.1]hept-3-yl]-1-azetidinecarboximidamide as a white solid. LC/MS: M+H 517.20 at 2.19 minutes, Method D.

General Method for the Preparation of Nitrogen-Bound C-2 Analogs

Step 1. Synthesis of 2-Amino Analogs

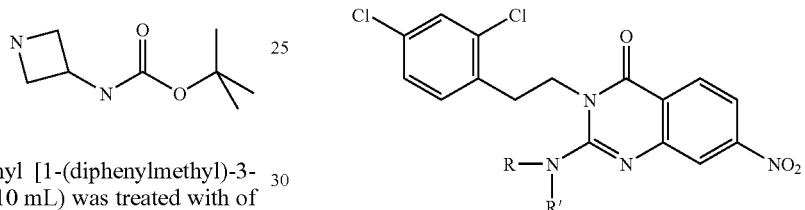

To a stirred solution 2-chloro-3-[2-(2,4-dichlorophenyl)ethyl]-7-nitro-4(3H)-quinazolinone (1 equivalents) in acetonitrile (1.0 M) was added the corresponding amine (2 equivalents) and the reaction mixture was heated to reflux until the reaction was completed as monitored by HPLC (ca. 30 min). The reaction mixture was then cooled to RT and the solvent

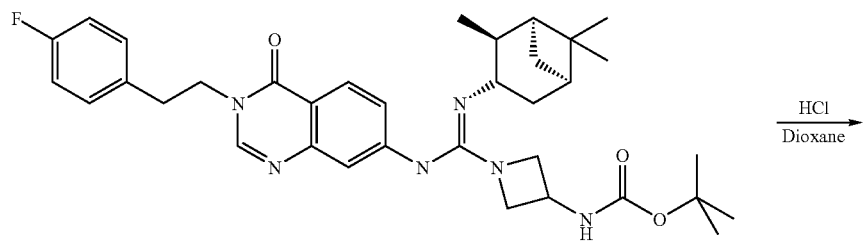

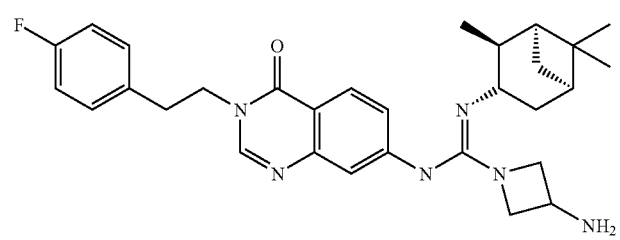

was removed in vacuo. The crude product was purified via silica gel flash chromatography (0-5% MeOH/CH$_2$Cl$_2$ eluent).

Step 2. Reduction of Nitro to Aniline

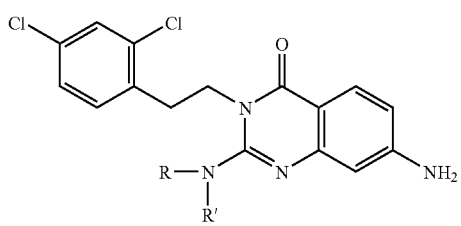

To a stirred solution of the nitro compound (1 equiv) in absolute ethanol (1.0 M) was added iron powder (2.5 equivalents) and acetic acid (14 equivalents). The reaction mixture was heated to reflux until the reaction was complete as monitored by HPLC. The reaction mixture was then cooled to RT, diluted with EtOAc, and washed with sat. NaHCO$_3$. The aqueous layer was re-extracted with EtOAc (×2) and the combined organic layers were dried over Na$_2$SO$_4$, filtered, and concentrated in vacuo. The crude solid was used in the next step without purification.

Step 3. Conversion of Aniline to Thiourea

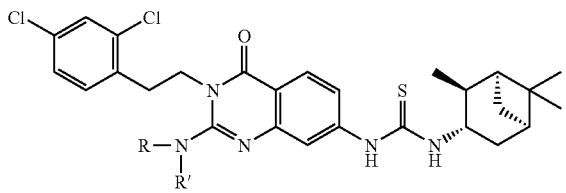

To a stirred solution of crude aniline (1 equiv) in acetone (1.0 M) at 0° C. was added Na$_2$CO$_3$ (2 equivalents) followed by thiophosgene (3 equivalents) dropwise via syringe. The reaction mixture was stirred at 0° C. for 10 minutes then allowed to warm to room temperature. A solid precipitated from solution as the reaction progressed. When the starting material was completely consumed as monitored by HPLC, the reaction mixture was concentrated in vacuo, diluted with acetone, and then concentrated again to remove excess thiophosgene. The material was then diluted with EtOAc and washed with water. All of the solid was dissolved. The aqueous layer was re-extracted with EtOAc (×2) and the combined organic layers were dried over Na$_2$SO$_4$, filtered, and concentrated in vacuo. The crude material was then dissolved in THF (1.0 M) and (1S,2S,3S,5R)-(+)-isopinocampheylamine (1.3 equiv) was added via syringe. The reaction mixture was stirred at RT for 30 min then concentrated in vacuo. The crude material was purified via silica gel flash chromatography (0-5% MeOH/CH$_2$Cl$_2$ eluent).

Step 4. Conversion of Thiourea to Guanidine

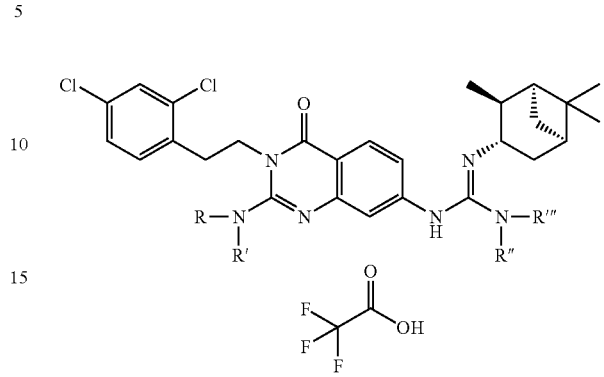

To a stirred solution of thiourea (1 equivalents) in THF (1.0 M) was added EDC (1.5 equivalents) and the reaction mixture was heated to reflux. When the starting material was completely consumed as monitored by HPLC, the reaction mixture was cooled to RT and then the corresponding amine (2 equivalents) and Et$_3$N (2 equivalents) were added. The reaction mixture was stirred at room temperature for 1 hour then concentrated in vacuo. The crude material was purified via preparative reversed-phase HPLC (MeCN/water eluent) and lyophilized to produce the TFA salt.

General Procedure for the Synthesis of Aryl Guanidines

Unless otherwise noted, a THF solution of a carbodiimide such as Carbodiimide A or Carbodiimide B was stirred with approximately 1.5 equivalents of primary or secondary amine at room temperature for 10 minutes. (In cases where the amine was in a salt form, the amine was dissolved in minimal methanol and 2 equivalents of triethylamine was added.) The reaction were concentrated under a stream of nitrogen, dissolved in methanol and purified by preparative HPLC.

Synthesis of N-(3-{2-[2-Fluoro-4-(Methyloxy)Phenyl]Ethyl}-4-OXO-3,4-Dihydro-7-Quinazolinyl)-N'-4H-1,2,4-Triazol-4-YL-N"-[(1R,2S,3S,5S)-2,6,6-Trimethylbicyclo[3.1.1]Hept-3-YL]Guanidine Trifluoroacetate

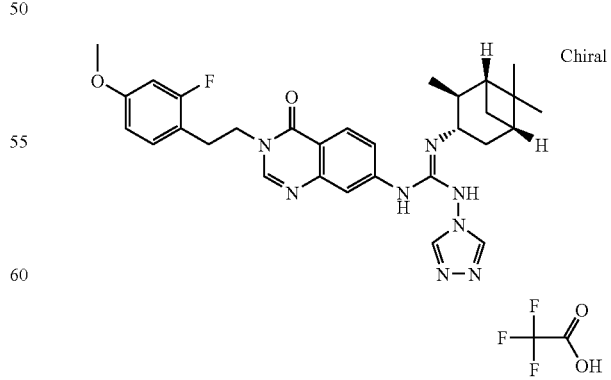

N-(3-{2-[2-fluoro-4-(methyloxy)phenyl]ethyl}4-oxo-3,4-dihydro-7-quinazolinyl)-N'-[(1S,2S, 3S, 5R)-2,6,6-trimethylbicyclo[3.1.1]hept-3-yl]carbodiimide (4 mL, 23 mM solution in THF), 4H-1,2,4-triazol-4-amine (49 mg) and excess NaH were stirred together and heated at 50° C. for 30 minutes. The reaction was quenched with 1 mL H₂O and 5 mL of ethyl acetate. The mixture was passed through a Varian Chem Elut cartridge followed by 50 mL of ethyl acetate. The ethyl acetate solution was dried over MgSO₄ and concentrated. This crude material was dissolved in 1 mL of methanol, purified by preparative HPLC and freeze-dried to give the TFA salt of the title compound.

Synthesis of cis-4-Fluorocyclohexylamine

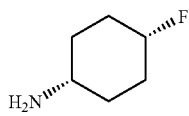

Step 1. Synthesis of trans-(t-butoxy)-N-(4-hydroxy-cyclohexyl)-carboxamide

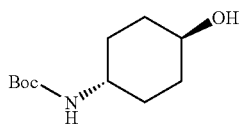

A suspension of trans-4-aminocyclohexanol (1 equivalent) in THF (0.1 M) was treated with (Boc)₂O (1 equivalent). The mixture was stirred at room temperature overnight, dissolved in chloroform, and washed with water to yield a solid that was used without further purification.

Step 2. Synthesis of cis-(t-butoxy)-N-(4-fluorocyclohexyl)carboxamide

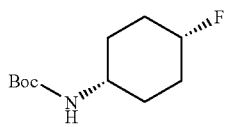

To a solution of (t-butoxy)-N-(4-hydroxycyclohexyl)carboxamide (1 equivalent) in CH₂Cl₂ (1 M) cooled to −78° C. was added dropwise a solution of DAST (1 equivalent) in CH₂Cl₂ (0.5 M). The mixture was stirred at −78° C. for 4 hours, and then allowed to rise to room temperature. The solution was poured into saturated NaHCO₃ and extracted with chloroform, dried, and evaporated. The resulting crude product was purified on silica gel, eluting with ethyl acetate/hexane 5:95.

Step 3. Synthesis of cis-4-fluorocyclohexylamine

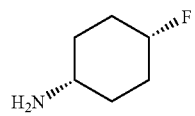

A solution of cis-(t-butoxy)-N-(4-fluorocyclohexyl)carboxamide (6.51 mmol) in CH₂Cl₂ (20 mL) was treated with TFA (10 mL) at room temperature. The reaction mixture was stirred for 2 hours, the solvent was removed in vacuo, and the crude product was dissolved in water and washed with chloroform. The acidic aqueous phase was cooled at 0° C. and made basic by the addition of solid KOH. The resulting mixture was extracted with CH₂Cl₂, dried and filtered, yielding the title compound which was used without further purification and as a 0.3 M solution in CH₂Cl₂.

Synthesis of 4,4-Difluorocyclohexylamine

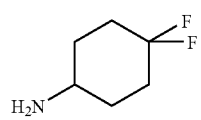

Step 1. Synthesis of N-(4,4-difluorocyclohexyl)(t-butoxy)carboxamide

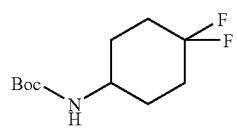

A solution of (t-butoxy)-N-(4-oxocyclohexyl)carboxamide (2.5 g, 11.7 mmol) in CH₂Cl₂ (45 mL) was treated with a solution of DAST (2.63 mL, 19.93 mmol) in CH₂Cl₂ (6 mL) at room temperature. EtOH (141 μl, 2.3 mmol) was added, and the mixture was stirred at room temperature overnight. The solution was poured into saturated NaHCO₃ and extracted with chloroform, dried, and evaporated to yield a 1:1 mixture of the title compound and (t-butoxy)-N-(4-fluorocyclohex-3-enyl)carboxamide. This mixture was dissolved in CH₂Cl₂ (40 mL) and MeOH (14 mL) and cooled to −78° C. Ozone was bubbled into the solution for 50 minutes until it turned green and Me₂S was added (3 equivalents). The reaction mixture was allowed to warm to room temperature, chloroform was added and the organic phase was washed with water, dried, and evaporated to yield the title compound which was used without further purification.

Step 2. Synthesis of 4,4-difluorocyclohexylamine

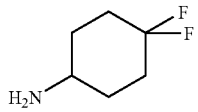

A solution of N-(4,4-difluorocyclohexyl)(t-butoxy)carboxamide (6.51 mmol) in CH$_2$Cl$_2$ (20 mL) was treated with TFA (10 mL) at room temperature. The reaction mixture was stirred for 2 hours, the solvent was removed in vacuo, and the crude product was dissolved in water and washed with chloroform. The acidic aqueous phase was cooled at 0° C. and made basic by the addition of solid KOH. The resulting mixture was extracted with CH$_2$Cl$_2$, dried, and filtered yielding the title compound which was used without further purification as a 0.3 M solution in CH$_2$Cl$_2$.

Procedure 1 Synthesis of 6-fluoro Analog of 7-azido-quinazoline-4-one (1)

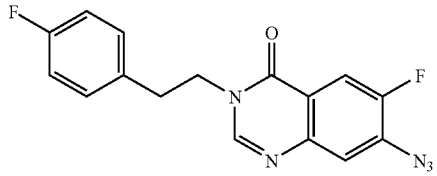

1

Step 1: Synthesis of (2-amino-4,5-difluorophenyl)-N-[2-(4-fluorophenyl)ethyl]-carboxamide

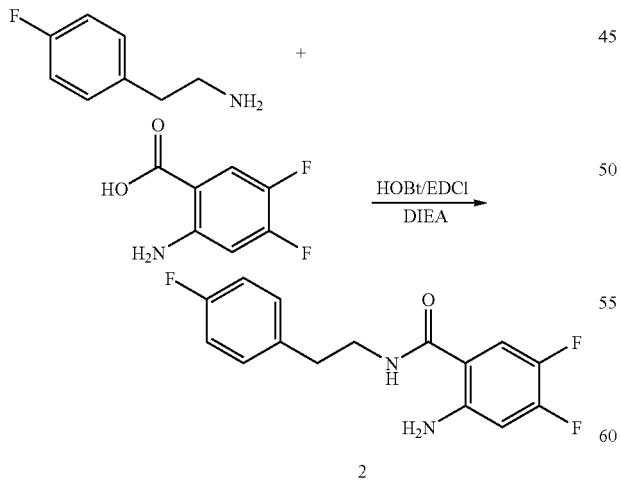

2

To a stirred solution of 4,5-difluoro anthranilic acid (2.0 g, 11.6 mmol) in anhydrous THF (30 mL) was added hydroxybenzotriazole hydrate (HOBt) (1.56 g, 11.6 mmol), diisopropylethyl amine (2.01 mL, 11.6 mmol), and 4-fluorophenylethyl amine (1.52 mL, 11.6 mmol). After all of the HOBt had completely dissolved, EDCl (2.21 g, 11.6 mmol) was added and the resulting orange solution was stirred at room temperature for 16 hours. The solvent was removed, and the residue was chromatographed on silica eluting with 15% EtOAc in hexanes giving the desired benzamide (2) as white crystals (3.07 g, 10.4 mmol, 90%).

Step 2: Synthesis of 6,7-difluoro-3-[2-(4-fluorophenyl)ethyl]-3-hydroquinazolin-4-one

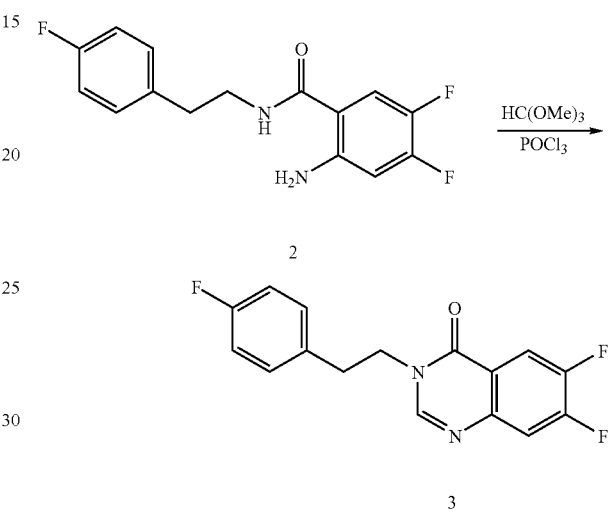

The starting benzamide (2) was dissolved in trimethyl orthoformate (20 mL) and heated at 120° C. under a stream of nitrogen for 3 hours. The solution was cooled, and the solvent was removed by rotary evaporation. The residue was triturated with hexanes, and the solids collected by filtration, washed with hexanes, and dried on the pump. The formamide intermediate was isolated as a white solid and confirmed by NMR. This intermediate was suspended in POCl$_3$ (10 mL) and heated to 140° C. for 3 minutes. The reaction was cooled, poured over crushed ice, made slightly alkaline with saturated sodium bicarbonate solution, and extracted with EtOAc. The organic layer was collected and dried over magnesium sulfate. Product (3) was isolated as a white solid (1.94 g, 6.38 mmol, 75% for 2 steps).

Step 3: Synthesis of 7-(azadiazomvinyl)-6-fluoro-3-[2-(4-fluorophenyl)ethyl]-3-hydroquinazolin-4-one

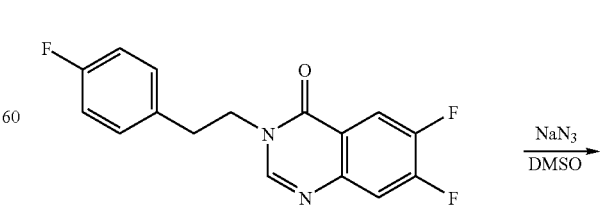

3

-continued

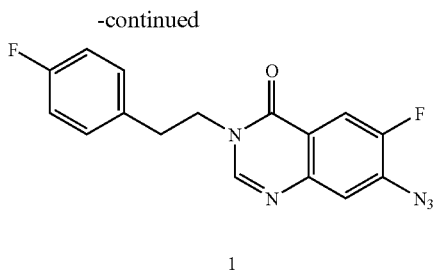

1

Difluoroquinazoline (3) (1.46 g, 4.6 mmol) was dissolved in DMSO (10 mL), and sodium azide (3 g, 46.0 mmol) was added. The resulting mixture was heated to 70° C. with stirring for 4 hours. The reaction was monitored by NMR. The reaction was cooled and diluted with water, and the resulting precipitate collected by filtration and washed with water. The solid was dissolved in methylene chloride and dried (MgSO$_4$) in order to remove trace water. Product (1) was isolated as an off-white solid (1.43 g, 4.37 mmol, 95%).

Following the formation of compound 1, final guanidine quinazolinones were formed following the synthetic method described below (Procedure 1A):

Procedure 1A

To a solution of (1) (1 equivalent) in THF was added trimethylphosphine (1.5 equivalents), and the mixture was stirred at room temperature for 10 minutes. To the iminophosphorane solution was added (1S,2S,3S,5R)-2,6,6-trimethylbicyclo[3.1.1]hept-3-yl isocyanate (1.6 equivalents). The solution was heated at 70° C. overnight. To half of the carboimide solution was added a THF solution of (6S,2R)-2,6-dimethylpiperazine (2 equivalents). After being heated at 70° C. for 2 hours, the residue was subjected to HPLC purification to give the guanidine product as its TFA salt.

The 2-fluoro-4-methoxy, 2,4-difluoro and 2,4-dichloro analogs were synthesized via the same pathway described above. Compounds of the group synthesized via the pathway described above include Examples 42, 44, and 45.

Example 1

Synthesis of (3R,5S)-N-(3-{2-[2-fluoro-4-(methyloxy)-phenyl]ethyl}-4-oxo-3,4-dihydroquinazolin-7-yl)-3,5-dimethyl-N'-[(1S,2S,5R)-2,6,6-trimethylbicyclo[3.1.1]hept-3-yl]piperazine-1-carboximidamide

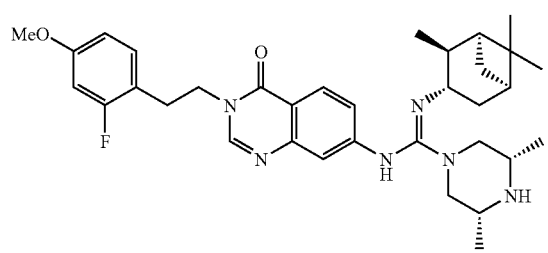

Step 1. Synthesis of (c): 2-amino-N-[2-(2-fluoro-4-methoxy-phenyl)-ethyl]-4-nitro-benzamide

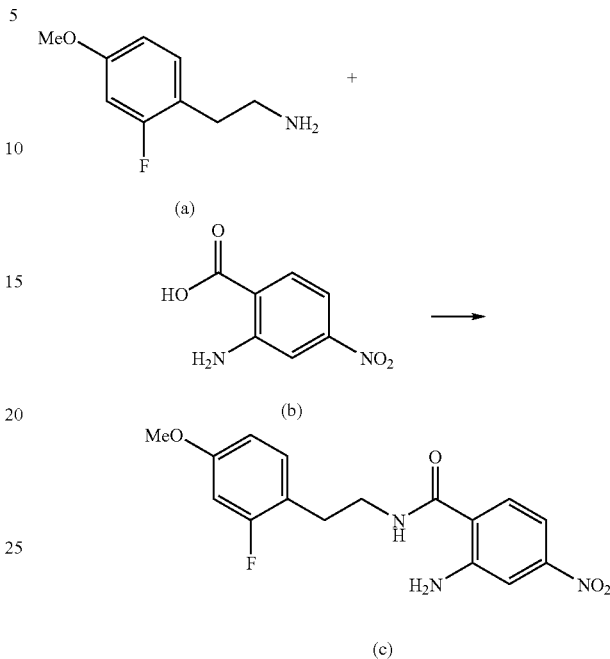

2-Fluoro-4-methoxyphenylethylamine ((a):1 equivalent), 4-nitroanthranilic acid ((b): 1 equivalent), HBTU (1.5 equivalents), and dry THF (0.5 M in (a)) were added to a dry round bottom flask. The mixture was allowed to stir for 10 hours at room temperature. The reaction was then dry loaded onto silica gel and purified via flash chromatography using hexanes/ethyl acetate. The pure fractions were combined and concentrated in vacuo to yield the product ((c): 2-amino-N-[2-(2-fluoro-4-methoxy-phenyl)-ethyl]-4-nitro-benzamide) as a pure solid.

Step 2. Synthesis of (d): 3-[2-(2-fluoro-4-methoxy-phenyl)-ethyl]-7-nitro-3H-quinazolin-4-one

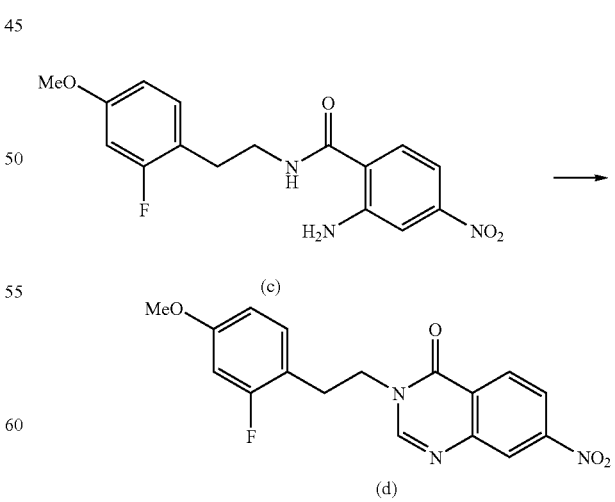

The pure product ((c): 1 equivalent) of Step 1, Gold's reagent, and dioxane (0.5 M in (c)) were added to a dry round bottom flask, fitted with a condenser, and heated to reflux for 16 hours. Once complete product conversion was verified by LC/MS, acetic acid (1 equivalent) and sodium acetate (1 equivalent) were added to the reaction. The subsequent mixture was heated to reflux for 3 hours. Then, the reaction was concentrated in vacuo, taken up in ethyl acetate, and washed with water. After the organic layer was isolated, the aqueous layer was extracted with two more portions of ethyl acetate. The organic layers were then combined, dried over sodium sulfate, filtered through a cotton plug, and concentrated. The crude product mixture was purified via flash chromatography using a mixture of $CH_2Cl_2$/MeOH. The pure fractions were combined and concentrated in vacuo to yield the pure product ((d): 3-[2-(2-fluoro-4-methoxy-phenyl)-ethyl]-7-nitro-3H-quinazolin-4-one) as a pure solid.

Step 3. Synthesis of (e): 7-amino-3-[2-(2-fluoro-4-methoxy-phenyl)-ethyl]-3H-quinazolin-4-one

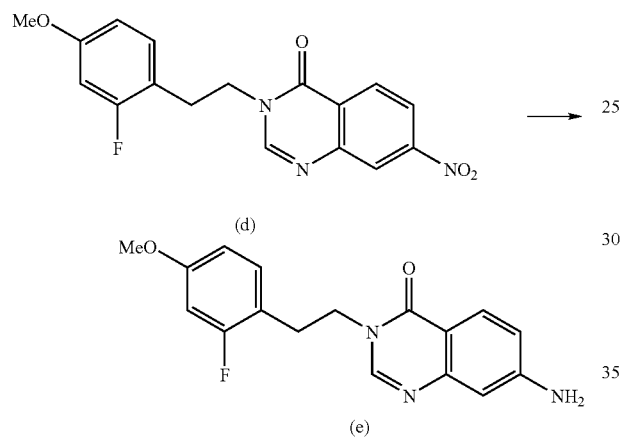

To a solution of (d), prepared as described in Step 2, in MeOH (0.25 M in (d)) was added 10% Pd/C (0.1 equivalent). The mixture was sealed with a septum and degassed with nitrogen for 10 minutes. Hydrogen was then bubbled through the solution for 20 minutes. Once reaction completion was verified by LC/MS, the reaction was degassed with nitrogen for 10 minutes. The mixture was filtered through Celite® and concentrated in vacuo to yield the product ((e): 7-amino-3-[2-(2-fluoro-4-methoxy-phenyl)-ethyl]-3H-quinazolin-4-one). The product was used in the next reaction without further purification.

Step 4. Synthesis of (f): 3-[2-(2-fluoro-4-methoxy-phenyl)-ethyl]-7-isothiocyanato-3H-quinazolin-4-one

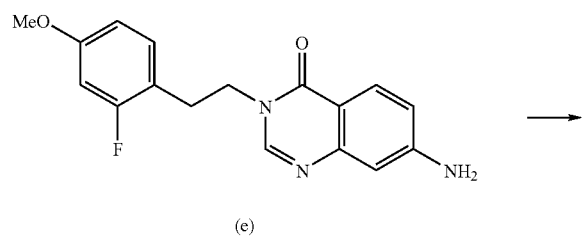

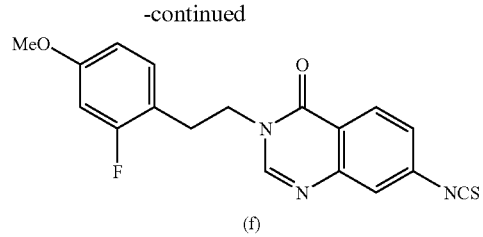

To a mixture of (e), prepared as described in Step 3, (1 equivalent) and $NaHCO_3$ (3 equivalents) in acetone (0.1 M in (e)) was added thiophosgene (3 equivalents) dropwise. The resulting slurry was stirred at room temperature for three hours. Once reaction completion was verified by LC/MS, the reaction was concentrated in vacuo to remove solvent and excess thiophosgene. The mixture was then taken up in ethyl acetate and washed with water. After the organic layer was isolated, the aqueous layer was extracted with two more portions of ethyl acetate. The organic layers were then combined, dried over sodium sulfate, filtered through a cotton plug, and concentrated in vacuo to yield the product ((f): 3-[2-(2-fluoro-4-methoxy-phenyl)-ethyl]-7-isothiocyanato-3H-quinazolin-4-one). The crude product was used in the next reaction without further purification.

Step 5. Synthesis of (g): 1-{3-[2-(2-fluoro-4-methoxy-phenyl)-ethyl]-4-oxo-3,4-dihydro-quinazolin-7-yl}-3-(2,6,6-trimethyl-bicyclo[3.1.1]hept-3-yl)-thiourea

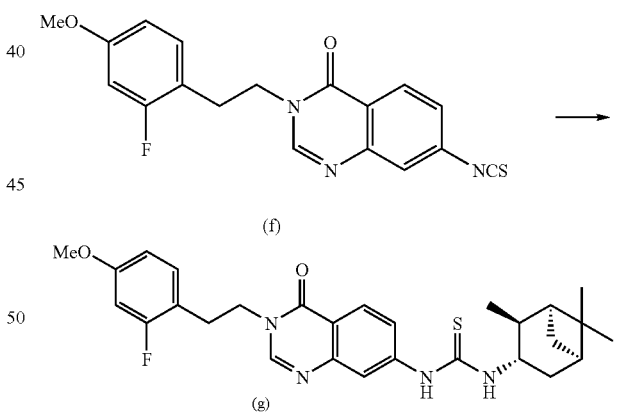

To a solution of (f, prepared as described in Step 4, (1 equivalent) in THF (0.5 M in (f) was added (1S,2S,3S,5R)-(+)-isopinocampheylamine (1.5 equivalents). The reaction was stirred at room temperature for 10 hours. The crude product mixture was then concentrated in vacuo, dissolved in methylene chloride, and purified via flash chromatography using hexanes/ethyl acetate. The pure fractions were combined and concentrated in vacuo to yield the pure product ((g): 1-{3-[2-(2-fluoro-4-methoxy-phenyl)-ethyl]-4-oxo-3,4-dihydro-quinazolin-7-yl}-3-(2,6,6-trimethyl-bicyclo[3.1.1]hept-3-yl)-thiourea).

Step 6. Synthesis of (h): (3R,5S)—N-(3-{2-[2-fluoro-4-(methyloxy)phenyl]ethyl}-4-oxo-3,4-dihydroquinazolin-7-yl)-3,5-dimethyl-N'-[(1S,2S,5R)-2,6,6-trimethyl bicyclo[3.1.1]hept-3-yl]piperazine-1-carboximidamide

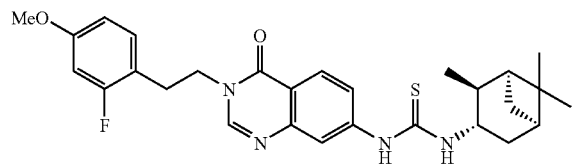

(g)

↓

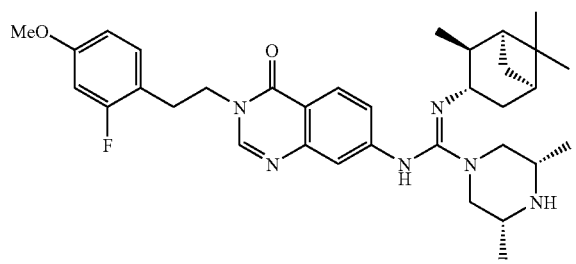

To a solution of (g), prepared as described in Step 5, (1 equivalent) in dry THF (0.1 M in (g)) in a dry round bottom flask was added 1-[3-(dimethylamino)-propyl]-3-ethylcarbodiimide hydrochloride (2 equivalents). The reaction was fitted with a condenser and heated to 80° C. for 1 hour. The resulting solution was allowed to cool to room temperature for 20 minutes. A solution of cis-2,6-dimethylpiperazine (2 equivalents; 0.5 M in CH₂Cl₂) was then added to the reaction, and the resulting mixture was stirred at room temperature for 10 minutes. The mixture was then diluted with ethyl acetate and washed with water. After the organic layer was isolated, the aqueous layer was extracted with two more portions of ethyl acetate. The organic layers were then combined and concentrated in vacuo. The crude mixture was dissolved in DMSO and purified via preparative HPLC using water (0.1% TFA)/acetonitrile (0.1% TFA). The pure fractions were combined and concentrated in vacuo to remove the majority of acetonitrile. Sodium carbonate (15 equivalents) was then added to the resulting aqueous solution and the slurry was allowed to sit at room temperature for 1 hour with occasional swirling. The basic aqueous solution was then extracted with 3 separate portions of ethyl acetate. The organic layers were combined, dried over sodium sulfate, filtered through a cotton plug, and concentrated in vacuo to yield product (h) as a free base. The resulting solid was then dissolved in an aqueous HCl solution (1 M; 15 equivalents) and concentrated in vacuo. The resulting mixture was dissolved in a 1:1 water/acetonitrile mixture and lyophilized to yield the pure Bis-HCl salt product ((h): (3R,5S)—N-(3-{2-[2-fluoro-4-(methyloxy)phenyl]ethyl}4-oxo-3,4-dihydroquinazolin-7-yl)-3,5-dimethyl-N'-[(1 S,2S,5R)-2,6,6-trimethylbicyclo[3.1.1]hept-3-yl]piperazine-1-carboximidamide.

Synthesis of Compounds of Structure IIIA, IIIB, IIIF, and IIIG

Compounds of formula IIIA, IIIB, IIIF, and IIIG are prepared using the methodology described above using an appropriately substituted pyridine, pyrazine, or pyrimidine benzoic acid, respectively, in place of the 4-nitroanthranilic acid (b) in Step 1. Steps 2-6 may then be carried out to give the final product. One skilled in the art will also recognize that the pyridine may be further substituted to produce variously substituted compounds where R⁴, R⁵, and/or R⁶ are any of the groups herein described such as, but not limited to, fluoro, chloro, alkyl, and alkaryl.

Synthesis of Compounds of Structure IIIC, IIID, and IIIE

Compounds of formula IIIC, IIID, and IIIE are prepared using the methodology described above using an appropriately fluorine-substituted 4-nitroanthranilic acid in place of 4-nitroanthranilic acid (b) in Step 1. Steps 2-6 may then be carried out to give the final product. One skilled in the art will recognize that a fluorine-substituted 4-nitroanthranilic acid may be used which includes further substituents to produce variously substituted compounds where R⁴, R⁵, and/or R⁶ are any of the groups herein described such as, but not limited to, fluoro, chloro, alkyl, and alkaryl.

Synthesis of Compounds of Structure IC

Compounds of formula IC are prepared using the methodology described above using an appropriately substituted 5-nitroanthranilic acid in place of 4-nitroanthranilic acid (b) in Step 1. Steps 2-6 may then be carried out to give the final product. One skilled in the art will recognize that a fluorine-substituted 5-nitroanthranilic acid may be used which includes further substituents to produce variously substituted compounds where R⁴, R⁵, and/or R⁶ are any of the groups herein described such as, but not limited to, fluoro, chloro, alkyl, and alkaryl.

Example 2

Synthesis of 7-{[1-((5S,3R)-3,5-dimethylpiperazinyl)-2-((2S,3S,1R,5R)-2,6,6-trimethylbicyclo[3.1.1]hept-3-yl)(1Z)-2-azavinyl]amino}-3-[2-(2,4-dichlorophenyl)ethyl]-1,3-dihydroquinazoline-2,4-dione

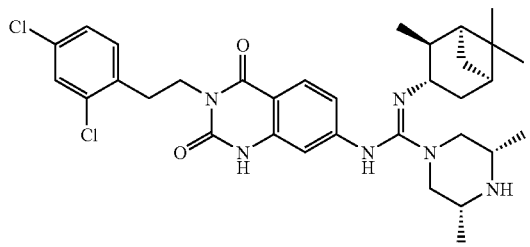

Step 1. Synthesis of (c): 2-amino-N-[2-(2,4-dichlorophenyl)-ethyl]-4-nitro-benzamide

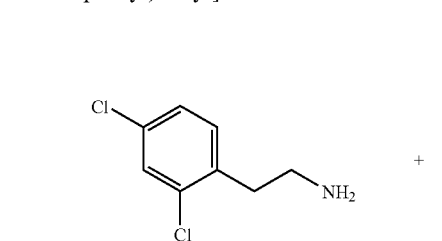

(a)

(b)

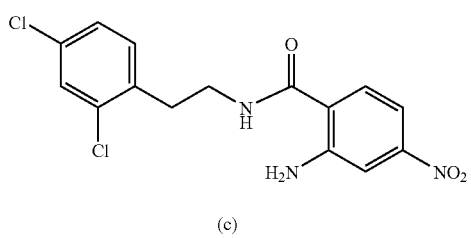

(c)

2,4-Dichlorophenylethylamine ((a):1 equivalent), 4-nitroanthranilic acid ((b): 1 equivalent), HBTU (1.5 equivalents), and dry THF (0.5 M in (a)) were added to a dry round bottom flask. The mixture was allowed to stir for 10 hours at room temperature. The reaction was then dry loaded onto silica gel and purified via flash chromatography using hexanes/ethyl acetate. The pure fractions were combined and concentrated in vacuo to yield the product ((c): 2-amino-N-[2-(2,4-dichloro-phenyl)ethyl]-4-nitrobenzamide) as a pure solid.

Step 2. Synthesis of (d): 3-[2-(2,4-dichlorophenyl)ethyl]-7-nitro-1,3-dihydroquinazoline-2,4-dione

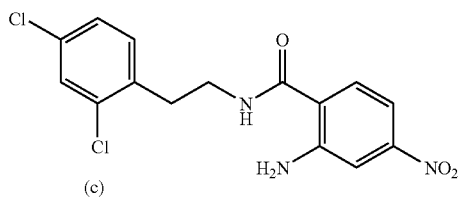

(c)

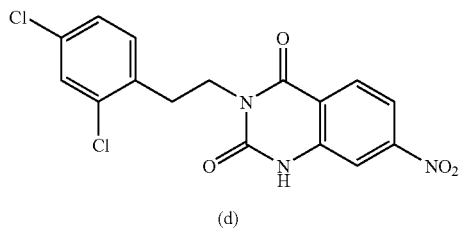

(d)

To a 0.3M solution of (c), prepared as described in Step 1 (2.5 g, 7.5 mmol (c)) in dioxane was added 40 mL of a 20% phosgene solution in toluene, followed by 15 mL triethylamine. After stirring for 1 hour at room temperature, solvent was removed by rotary evaporation followed by high vacuum. The residue was dissolved in ethyl acetate and washed three times with water. After drying with sodium sulfate and rotary evaporation, an orange-brown solid ((d): 3-[2-(2,4-dichlorophenyl)ethyl]-7-nitro-1,3-dihydroquinazoline-2,4-dione) was obtained in over 90% yield.

Step 3. Synthesis of (e): 7-amino-3-[2-(2,4-dichlorophenyl)ethyl]-1,3-dihydroquinazoline-2,4-dione

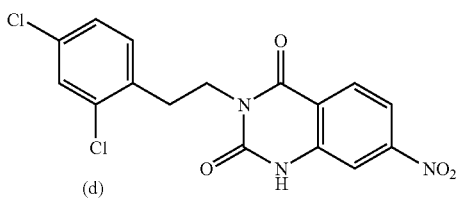

(d)

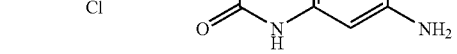

(e)

To a solution of (d), prepared as described in Step 2, in MeOH (0.25 M in (d)) was added 10% Pd/C (0.1 equivalents). The mixture was sealed with a septum and degassed with nitrogen for 10 minutes. Hydrogen was then bubbled through the solution for 20 minutes. Once reaction completion was verified by LC/MS, the reaction was degassed with nitrogen for 10 minutes. The mixture was filtered through Celite® and concentrated in vacuo to yield the product ((e)) 7-amino-3-[2-(2,4-dichlorophenyl)ethyl]-1,3-dihydroquinazoline-2,4-dione). The product was used in the next reaction without further purification.

Step 4. Synthesis of (f): 3-[2-(2,4-dichlorophenyl)ethyl]-2,4-dioxo-1,3-dihydroquinazolin-7-isothiocyanate

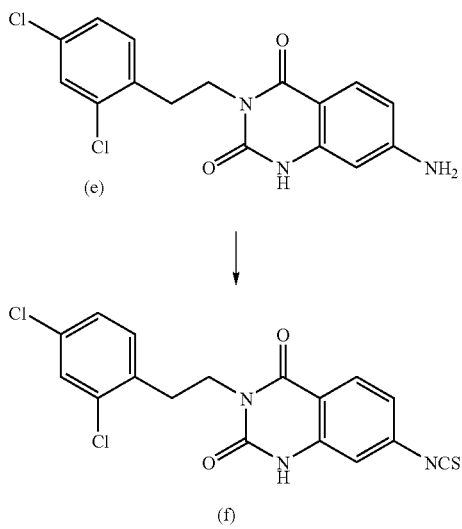

To a mixture of (e), prepared as described in Step 3, (1 equivalent) and NaHCO$_3$ (3 equivalents) in acetone (0.1 M in (e)) was added thiophosgene (3 equivalents) dropwise. The resulting slurry was stirred at room temperature for three hours. Once reaction completion was verified by LC/MS, the reaction was concentrated in vacuo to remove solvent and excess thiophosgene. The mixture was then taken up in ethyl acetate and washed with water. After the organic layer was isolated, the aqueous layer was extracted with two more portions of ethyl acetate. The organic layers were then combined, dried over sodium sulfate, filtered through a cotton plug, and concentrated in vacuo to yield the product ((f): 3-[2-(2,4-dichlorophenyl)ethyl]-2,4-dioxo-1,3-dihydroquinazolin-7-isothiocyanate). The crude product was used in the next reaction without further purification.

Step 5. Synthesis of (g): 7-({[((2S,3S,1R,5R)-2,6,6-trimethylbicyclo[3.1.1]hept-3-yl)amino]thioxomethyl}amino)-3-[2-(2,4-dichlorophenyl)ethyl]-1,3-dihydroquinazoline-2,4-dione

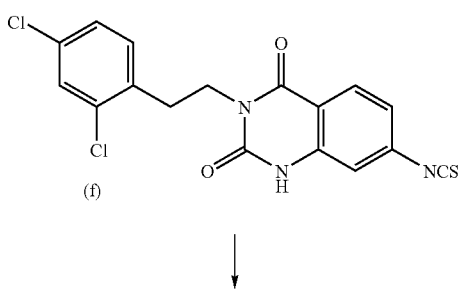

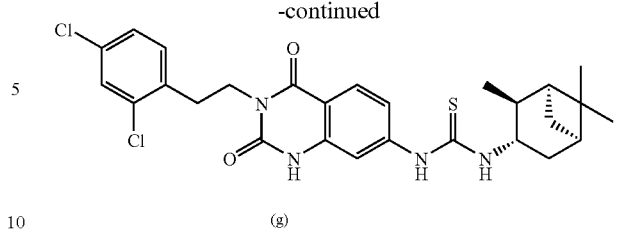

To a solution of (f), prepared as described in Step 4, (1 equivalent) in THF (0.5 M in (f)) was added (1S,2S,3S,5R)-(+)-isopinocampheylamine (1.5 equivalents). The reaction was stirred at room temperature for 10 hours. The crude product mixture was then concentrated in vacuo, dissolved in methylene chloride, and purified via flash chromatography using hexanes/ethyl acetate. The pure fractions were combined and concentrated in vacuo to yield the pure product ((g 7-({[((2S,3S,1R,5R)-2,6,6-trimethylbicyclo[3.1.1]hept-3-yl)amino]thioxomethyl}amino)-3-[2-(2,4-dichlorophenyl)ethyl]-1,3-dihydroquinazoline-2,4-dione).

Step 6. Synthesis of (h): 7-{[1-((5S,3R)-3,5-dimethylpiperazinyl)-2-((2S,3S,1R,5R)-2,6,6-trimethylbicyclo[3.1.1]hept-3-yl)(1Z)-2-azavinyl]amino}-3-[2-(2,4-dichlorophenyl)ethyl]-1,3-dihydroquinazoline-2,4-dione

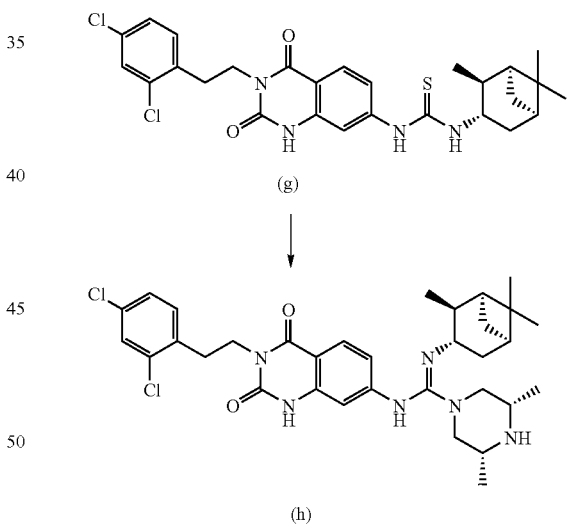

To a solution of (g), prepared as described in Step 5, (1 equivalent) in dry THF (0.1 M in (g)) in a dry round bottom flask was added 1-[3-(dimethylamino)-propyl]-3-ethylcarbodiimide hydrochloride (2 equivalents). The reaction flask was fitted with a water-cooled condenser and heated to 80° C. for 1 hour under a nitrogen atmosphere. The resulting solution was cooled to 0° C. for 20 minutes. A solution of cis-2,6-dimethylpiperazine (2 equivalents; 0.5 M in CH$_2$Cl$_2$) was then added to the reaction, and the resulting mixture was stirred at 0° C. for 10 minutes. The mixture was then diluted with ethyl acetate and washed with water. After the organic layer was isolated, the aqueous layer was extracted with two more portions of ethyl acetate. The organic layers were then combined and concentrated in vacuo. The crude mixture was dissolved in DMSO/acetonitrile and purified via preparative HPLC using water (0.1% TFA)/acetonitrile (0.1% TFA). The pure fractions were combined and concentrated in vacuo to remove the majority of acetonitrile. Sodium hydroxide (10 equivalents) was then added to the resulting aqueous solution and the slurry was allowed to sit at room temperature for 1 hour with occasional swirling. The basic aqueous solution was then extracted with 3 separate portions of ethyl acetate. The organic layers were combined, dried over sodium sulfate, filtered through a cotton plug, and concentrated in vacuo to yield product (h) as a free base. The resulting solid was then dissolved in an aqueous HCl solution (1 M; 15 equivalents) and concentrated in vacuo. The resulting mixture was dissolved in a 1:1 water/acetonitrile mixture and lyophilized to yield the pure Bis-HCl salt product ((h): 7-{[1-((5S,3R)-3,5-dimethylpiperazinyl)-2-((2S,3S,1R,5R)-2,6,6-trimethylbicyclo[3.1.1 ]hept-3-yl)(1Z)-2-azavinyl]amino}-3-[2-(2,4-dichlorophenyl)ethyl]-1 ,3-dihydroquinazoline-2,4-dione).

Synthesis of Compounds of Structure IVA and IVB

Compounds of formula IVA and IVB are prepared using the methodology described above using an appropriately substituted pyridine in place of the 4-nitroanthranilic acid (b) in Step 1b. Procedure 1A may then be carried out to give the final product. One skilled in the art will also recognize that the pyridine may be further substituted to produce variously substituted compounds where $R^4$, $R^5$, and/or $R^6$ are any of the groups herein described such as, but not limited to, fluoro, chloro, alkyl, and alkaryl.

Compounds are prepared using the methodology described above in Procedure A. Procedure 1A may then be carried out to give the final product. One skilled in the art will recognize that a fluorine-substituted 4-nitroanthranilic acid may be used which includes further substituents to produce variously substituted compounds where $R^4$, $R^5$, and/or $R^6$ are any of the groups herein described such as, but not limited to, fluoro, chloro, alkyl, and alkaryl.

Example 3

Synthesis of 7-{[1-((3S)-3-methylpiperazinyl)(1Z)-2-aza-2-(4,4-difluorocyclohexyl)vinyl]amino}-3-[2-(2-fluoro-4-methoxyphenyl)ethyl]-3-hydroquinazolin-4-one

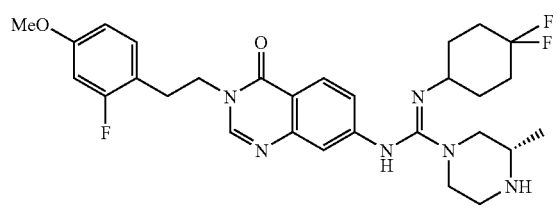

Step 1. Synthesis of (b): 7-({[(4,4-difluorocyclohexyl)amino]-thioxomethyl}amino)-3-[2-(2-fluoro-4-methoxyphenyl)ethyl]-3-hydroquinazolin-4-one

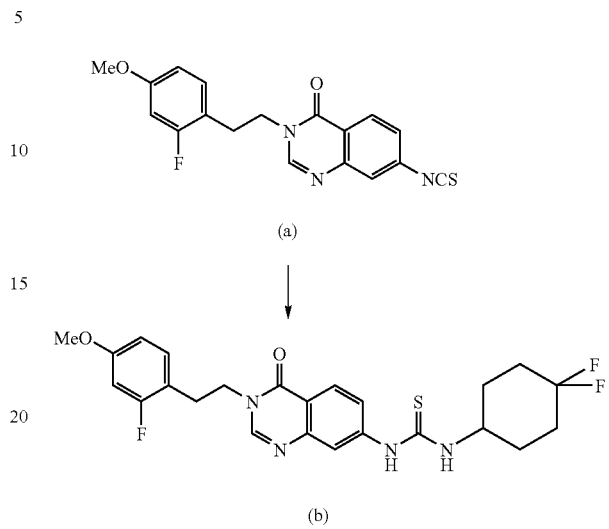

To a solution of (a), prepared as (f) described in Step 4 of Example 1, (1 equivalent) in THF (0.5 M in (a)) was added 4,4-difluorocyclohexylamine prepared as described above (1.5 equivalents). The reaction was stirred at room temperature for 10 hours. The crude product mixture was then concentrated in vacuo, dissolved in methylene chloride, and purified via flash chromatography using hexanes/ethyl acetate. The pure fractions were combined and concentrated in vacuo to yield the pure product ((b): 7-({[(4,4-difluorocyclohexyl)amino]-thioxomethyl}amino)-3-[2-(2-fluoro-4-methoxyphenyl)ethyl]-3-hydroquinazolin-4-one).

Step 2. Synthesis of (c): 7-{[1-((3S)-3-methylpiperazinyl)(1Z)-2-aza-2-(4,4-difluorocyclohexyl)vinyl]amino}-3-[2-(2-fluoro-4-methoxyphenyl)-ethyl]-3-hydroquinazolin-4-one

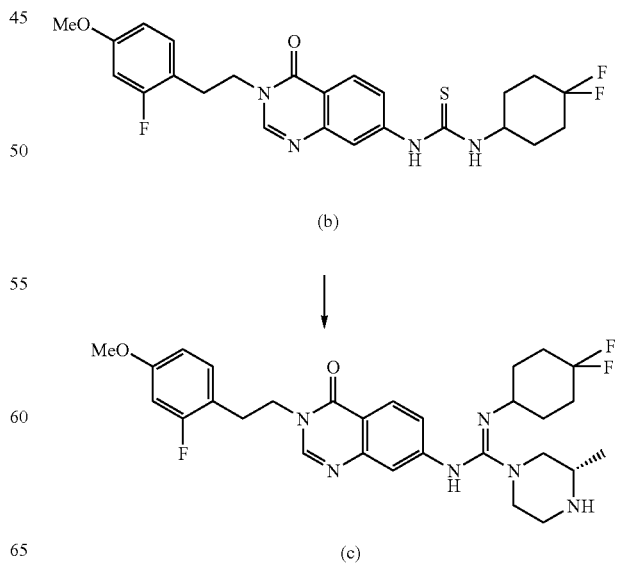

To a solution of (b), prepared as described in Step 1, (1 equivalent) in dry THF (0.1 M in (b)) in a dry round bottom flask was added 1-[3-(dimethylamino)-propyl]-3-ethylcarbodiimide hydrochloride (2 equivalents). The reaction was fitted with a condenser and heated to 80° C. for 1 hour. The resulting solution was allowed to cool to room temperature for 20 minutes. A solution of (S)-2-methylpiperazine (2 equivalents; 0.5 M in CH$_2$Cl$_2$) was then added to the reaction, and the resulting mixture was stirred at room temperature for 10 minutes. The mixture was then diluted with ethyl acetate and washed with water. After the organic layer was isolated, the aqueous layer was extracted with two more portions of ethyl acetate. The organic layers were then combined and concentrated in vacuo. The crude mixture was dissolved in DMSO and purified via preparative HPLC using water (0.1% TFA)/acetonitrile (0.1% TFA). The pure fractions were combined and concentrated in vacuo to remove the majority of acetonitrile. Sodium carbonate (15 equivalents) was then added to the resulting aqueous solution and the slurry was allowed to sit at room temperature for 1 hour with occasional swirling. The basic aqueous solution was then extracted with 3 separate portions of ethyl acetate. The organic layers were combined, dried over sodium sulfate, filtered through a cotton plug, and concentrated in vacuo to yield product (c) as a free base. The resulting solid was then dissolved in an aqueous HCl solution (1 M; 15 equivalents) and concentrated in vacuo. The resulting mixture was dissolved in a 1:1 water/acetonitrile mixture and lyophilized to yield the pure Bis-HCl salt product ((c): 7-{[1-((3S)-3-methylpiperazinyl)(1Z)-2-aza-2-(4,4-difluorocyclohexyl)vinyl]amino}-3-[2-(2-fluoro-4-methoxyphenyl)-ethyl]-3-hydroquinazolin-4-one).

Method 1 Synthesis of 3-[2-(4-fluorophenyl)ethyl]-7-nitro-2-(4-pyridyl)-3-hydroquinazolin-4-one

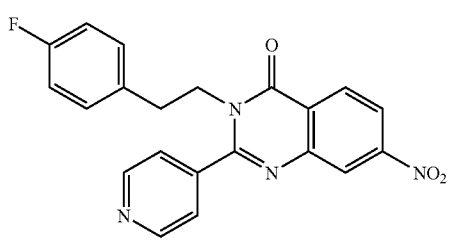

Pyridine 4-carboxylic acid was stirred in POCl$_3$ at room temperature for about 5 minutes. To the stirred solution was then added 0.9 equivalents of (2-amino-4-nitrophenyl)-N-[2-(4-fluorophenyl)ethyl]carboxamide. The resulting mixture was then stirred for about 15 minutes at room temperature in a microwave tube, which was then heated to 165° C. in a microwave for 10 minutes. LC/MS indicated completion of the reaction. The POCl$_3$ was evaporated, and the residue was dissolved in CH$_2$Cl$_2$ and washed with saturated sodium bicarbonate solution. The combined organic layers were dried over MgSO$_4$ and concentrated in vacuo and chromatographed on silica gel, eluting with a gradient of EtOAc in Hexanes. The resulting product, 3-[2-(4-fluorophenyl)ethyl]-7-nitro-2-(4-pyridyl)-3-hydroquinazolin-4-one, was then converted to Example 77 using the procedures described in Scheme 1a.

Method 2 Synthesis of 2-[2-(2-fluoro-4-methoxyphenyl)ethyl]-3-methyl-7-nitro-3-hydroquinazolin 4-one

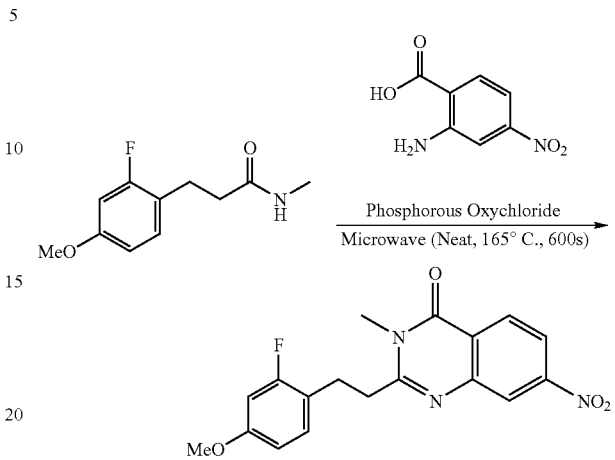

3-(2-Fluoro-4-methoxy-phenyl)-N-methyl-propionamide was synthesized using an EDCl mediated coupling of 3-(2-fluoro-4-methoxy-phenyl)-N-methyl-propionic acid and methylamine (2M solution in THF). The amide was then taken up in POCl$_3$ in a microwave vessel and the mixture was stirred about 3 minutes. To the stirred solution was added about 1 equivalent of 4-nitroanthranilic acid. The unsealed vial was stirred for 10 minutes until there was a color change from red to yellow. The vial was then sealed and reacted in a microwave unit at 165° C. for 600 seconds. Reaction completion was checked with LC/MS. 2-[2-(2-Fluoro-4-methoxyphenyl)ethyl]-3-methyl-7-nitro-3-hydroquinazolin-4-one was then purified by column chromatography, eluting with EtOAc in hexanes. 2-[2-(2-Fluoro-4-methoxyphenyl)ethyl]-3-methyl-7-nitro-3-hydroquinazolin-4-one was then converted to Example 90 using the procedures described above through the corresponding thiourea (Scheme 1a).

Method 3 Synthesis of 3-[2-(2-fluoro-4-methoxyphenyl)ethyl]-2-(4-methylpiperazinyl)-7-nitro-3-hydroquinazolin-4-one (B) and 3-[2-(2-fluoro-4-methoxyphenyl)ethyl]-2-[imino(4-methylpiperazinyl)-methyl]-7-nitro-3-hydroquinazolin-4-one (C)

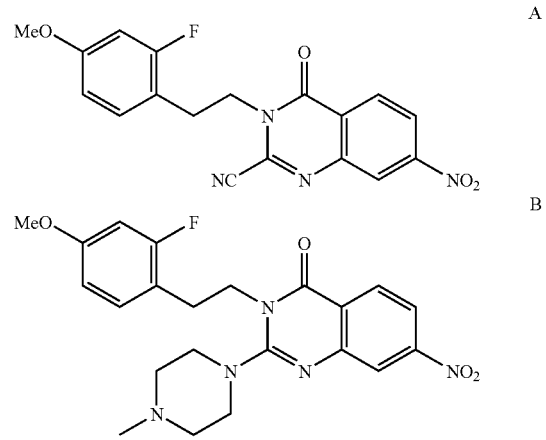

-continued

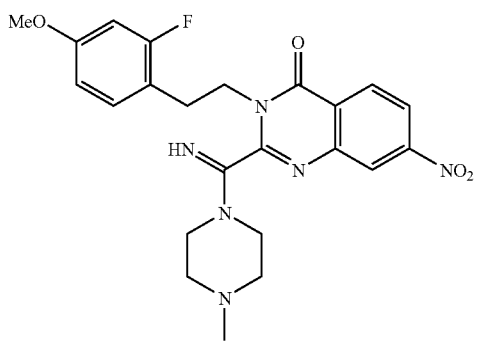

The synthesis of nitrile A was first conducted as described in J. Heterocyclic Chem., 35, 659 (1998)). Nitrile A was heated in an excess of N-methylpiperazine to 110° C. in a microwave for 600 seconds and analyzed by LC/MS to provide B and C. Products B and C were separated by column chromatography on silica gel eluting with 10% MeOH in $CH_2Cl_2$. Compound B was the first to come off the column. Compounds B and C were then respectively converted to Examples 99 and 71 using the procedures described herein.

Method 4 Synthesis of 3-[2-(2-fluoro-4-methoxyphenyl)ethyl]-7-nitro-2-(1,2,3,4-tetraazol-5-yl)-3-hydroquinazolin-4-one

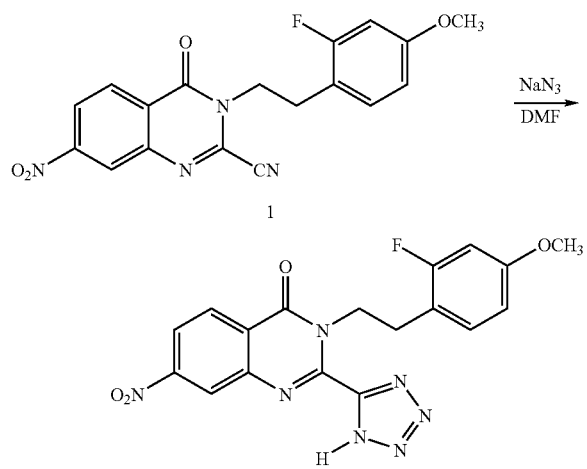

Nitrile 1 shown above (0.9 g, 2.4 mmoles) was dissolved in dry DMF (5 mL). Sodium azide (0.8 g, 12.2 mmoles),was added and the mixture was heated at 125° C. for 1 hour. The reaction was cooled, diluted with water (25 mL), and filtered. The collected solid was redissolved in THF/EtOAc 1:1 (25 mL), washed with water (25 mL), and dried over $MgSO_4$. Filtration and solvent removal afforded 650 mg of a brown solid. The $^1$H NMR (DMSO-D6, 300 MHz) was consistent with desired product formation. The product was converted to Example 78 using the procedures described herein.

Method 5 Synthesis of 3-[2-(4-fluorophenyl)ethyl]-2-[(4-methylpiperazinyl)-methyl]-7-nitro-3-hydroquinazolin-4-one (3)

Step 1 Synthesis of 2-chloro-N-[2-(4-fluoro-phenyl)-ethyl]-acetamide (1)

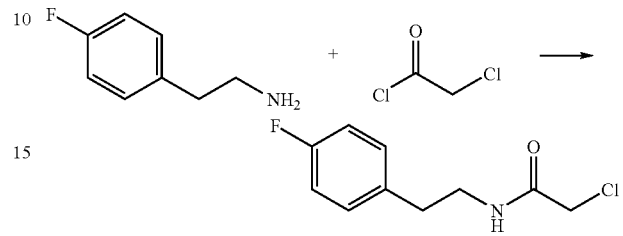

To a solution of 4-fluorophenylethylamine (1.0 equivalent) in dried THF was added Hunig's base (DIEA) (1 equivalent). The mixture was then stirred for 3 minutes at 0° C. Thereafter, a solution of chloroacetylchloride (1.0 equivalent) in THF was added via a syringe over a period of 7 minutes. The reaction mixture was then stirred at room temperature for 1 hour after which time the reaction mixture was condensed in vacuo, quenched with water, extracted with ethyl acetate (3×) and dried over $Na_2SO_4$. After concentration in vacuo, compound 1 shown above was obtained, which was carried on further without further purification. LC/MS=M+H 216.1 at 2.18 minutes.

Step 2 Synthesis of 2-chloromethyl-3-[2-(4-fluorophenyl)-ethyl]-7-nitro-3H-quinazolin-4-one (2)

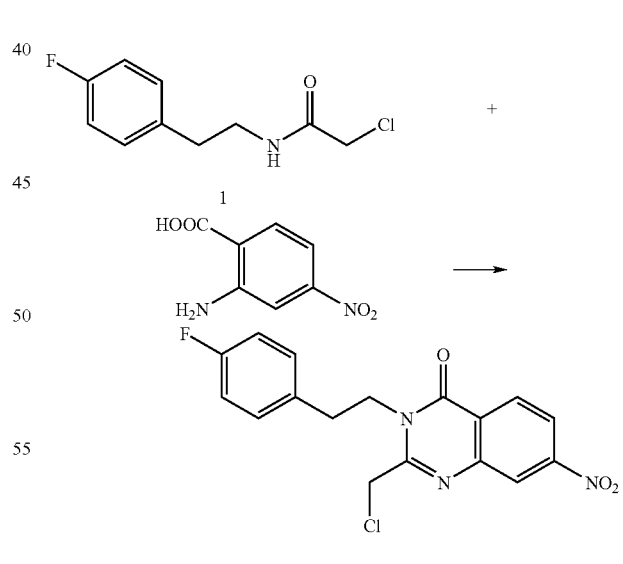

Compound 1 (1.2 equivalents) was dissolved in neat $POCl_3$ and allowed to stir under $N_2$ for 5 minutes. Solid 4-nitroanthranilic acid (1.0 equivalent) was then added, and the mixture was allowed to stir at room temperature for 10 minutes until the color changed to yellow from red. Thereafter, the reaction mixture was refluxed at 100° C. for 2 hours, followed by removal of POCl₃ in vacuo (addition of triethylamine to the rotovap condenser). The crude product so obtained was neutralized with a saturated solution of NaHCO₃, extracted with ethyl acetate (3 times), dried over Na₂SO₄, and condensed in vacuo. Purification of the crude product was carried out with column chromatography in several batches using a gradient of EtOAc in hexanes. LC/MS=M+H 3.62 at 3.5 minutes.

Step 3 Synthesis of 3-[2-(4-fluorophenyl)ethyl]-2-[(4-methylpiperazinyl)-methyl]-7-nitro-3-hydroquinazolin-4-one (3)

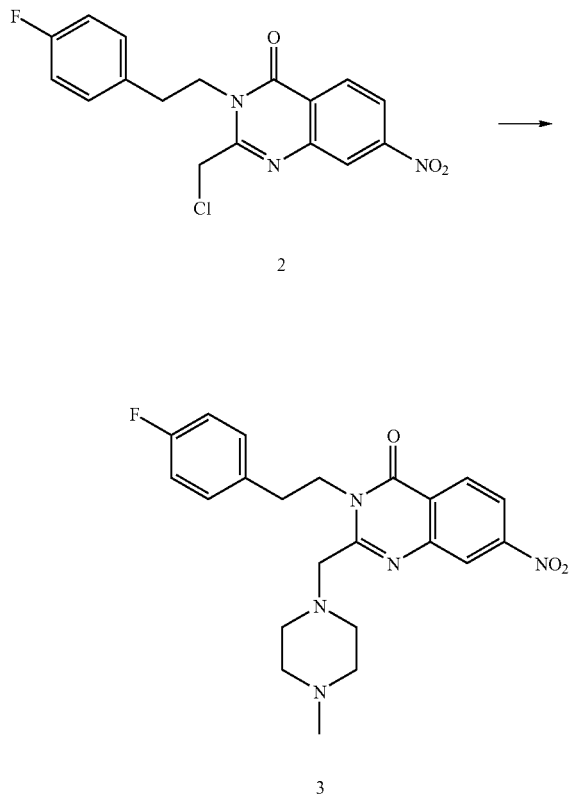

A solution of 2 (1 equivalent) and 4-methylpiperazine (3 equivalents) in 2 mL NMP were heated at 80° C. After stirring for 18 hours, the dark brown solution was diluted with ethyl acetate and washed twice with water. The organic phase was then dried with sodium sulfate, filtered and concentrated in vacuo, and taken on to the next step without further purification. Compound 3 was then converted to Example 69 using the procedures described herein. This procedure yielded a dark oil, and small amounts of NMP may remain in the product. Formation of some analogous compounds required the addition of three equivalents of diisopropyl ethyl amine. Similar chemistry was used to prepare Examples 67, 70, 72, 74, 75, 79, and 81 as identified in the following tables.

Step 3a Synthesis of 2-[(2,4-difluorophenoxy)methyl]-3-methyl-7-nitro-3-hydroquinazolin-4-one

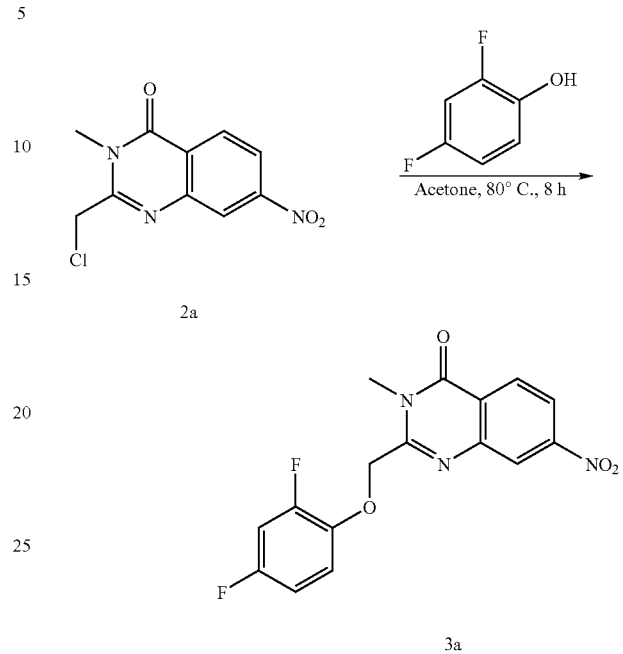

2,4-Difluorophenol (2.5 equivalents) was added to 2-(chloromethyl)-3-methyl-7-nitro-3-hydroquinazolin-4-one (2a) in acetone and refluxed for 8 hours. The solution was then cooled to room temperature, washed with saturated sodium bicarbonate, dried and filtered over sodium sulfate and concentrated in vacuo to afford 2-[(2,4-difluorophenoxy)methyl]-3-methyl-7-nitro-3-hydroquinazolin-4-one in quantitative yields. Compound 3a was then converted to Example 88 using the procedures described herein. Similar chemistry was used to prepare Examples 68, 89, 92, 93, 94, 95, 96, 97, 98, and 100 as identified in the following tables.

Method 6 Synthesis of 3-[2-(2-fluoro-4-methoxyphenyl)ethyl]-7-nitrobenzo[d]1,2,3-triazin-4-one

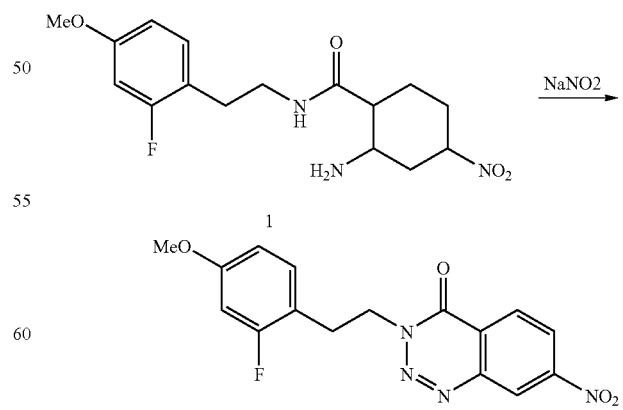

A mixture of benzamide (1) (3.42 mmol), water (40 mL), and concentrated HCl (12 mL) was cooled in an ice bath, and a solution of NaNO₂ (3.6 mmol) in water (5 mL) was added drop wise. The mixture was stirred for 1 hour, and 20 mL 10 N NaOH was added. The stirring was continued for another hour, and the reaction was neutralized with AcOH, extracted with methylene chloride, and dried over MgSO$_4$. The crude product was chromatographed on silica (30%) EtOAc/hexanes) yielding the desired product as a yellow solid. The purified compound was then converted to Example 102 using the procedures described herein.

Method 7 Synthesis of 6-amino-2-[2-(2-fluoro-4-methoxyphenyl)ethyl]-2-hydroisoquinolin-1-one Step 1

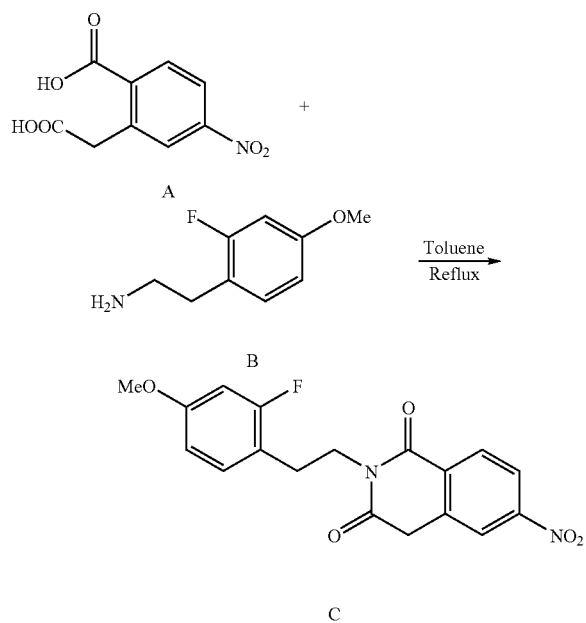

The diacid A (1 equivalent) was added to a flask equipped with a reflux condenser and dean stark trap and charged with dry toluene. The mixture was heated to reflux and then 2-(2-fluoro-4-methoxy-phenyl)-ethylamine B (1 equivalent) was added. The reaction was kept at reflux overnight, and then the toluene was removed by rotary evaporation. Purification by flash chromatography using ethyl acetate/hexanes provided the product C in 30% yield.

Step 2

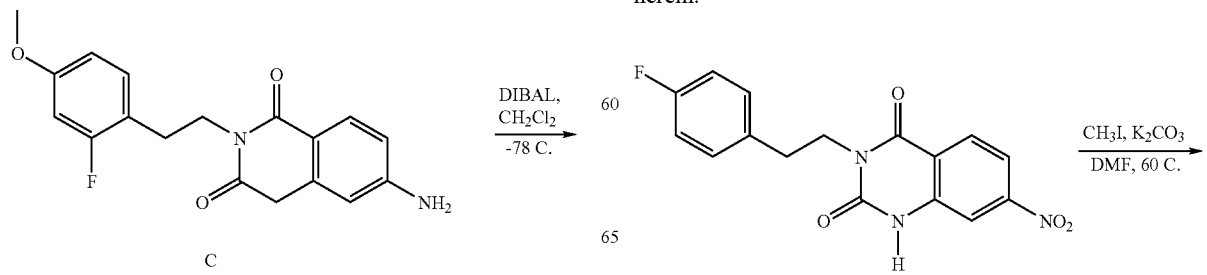

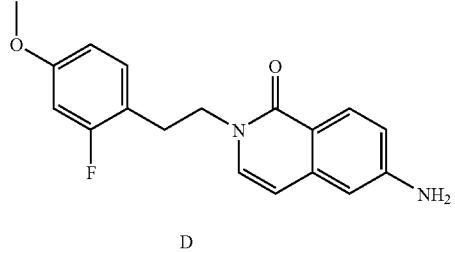

The imide (C) was dissolved in CH$_2$Cl$_2$ and cooled to −78° C. 3 equivalents of DIBAL (1M in CH$_2$Cl$_2$) were added, and the reaction was stirred at −78° C. for 1 hour when LC/MS indicated completion of the reaction. The solution was then diluted with ether and 10 equivalents of NaF and 4 equivalents water were added. The reaction was then stirred for an hour. The reaction was then filtered through Celite® to yield the crude pyridone amine (D). Compound D was then converted to Example 103 using the procedures described herein. Similar chemistry was used to prepare Example 104 as identified in the final table.

As noted below, the compounds in the following tables were prepared using the methodology described herein from commercially available starting materials which are readily recognizable by those skilled in the art or by using known synthetic methods. For example, Example 11 was prepared using the methodology described in Scheme 1a and the appropriate amino indanol. Examples 14 and 18 which include hydroxymethyl-substituted arylalkyl groups were also prepared using the general methodology of Scheme 1a with the appropriate amino alcohol. N-cyano substituted piperazine compound Example 36 was prepared by: first, mono-Boc protecting 2,6-trans dimethylpiperazine; second, treating the mono-Boc protected compound with cyanogen bromide (2.5 equivalents) and Hunig's base (1.1 equivalent); third, purifying the resulting nitrile piperazine compound on silica gel; fourth, deprotecting the purified compound; and fifth, reacting the resulting purified nitrile trans dimethyl piperazine compound using the methods described herein to produce Example 36. Compounds such as Examples 73 and 76 were prepared using the procedure of Method 2 with the appropriated amides of methacrylic acid and acetic acid.

Compounds of formula IB where R$^2$ is an alkyl group such as Example 59 where R$^2$ is a methyl group may be prepared by alkylating a dione where R$^2$ is H prepared as described herein. For example, Example 59 was prepared using the methylation procedure shown below (reaction of dione with methyl iodide and potassium carbonate (1:2:2) in DMF at 60° C. to produce the nitro compound which was then converted to Example 59 using the standard procedures described herein.

-continued

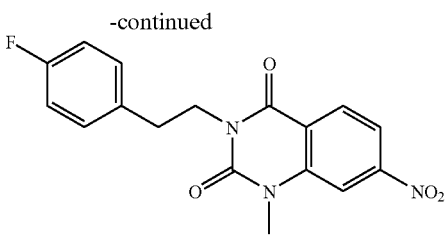

The compounds in the following tables were prepared using the methodology described in the above procedures, methods, and examples. The starting materials used in the syntheses are recognizable to one of skill in the art and are commercially available or may be prepared using known methods. The synthesis of various guanidine compounds is known in the art. Such synthesis information may be found in the following references each of which is hereby incorporated by reference in its entirety as if fully set forth herein: PCT publication WO 02/18327; PCT publication WO 03/099818; U.S. patent application Ser. No. 09/945,384; U.S. patent application Ser. No. 10/444,495; U.S. Provisional Patent Application Ser. No. 60/230,565; U.S. Provisional Patent Application Ser. No. 60/245,579; U.S. Provisional Application Ser. No. 60/282,847; U.S. Provisional Application Ser. No. 60/353,183; U.S. Provisional Application Ser. No. 60/353,188; U.S. Provisional Application Ser. No. 60/382,762; U.S. Provisional Application Ser. No. 60/441,019; U.S. Provisional Application Ser. No. 60/473,317; U.S. Provisional Application Ser. No. 60/523,336; and U.S. Provisional Application Ser. No. 60/524,491.

Table of Examples 4-66

| No. | Structure | | Name | MH+ |
|---|---|---|---|---|
| 4 | 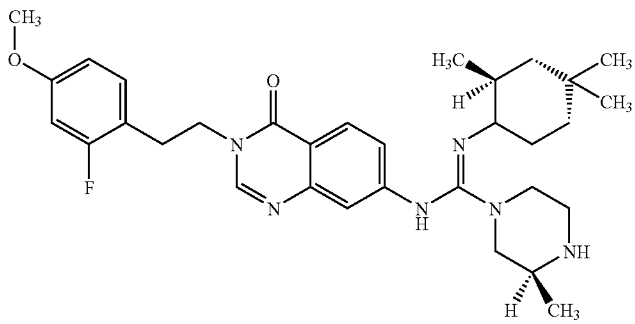 | Chiral | (3S)-N-(3-{2-[2-fluoro-4-(methyloxy)phenyl]ethyl}-4-oxo-3,4-dihydroquinazolin-7-yl)-3-methyl-N'-[(1S,2S,5R)-2,6,6-trimethylbicyclo[3.1.1]hept-3-yl]piperazine-1-carboximidamide | 575.7 |
| 5 | 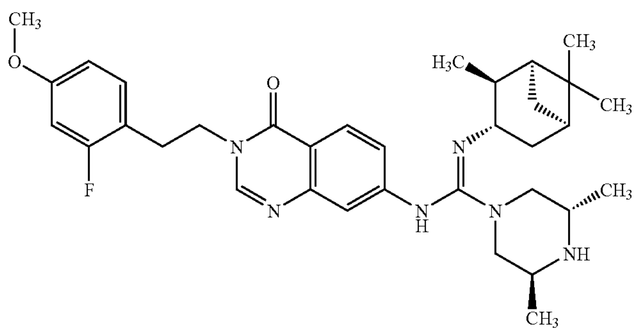 | Chiral | (3S,5S)-N-(3-{2-[2-fluoro-4-(methyloxy)phenyl]ethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 589.8 |
| 6 | 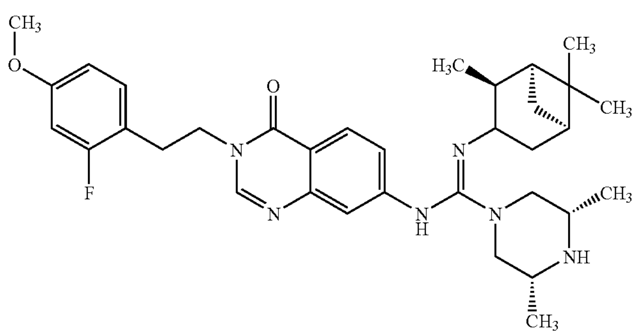 | Chiral | (3R,5S)-N-(3-{2-[2-fluoro-4-(methyloxy)phenyl]ethyl}-4-oxo-3,4-dihydroquinazolin-7-yl)-3,5-dimethyl-N'-[(1S,2S,5R)-2,6,6-trimethylbicyclo[3.1.1]hept-3-yl]piperazine-1-carboximidamide | 589.8 |

-continued

| No. | Structure | Name | MH+ |
|---|---|---|---|
| 7 | Chiral | (3S)-N-(3-{2-[2-fluoro-4-(methyloxy)phenyl]ethyl}-4-oxo-3,4-dihydroquinazolin-7-yl)-3-methyl-N'-[4-(trifluoromethyl)cyclohexyl]piperazine-1-carboximidamide | 589.6 |
| 8 | Chiral | N-[2-(dimethylamino)ethyl]-N'-(3-{2-[2-fluoro-4-(methyloxy)phenyl]ethyl}-4-oxo-3,4-dihydroquinazolin-7-yl)-n-(phenylmethyl)-N''-[(1S,2S,5R)-2,6,6-lNL trimethyl-bicyclo[3.1.1]hept-3-yl]guanidine | 653.9 |
| 9 | Chiral | (3S)-N-{3-[2-(4-fluorophenyl)ethyl]-4-oxo-3,4-dihydroquinazolin-7-yl-3-methyl-N'-[(1S,2S,5R)-2,6,6-trimethylbicyclo[3.1.1]hept-3-yl]piperazine-1-carboximidamide | 545.7 |
| 10 | Chiral | (3S)-N-{3-[2-(2,4-difluorophenyl)ethyl]-4-oxo-3,4-dihydroquinazolin-7-yl}-3-methyl-N'-[(1S,2S,5R)-2,6,6-trimethylbicyclo[3.1.1]hept-3-yl]piperazine-1-carboximidamide | 563.7 |
| 11 | Chiral | (3S)-N-{3-[(1R,2S)-2-hydroxy-2,3-dihydro-1H-inden-1-yl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 557.7 |

-continued

| No. | Structure | Name | MH+ |
|---|---|---|---|
| 12 | Chiral | (3S)-N'-(4,4-difluorocyclohexyl)-N-(3-{2-[2-fluoro-4-(methyloxy)phenyl]ethyl}-4-oxo-3,4-dihydroquinazolin-7-yl)-3-methylpiperazine-1-carboximidamide | 557.6 |
| 13 | Chiral | (3S)-N'-(4-fluorocyclohexyl)-N-(3-{2-[2-fluoro-4-(methyloxy)phenyl]ethyl}-4-oxo-3,4-dihydroquinazolin-7-yl)-3-methylpiperazine-1-carboximidamide | 539.6 |
| 14 | Chiral | (3S)-N-{3-[(1S)-1-(hydroxymethyl)-3-methylbutyl]-4-oxo-3,4-dihydroquinazolin-7-yl}-3-methyl-N'-[(1S,2S,5R)-2,6,6-trimethylbicyclo[3.1.1]hept-3-yl]piperazine-1-carboximidamide | 523.7 |
| 15 | 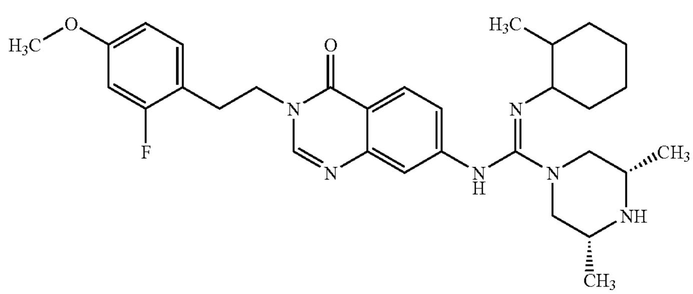 | (3R,5S)-N-(3-{2-[2-fluoro-4-(methyloxy)phenyl]ethyl}-4-oxo-3,4-dihydroquinazolin-7-yl)-3,5-dimethyl-N'-(2-methylcyclohexyl)piperazine-1-carboximidamide | 549.7 |
| 16 | 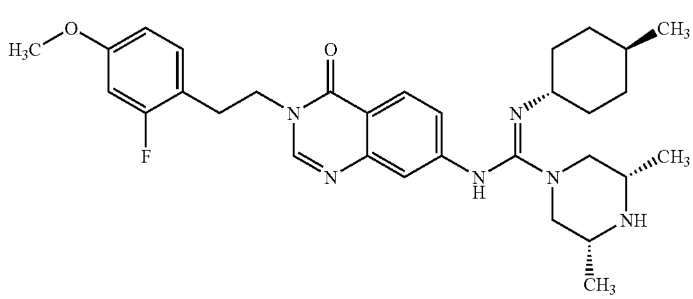 | (3R,5S)-N-(3-{2-[2-fluoro-4-(methyloxy)phenyl]ethyl}-4-oxo-3,4-dihydroquinazolin-7-yl)-3,5-dimethyl-N'-(4-methylcyclohexyl)piperazine-1-carboximidamide | 549.7 |

| No. | Structure | Name | MH+ |
|---|---|---|---|
| 17 | Chiral | (3S,5S)-N-{3-[2-(2,4-difluorophenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 577.7 |
| 18 | Chiral | (3R,5S)-N-{3-[(1S)-2-[2-fluoro-4-(methyloxy)phenyl]-1-(hydroxymethyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 619.8 |
| 19 | Chiral | (3S,5S)-N-{3-[(1S)-2-[2-fluoro-4-(methyloxy)phenyl]-1-(hydroxymethyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 619.8 |
| 20 | Chiral | (3R,5S)-N-{3-[2-(4-fluorophenyl)ethyl]-4-oxo-3,4-dihydroquinazolin-7-yl-3,5-dimethyl-N'-[(1S,2S,3S,5R)-2,6,6-trimethylbicyclo[3.1.1]hept-3-yl]piperazine-1-carboximidamide | 559.7 |
| 21 | Chiral | (3R)-3-(dimethylamino)-N-(3-{2-[2-fluoro-4-(methyloxy)phenyl]ethyl}-4-oxo-3,4-dihydroquinazolin-7-yl)-N'-[(1S,2S,3S,5R)-2,6,6-trimethylbicyclo[3.1.1]hept-3-yl]pyrrolidine-1-carboximidamide | 589.8 |

| No. | Structure | | Name | MH+ |
|---|---|---|---|---|
| 22 | 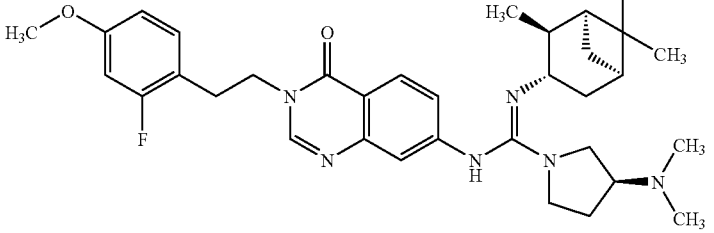 | Chiral | (3S)-3-(dimethylamino)-N-(3-{2-[2-fluoro-4-(methyloxy)phenyl]ethyl}-4-oxo-3,4-dihydroquinazolin-7-yl)-N'-[(1S,2S,3S,5R)-2,6,6-trimethylbicyclo[3.1.1]hept-3-yl]pyrrolidine-1-carboximidamide | 589.8 |
| 23 | 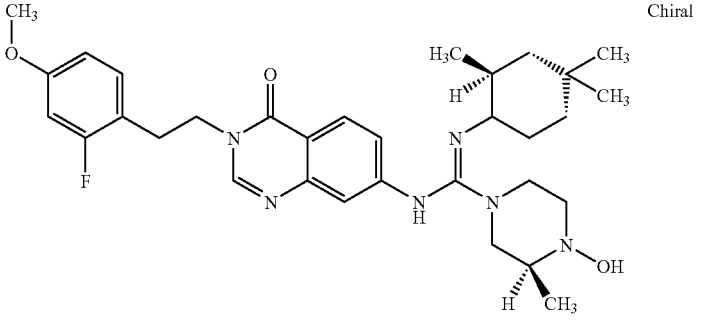 | Chiral | (3S)-N-(3-{2-[2-fluoro-4-(methyloxy)phenyl]ethyl}-4-oxo-3,4-dihydroquinazolin-7-yl)-4-hydroxy-3-methyl-N'-[(1S,2S,SR)-2,6,6-trimethylbicyclo[3.1.1]hept-3-yl]piperazine-1-carboximidamide | 591.7 |
| 24 | 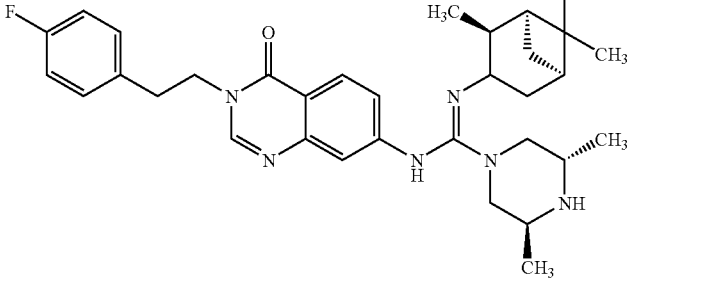 | Chiral | (3S,5S)-N-{3-[2-(4-fluorophenyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 559.7 |
| 25 | 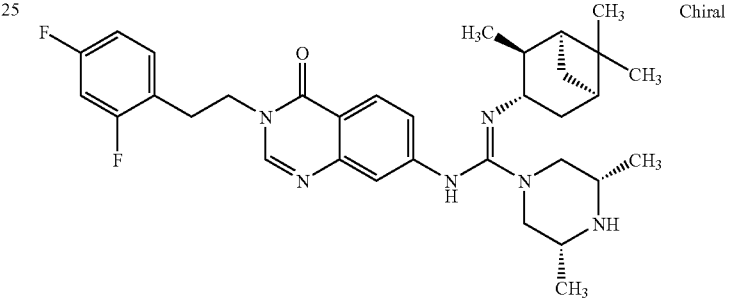 | Chiral | (3R,5S)-N-{3-[2-(2,4-difluorophenyl)ethyl]-4-oxo-3,4-dihydroquinazolin-7-yl}-3,5-dimethyl-N'-[(1S,2S,3S,5R)-2,6,6-trimethylbioyclo[3.1.1]hept-3-yl]piperazine-1-carboximidamide | 577.7 |
| 26 | 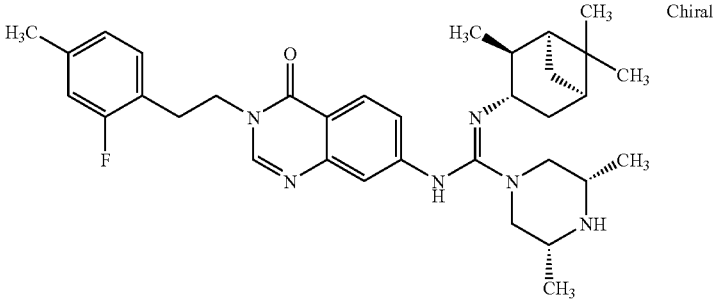 | Chiral | (3R,5S)-N-{3-[2-(2-fluoro-4-methylphenyl)ethyl]-4-oxo-3,4-dihydroquinazolin-7-yl}-[(1S,2S,3S,5R)-2,6,6-trimethylbicyclo[3.1.1]hept-3-yl]piperazine-1-carboximidamide | 573.8 |

-continued

| No. | Structure | Name | MH+ |
|---|---|---|---|
| 27 | Chiral | (3S,5S)-N-{3-[2-(2-fluoro-4-methylphenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 573.8 |
| 28 | Chiral | (3R,5S)-N-{3-[(1S)-2-(4-fluorophenyl)-1-(hydroxymethyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 589.8 |
| 29 | Chiral | (3S)-N-{3-[2-(4-fluorophenyl)ethyl]-4-oxo-3,4-dihydroquinazolin-7-yl}-4-hydroxy-3-methyl-N'-[(1S,2S,5R)-2,6,6-trimethylbicyclo[3.1.1]hept-3-yl]piperazine-1-carboximidamide | 561.7 |
| 30 | Chiral | (3R,5S)-N-{3-[2-(4-chlorophenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 576.2 |
| 31 | Chiral | (3R,5S)-N-{3-[2-(2,4-dichlorophenyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 610.6 |

-continued

| No. | Structure | Name | MH+ |
|---|---|---|---|
| 32 | Chiral | (3R,5S)-N-{3-[(1S)-2-(4-chlorophenyl)-1-(hydroxymethyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 606.2 |
| 33 | Chiral | (3R,5S)-N-{3-[(1S)-2.hydroxy-1-(phenylmethyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 571.8 |
| 34 | Chiral | (3R,5S)-N-{3-[2-(4-chloro-2-fluorophenyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 594.2 |
| 35 | 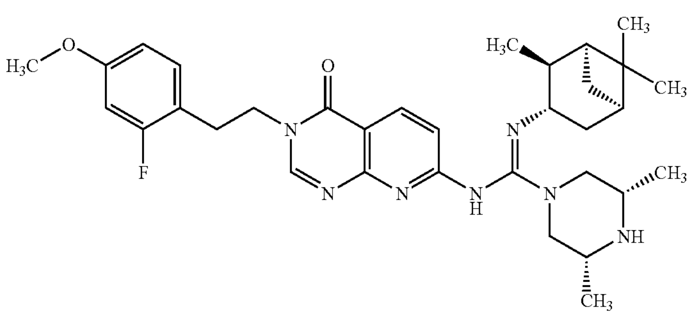 | (3R,5S)-N-(3-{2-[2-fluoro-4-(methyloxy)phenyl]ethyl}-4-oxo-3,4-dihydropyrido[2,3-d]pyrimidin-7-yl)-3,5-dimethyl-N'-[(1S,2S,3S,5R)-2,6,6-trimethylbicyclo[3.1.1]hept-3-yl]piperazine-1-carboximidamide | 590.8 |
| 36 | Chiral | (3S,5S)-4-cyano-N-(3-{2-[2-fluoro-4-(methyloxy)phenyl]ethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 614.8 |

| No. | Structure | | Name | MH+ |
|---|---|---|---|---|
| 37 | 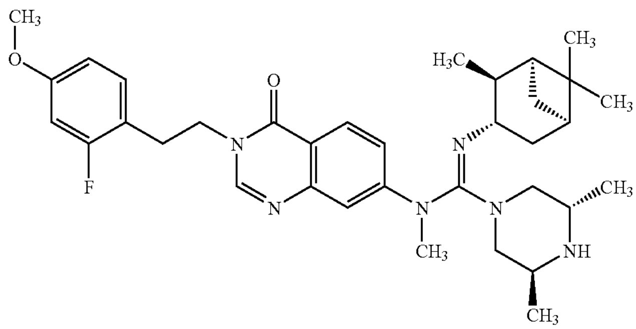 | Chiral | (3S,5S)-N-(3-{2-[2-fluoro-4-(methyloxy)phenyl]ethyl}-4-oxo-3,4-dihydroquinazolin-7-yl)-N,3,5-trimethyl-N'-[(1S,2S,3S,5R)-2,6,6-trimethylbicyclo[3.1.1]hept-3-yl]piperazine-1-carboximidamide | 603.8 |
| 38 | 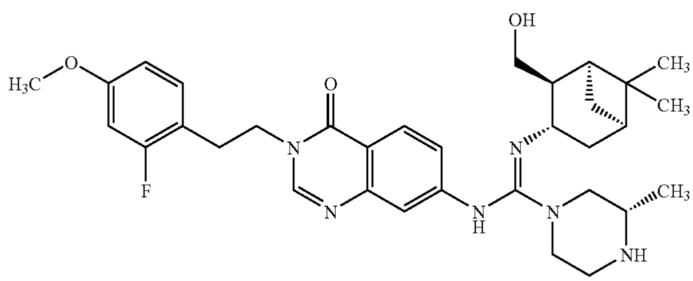 | Chiral | (3S)-N-(3-{2-[2-fluoro-4-(methyloxy)phenyl]ethyl}-4-oxo-3,4-dihydroquinazolin-7-yl)-N'-[(1S,2S,3S,5R)-2-(hydroxymethyl)-6,6-dimethylbicyclo[3.1.1]hept-3-yl]-3-methylpiperazine-1-carboximidamide | 591.7 |
| 39 | 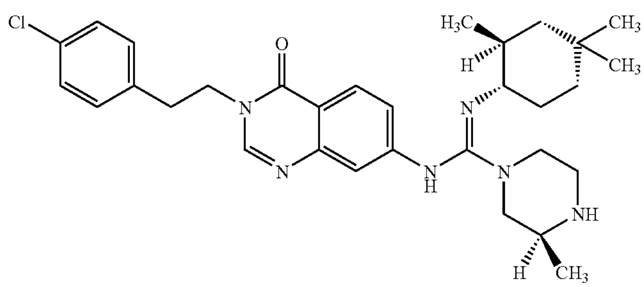 | Chiral | (3S)-N-{3-[2-(4-chlorophenyl)ethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 562.2 |
| 40 | 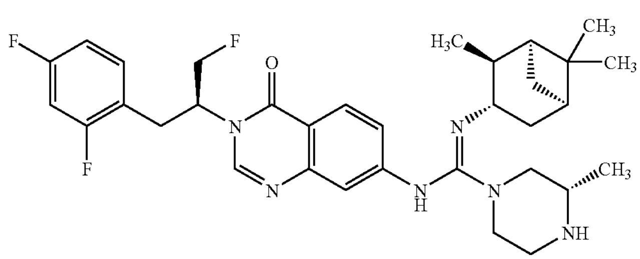 | Chiral | (3S)-N-{3-[(1S)-2-(2,4-difluorophenyl)-1-(fluoromethyl)ethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 595.7 |
| 41 | 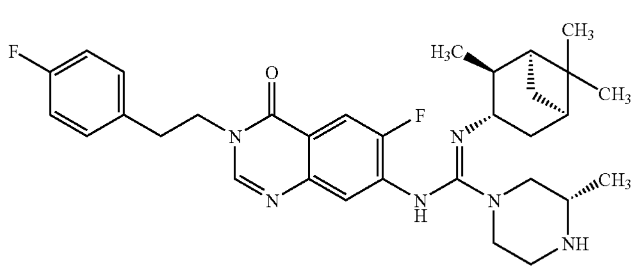 | Chiral | (3S)-N-{6-fluoro-3-[2-(4-fluorophenyl)ethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 563.7 |

-continued

| No. | Structure | | Name | MH+ |
|---|---|---|---|---|
| 42 | 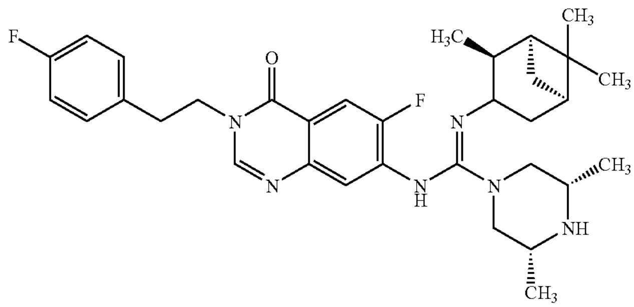 | Chiral | (3R,5S)-N-{6-fluoro-3-[2-(4-fluorophenyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 577.7 |
| 43 | 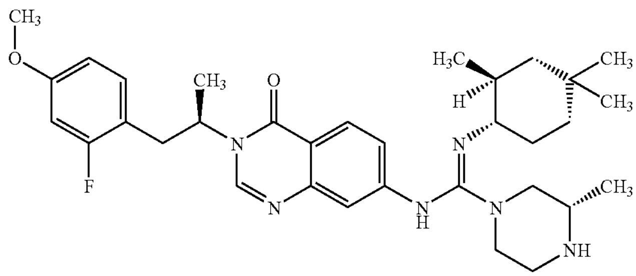 | Chiral | (3S)-N-(3-{(1R)-2-[2-fluoro-4-(methyloxy)phenyl]-1-methylethyl}-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 589.8 |
| 44 | 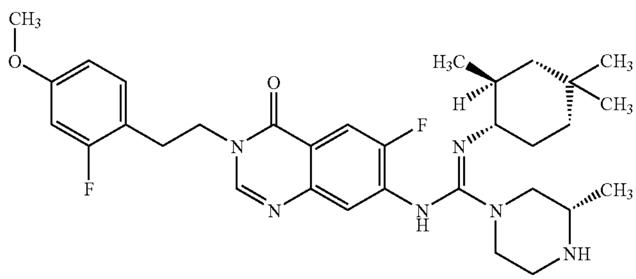 | Chiral | (3S)-N-(6-fluoro-3-{2-[2-fluoro-4-(methyloxy)phenyl]ethyl}-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 593.7 |
| 45 | 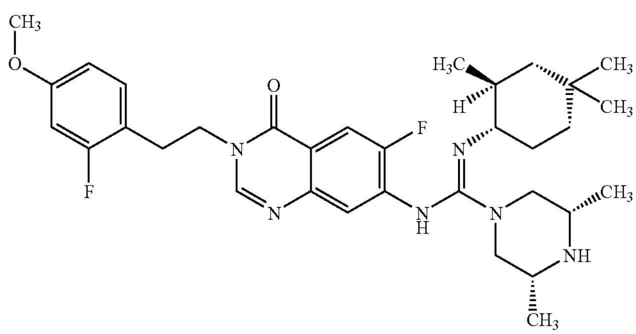 | Chiral | (3R,5S)-N-(6-fluoro-3-{2[2-fluoro-4-(methyloxy)phenyl]ethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 607.8 |
| 46 | 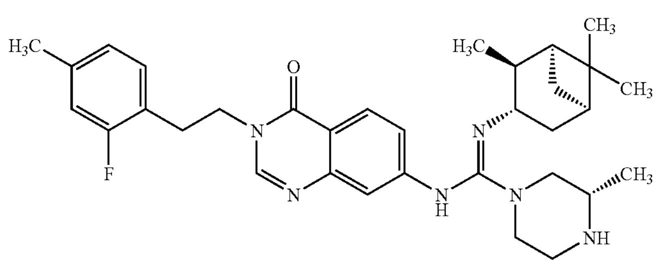 | Chiral | (3S)-N-{3-[2-(2-fluoro-4-methylphenyl)ethyl]-4-oxo-3,4-dihydroquinazolin-7-yl}-3-methyl-N'-[(1S,2S,3S,5R)-2,6,6-trimethylbicyolo[3.1.1]hept-3-yl]piperazine-1-carboximidamide | 559.7 |

-continued

| No. | Structure | | Name | MH+ |
|---|---|---|---|---|
| 47 | 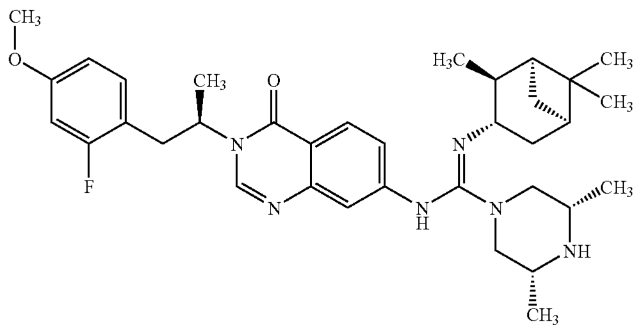 | Chiral | (3R,5S)-N-(3-{(1R)-2-[2-fluoro-4-(methyloxy)phenyl]-1-methylethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 603.8 |
| 48 | 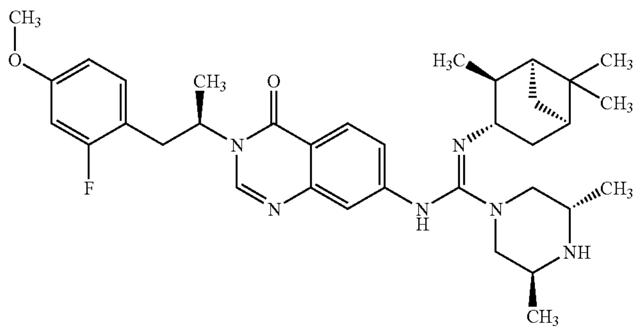 | Chiral | (3S,5S)-N-(3-{(1R)-2-[2-fluoro-4-(methyloxy)phenyl]-1-methylethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 603.8 |
| 49 | 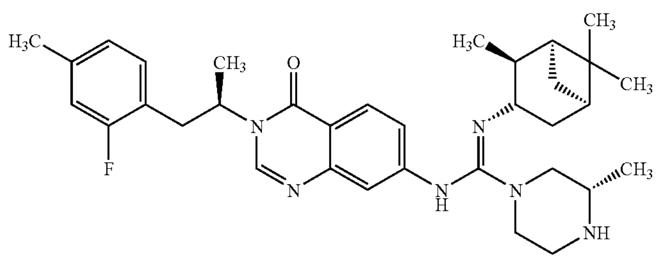 | Chiral | (3S)-N-{3-[(1R)-2-(2-fluoro-4-methylphenyl)-1-methylethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 573.8 |
| 50 | 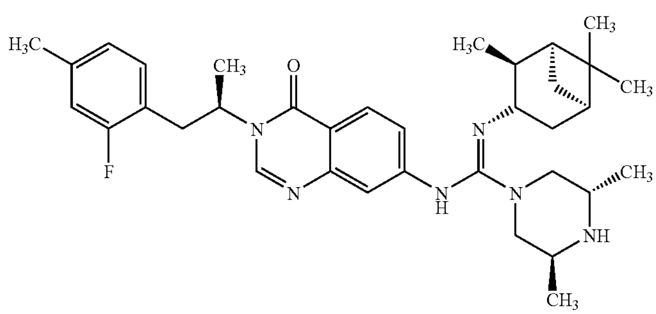 | Chiral | (3S,5S)-N-{3-[(1R)-2-(2-fluoro-4-methylphenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 587.8 |
| 51 | 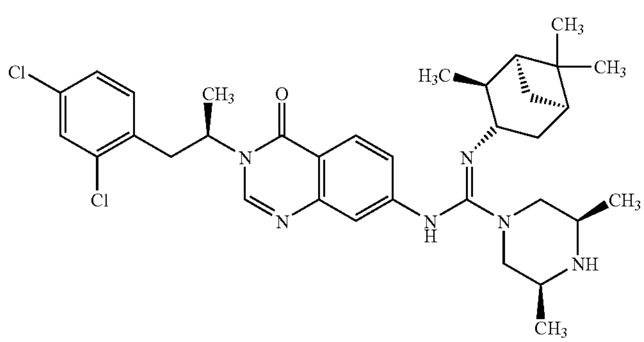 | Chiral | (3R,5S)-N-{3-[(1R)-2-(2,4-dichlorophenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 642.7 |

-continued

| No. | Structure | | Name | MH+ |
|---|---|---|---|---|
| 52 | 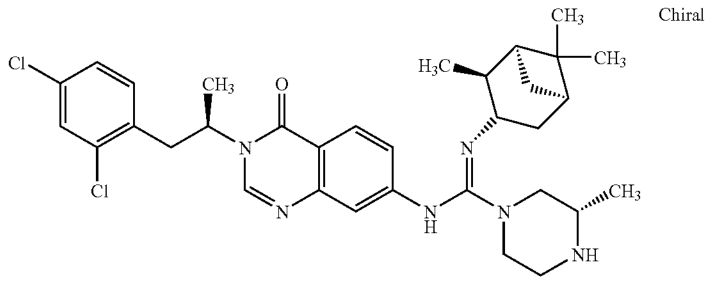 | Chiral | (3S)-N-{3-[(1R)-2-(2,4-dichlorophenyl)-1-methylethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 610.6 |
| 53 | 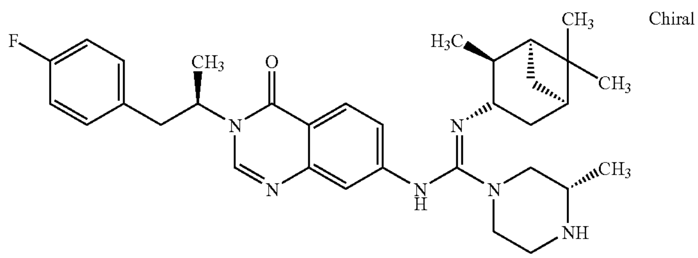 | Chiral | (3S)-N-{3-[(1R)-2-(4-fluorophenyl)-1-methylethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 559.7 |
| 54 | 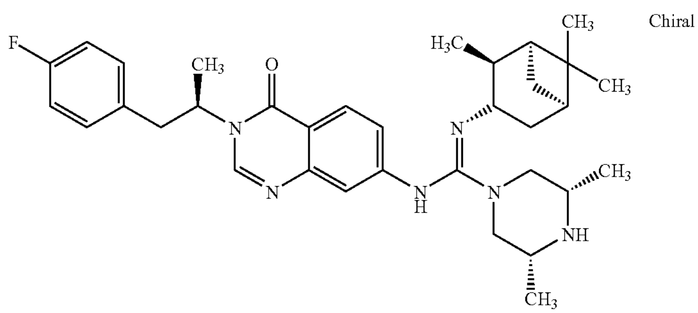 | Chiral | (3R,5S)-N-{3-[(1R)-2-(4-fluorophenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 573.8 |
| 55 | 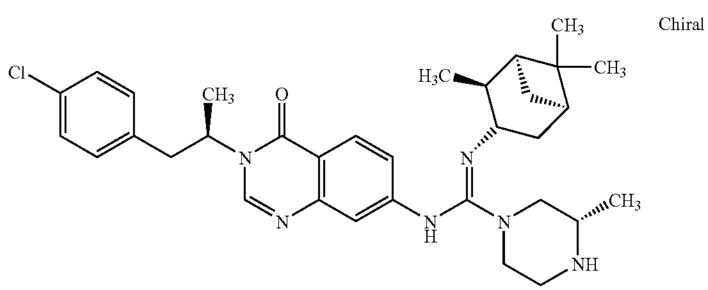 | Chiral | (3S)-N-{3-[(1R)-2-(4-chlorophenyl)-1-methylethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 576.2 |
| 56 | 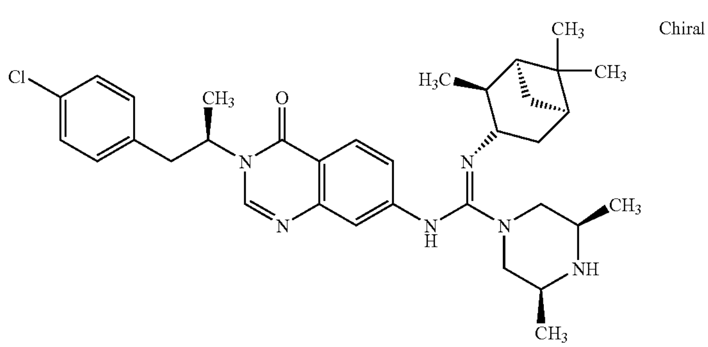 | Chiral | (3R,5S)-N-{3-[(1R)-2-(4-chlorophenyl)-1-methylethyl-]4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 590.2 |

-continued

| No. | Structure | Name | MH+ |
|---|---|---|---|
| 57 | Chiral | (3R,5S)-N-{3-[(1R)-2-(4-bromophenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 634.7 |
| 58 | Chiral | (3R,5S)-N-{3-[2-(2,4-difluorophenyl)ethyl]-2,4-dioxo-1,2,3,4-tetrahydroquinazolin-7-yl}-3,5-dimethyl-N'-[(1S,2S,5R)-2,6,6-trimethylbicyclo[3.1.1]hept-3-yl]piperazine-1-carboximidamide | 593.7 |
| 59 | Chiral | (3S)-N-{3-[2-4-fluorophenyl)ethyl]-1-methyl-2,4-dioxo-1,2,3,4-tetrahydroquinazolin-7-yl}-3-methyl-N'-[(1S,2S,5R)-2,6,6-trimethylbicyclo[3.1.1]hept-3-yl]piperazine-1-carboximidamide | 575.7 |
| 60 | 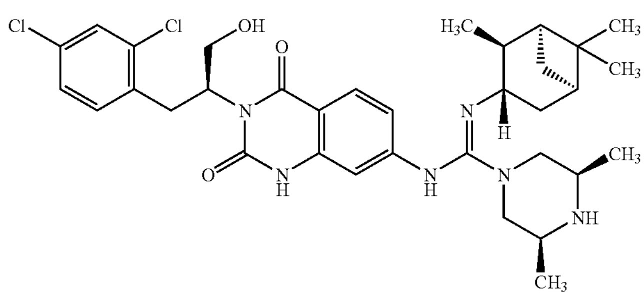 | (3R,5S)-N-{3-[(1S)-2-(2,4-dichlorophenyl)-1-(hydroxymethyl)ethyl]-2,4-dioxo-1,2,3,4-tetrahydroquinazolin-7-yl}-3,5-dimethyl-N'-[(1S,2S,3S,5R)-2,6,6-trimethylbicyclo[3.1.1]hept-3-yl]piperazine-1-carboximidamide | 656.7 |
| 61 | Chiral | (3S)-N-(2-hydroxy-3-methyl-4-oxo-3,4-dihydroquinazolin-7-yl)-3-metyl-N'-[(1S,2S,3S,5R)-2,6,6-trimetylbicyclo[3.1.1]hept-3-yl]piperazine-1-carboximidamide | 453.6 |

| No. | Structure | Name | MH+ |
|---|---|---|---|
| 62 | Chiral | (3S)-N-[3-(2-{4-[(4-fluorophenyl)carbonyl]piperidin-1-yl}ethyl)-2,4-dioxo-1,2,3,4-tetrahydroquinazolin-7-yl]-3-methyl-N'-[(1S,2S,3S,5R)-2,6,6-trimethylbicyclo[3.1.1]hept-3-yl]piperazine-1-carboximidamide | 672.9 |
| 63 | Chiral | (3S)-N-{3-[2-(2,4-dichlorophenyl)ethyl]-2,4-dioxo-1,2,3,4-tetrahydroquinazolin-7-yl}-3-methyl-N'-[(1S,2S,3S,5R)-2,6,6-trimethylbicyclo[3.1.1]hept-3-yl]piperazine-1-carboximidamide | 612.6 |
| 64 | Chiral | (3S)-N-(3-{2-[2-fluoro-4-(methyloxy)phenyl]ethyl}-2,4-dioxo-1,2,3,4-tetrahydroquinazolin-7-yl)-3-methyl-N'-[(1S,2S,3S,5R)-2,6,6-trimethylbicyclo[3.1.1]hept-3-yl]piperazine-1-carboximidamide | 591.7 |
| 65 | Chiral | (3R,5S)-N-(3-{2-[2-fluoro-4-(methyloxy)phenyl]ethyl}-2,4-dioxo-1,2,3,4-tetrahydroquinazolin-7-yl)-3,5-dimethyl-N'-[(1S,2S,3S,5R)-2,6,6-trimethylbicyclo[3.1.1]hept-3-yl]piperazine-1-carboximidamide | 605.8 |
| 66 | Chiral | (3S)-N'-(4,4-difluorocyclohexyl)-N-(3-{2-[2-fluoro-4-(methyloxy)phenyl]ethyl}-2,4-dioxo-1,2,3,4-tetrahydroquinazolin-7-yl)-3-methylpiperazine-1-carboximidamide | 573.6 |

Table of Examples 67-101

| No. | Structure | | Name | MH+ |
|---|---|---|---|---|
| 67 | 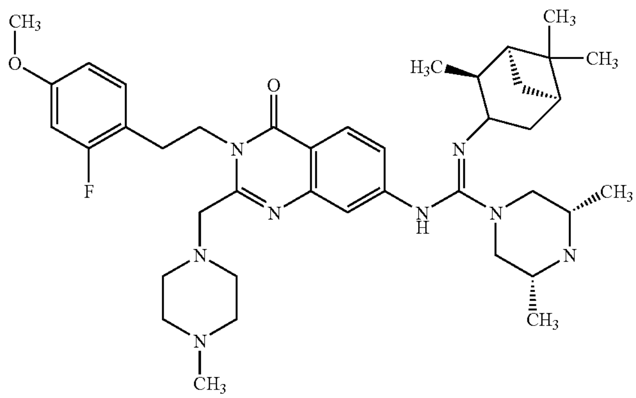 | Chiral | (3R,5S)-N-{3-{2-[2-fluoro-4-(methyloxy)phenyl]ethyl}-2-[(4-methylpiperazin-1-yl)methyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 701.9 |
| 68 | 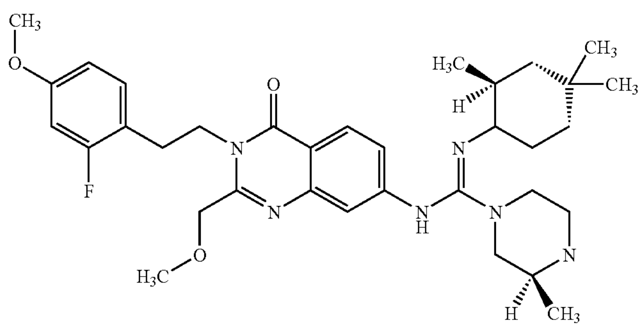 | Chiral | (3S)-N-{3-{2-[2-fluoro-4-(methyloxy)phenyl]ethyl}-2-[(methyloxy)methyl]-4-oxo-3,4-dihydroquinazolin-7-yl}-3-methyl-N'-[(1S,2S,5R)-2,6,6-trimethylbicyclo[3.1.1]hept-3-yl]piperazine-1-carboximidamide | 619.8 |
| 69 | 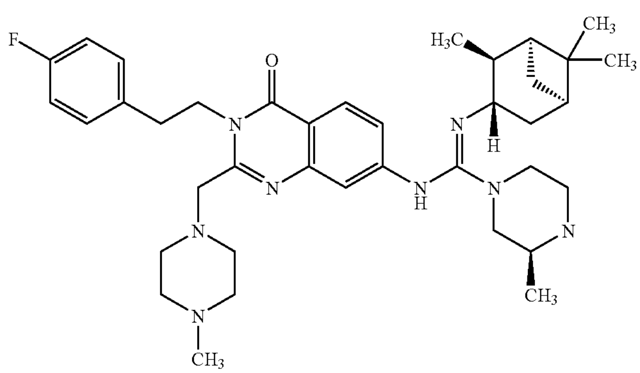 | Chiral | (3S)-N-{3-[2-(4-fluorophenyl)ethyl]-2-[(4-methylpiperazin-1-yl)methyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 657.9 |
| 70 | 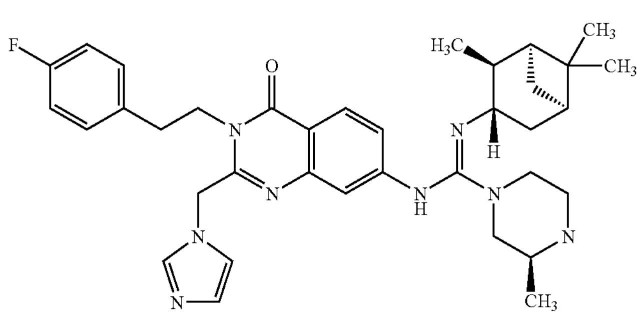 | Chiral | (3S)-N-[3-[2-(4-fluorophenyl)ethyl]-2-(1H-imidazol-1-ylmethyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 625.8 |

-continued

| No. | Structure | | Name | MH+ |
|---|---|---|---|---|
| 71 | 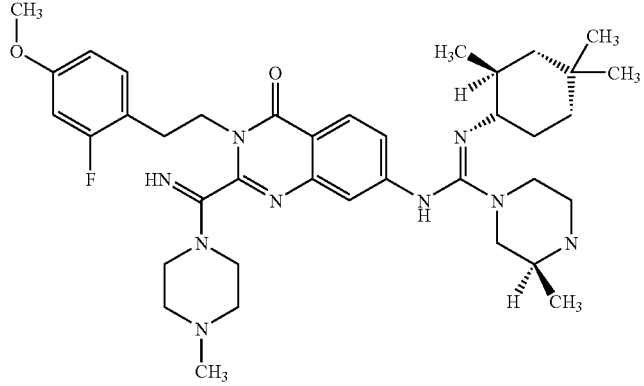 | Chiral | (3S)-N-{3-{2-[2-fluoro-4-(methyloxy)phenyl]ethyl}-2-[imino(4-methylpiperazin-1-yl)methyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 700.9 |
| 72 | 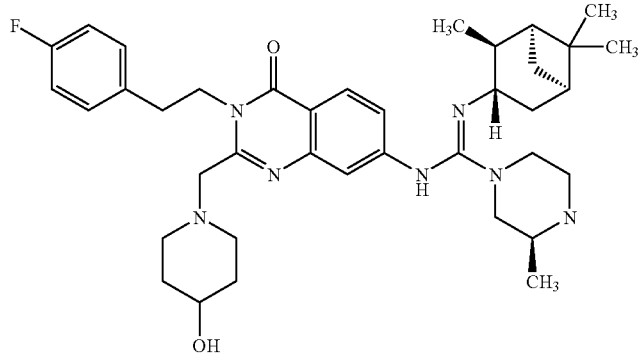 | Chiral | (3S)-N-{3-[2-(4-fluorophenyl)ethyl]-2-[(4-hydroxypiperidin-1-yl)methyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 658.9 |
| 73 | 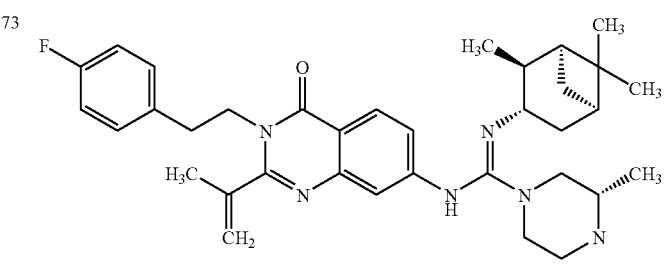 | Chiral | (3S)-N-[3-[2-(4-fluorophenyl)ethyl]-2-(1-methylethenyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 585.8 |
| 74 | 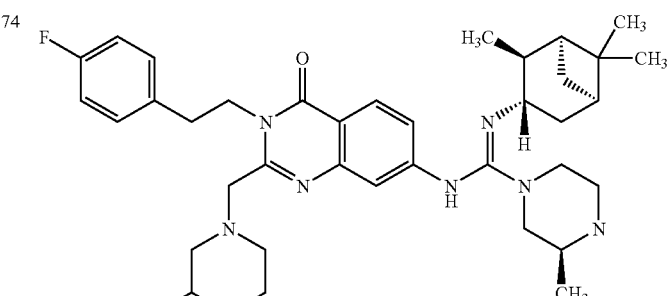 | Chiral | (3S)-N-{3-[2-(4-fluorophenyl)ethyl]-2-[(3-hydroxypiperidin-1-yl)methyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 658.9 |

-continued

| No. | Structure | Name | MH+ |
|---|---|---|---|
| 75 | Chiral | (3S)-N-[3-[2-(4-fluorophenyl)ethyl]-4-oxo-2-(2H-tetrazol-2-ylmethyl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 627.8 |
| 76 | Chiral | (3S)-N-(3-{2-[2-fluoro-4-(methyloxy)phenyl]ethyl}-2-methyl-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 589.8 |
| 77 | Chiral | (3S)-N-{3-[2-(4-fluorophenyl)ethyl]-4-oxo-2-pyridin-4-yl-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 622.8 |
| 78 | Chiral | (3S)-N-[3-{2-[2-fluoro-4-(methyloxy)phenyl]ethyl}-4-oxo-2-(2H-tetrazol-5-yl)-3,4-dihydroquinazolin-7-yl]-3-methyl-N'-(1S,2S,3S,5R)-2,6,6-trimethylbicyclo[3.1.1]hept-3-yl]piperazine-1-carboximidamide | 643.8 |
| 79 | Chiral | (3S)-N-(3-[2-(4-fluorophenyl)ethyl]-2-(morpholin-4-ylmethyl)-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 644.8 |

| No. | Structure | Name | MH+ |
|---|---|---|---|
| 80 | 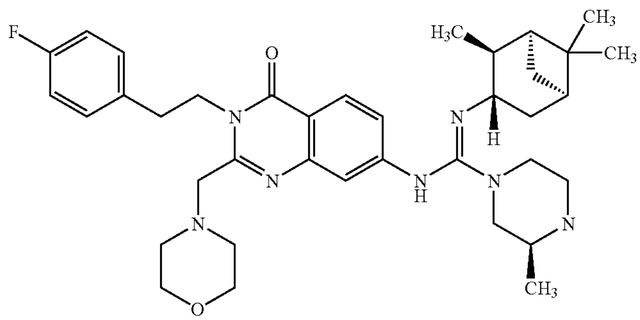 | (3S)-N-[3-[2-(4-fluorophenyl)ethyl]-2-(1H-imidazol-1-ylmethyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide Chiral | 625.8 |
| 81 | 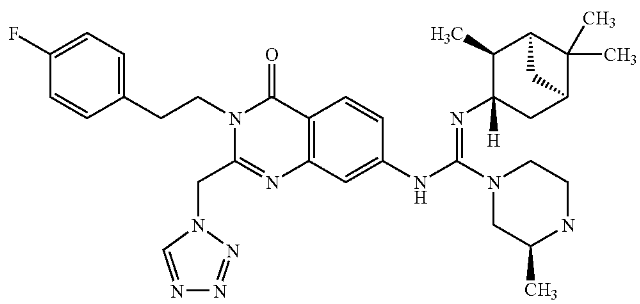 | (3S)-N-[3-[2-(4-fluorophenyl)ethyl]-4-oxo-2-(1H-tetrazol-1-ylmethyl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide Chiral | 627.8 |
| 82 | 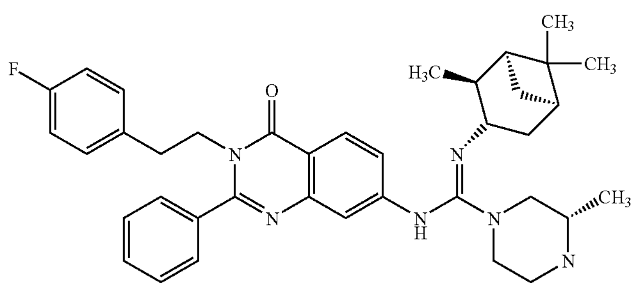 | (3S)-N-{3-[2-(4-fluorophenyl)ethyl]-4-oxo-2-phenyl-3,4-dihydroquinazolin-7-yl}-3-methyl-N-[(1S,2S,3S,5R)-2,6,6-trimethylbicyclo[3.1.1]hept-3-yl]piperazine-1-carboximidamide Chiral | 621.8 |
| 83 | 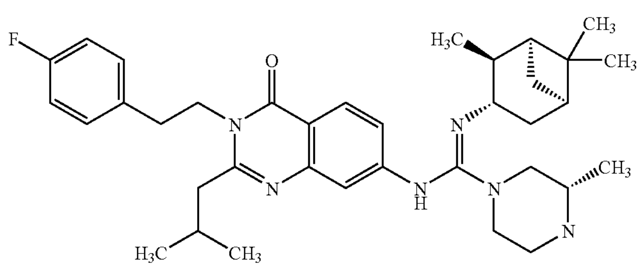 | (3S)-N-[3-[2-(4-fluorophenyl)ethyl]-2-(2-methylpropyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide Chiral | 601.8 |
| 84 | 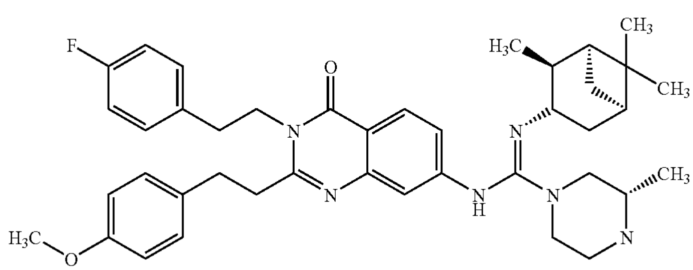 | (3S)-N-(3-[2-(4-fluorophenyl)ethyl]-2-{2-[4-(methyloxy)phenyl]ethyl}-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide Chiral | 679.9 |

-continued

| No. | Structure | Name | MH+ |
|---|---|---|---|
| 85 | Chiral | (3S)-N-[3-[2-(4-fluorophenyl)ethyl]-2-(4-methylcyclohexyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 641.9 |
| 86 | Chiral | (3S)-N-(2,3-bis{2-[2-fluoro-4-(methyloxy)phenyl]ethyl}-4-oxo-3,4-dihydroquinazolin-7-yl)-3-methyl-N'(1S,2S,5R)-2,6,6-trimethylbicyclo[3.1.1]hept-3-yl]piperazine-1-carboximidamide | 727.9 |
| 87 | Chiral | (3S)-N-[3-[2-(4-fluorophenyl)ethyl]-4-oxo-2-(2-phenylethyl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 649.9 |
| 88 | Chiral | (3S)-N-(2-{[(2,4-difluorophenyl)oxy]methyl}-3-methyl-4-oxo-3,4-)dihydroquinazolin-7-yl)-3N'-](1S,2S,5R)-2,6,6-trimethylbicyclo[3.1.1]hept-3-yl]piperazine-1-carboximidamide | 580.7 |
| 89 | Chiral | (3S)-N-[2-({[2-fluoro-4-(methyloxy)phenyl]oxy}methyl)-3-methyl-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 592.7 |

-continued

| No. | Structure | | Name | MH+ |
|---|---|---|---|---|
| 90 | 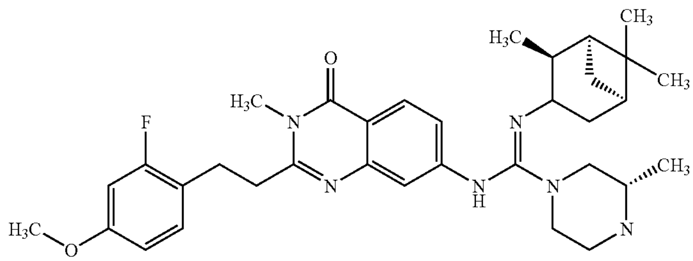 | Chiral | (3S)-N-(2-{2-[2-fluoro-4-(methyloxy)phenyl]ethyl}-3-methyl-4-oxo-3,4-dihydroquinazolin-7-yl)-3-methyl-N'-[(1S,2S,5R)-2,6,6-trimethylbicyclo[3.1.1]hept-3-yl]piperazine-1-carboximidamide | 590.8 |
| 91 | 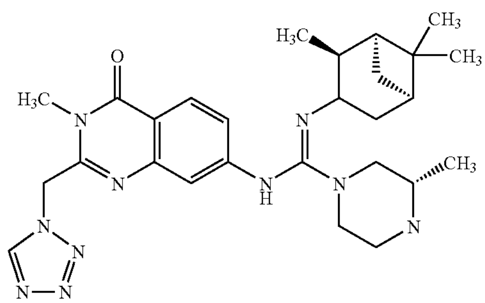 | Chiral | (3S)-3-methyl-N-[3-methyl-4-oxo-2-(1H-tetrazol-1-ylmethyl)-3,4-dihydroquinazolin-7-yl]-N'-[(1S,2S,5R)-2,6,6-trimethylbicyclo[3.1.1]hept-3-yl]piperazine-1-carboximidamide | 520.7 |
| 92 | 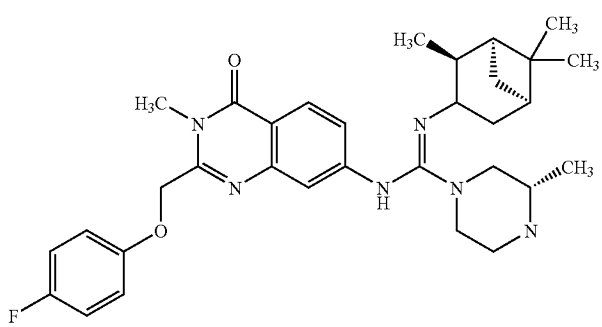 | Chiral | (3S)-N-(2-{[(4-fluorophenyl)oxy]methyl}-3-methyl-4-oxo-3,4-N'-[(1S,2S,5R)-2,6,6-dihydroquinazolin-7-yl)-3-methyl-trimethylbicyclo[3.1.1]hept-3-yl]piperazine-1-carboximidamide | 562.7 |
| 93 | 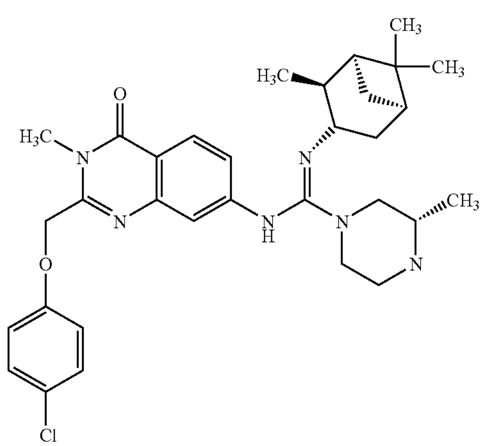 | Chiral | (3S)-N-(2-{[(4-chlorophenyl)oxy]methyl}-3-methyl-4-oxo-3,4-dihydroquinazolin-7-yl)-3-methyl-N'-[(1S,2S,3S,5R)-2,6,6-trimethybicyclo[3.1.1]hept-3-yl]piperazine-1-carboximidamide | 579.2 |

-continued

| No. | Structure | | Name | MH+ |
|---|---|---|---|---|
| 94 | 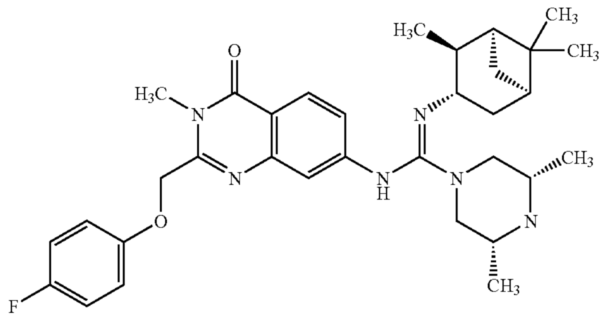 | Chiral | (3R,5S)-N-(2-{[(4-fluorophenyl)oxy]methyl}-3-methyl-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 576.7 |
| 95 | 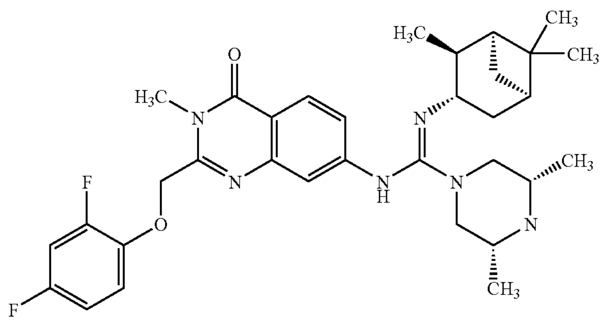 | Chiral | (3R,5S)-N-(2-{[(2,4-difluorophenyl)oxy]methyl}-3-methyl-4-oxo-3,4-dihydroquinazolin-7-yl)-3,5-dimethyl-N'-[(1S,2S,5R)-2,6,6-trimethylbicyclo[3.1.1]hept-3-yl]piperazine-1-carboximidamide | 594.7 |
| 96 | 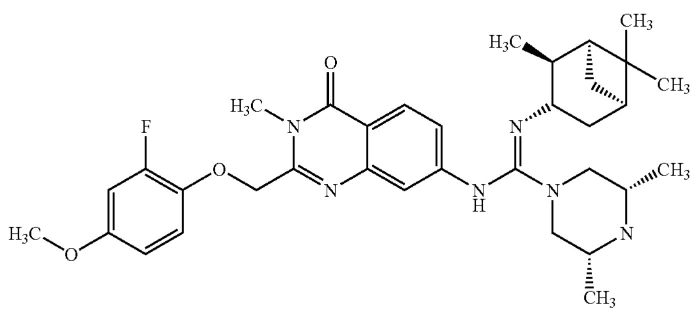 | Chiral | (3R,5S)-N-[2-({[2-fluoro-4-(methyloxy)phenyl]oxy}methyl)-3-methyl-4-oxo-3,4-dihydroquinazolin-7-yl]-3,5-dimethyl-N'-[(1S,2S,3S,5R)-2,6,6-trimethylbicyclo[3.1.1]hept-3-yl]piperazine-1-carboximidamide | 606.8 |
| 97 | 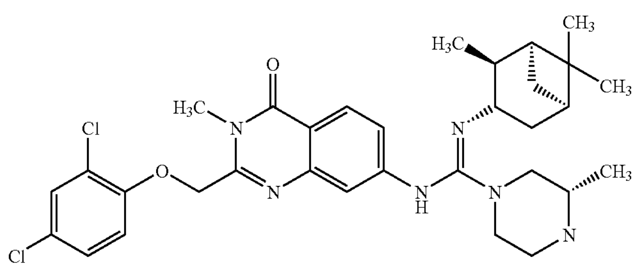 | Chiral | (3S)-N-(2-{[(2,4-dichlorophenyl)oxy]methyl}-3-methyl-4-oxo-3,4-dihydroquinazolin-7-yl)-3-methyl-N'[(1S,2S,3S,5R)-2,6,6-trimethylbicyclo-[3.1.1]hept-3-yl]piperazine-1-carboximidamide | 613.6 |
| 98 | 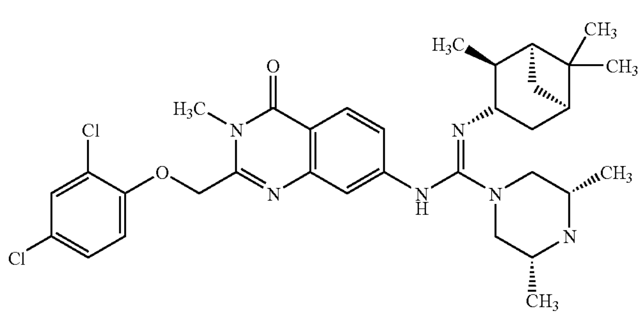 | Chiral | (3R,5S)-N-(2-{[(2,4-dichlorophenyl)oxy]methyl}-3-methyl-4-oxo-3,4-dihydroquinazolin-7-yl)-3,5-dimethyl-N'-[(1S,2S,5R)-2,6,6-trimethlbicyclo[3.1.1]hept-3-yl]piperazine-1-carboximidamide | 627.6 |

-continued

| No. | Structure | | Name | MH+ |
|---|---|---|---|---|
| 99 | 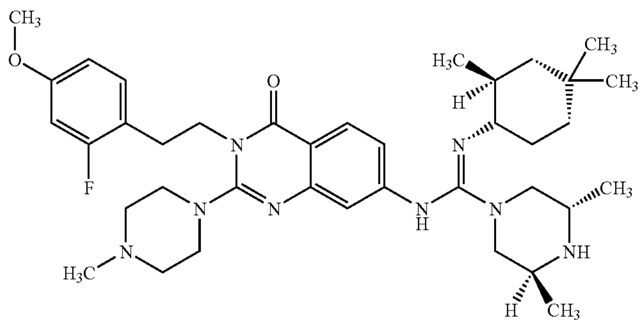 | Chiral | (3S)-N-[3-{2-[2-fluoro-4-(methyloxy)phenyl]ethyl}-2-(4-[nl methylpiperazin-1-yl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 673.9 |
| 100 | 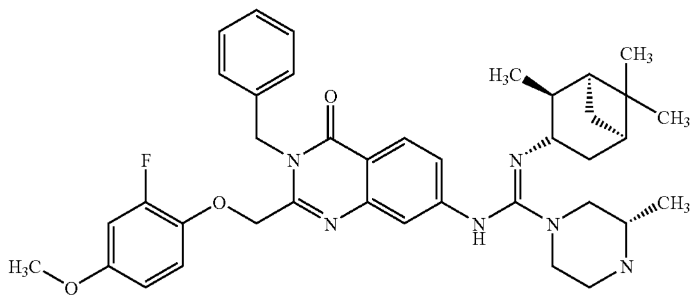 | Chiral | (3S)-N-[2-({[2-fluoro-4-(methyloxy)phenyl]oxy}methyl)-4-oxo-3-(phenylmethyl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 667.8 |
| 101 | 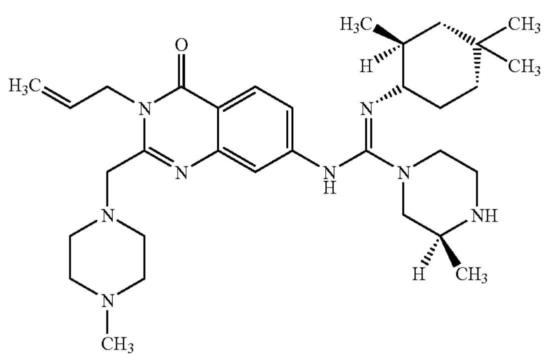 | Chiral | (3S)-3-methyl-N-{2-[(4-methylpiperazin-1-yl)methyl]-4-oxo-3-prop-2-enyl-3,4-dihydroquinazolin-7-yl}-N'-[(1S,2S,3S,5R)-2,6,6-trimethylbicyclo[3.1.1]hept-3-yl]piperazine-1-carboximidamide | 575.8 |

Table of Examples 102-112

| No. | Structure | | Name | MW+ |
|---|---|---|---|---|
| 102 | 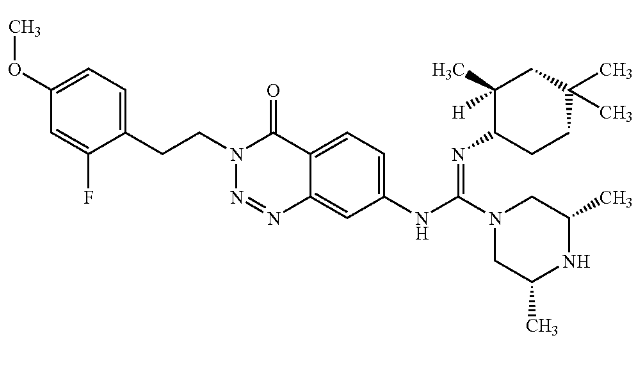 | Chiral | (3R,5S)-N-(3-{2-[2-fluoro-4-(methyloxy)phenyl]ethyl}-4-oxo-3,4-dihydro-1,2,3-benzotriazin-7-yl)-3,5-dimethyl-N'-[(1S,2S,3S,5R)-2,6,6-trimethylbicyclo[3.1.1]hept-3-yl]piperazine-1-carboximidamide | 590.8 |

-continued

| No. | Structure | | Name | MW+ |
|---|---|---|---|---|
| 103 | 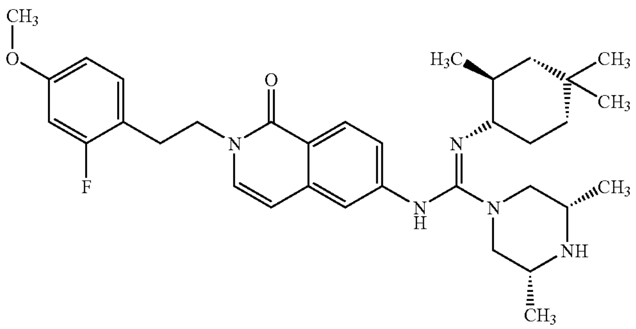 | Chiral | (3R,5S)-N-(2-{2-[2-fluoro-4-(methyloxy)phenyl]ethyl}-1-oxo-1,2-dihydroisoquinolin-6-yl)-3,5-dimethyl-N'-[(1S,2S,3S,5R)-2,6,6-trimethylbicyclo[3.1.1]hept-3-yl]piperazine-1-carboximidamide | 588.8 |
| 104 | 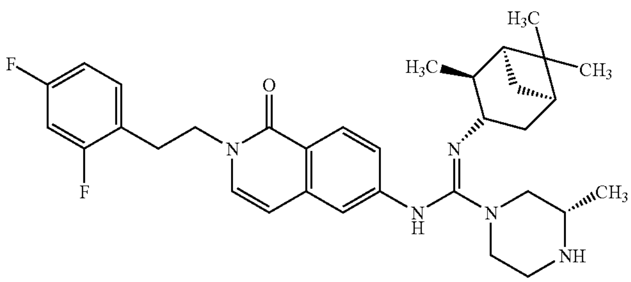 | | (3S)-N-{2-[2-(2,4-difluorophenyl)ethyl]-1-oxo-1,2-dihydroisoquinolin-6-yl}-3-methyl-N'-[(1S,2S,3S,5R)-2,6,6-trimethylbicyclo[3.1.1]hept-3-yl]piperazine-1-carboximidamide | 562.7 |
| 105 | 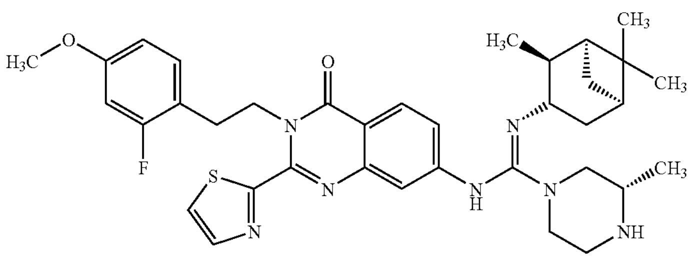 | | (3S)-N-[3-{2-[2-fluoro-4-(methyloxy)phenyl]ethyl}-4-oxo-2-(1,3-thiazol-2-yl)-3,4-dihydroquinazolin-7-yl]-3-methyl-N'-[(1S,2S,3S,5R)-trimethylbicyclo[3.1.1]hept-3-yl]piperazine-1-carboximidamide | 658.9 |
| 106 | 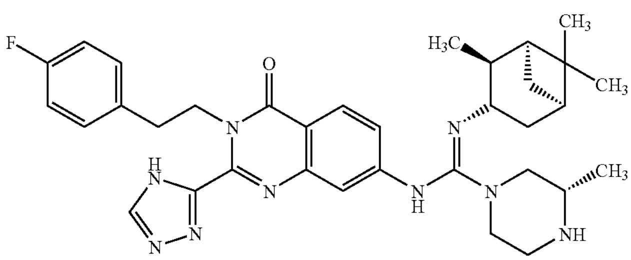 | | (3S)-N-[3-[2-(4-fluorophenyl)ethyl]-4-oxo-2-(4H-1,2,4-triazol-3-yl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 612.8 |
| 107 | 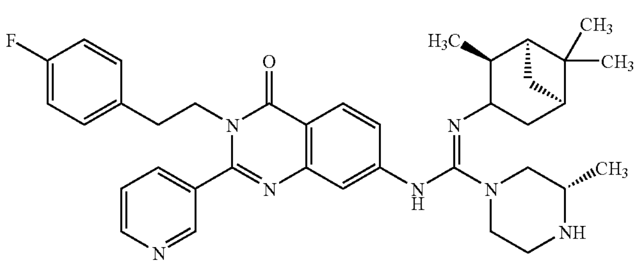 | Chiral | (3S)-N-{3-[2-(4-fluorophenyl)ethyl]-4-oxo-2-pyridin-3-yl-3,4-dihydroquinazolin-7-yl}-3-methyl-N'-[(1S,2S,5R)-2,6,6-trimethylbicyclo[3.1.1]hept-3-yl]piperazine-1-carboximidamide | 622.8 |

-continued

| No. | Structure | | Name | MW+ |
|---|---|---|---|---|
| 108 | 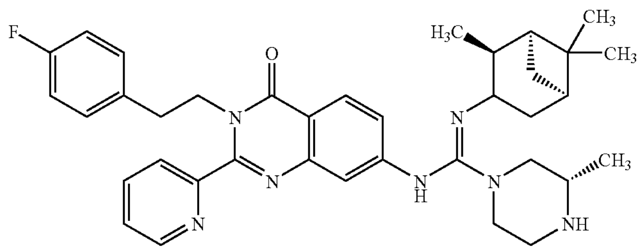 | Chiral | (3S)-N-{3-[2-(4-fluorophenyl)ethyl]-4-oxo-2-pyridin-2-yl-3,4-dihydroquinazolin-7-yl}-3-methyl-N'-[(1S,2S,5R)-2,6,6-trimethylbicyclo[3.1.1]hept-3-yl]piperazine-1-carboximidamide | 622.8 |
| 109 | 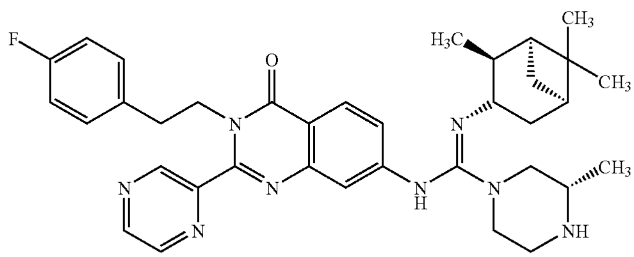 | Chiral | (3S)-N-{3-[2-(4-fluorophenyl)ethyl]-4-oxo-2-pyrazin-2-yl-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 623.8 |
| 110 | 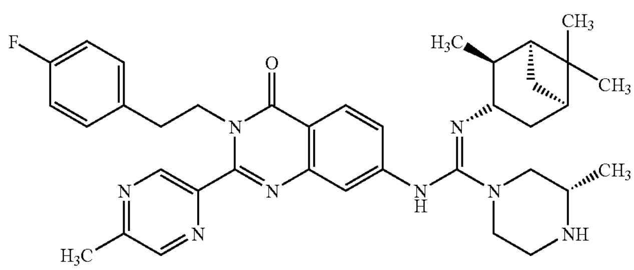 | Chiral | (3S)-N-[3-[2-(4-fluorophenyl)ethyl]-2-(5-methylpyrazin-2-yl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 637.8 |
| 111 | 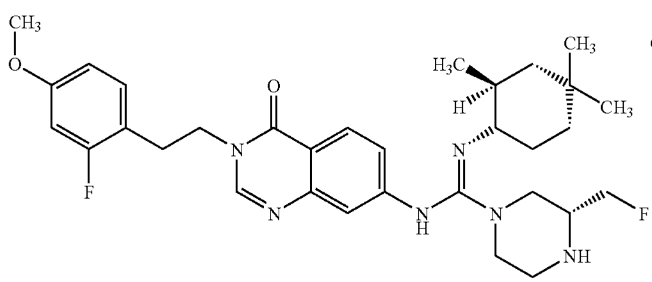 | Chiral | (3R)-3-(fluoromethyl)-N-(3-{2-[2-fluoro-4-(methyloxy)phenyl]ethyl}-4-oxo-3,4-dihydroquinazolin-7-yl)-N'-[(1S,2S,3S,5R)-2,6,6-trimethylbicyclo[3.1.1]hept-3-yl]piperazine-1-carboximidamide | 593.7 |
| 112 | 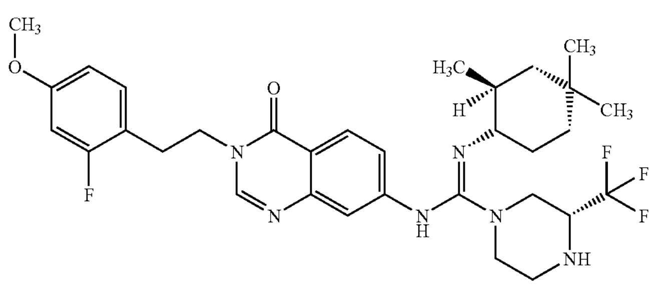 | Chiral | (3R)-N-(3-{2-[2-fluoro-4-(methyloxy)phenyl]ethyl}-4-oxo-3,4-dihydroquinazolin-7-yl)-3-(trifluoromethyl)-N'-trimethylbicyclo[3.1.1]hept-3-[(1S,2S,3S,5R)-2,6,6-yl]piperazine-1-carboximidamide | 629.7 |

Table of Examples 113-215

| No. | Structure | Name | MH+ |
|---|---|---|---|
| 113 | 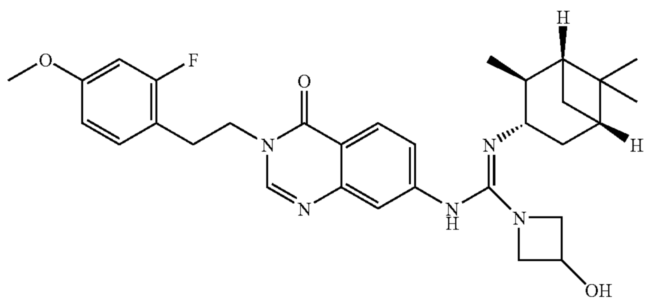 | N-{3-[2-(2-fluoro-4-methoxy-phenyl)ethyl]-4-oxo-3,4-dihydroquinazolin-7-yl}-3-hydroxy-N'-[(1R,2S,3S,5S)-2,6,6-trimethyl-bicyclo[3.1.1]hept-3-yl]azetidine-1-carboximidamide | 548.2 |
| 114 | 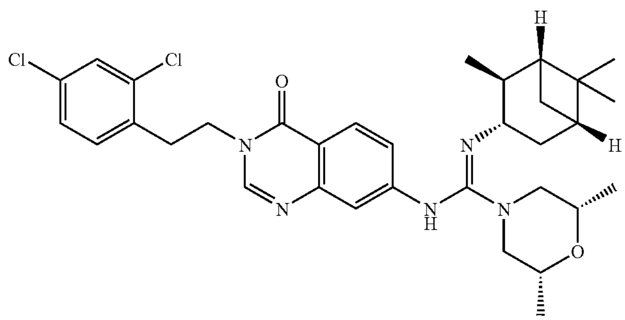 | (2R,6S)-N-{3-[2-(2,4-dichlorophenyl)ethyl]-4-oxo-3,4-dihydroquinazolin-7-yl}-2,6-dimethyl-N'-[(1R,2S,3S,5S)-2,6,6-trimethyl-bicyclo[3.1.1]hept-3-yl]morpholine-4-carboximidamide | 610.3 |
| 115 | 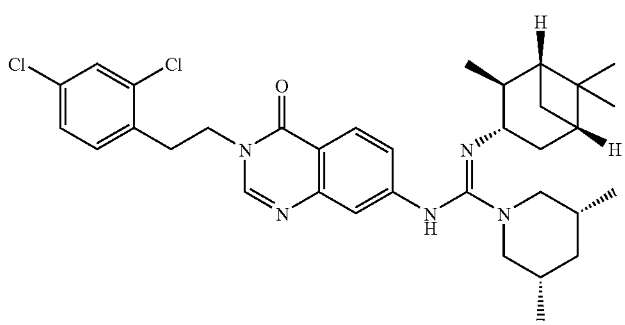 | (3R,5S)-N-{3-[2-(2,4-dichlorophenyl)ethyl]-4-oxo-3,4-dihydroquinazolin-7-yl}-3,5-dimethyl-N'-[(1R,2S,3S,5S)-2,6,6-trimethyl-bicyclo[3.1.1]hept-3-yl]piperidine-1-carboximidamide | 608.30 |
| 116 | 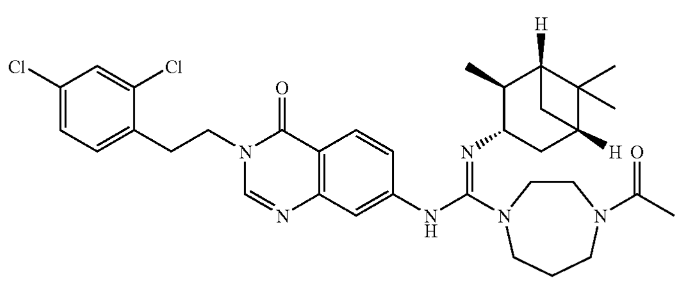 | 4-acetyl-N-{3-[2-(2,4-dichlorophenyl)ethyl]-4-oxo-3,4-dihydroquinazolin-7-yl}-trimethylbicyclo[3.1.1]hept-3-N'-[(1R,2S,3S,5S)-2,6,6-yl]-1,4-diazepane-1-carboximidamide | 637.4 |
| 117 | 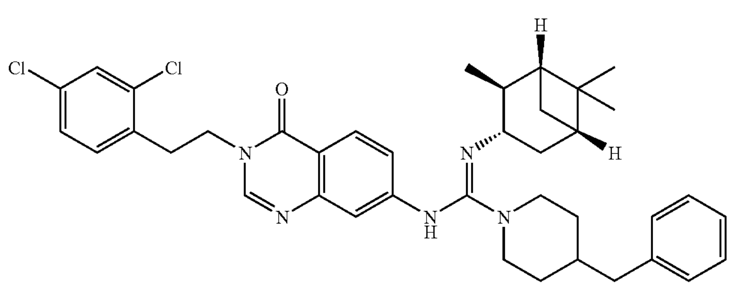 | 4-benzyl-N-{3-[2-(2,4-dichlorophenyl)ethyl]-4-oxo-3,4-dihydroquinazolin-7-yl}-trimethylbicyclo[3.1.1]hept-3-yl]piperidine-1-carboximidamide | 670.3 |

-continued

| No. | Structure | Name | MH+ |
|---|---|---|---|
| 118 | 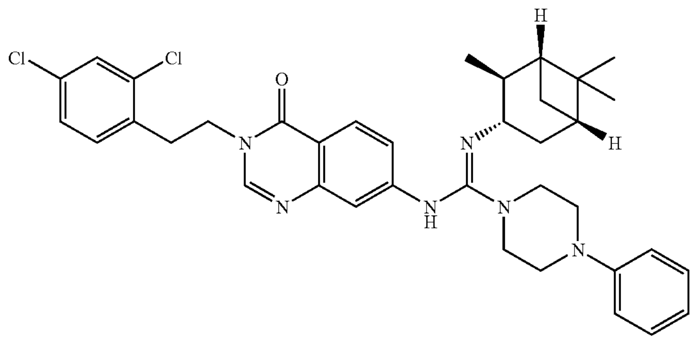 | N-{3-(2-(2,4-dichlorophenyl)-ethyl]-4-oxo-3,4-dihydroquinazolin-7-yl}-4-phenyl-N'-[(1R,2S,3S,5S)-2,6,6-trimethylbicyclo[3.1.1]hept-3-yl]piperazine-1-carboximidamide | 657.3 |
| 119 | 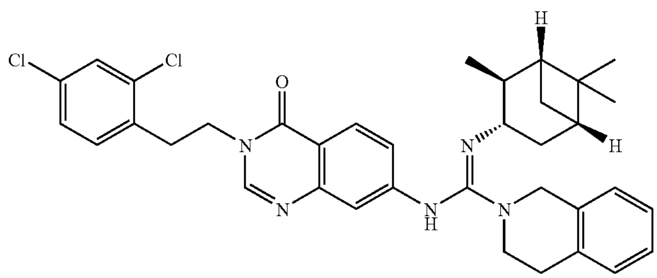 | N-{3-[2-(2,4-dichlorophenyl)ethyl]-4-oxo-3,4-dihydroquinazolin-7-yl}-N'-[(1R,2S,3S,5S)-2,6,6-trimethylbicyclo[3.1.1]hept-3-yl]-3,4-dihydroisoquinoline-2(1H)-carboximidamide | 628.3 |
| 120 | 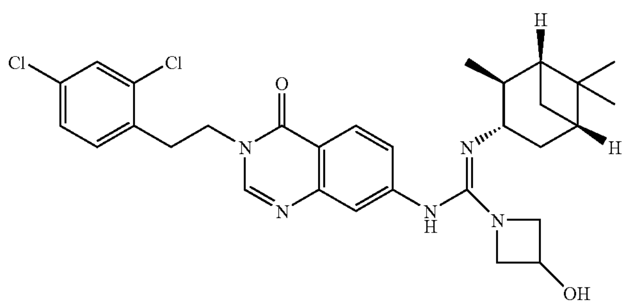 | N-{3-[2-(2,4-dichlorophenyl)-ethyl]-4-oxo-3,4-dihydroquinazolin-7-yl}-3-hydroxy-N'-[(1R,2S,3S,5S)-2,6,6-trimethyl-bicyclo[3.1.1]hept-3-yl]azetidine-1-carboximidamide | 568.2 |
| 121 | 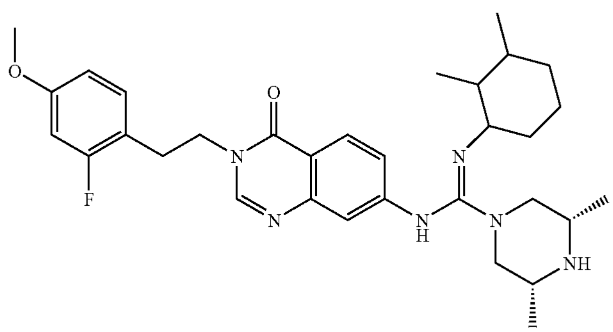 | N-(2,3-Dimethyl-cyclohexyl)-N-{3-[2-(2-fluoro-4-methoxy-phenyl)-ethyl]-4-oxo-3,4-dihydro-quinazolin-7-yl}-3,5-dimethyl-piperazine-1-carboxamidine | 563.2 |
| 122 | 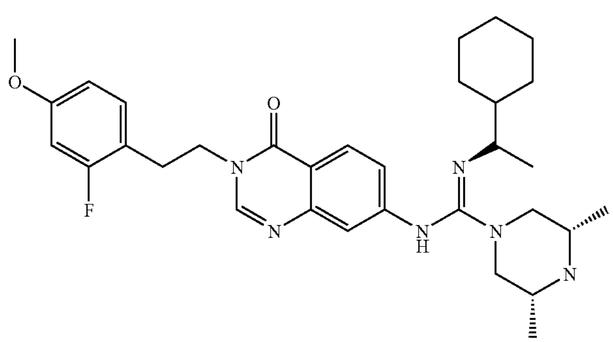 | N-(1-Cyclohexyl-ethyl)-N'-{3-[2-(2-fluoro-4-methoxy-phenyl)-ethyl]-4-oxo-3,4-dihydro-quinazolin-7-yl}-3,5-dimethyl-piperazine-1-carboxamidine | 563.3 |

-continued

| No. | Structure | Name | MH+ |
|---|---|---|---|
| 123 | 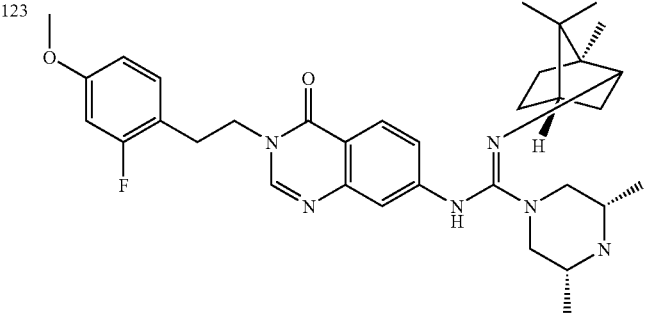 | N-{3-[2-(2-Fluoro-4-methoxy-phenyl)-ethyl]-4-oxo-3,4-dihydro-quinazolin-7-yl}-3,5-dimethyl-N'-(1,7,7-trimethyl-bicyclo[2.2.1]hept-2-yl)-piperazine-1-carboxamidine | 589.2 |
| 124 | 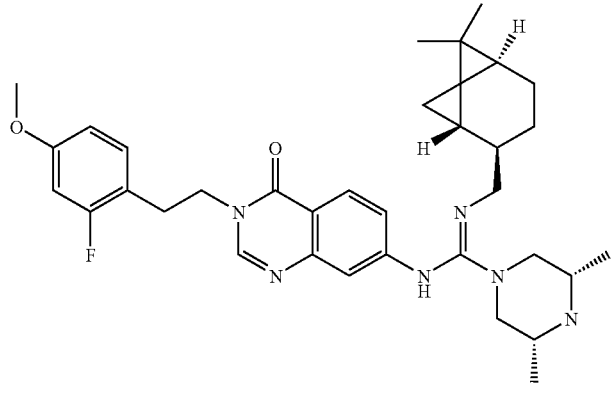 | N-(6,6-Dimethyl-bicyclo[3.1.1]hept-2-ylmethyl)-N'-{3-[2-(2-fluoro-4-methoxy-phenyl)-ethyl]-4-oxo-3,4-dihydroquinazolin-7-yl}-3,5-dimethyl-piperazine-1-carboxamidine | 589.2 |
| 125 | 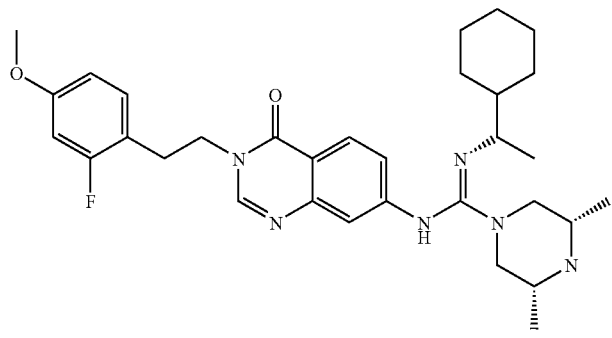 | N-(1-Cyclohexyl-ethyl)-N'-{3-[2-(2-fluoro-4-methoxy-phenyl)-ethyl]-4-oxo-3,4-dihydro-quinazolin-7-yl}-3,5-dimethyl-piperazine-1-carboxamidine | 563.3 |
| 126 | 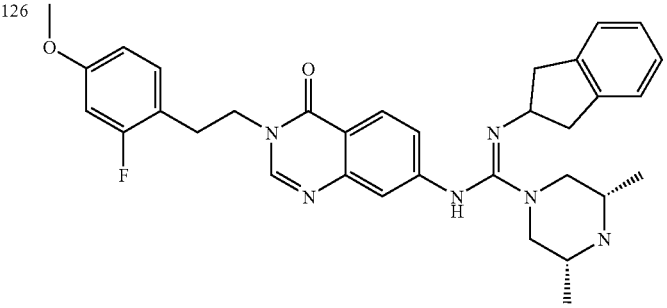 | N-{3-[2-(2-Fluoro-4-methoxy-phenyl)-ethyl]-4-oxo-3,4-dihydro-quinazolin-7-yl}-N-indan-2-yl-3,5-dimethyl-piperazine-1-carboxamidine | 569.2 |

-continued

| No. | Structure | Name | MH+ |
|---|---|---|---|
| 127 | 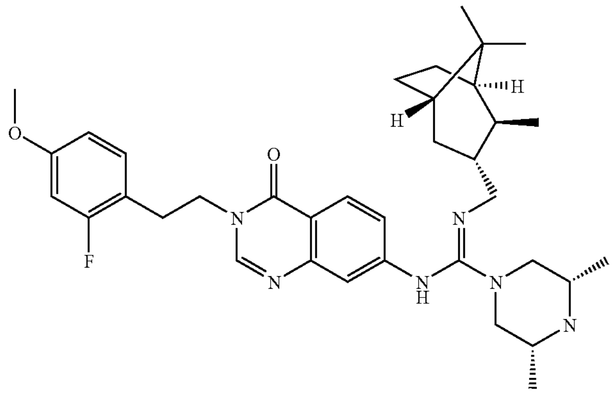 | N-{3-[2-(2-Fluoro-4-methoxy-phenyl)-ethyl]-4-oxo-3,4-dihydro-quinazolin-7-yl}-3,5-dimethyl-N'-(2,6,6-trimethyl-bicyclo[3.1.1]hept-3-ylmethyl)-piperazine-1-carboxamidine | 603.4 |
| 128 | 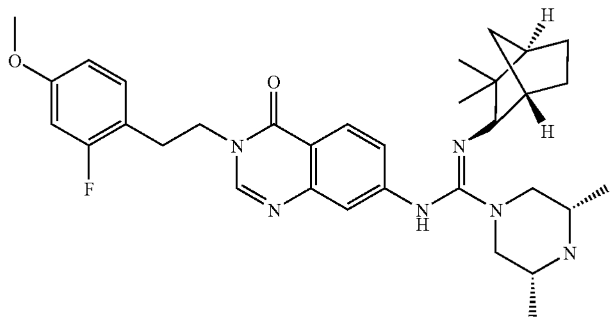 | N-{3-[2-(2-Fluoro-4-methoxy-phenyl)-ethyl]-4-oxo-3,4-dihydro-quinazolin-7-yl}-3,5-dimethyl-N'-(1,3,3-trimethyl-bicyclo[2.2.1]hept-2-yl)-piperazine-1-carboxamidine | 590.3 |
| 129 | 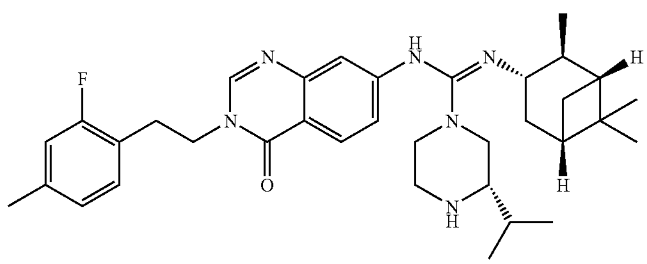 | (3S)-N-{3-[2-(2-fluoro-4-methylphenyl)ethyl]-4-oxo-3,4-dihydroquinazolin-7-yl}-3-isopropyl-N'-[(1R,2S,3S,5S)-2,6,6-trimethyl-bicyclo[3.1.1]hept-3-yl]-piperazine-1-carboximidamide | 587.3 |
| 130 | 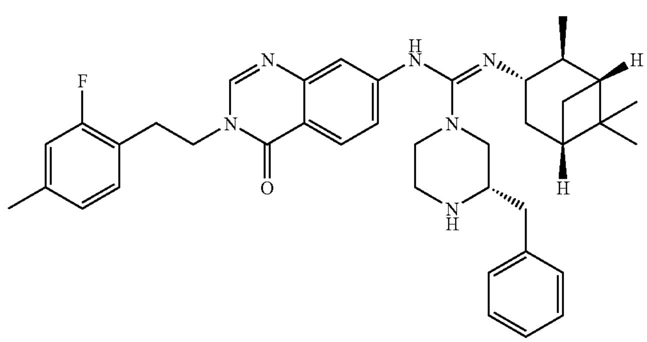 | (3S)-3-benzyl-N-{3-[2-(2-fluoro-4-methylphenyl)ethyl]-4-oxo-3,4-dihydroquinazolin-7-yl}-M-[(1R,2S,3S,5S)-2,6,6-trimethylbicyclo[3.1.1]hept-3-yl]piperazine-1-carboximidamide | 635.3 |
| 131 | 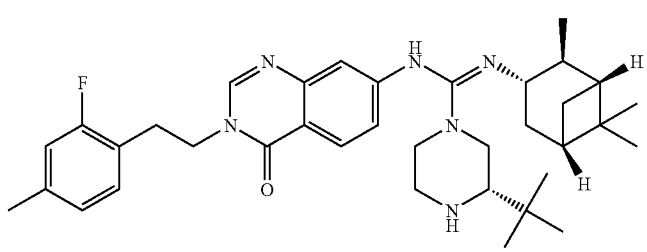 | (3S)-3-tert-butyl-N-{3-[2-(2-fluoro-4-methylphenyl)ethyl]-4-oxo-3,4-dihydroquinazolin-7-yl}-N'-[(1R,2S,3S,5S)-2,6,6-trimethylbicyclo[3.1.1]hept-3-yl]piperazine-1-carboximidamide | 601.3 |

-continued

| No. | Structure | Name | MH+ |
|---|---|---|---|
| 132 | 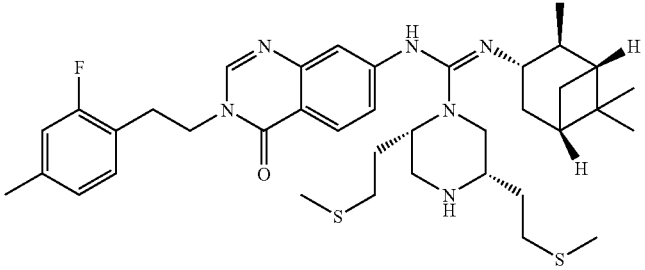 | (2S,5S)-N-{3-[2-(2-fluoro-4-methylphenyl)ethyl]-4-oxo-3,4-dihydroquinazolin-7-yl}-2,5-bis[2-(methylthio)ethyl]-N'-[(1R,2S,3S,5S)-2,6,6-trimethylbicyclo[3.1.1]hept-3-yl]piperazine-1-carboximidamide | 693.4 |
| 133 | 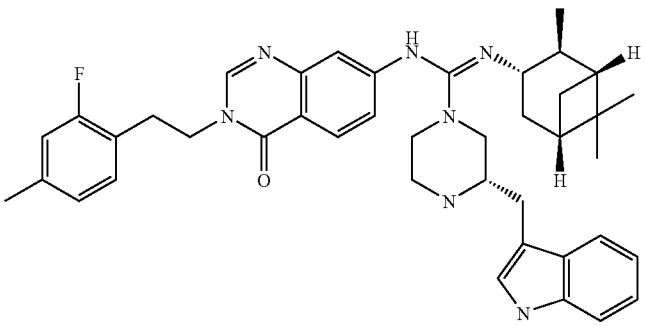 | (3S)-N-{3-[2-(2-fluoro-4-methylphenyl)ethyl]-4-oxo-(1H-indol-3-ylmethyl)N'-[(1R,2S,3S,5S)-2,6,6-trimethylbicyclo[3.1.1]hept-3-yl]piperazine-1-carboximidamide | 674.4 |
| 134 | 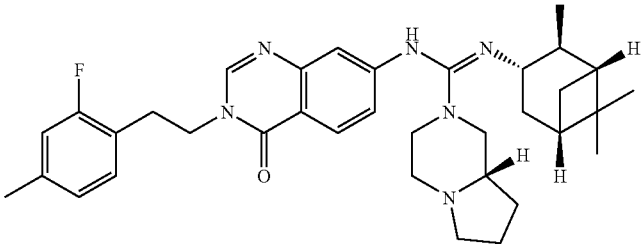 | (8aS)-N-{3-[2-(2-fluoro-4-methylphenyl)ethyl]-4-oxo-3,4-dihydroquinazolin-7-yl}-[(1R,2S,3S,5S)-2,6,6-trimethylbicyclo[3.1.1]hept-3-yl]hexahydropyrrolo[1,2-a]pyrazine-2(1H)-carboximidamide | 585.3 |
| 135 | 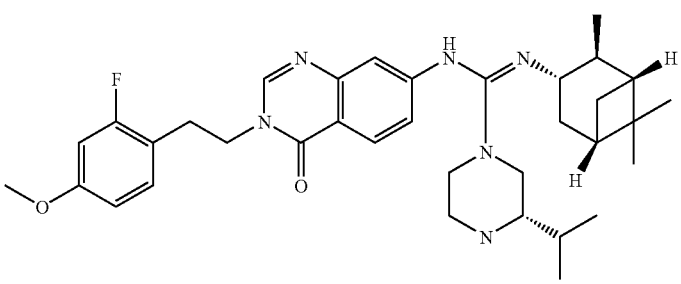 | (3S)-N-{3-[2-(2-fluoro-4-methoxyphenyl)ethyl]-4-oxo-3,4-dihydroquinazolin-7-yl}-3-isopropyl-N'-[1R,2S,3S,5S)-2,6,6-trimethylbicyclo[3.1.1]hept-3-yl]piperazine-1-carboximidamide | 603.3 |
| 136 | 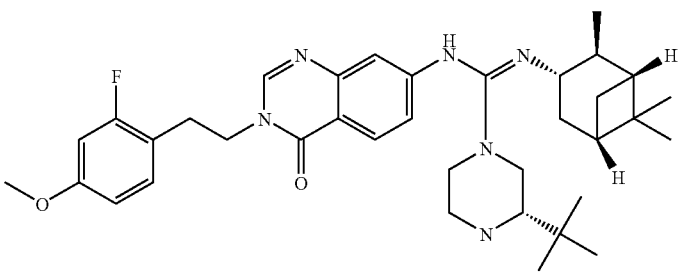 | (3S)-3-tert-butyl-N-{3-[2-(2-fluoro-4-methoxyphenyl)ethyl]-4-oxo-3,4-dihydroquinazolin-7-yl}-N'-[(1R,2S,3S,5S)-2,6,6-trimethylbicyclo[3.1.1]hept-3-yl]piperazine-1-carboximidamide | 617.4 |

| No. | Structure | Name | MH+ |
|---|---|---|---|
| 137 | 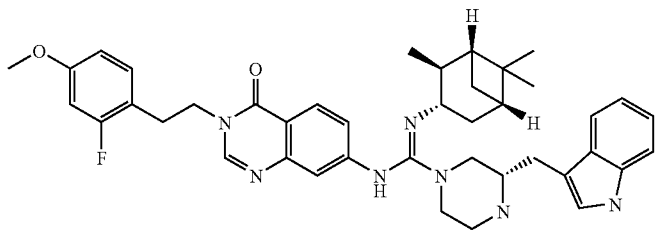 | (3S)-N-{3-[2-(2-fluoro-4-methoxyphenyl)ethyl]-4-oxo-3,4-dihydroquinazolin-7-yl}-3-(1H-indol-3-ylmethyl)-N'-[(1R,2S,3S,5S)-2,6,6-trimethylbicyclo[3.1.1]hept-3-yl]piperazine-1-carboximidamide | 690.4 |
| 138 | 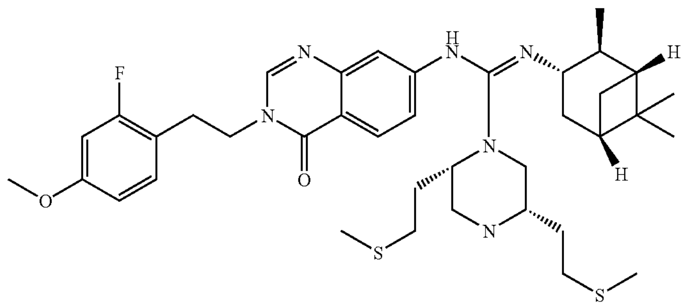 | (2S,5S)-N-{3-[2-(2-fluoro-4-methoxyphenyl)ethyl]-4-oxo-3,4-dihydroquinazolin-7-yl}-2,5-bis[2-(methythio)ethyl]-N'-[(1R,2S,3S,5S)-2,6,6-trimethylbicyclo[3.1.1]hept-3-yl]piperazine-1-carboximidamide | 709.4 |
| 139 | 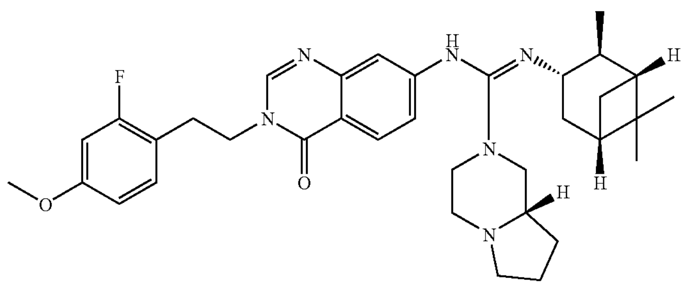 | (8aS)-N-{3-[2-(2-fluoro-4-methoxyphenyl)ethyl]-4-oxo-3,4-dihydroquinazolin-7-yl}-N'-[(1R,2S,3S,5S)-2,6,6-trimethylbicyclo[3.1.1]hept-3-yl]hexahydropyrrolo[1,2-a]pyrazine-2(1H)-carboximidamide | 601.4 |
| 140 | 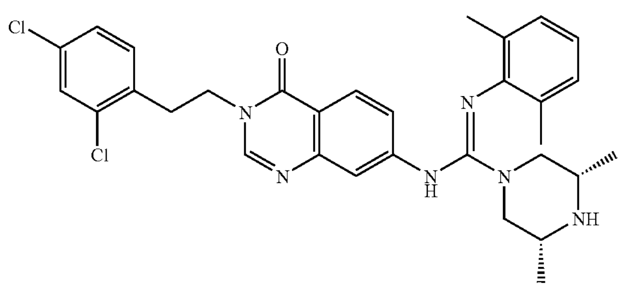 | (3R,5S)-N-{3-[2-(2,4-dichlorophenyl)ethyl]-4-oxo-3,4-dihydroquinazolin-7-yl}-N'-(2,6-dimethylphenyl)-3,5-dimethylpiperazine-1-carboximidamide | 577.2 |
| 141 | 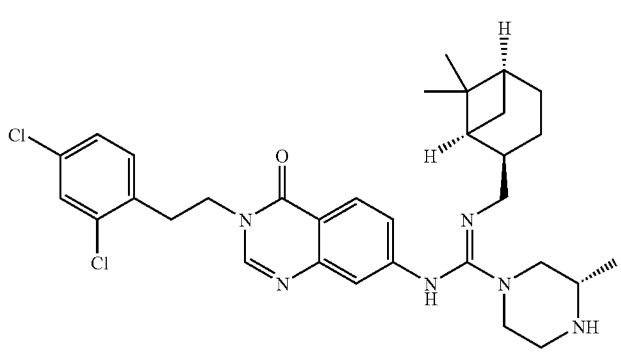 | (3S)-N-{3-[2-(2,4-dichlorophenyl)ethyl]-4-oxo-3,4-dihydroquinazolin-7-yl}-N'-{[(1S,2R,5S)-6,6-dimethylbicyclo[3.1.1]hept-2-yl]methyl}-3-methylpiperazine-1-carboximidamide | 595.1 |

-continued

| No. | Structure | Name | MH+ |
|---|---|---|---|
| 142 | 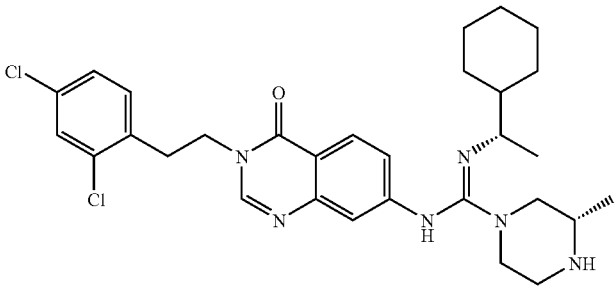 | (3S)-N'-[(1S)-1-cyclohexylethyl]-N-{3-[2-(2,4-dichloro-phenyl)ethyl]-4-oxo-3,4-dihydroquinazolin-7-yl}-3-methylpiperazine-1-carboximidamide | 571.2 (MH +3) |
| 143 | 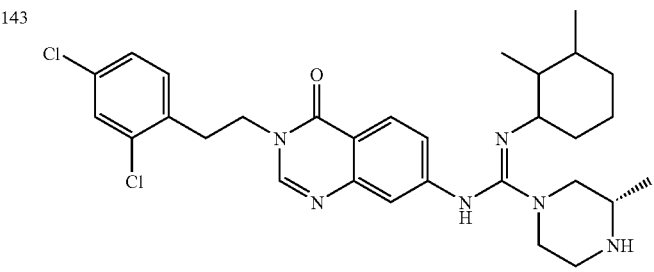 | (3S)-N-{3-[2-(2,4-dichlorophenyl)ethyl]-4-oxo-3,4-dihydroquinazolin-7-yl}-methylpiperazine-1-N'-(2,3-dimethylcyclohexyl)-3-carboximidamide | 570.2 (MH +2) |
| 144 | 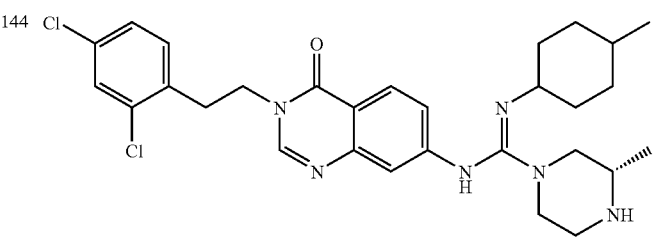 | (3S)-N-{3-[2-(2,4-dichlorophenyl)ethyl]-4-oxo-3,4-dihydroquinazolin-7-yl}-3-methyl-N'-(4-methyl-cyclohexyl)piperazine-1-carboximidamide | 558.0 (MH +3) |
| 145 | 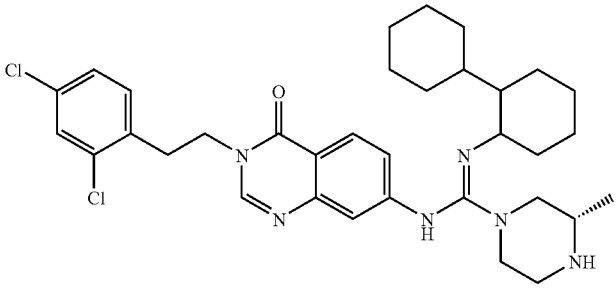 | (3S)-N'-[1,1'bi(cyclohexyl)-2-yl]-N-{3-[2-(2,4-dichloro-phenyl)ethyl]-4-oxo-3,4-dihydroquinazolin-7-yl}-3-methylpiperazine-1-carboximidamide | 623.2 |
| 146 | 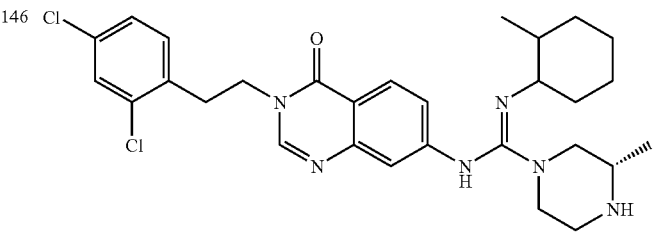 | (3S)-N-{3-[2-(24-dichlorophenyl)ethyl]-4-oxo-3,4-dihydroquinazolin-7-yl}-3-methyl-N'-(2-methylcyclohexyl)piperazine-1-carboximidamide | 555.2 |

| No. | Structure | Name | MH+ |
|---|---|---|---|
| 147 | 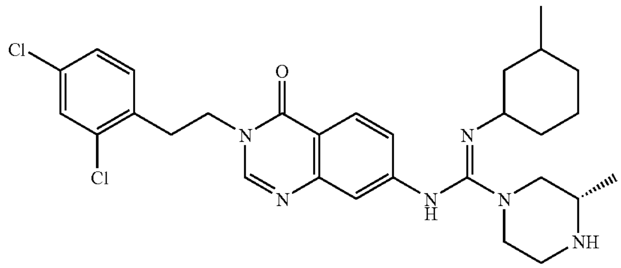 | (3S)-N-{3-[2-(2,4-dichlorophenyl)ethyl]-4-oxo-3,4-dihydroquinazolin-7-yl}-3-methyl-N'(3-methylcyclohexyl)piperazine 1-carboximidamide | 557.8 (MH +3) |
| 148 | 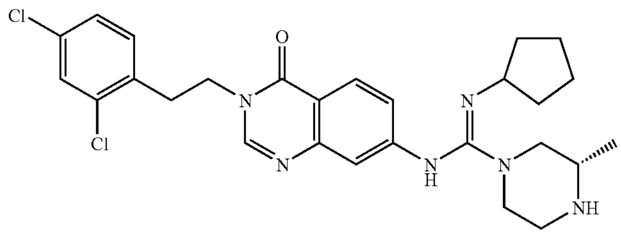 | (3S)-N'-cyclopentyl-N-{3-[2-(2,4-dichlorophenyl)ethyl]-4-oxo-3,4-dihydroquinazolin-7-yl}-3-methylpiperazine-1-carboximidamide | 527.2 |
| 149 | 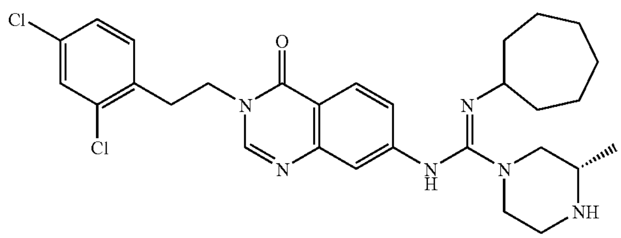 | (3S)-N'-cycloheptyl-N-{3-[2-(2,4-dichlorophenyl)ethyl]-4-oxo-3,4-dihydroquinazolin-7-yl}-3-methylpiperazine-1-carboximidamide | 558.1 (MH +3) |
| 150 | 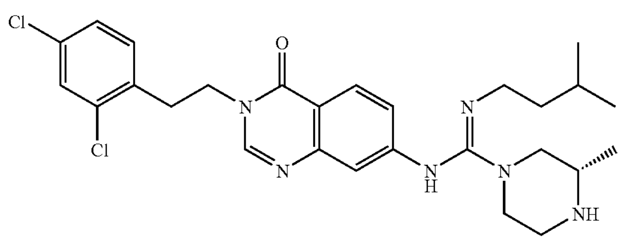 | (3S)-N-{3-[2-(2,4-dichlorophenyl)ethyl]-4-oxo-3,4-dihydroquinazolin-7-yl}-N'-isopentyl-3-methylpiperazine-1-carboximidamide | 532.2 (MH +3) |
| 151 | 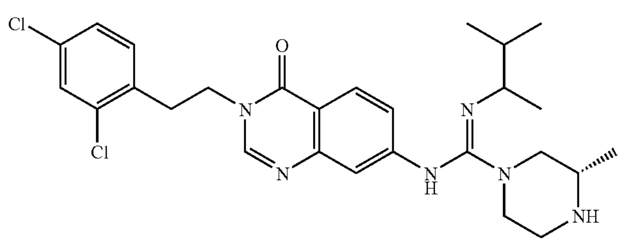 | (3S)-N-{3-[2-(2,4-dichlorophenyl)ethyl]-4-oxo-3,4-dihydroquinazolin-7-yl}-N'-(1,2-dimethylpropyl)-3-methylpiperazine-1-carboximidamide | 532.2 (MH +3) |
| 152 | 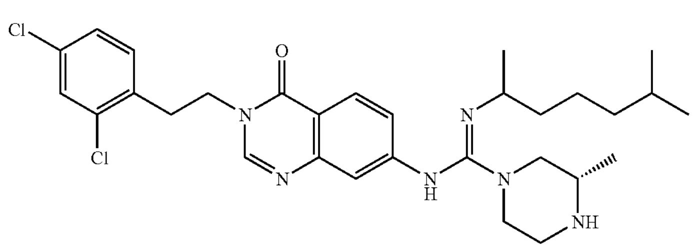 | (3S)-N-{3-[2-(2,4-dichlorophenyl)ethyl]-4-oxo-3,4-dihydroquinazolin-7-yl}-N'-(1,5-dimethylhexyl)-3-methylpiperazine-1-carboximidamide | 574.2 (MH +3) |

-continued

| No. | Structure | Name | MH+ |
|---|---|---|---|
| 153 | 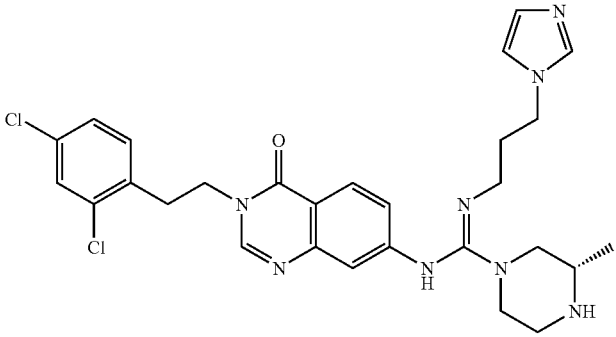 | (3S)-N-{3-[2-(2,4-dichlorophenyl)ethyl]-4-oxo-3,4-dihydroquinazolin-7-yl}-N'-[3-(1H-imidazol-1-yl)propyl]-3-methylpiperazine-1-carboximidamide | 567.2 |
| 154 | 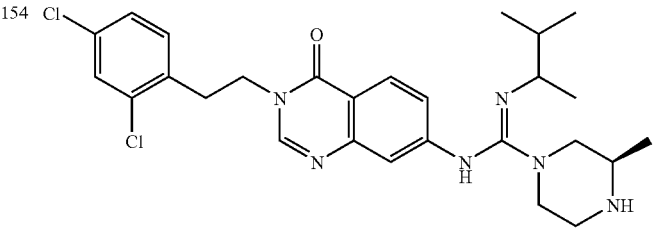 | (3R)-N-{3-[2-(2,4-dichlorophenyl)ethyl]-4-oxo-3,4-dihydroquinazolin-7-yl}-N'-(1,2-dimethylpropyl)-3-methylpiperazine-1-carboximidamide | 531.2 (MH +3) |
| 155 | 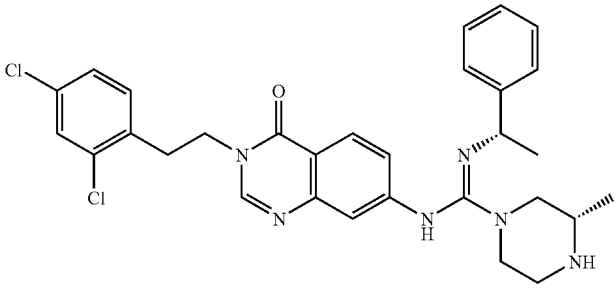 | (3S)-N-{3-[2-(2,4-dichlorophenyl)ethyl]-4-oxo-3,4-dihydroquinazolin-7-yl}-3-methyl-N'-[(1S)-1-phenylethyl]piperazine-1-carboximidamide | 563.8 |
| 156 | 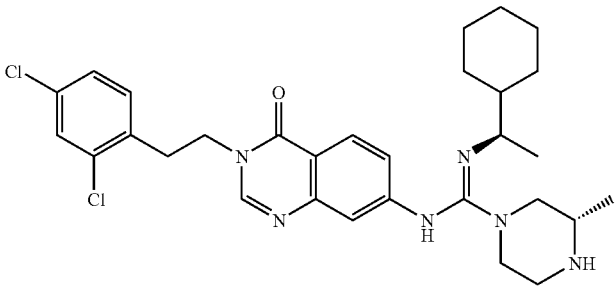 | (3S)-N'-[(1R)-1-cyclohexylethyl]-N-{3-[2-(2,4-dichlorophenyl)ethyl]-4-oxo-3,4-dihydroquinazolin-7-yl}-3-methylpiperazine-1-carboximidamide | 569.2 |
| 157 | 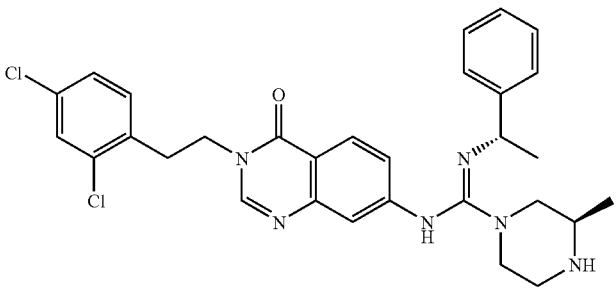 | (3R)-N-{3-[2-(2,4-dichlorophenyl)ethyl]-4-oxo-3,4-dihydroquinazolin-7-yl}-3-methyl-N'-[(1S)-1-phenylethyl]piperazine-1-carboximidamide | 563.2 |

| No. | Structure | Name | MH+ |
|---|---|---|---|
| 158 | 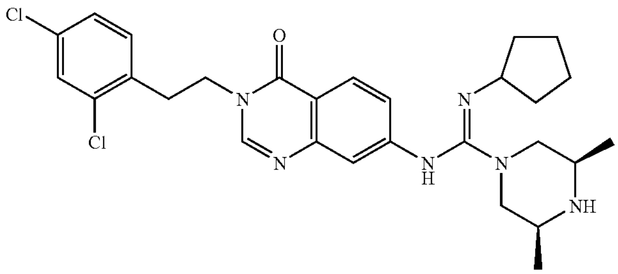 | (3R,5S)-N'-cyclopentyl-N-{3-[2-(2,4-dichlorophenyl)ethyl]-4-oxo-3,4-dihydroquinazolin-7-yl}-3,5-dimethylpiperazine-1-carboximidamide | 541.1 |
| 159 | 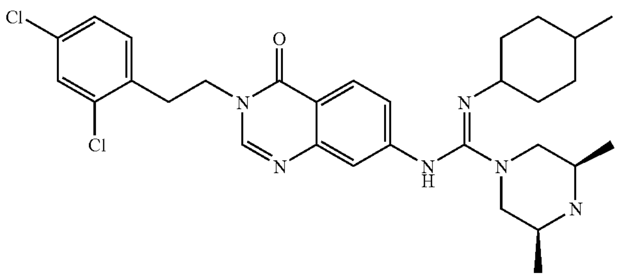 | (3R,5S)-N-{3-[2-(2,4-dichlorophenyl)ethyl]-4-oxo-3,4-dihydroquinazolin-7-yl}-3,5-dimethyl-N'-(4-methylcyclohexyl)piperazine-1-carboximidamide | 569.0 |
| 160 | 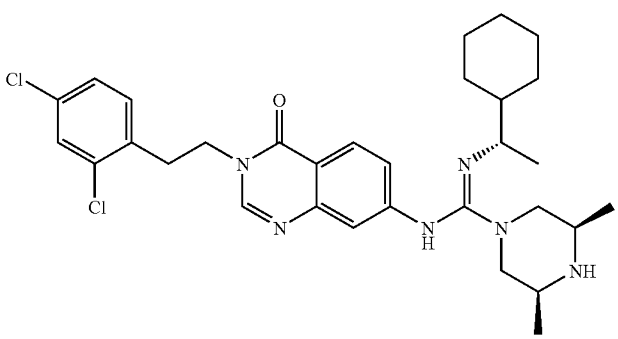 | (3R,5S)-N'-[(1S)-1-cyclohexylethyl]-N-{3-[2-(2,4-dichlorophenyl)ethyl]-4-oxo-3,4-dihydroquinazolin-7-yl}-3,5-dimethylpiperazine-1-carboximidamide | 583.1 |
| 161 | 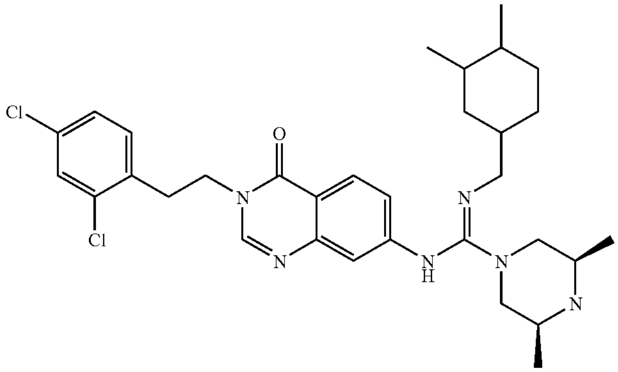 | (3R,5S)-N-{3-[2-(2,4-dichlorophenyl)ethyl]-4-oxo-3,4-dihydroquinazolin-7-yl}-N'-(2,3-dimethylcyclohexyl)-3,5-dimethylpiperazine-1-carboximidamide | 583.1 |

-continued

| No. | Structure | Name | MH+ |
|---|---|---|---|
| 162 | 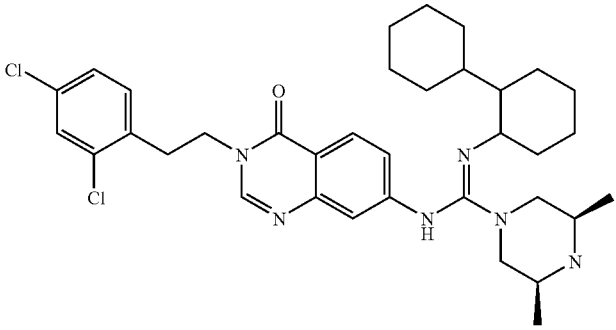 | (3R,5S)-N'-[1,1-bi(cyclohexyl)-2-yl]-N-{3-[2-(2,4-dichlorophenyl)ethyl]-4-oxo-3,4-dihydroquinazolin-7-yl}-3,5-dimethylpiperazine-1-carboximidamide | 637.2 |
| 163 | 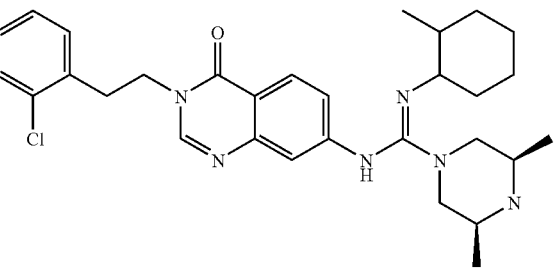 | (3R,5S)-N-{3-[2-(2,4-dichlorophenyl)ethyl]-4-oxo-3,4-dihydroquinazolin-7-yl}-3,5-dimethyl-N'-(2-methylcyclohexyl)piperazine-1-carboximidamide | 569.2 |
| 164 | 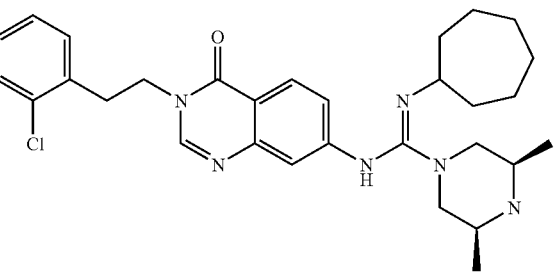 | (3R,5S)-N'-cycloheptyl-N-{3-[2-(2,4-dichlorophenyl)ethyl]-4-oxo-3,4-dihydroquinazolin-7-yl}-3,5-dimethylpiperazine-1-carboximidamide | 637.0 |
| 165 | 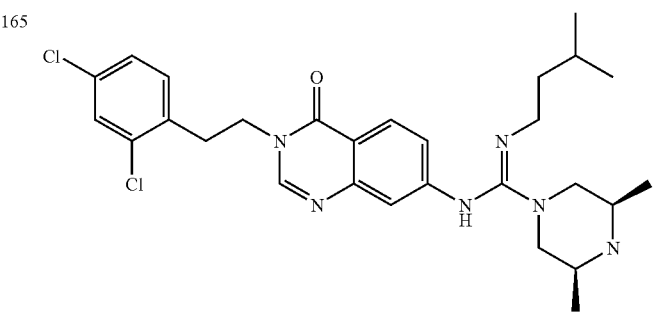 | (3R,5S)-N-{3-[2-(2,4-dichlorophenyl)ethyl]-4-oxo-3,4-dihydroquinazolin-7-yl}-N'-isopentyl-3,5-dimethylpiperazine-1-carboximidamide | 543.0 |
| 166 | 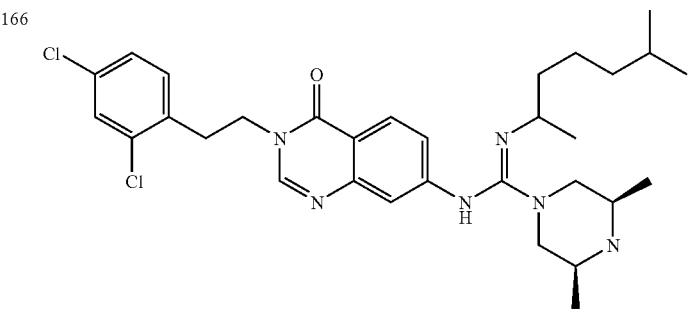 | (3R,5S)-N-{3-[2-(2,4-dichlorophenyl)ethyl]-4-oxo-3,4-dihydroquinazolin-7-yl}-N'-(1,5-dimethylhexyl)-3,5-dimethylpiperazine-1-carboximidamide | 585.1 |

-continued

| No. | Structure | Name | MH+ |
|---|---|---|---|
| 167 | 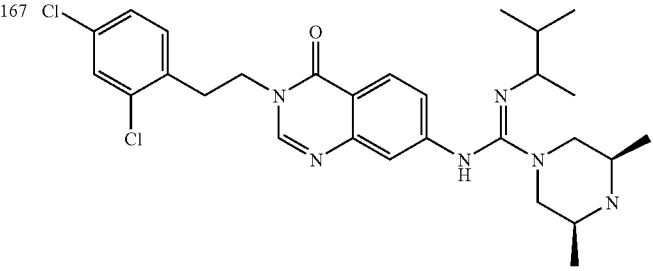 | (3R,5S)-N-{3-[2-(2,4-dichlorophenyl)ethyl]-4-oxo-3,4-dihydroquinazolin-7-yl}-N'-(1,2-dimethylpropyl)-3,5-dimethylpiperazine-1-carboximidamide | 543.0 |
| 168 | 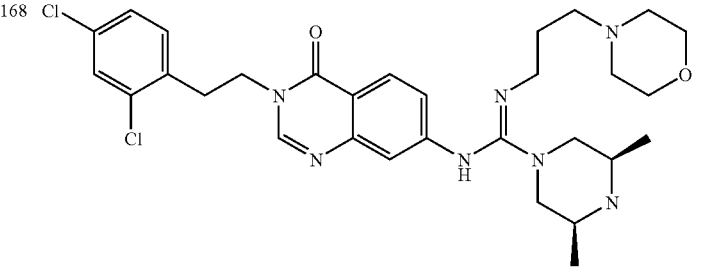 | (3R,5S)-N-{3-[2-(2,4-dichlorophenyl)ethyl]-4-oxo-3,4-dihydroquinazolin-7-yl}-3,5-dimethyl-N'-(3-morpholin-4-ylpropyl)piperazine-1-carboximidamide | 600.1 |
| 169 | 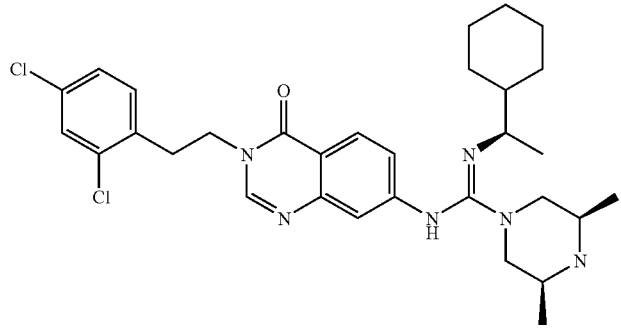 | (3R,5S)-N'-[(1R)-1-cyclohexylethyl]-N-{3-[2-(2,4-dichlorophenyl)ethyl]-4-oxo-3,4-dihydroquinazolin-7-yL}-3,5-dimethylpiperazine-1-carboximidamide | 583.1 |
| 170 | 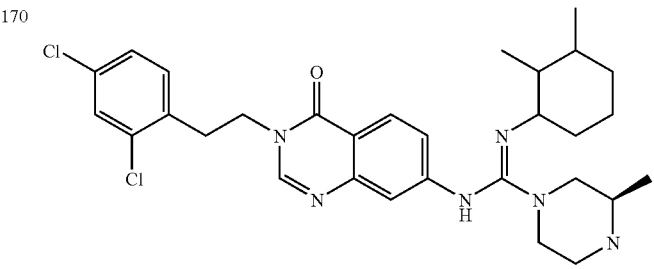 | (3R)-N-{3-[2-(2,4-dichlorophenyl)ethyl]-4-oxo-3,4-dihydroquinazolin-7-yl}-N'-(2,3-dimethylcyclohexyl)-3-methylpiperazine-1-carboximidamide | 569.0 |
| 171 | 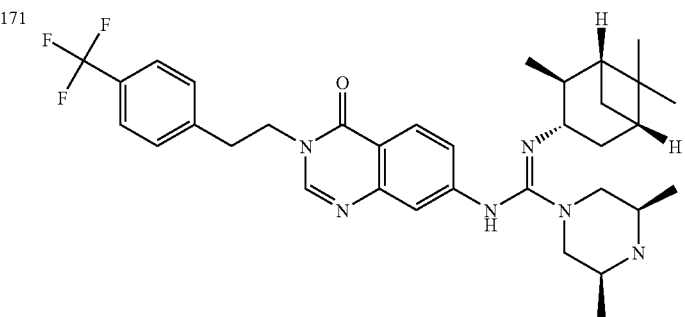 | (3R,5S)-3,5-dimethyl-N-(4-oxo-3-{2-[4-(trifluoromethyl)-phenyl]ethyl}-3,4-dihydroquinazoiin-7-yl)-N'-[(1R,2S,3S,5S)-2,6,6-trimethylbicyclo[3.1.1]hept-3-yl]piperazine-1-carboximidamide | 607.3 |

-continued

| No. | Structure | Name | MH+ |
|---|---|---|---|
| 172 | 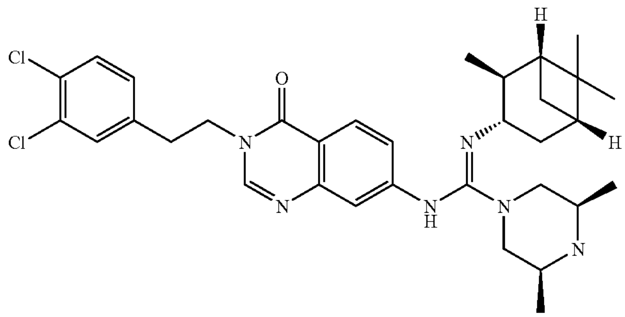 | (3R,5S)-N-{3-[2-(3,4-dichlorophenyl)ethyl]-4-oxo-3,4-dihydroquinazolin-7-yl}-[3,5-dimethyl-N'-[(1R,2S,3S,5S)-2,6,6-trimethyl-bicyclo[3.1.1]hept-3-yl]piperazine-1-carboximidamide | 607.2 |
| 173 | 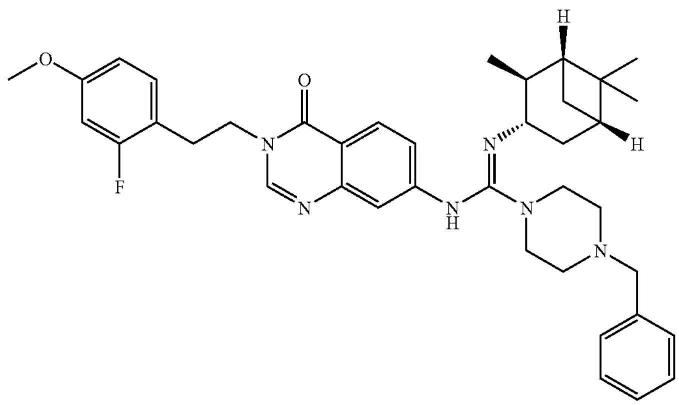 | N-(3-{2-[2-fluoro-4-(methyloxy)phenyl]ethyl}-4-oxo-3,4-dihydro-7-quinazolinyl)-4-(phenylmethyl)-N'-[(1R,2S,3S,5S)-2,6,6-trimethylbicyclo[3.1.1]hept-3-yl]-1-piperazinecarboximidamide | 651.4 |
| 174 | 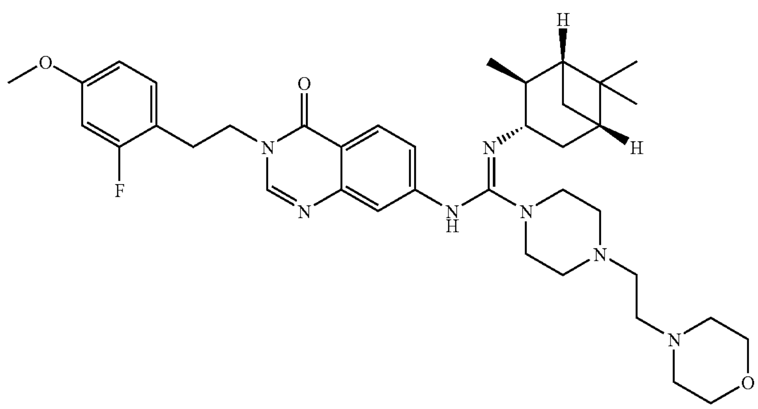 | (3-{2-[2-fluoro-4-(methyloxy)phenyl]ethyl}-4-oxo-3,4-dihydro-7-quinazolinyl)-4-[2-(4-morpholinyl)ethyl]-N'-[(1R,2S,3S,5S)-2,6,6-trimethylbicyclo[3.1.1]hept-3-yl]-1-piperazinecarboximidamide | 673.7 |
| 175 | 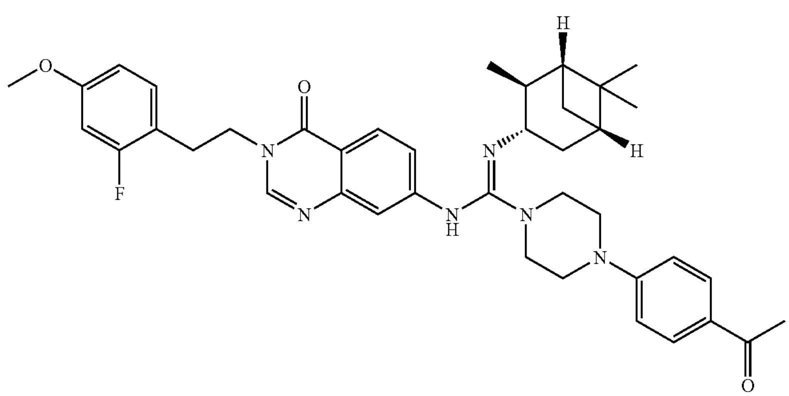 | 4-(4-acetylphenyl)-N-(3-{2-[2-fluoro-4-(methyloxy)phenyl]ethyl}-4-oxo-3,4-dihydro-7-quinazolinyl)-N'-[(1R,2S,3S,5S)-2,6,6-trimethyl-bicyclo]3.1.1]hept-3-yl]-1-piperazinecarboximidamide | 679.5 |

-continued

| No. | Structure | Name | MH+ |
|---|---|---|---|
| 176 | 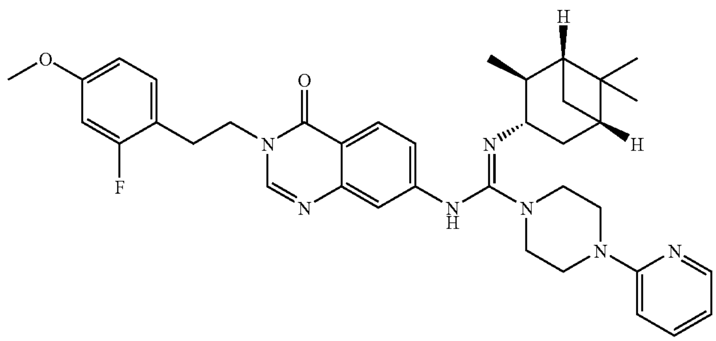 | N-(3-{2-(2-fluoro-4-(methyloxy)phenyl]ethyl}-4-oxo-3,4-dihydro-7-quinazolinyl)-4-(2-pyridinyl)-N'-[(1R,2S,3S,5S)-2,6,6-trimethyl-bicyclo[3.1.1]hept-3-yl]-1-piperazinecarboximidamide | 637.6 |
| 177 | 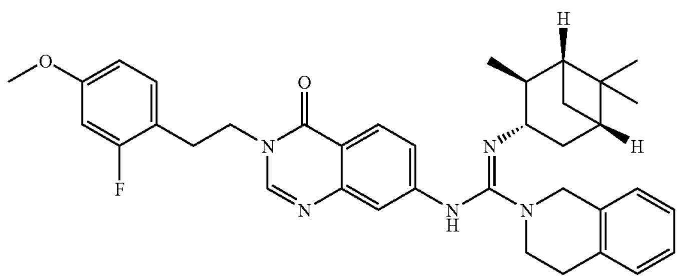 | N-(3-{2-[2-fluoro-4-(methyloxy)phenyl]ethyl}-4-oxo-3,4-dihydro-7-quinazolinyl)-N'-[(1R,2S,3S,5S)-2,6,6-trimethyl-bicyclo[3.1.1]hept-3-yl]-3,4-dihydro-2(1H)-isoquinolinecarboximidamide | 607.7 |
| 178 | 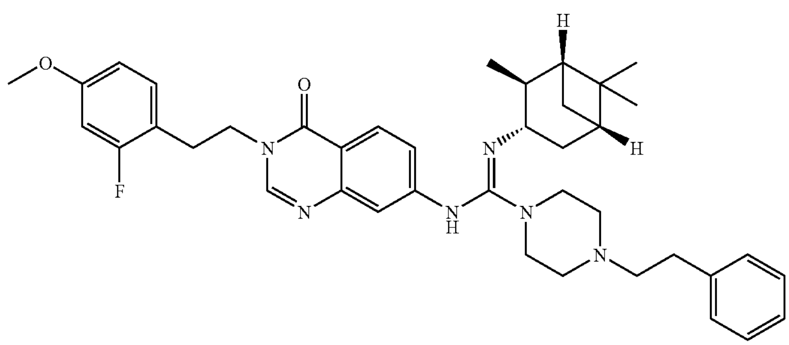 | N-(3-{2-[2-fluoro-4-(methyloxy)phenyl]ethyl}-4-oxo-3,4-dihydro-7-quinazolinyl)-4-(2-phenylethyl)-N'-[(1R,2S,3S,5S)-2,6,6-trimethyl-bicyclo(3.1.1]hept-3-yl]-1-piperazinecarboximidamide | 664.8 |
| 179 | 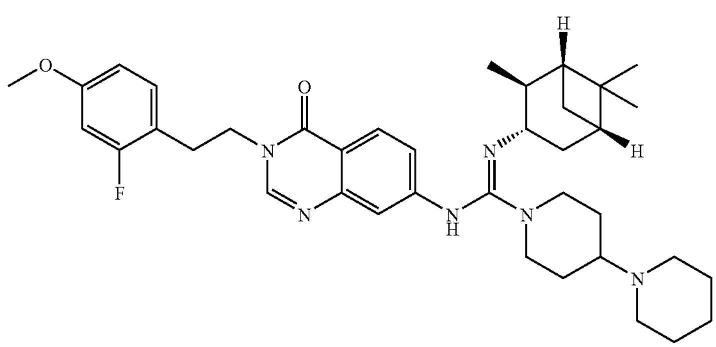 | N-(3-{2-[2-fluoro-4-(methyloxy)phenyl]ethyl}-4-oxo-3,4-dihydro-7-quinazolinyl)-N'-[(1R,2S,3S,5S)-2,6,6-trimethyl-bicyclo[3.1.1]hept-3-yl]-1,4'-bipiperidine-1'-carboximidamide | 642.7 |
| 180 | 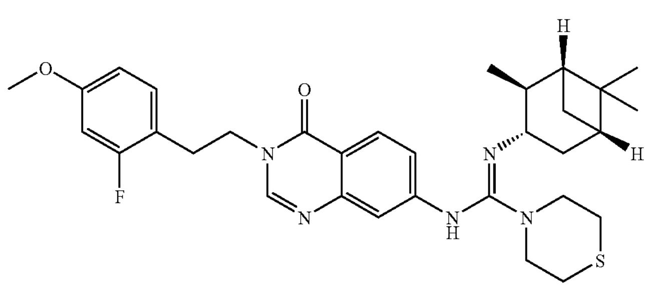 | N-(3-{2-(2-fluoro-4-(methyloxy)phenyl]ethyl}-4-oxo-3,4-dihydro-7-quinazolinyl)-N'-[(1R,2S,3S,5S)-2,6,6-trimethylbicyclo[3.1.1]hept-3-yl]-4-thiomorpholine-carboximidamide | 577.6 |

-continued

| No. | Structure | Name | MH+ |
|---|---|---|---|
| 181 | 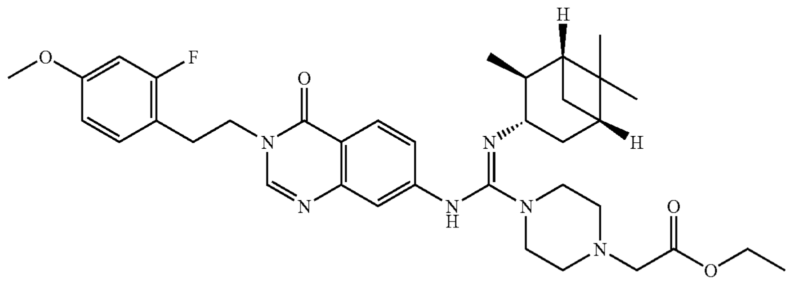 | ethyl[4-((Z)-[(3-{2-[2-fluoro-4-(methyloxy)phenyl]ethyl}-4-oxo-3,4-dihydro-7-quinazolinyl)amino]-[(1R,2S,5S)-2,6,6-trimethylbicyclo[3.1.1]hept-3-yl]imino}methyl)-1-piperazinyl]acetate | 647.3 |
| 182 | 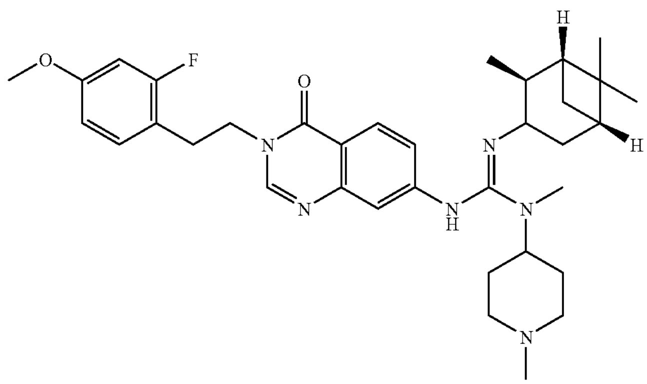 | N'-(3-{2-[2-fluoro-4-(methyloxy)phenyl]ethyl}-4-oxo-3,4-dihydro-7-quinazolinyl)-N-methyl-N-(1-methyl-4-piperidinyl)-N'-[(1R,2S,5S)-2,6,6-trimethyl-bicyclo[3.1.1]hept-3-ylguanidine | 603.3 |
| 183 | 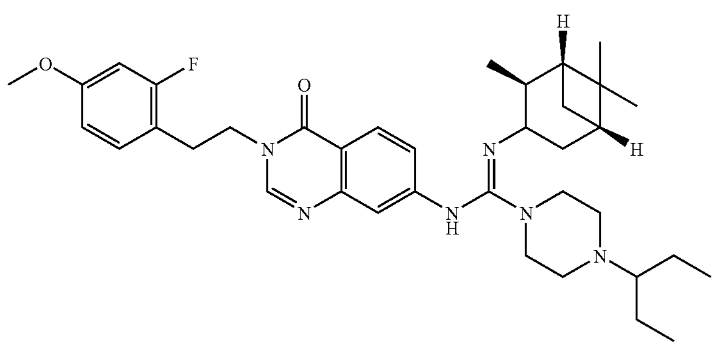 | 4-(1-ethylpropyl)-N-(3-{2-[2-fluoro-4-(methyloxy)phenyl]-ethyl}-4-oxo-3,4-dihydro-7-quinazolinyl)-N'-[(1R,2S,5S)-2,6,6-trimethyl-bicyclo[3.1.1]hept-3-yl]-1-piperazinecarboximidamide | 631.4 |
| 184 | 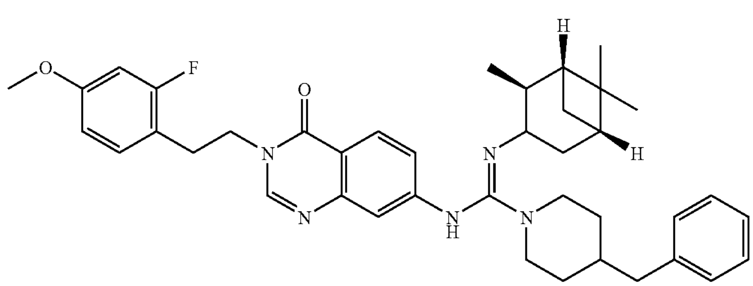 | N-(3-{2-[2-fluoro-4-(methyloxy)phenyl]ethyl}-4-oxo-3,4-dihydro-7-quinazolinyl)-4-(phenylmethyl)-N'-[(1R,2S,5S)-2,6,6-trimethylbicyclo[3.1.1]hept-3-yl]-1-piperidinecarboximidamide | 650.3 |

-continued

| No. | Structure | Name | MH+ |
|---|---|---|---|
| 185 | 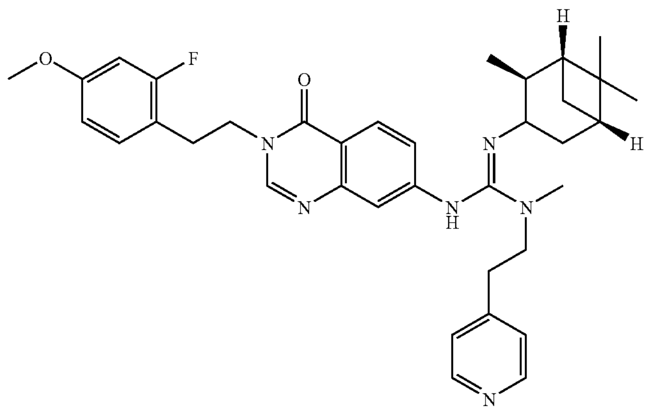 | N'-(3-{2-[2-fluoro-4-(methyloxy)phenyl]ethyl}-4-oxo-3,4-dihydro-7-quinazolinyl)-N-methyl-N-[2-(4-pyridinyl)ethyl]-N''-[(1R,2S,5S)-2,6,6-trimethylbicyclo[3.1.1]hept-3-yl]guanidine | 611.3 |
| 186 | 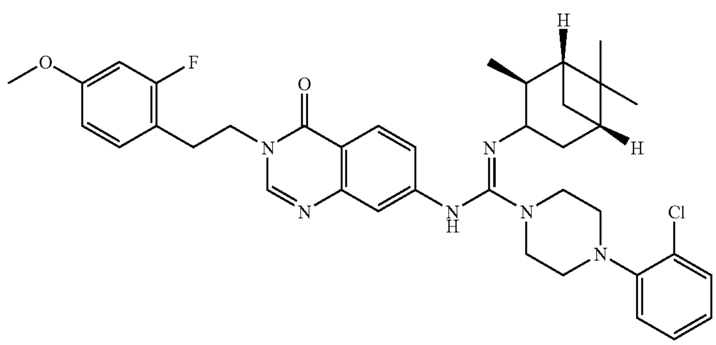 | 4-(2-chlorophenyl)-N-(3-{2-[2-fluoro-4-(methyloxy)-phenyl]ethyl}-4-oxo-3,4-dihydro-7-quinazolinyl)-N'-[(1R,2S,5S)-2,6,6-trimethyl-bicyclo[3.1.1]hept-3-yl]-1-piperazinecarboximidamide | 671.3 |
| 187 | 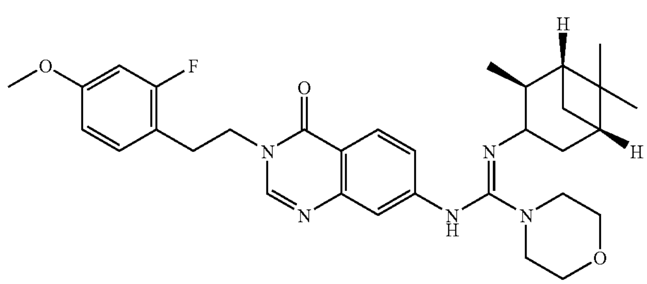 | N-(3-{2-[2-fluoro-4-(methyloxy)phenyl]ethyl}-4-oxo-3,4-dihydro-7-quinazolinyl)-N'-[(1R,2S,5S)-2,6,6-trimethyibicyclo[3.1.1]hept-3-yl]-4-morpholinecarboximidamide | 562.3 |
| 188 | 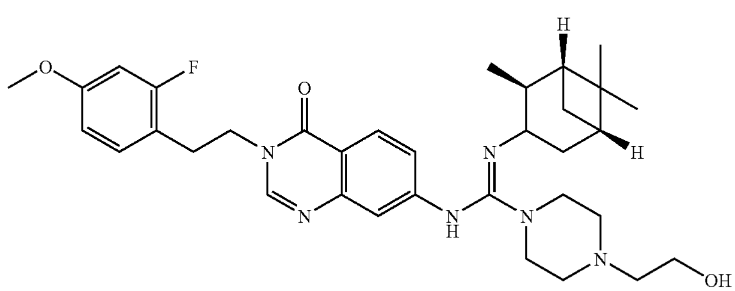 | N-(3-{2-[2-fluoro-4-(methyloxy)phenyl]ethyl}-4-oxo-3,4-dihydro-7-quinazolinyl)-4-(2-hydroxyethyl)-N'-[(1R,2S,5S)-2,6,6-trimethylbicyclo[3.1.1]hept-3-yl]-1-piperazinecarboximidamide | 605.3 |

-continued

| No. | Structure | Name | MH+ |
|---|---|---|---|
| 189 | 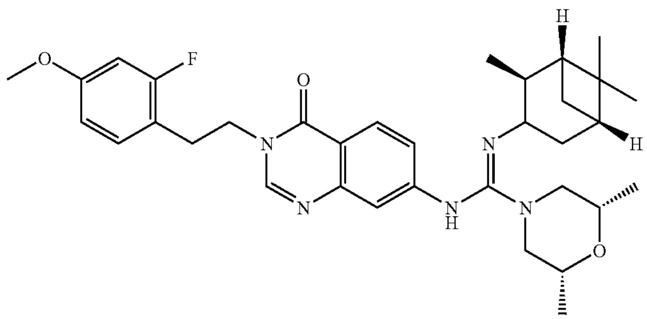 | (2R,6S)-N-(3-{2-[2-fluoro-4-(methyloxy)phenyl]ethyl}-4-oxo-3,4-dihydro-7-quinazolinyl)-2,6-dimethyl-N'-[(1R,2S,5S)-2,6,6-trimethylbicyclo[3.1.1]hept-3-yl]-4-morpholinecarboximidamide | 590.3 |
| 190 | 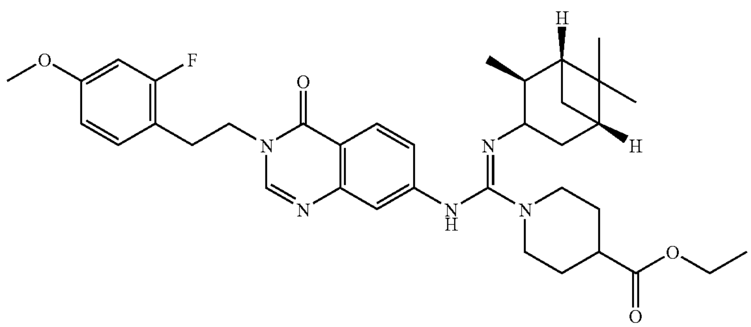 | ethyl 1-((Z)-[(3-{2-[2-fluoro-4-(methyloxy)phenyl]ethyl}-4-oxo-3,4-dihydro-7-quinazolinyl)amino[{[(1R,2S,5S)-2,6,6-trimethylbicyclo[3.1.1]hept-3-yl]imino}methyl)-4-piperidinecarboxylate | 632.3 |
| 191 | 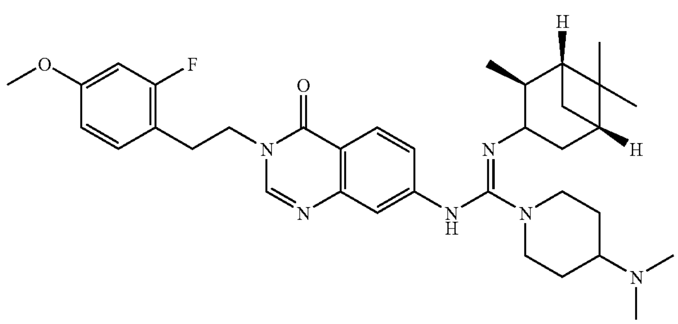 | 4-(dimethylamino)-N-(3-{2-[2-fluoro-4-(methyloxy)phenyl]ethyl}-4-oxo-3,4-dihydro-7-quinazolinyl)-N'-[(1R,2S,5S)-2,6,6-trimethylbicyclo[3.1.1]hept-3-yl]-1-piperidinecarboximidamide | 603.3 |
| 192 | 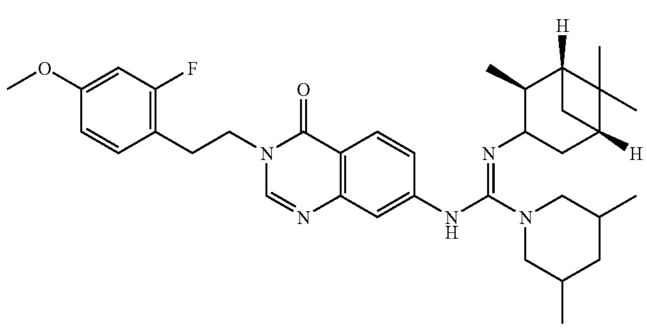 | N-(3-{2-[2-fluoro-4-(methyloxy)phenyl]ethyl}-4-oxo-3,4-dihydro-7-quinazolinyl)-3,5-dimethyl-N'-[(1R,2S,5S)-2,6,6-trimethylbicyclo[3.1.1]hept-3-yl]-1-piperidinecarboximidamide | 588.3 |

-continued

| No. | Structure | Name | MH+ |
|-----|-----------|------|-----|
| 193 | 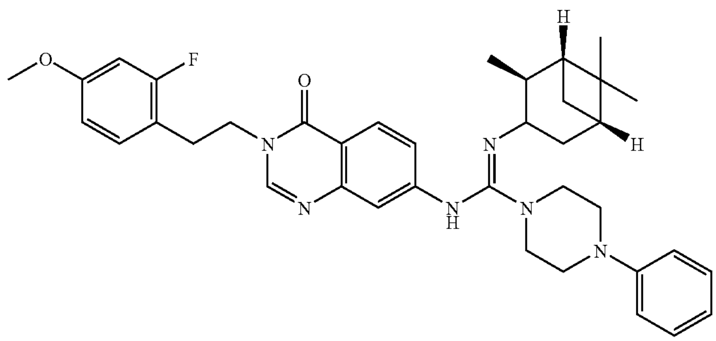 | N-(3-{2-[2-fluoro-4-(methyloxy)phenyl]ethyl}-4-oxo-3,4-dihydro-7-quinazolinyl)-4-phenyl-N'-[(1R,2S,5S)-2,6,6-trimethylbicyclo[3.1.1]hept-3-yl]-1-piperazinecarboximidamide | 637.3 |
| 194 | 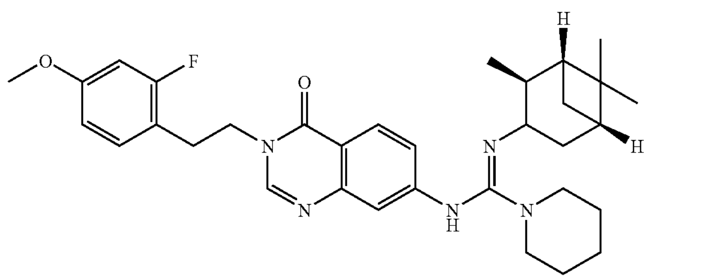 | N-(3-{2-[2-fluoro-4-(methyloxy)phenyl]ethyl}-4-oxo-3,4-dihydro-7-quinazolinyl)-N'-[(1R,2S,5S)-2,6,6-trimethyibicyclo[3.1.1]hept-3-yl]-1-piperidinecarboximidamide | 560.3 |
| 195 | 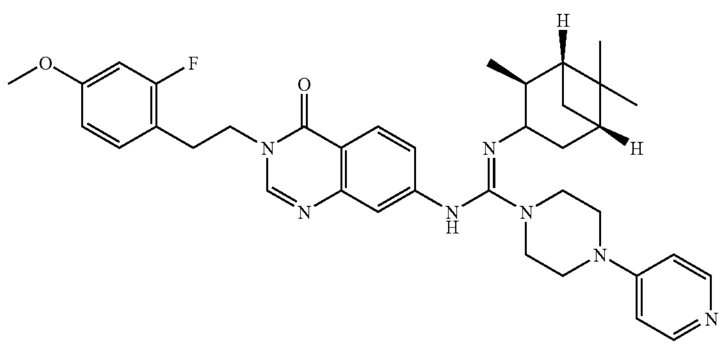 | N-(3-{2-[2-fluoro-4-(methyloxy)phenyl]ethyl}-4-oxo-3,4-dihydro-7-quinazolinyl)-4-(4-pyridinyl)-N'-[(1R,2S,5S)-2,6,6-trimethylbicyclo[3.1.1]hept-3-yl]-1-piperazinecarboximidamide | 636.7 |
| 196 | 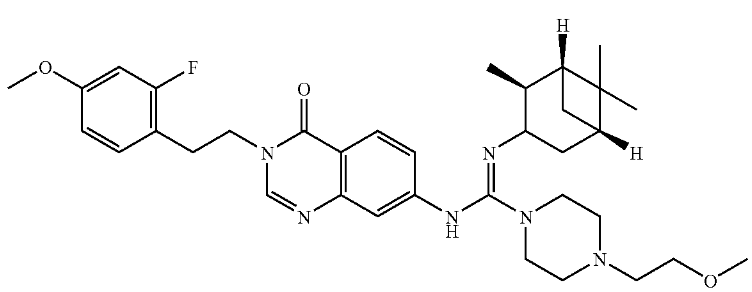 | N-(3-{2-[2-fluoro-4-(methyloxy)phenyl]ethyl}-4-oxo-3,4-dihydro-7-quinazolinyl)-4-[2-(methyloxy)ethyl]-N'-[(1R,2S,5S)-2,6,6-trimethylbicyclo[3.1.1]hept-3-yl]-1-piperazinecarboximidamide | 619.3 |
| 197 | 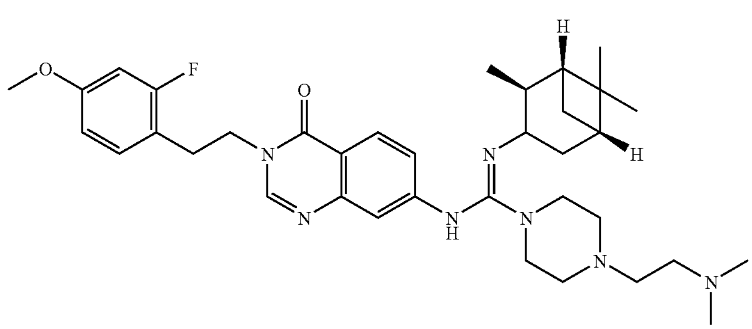 | 4-[2-(dimethylamino)ethyl]-N-(3-{2-[2-fluoro-4-(methyloxy)-phenyl]ethyl}-4-oxo-3,4-dihydro-7-quinazolinyl)-N'-[(1R,2S,5S)-2,6,6,-trimethyl-bicyclo[3.1.1]hept-3-yl]-1-piperazinecarboximidamide | 632.4 |

-continued

| No. | Structure | Name | MH+ |
|---|---|---|---|
| 198 | 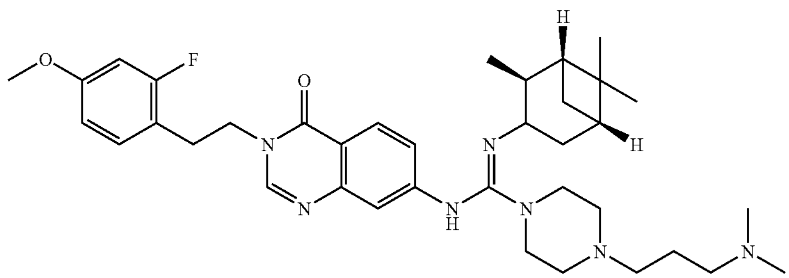 | 4-[3-(dimethylamino)propyl]-N-(3-{2-[2-fluoro-4-(methyloxy)-phenyl]ethyl}-4-oxo-3,4-dihydro-7-quinazolinyl)-N'-[(1R,2S,5S)-2,6,6-trimethyl-bicyclo[3.1.1]hept-3-yl]-1-piperazinecarboximidamide | 646.4 |
| 199 | 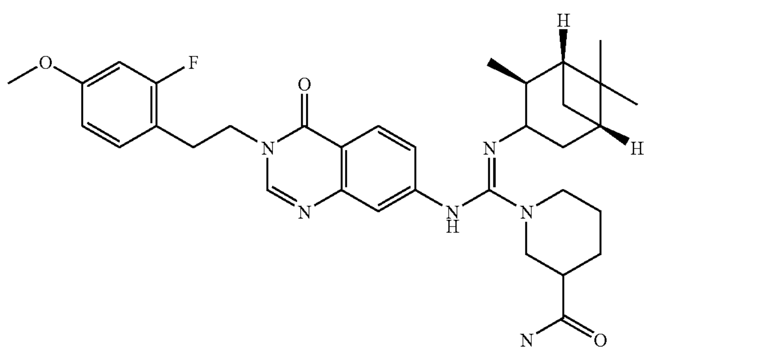 | 1-((Z)-[(3-{2-[2-fluoro-4-(methyloxy)-phenyl]ethyl}-4-oxo-3,4-dihydro-7-quinazolinyl)amino]{[(1R,2S,5S)-2,6,6-trimethyl-bicyclo[3.1.1]hept-3-yl]imino}methyl)-3-piperidinecarboxamide | 603.3 |
| 200 | 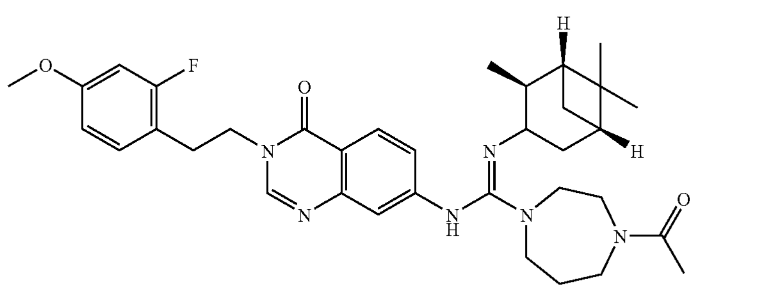 | 4-acetyl-N-(3-{2-[2-fluoro-4-(methyloxy)phenyl]ethyl}-4-oxo-3,4-dihydro-7-quinazolinyl)-N'(-[(1R,2S,5S)-2,6,6-trimethylbicyclo[3.1.1]hept-3-yl]hexahydro-1H-1,4-diazepine-1-carboximidamide | 617.3 |
| 201 | 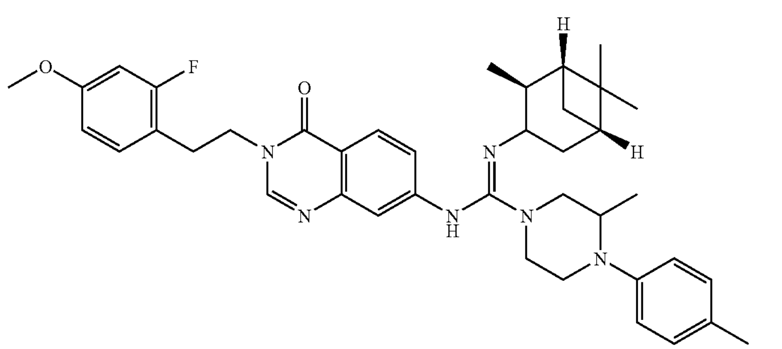 | N-(3-{2-[2-fluoro-4-(methyloxy)phenyl]ethyl}-4-oxo-3,4-dihydro-7-quinazolinyl)-3-methyl-4-(4-methylphenyl)-N'-[(1R,2S,5S)-2,6,6-trimethylbicyclo[3.1.1]hept-3-yl]-1-piperazinecarboximidamide | 665.4 |
| 202 | 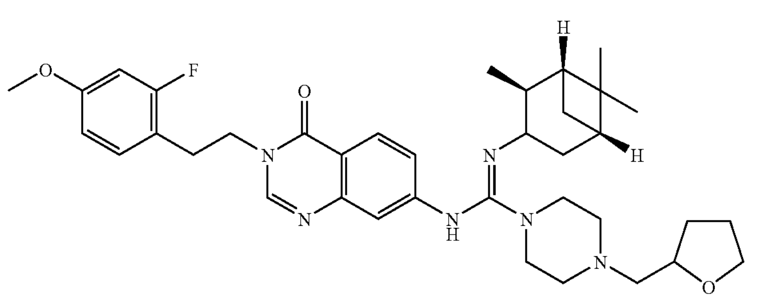 | N-(3-{2-[2-fluoro-4-(methyloxy)phenyl]ethyl}-4-oxo-3,4-dihydro-7-quinazolinyl)-4-(tetrahydro-2-furanylmethyl)-N'-[(1R,2S,5S)-2,6,6-trimethylbicyclo[3.1.1]hept-3-yl]-1-piperazinecarboximidamide | 645.4 |

-continued

| No. | Structure | Name | MH+ |
|---|---|---|---|
| 203 | 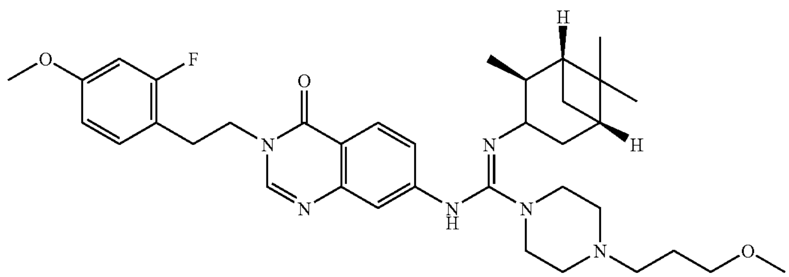 | N-(3-{2-[2-fluoro-4-(methyloxy)phenyl]ethyl}-4-oxo-3,4-dihydro-7-quinazolinyl)-4-[3-(methyloxy)propyl]-N'-[(1R,2S,5S)-2,6,6-trimethylbicyclo[3.1.1]hept-3-yl]-1-piperazinecarboximidamide | 628.4 |
| 204 | 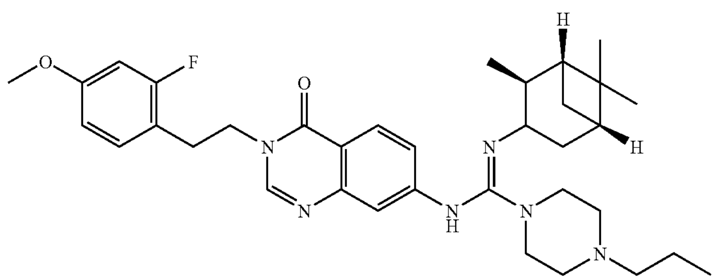 | N-(3-{2-[2-fluoro-4-(methyloxy)phenyl]ethyl}-4-oxo-3,4-dihydro-7-quinazolinyl)-4-propyl-N'-[(1R,2S,5S)-2,6,6-trimethylbicyclo[3.1.1]hept-3-yl]-1-piperazinecarboximidamide | 603.3 |
| 205 | 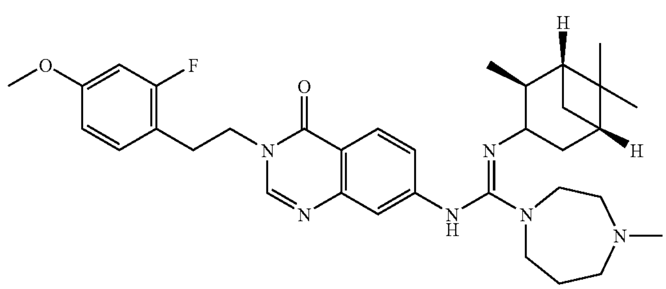 | N-(3-{2-[2-fluoro-4-(methyloxy)phenyl]ethyl}-4-oxo-3,4-dihydro-7-quinazlinyl)-4-methyl-N'-[(1R,2S,5S)-2,6,6-trimethylbicyclo[3.1.1]hept-3-yl]hexahydro-1H-1,4-diazepine-1-carboximidamide | 589.3 |
| 206 | 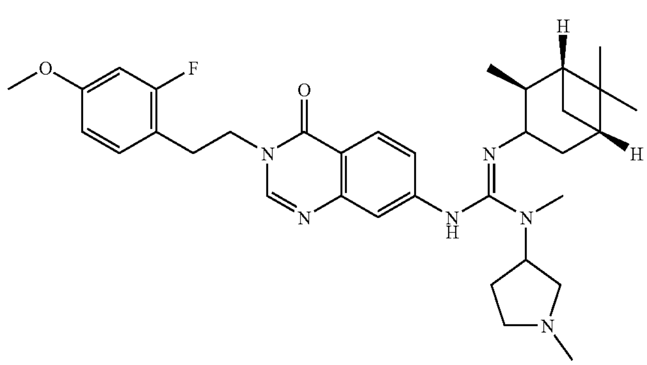 | N'-(3-{2-[2-fluoro-4-(methloxy)phenyl]ethyl}-4-oxo-3,4-dihydro-7-quinazolinyl-N-methy-N-N-(1-methyl-3-pyrrolidinyl)-N"-[(1R,2S,5S)-2,6,6-trimethyl-bicyclo[3.1.1]hept-3-yl]guanidine | 589.3 |

-continued

| No. | Structure | Name | MH+ |
|---|---|---|---|
| 207 | 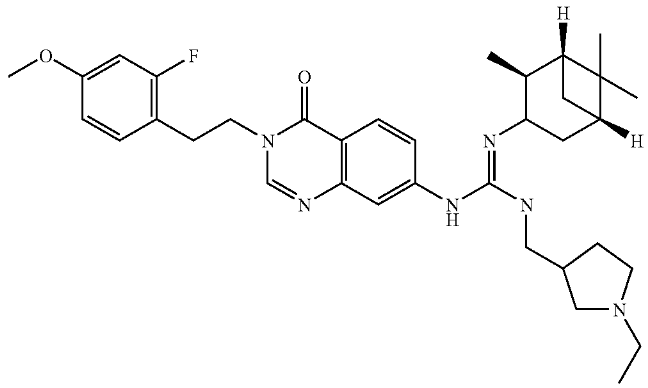 | N-[(1-ethyl-3-pyrrolidinyl)methyl]-N''-(3-{2-[2-fluoro-4-(methyloxy)phenyl]ethyl}-4-oxo-3,4-dihydro-7-quinazolinyl)-N''-[(1R,2S,5S)-2,6,6-trimethylbicyclo[3.1.1]hept-3-yl]guanidine | 603.3 |
| 208 | 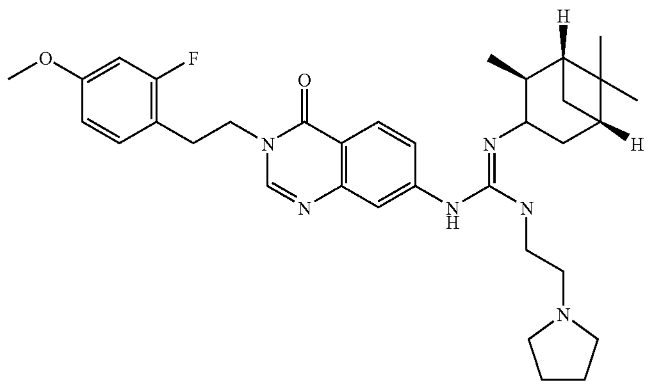 | N-(3-{2-[2-fluoro-4-(methyloxy)phenyl]ethyl}-4-oxo-3,4-dihydro-7-quinazolinyl)-N'-[2-(1-pyrrolidinyl)ethyl]-N''-[(1R,2S,5S)-2,6,6-trimethylbicyclo[3.1.1]hept-3-yl]guanidine | 589.3 |
| 209 | 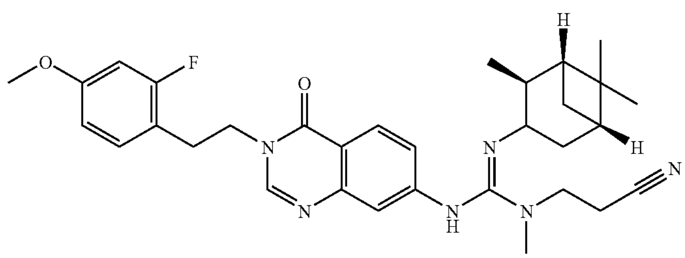 | N-(2-cyanoethyl)-N'-(3-{2-[2-fluoro-4-(methyloxy)phenyl]ethyl}-4-oxo-3,4-dihydro-7-quinazolinyl)-N-methyl-N''-[(1R,2S,5S)-2,6,6-trimethylbicyclo[3.1.1]hept-3-yl]guanidine | 559.2 |
| 210 | 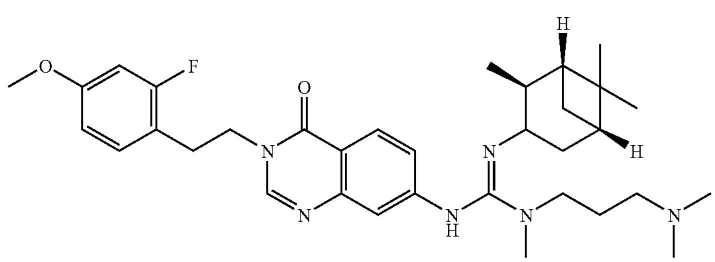 | N-[3-(dimethylamino)propyl]-N'-(3-{2-[2-fluoro-4-(methyloxy)-phenyl]ethyl}-4-oxo-3,4-dihydro-7-quinazolinyl)-N-methyl-N''-[(1R,2S,5S)-2,6,6-trimethylbicyclo[3.1.1]hept-3-yl]guanidine | 591.3 |
| 211 | 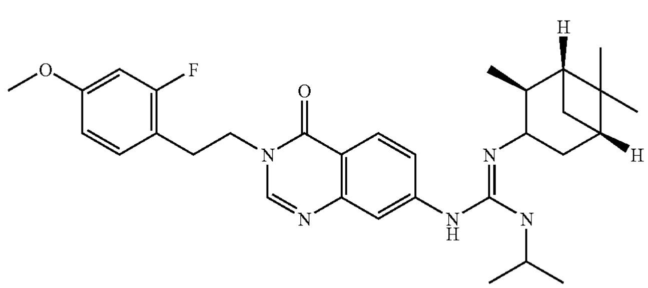 | N-(3-{2-[2-fluoro-4-(methyloxy)phenyl]ethyl}-4-oxo-3,4-dihydro-7-quinazolinyl)-N-(1-methylethyl)-N''-[(1R,2S,5S)-2,6,6-trimethylbicyclo[3.1.1]hept-3-yl]guanidine | 434.2 |

| No. | Structure | Name | MH+ |
|---|---|---|---|
| 212 | 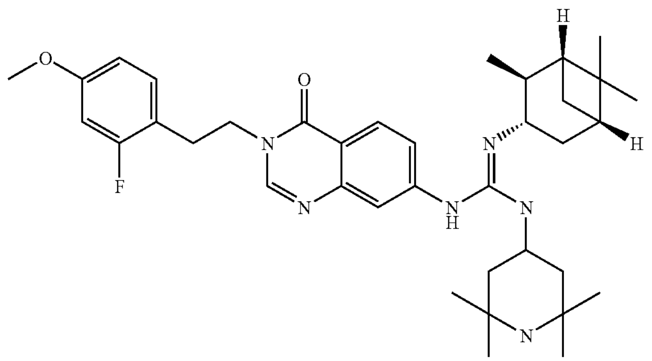 | N-(3-{2-[2-fluoro-4-(methyloxy)phenyl]ethyl}-4-oxo-3,4-dihydro-7-quinazolinyl)-N'-(2,2,6,6-tetramethyl-4-piperidinyl)-N"-[(1R,2S,3S,5S)-2,6,6-trimethyl-bicyclo[3.1.1]hept-3-yl]guanidine | 631.3 |
| 213 | 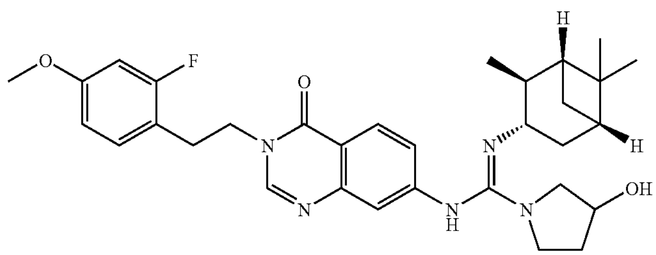 | N-(3-{2-[2-fluoro-4-(methyloxy)phenyl]ethyl}-4-oxo-3,4-dihydro-7-quinazolinyl)-3-hydroxy-N'-[(1R,2S,3S,5S)-2,6,6-trimethyl-bicyclo[3.1.1]hept-3-yl]-1-pyrrolidinecarboximidamide | 562.3 |
| 214 | 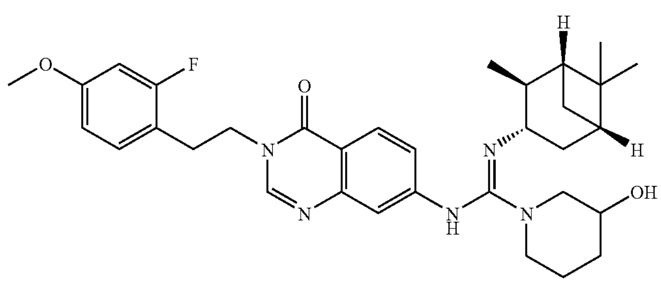 | N-(3-{2-[2-fluoro-4-(methyloxy)phenyl]ethyl}-4-oxo-3,4-dihydro-7-quinazolinyl)-3-hydroxy-N'-[(1R,2S,3S,5S)-2,6,6-trimethylbicyclo[3.1.1]hept-3-yl]-1-piperidinecarboximidamide | 576.3 |
| 215 | 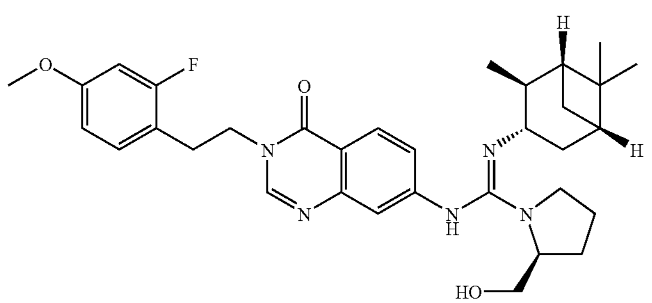 | (2S)-N-(3-{2-[2-fluoro-4-(methyloxy)phenyl]ethyl}-4-oxo-3,4-dihydro-7-quinazolinyl)-2-(hydroxymethyl)-N'-[(1R,2S,3S,5S)-2,6,6-trimethylbicyclo[3.1.1]hept-3-yl]-1-pyrrolidine-carboximidamide | 576.3 |

Table of Examples 216-258

| Ex. | Structure | Name | MH+ |
|---|---|---|---|
| 216 | 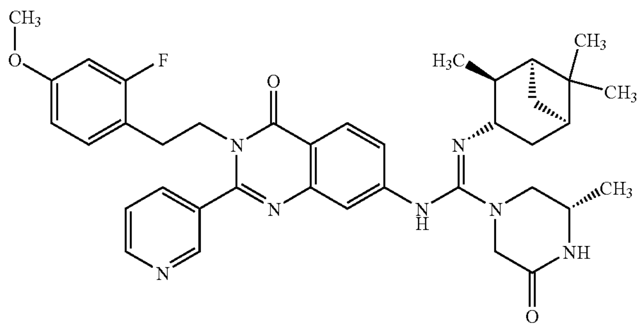 | (3S)-N-{3-[2-(2-fluoro-4-methoxyphenyl)ethyl]-4-oxo-2-pyridin-3-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 666.5 |
| 217 | 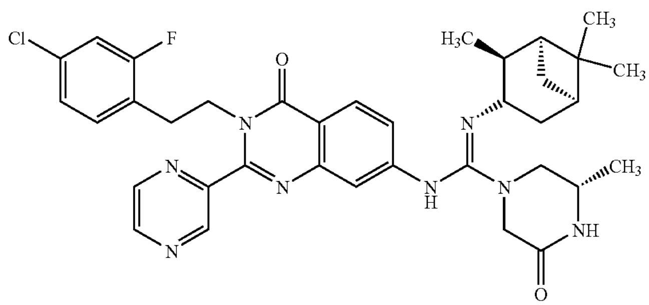 | (3S)-N-{3-[2-(4-chloro-2-fluorophenyl)ethyl]-4-oxo-2-pyrazin-2-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 671.3 |
| 218 | 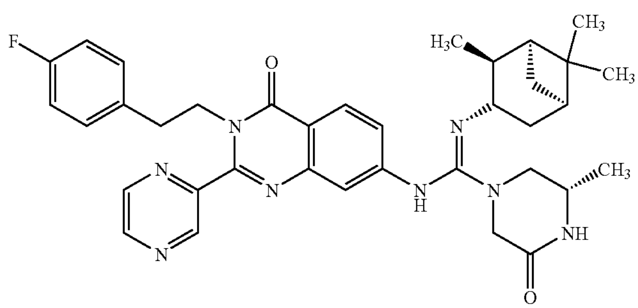 | (3S)-N-{3-[2-(4-fluorophenyl)ethyl]-4-oxo-2-pyrazin-2-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 637.4 |
| 219 | 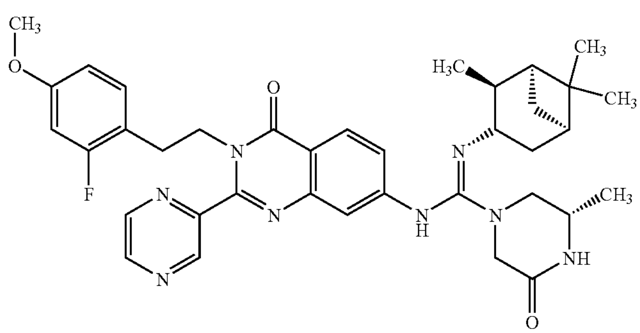 | (3S)-N-{3-[2-(2-fluoro-4-methoxyphenyl)ethyl]-4-oxo-2-pyrazin-2-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 667.5 |

-continued

| Ex. | Structure | Name | MH+ |
|---|---|---|---|
| 220 | 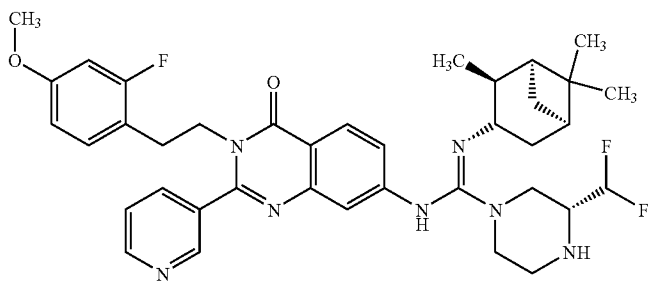 | (3R)-3-(difluoromethyl)-N-{3-[2-(2-fluoro-4-methoxyphenyl)ethyl]-4-oxo-2-pyridin-3-yl-3,4-dihydroquinazolin-7-yl}-N'-[(1S, 2S, 3S, 5R)-2,6,6-trimethylbicyclo[3.1.1]hept-3-yl]piperazine-1-carboximidamide | 688.3 |
| 221 | 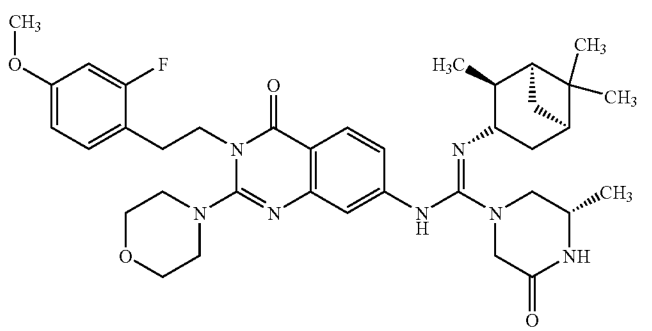 | (3S)-N-{3-[2-(2-fluoro-4-methoxyphenyl)ethyl]-2-morpholin-4-yl-4-oxo-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 674.6 |
| 222 | 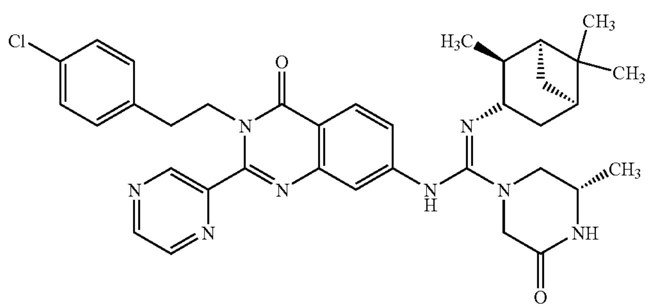 | (3S)-N-{3-[2-(4-chlorophenyl)ethyl]-4-oxo-2-pyrazin-2-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 653.5 |
| 223 | 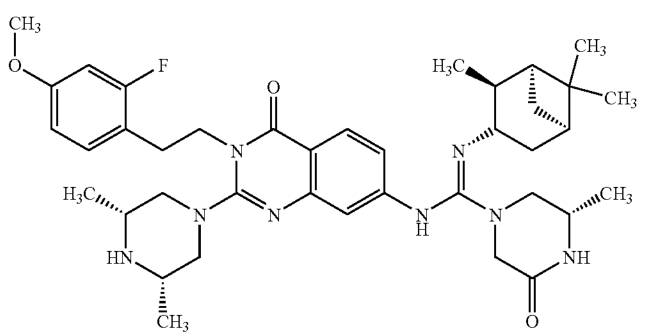 | (3S)-N-{2-[(3R, 5S)-3,5-dimethylpiperazin-1-yl]-3-[2-(2-fluoro-4-methoxyphenyl)ethyl]-4-oxo-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 701.5 |
| 224 | 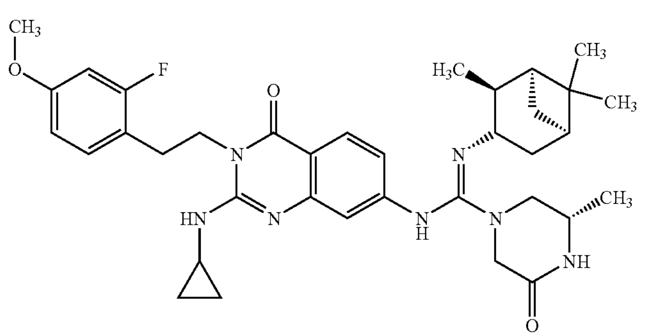 | (3S)-N-{2-(cyclopropylamino)-3-[2-(2-fluoro-4-methoxyphenyl)ethyl]-4-oxo-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 644.5 |

| Ex. | Structure | Name | MH+ |
| --- | --- | --- | --- |
| 225 | 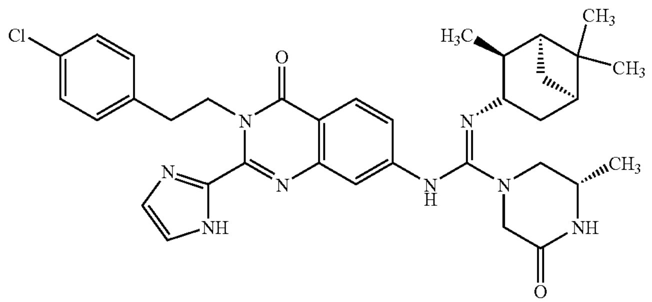 | (3S)-N-[3-[2-(4-chlorophenyl)ethyl]-2-(1H-imidazol-2-yl)-4-oxo-3,4-dihydroquinazolin-7-yl]-3-methyl-5-oxo-N'-[(1S, 2S, 3S, 5R)-2,6,6-trimethylbicyclo[3.1.1]hept-3-yl]piperazine-1-carboximidamide | 641.4 |
| 226 | 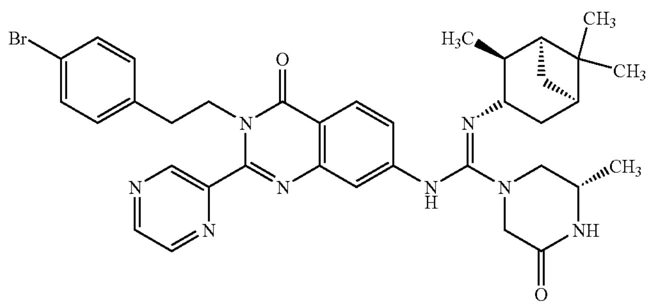 | (3S)-N-{3-[2-(4-bromophenyl)ethyl]-4-oxo-2-pyrazin-2-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 699.2 |
| 227 | 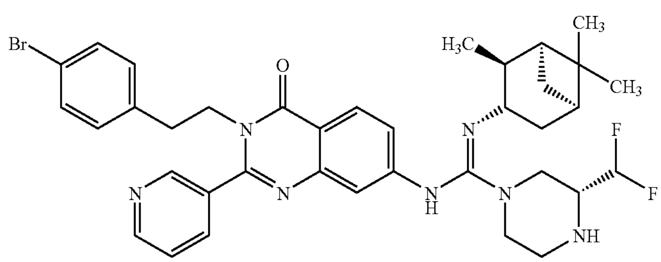 | (3R)-N-{3,-[2,-(4-bromophenyl)ethyl]-4-oxo-2-pyridin-3-yl-3,4-dihydroquinazolin-7-yl}-3-(difluoromethyl)-N'-[(1S, 2S, 3S, 5R)-2,6,6-trimethylbicyclo[3.1.1]hept-3-yl]piperazine-1-carboximidamide | 720.1 |
| 228 | 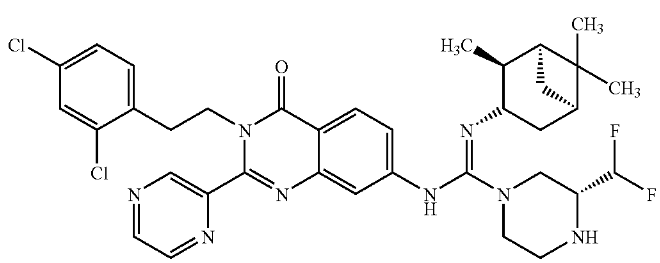 | (3R)-N-{3-[2-(2,4-dichlorophenyl)ethyl]-4-oxo-2-pyrazin-2-yl-3,4-dihydroquinazolin-7-yl}-3-(difluoromethyl)-N'-[(1S, 2S, 3S, 5R)-2,6,6-trimethylbicyclo[3.1.1]hept-3-yl]piperazine-1-carboximidamide | 709.5 |
| 229 | 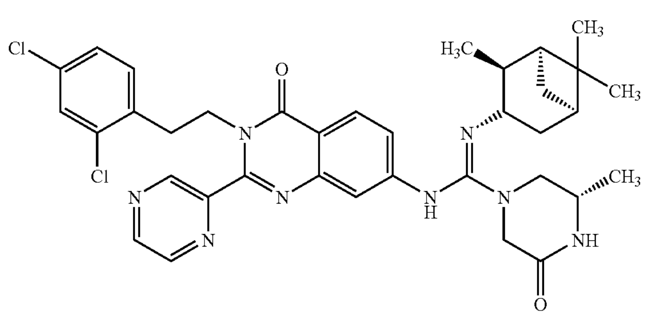 | (3S)-N-{3-[2-(2-dichlorophenyl)ethyl]-4-oxo-2-pyrazin-2-yl-3,4-dihydroquinazolin-7-yl}-3-methyl-5-oxo-N'-((1S, 2S, 3S, 5R)-2,6,6-trimethylbicyclo[3.1.1]hept-3-yl]piperazine-1-carboximidamide | 687.5 |

-continued

| Ex. | Structure | Name | MH+ |
|---|---|---|---|
| 230 | 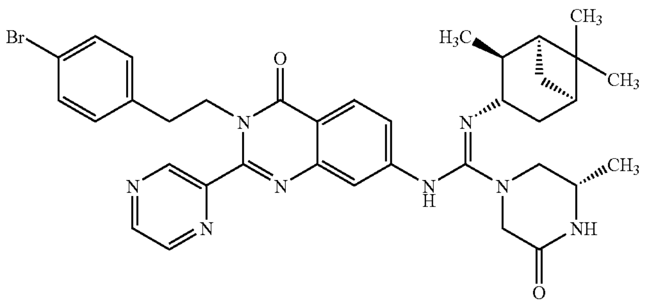 | (3S)-N-{3-[2-(4-bromophenyl)ethyl]-4-oxo-2-pyridin-3-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 696 |
| 231 | 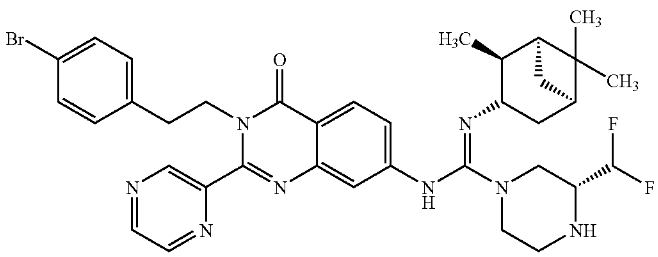 | (3R)-N-{3-[2-(4-bromophenyl)ethyl]-4-oxo-2-pyrazin-2-yl-3,4-dihydroquinazolin-7-yl}-3-(difluoromethyl)-N'-[(1S, 2S, 3S, 5R)-2,6,6-trimethylbicyclo[3.1.1]hept-3-yl]piperazine-1-carboximidamide | 719.4 |
| 232 | 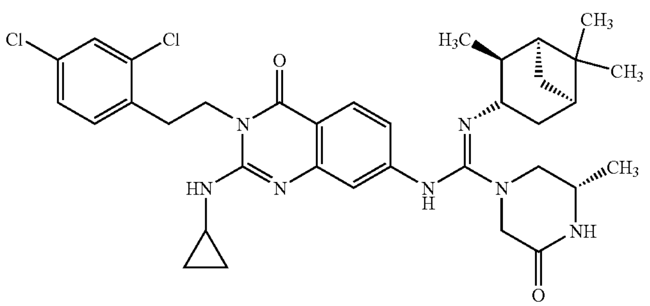 | (3S)-N-{2-(cyclopropylamino)-3-[2-(2,4-dichlorophenyl)ethyl]-4-oxo-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 664.4 |
| 233 | 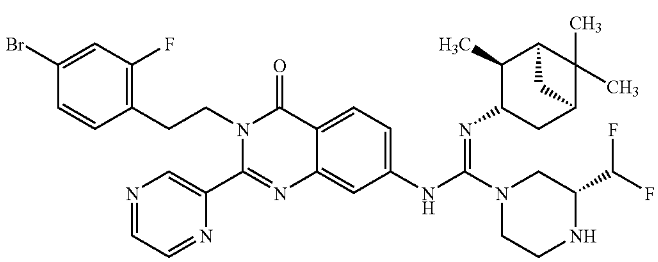 | (3R)-N-{3-[2-(4-bromo-2-fluorophenyl)ethyl]-4-oxo-2-pyrazin-2-yl-3,4-dihydroquinazolin-7-yl}-3-(difluoromethyl)-N'-[(1S, 2S, 3S, 5R)-2,6,6-trimethylbicyclo[3.1.1]hept-3-yl]piperazine-1-carboximidamide | 739.1 |
| 234 | 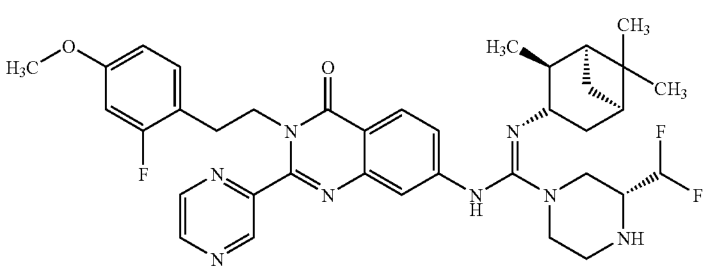 | (3R)-3-(difluoromethyl)-N-{3-[2-(2-fluoro-4-methoxyphenyl)ethyl]-4-oxo-2-pyrazin-2-yl-3,4-dihydroquinazolin-7-yl}-N'-((1S, 2S, 3S, 5R)-2,6,6-trimethylbicyclo[3.1.1]hept-3-yl]piperazine-1-carboximidamide | 689.5 |

-continued

| Ex. | Structure | Name | MH+ |
|---|---|---|---|
| 235 | 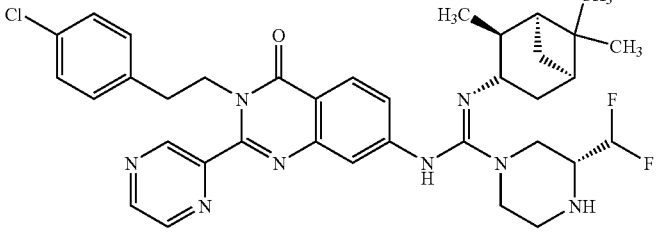 | (3R)-N-{3-[2-(4-chlorophenyl)ethyl]-4-oxo-2-pyrazin-2-yl-3,4-dihydroquinazolin-7-yl}-3-(difluoromethyl)-N'-[(1S, 2S, 3S, 5R)-2,6,6-trimethylbicyclo[3.1.1]hept-3-yl]piperazine-1-carboximidamide | 675.4 |
| 236 | 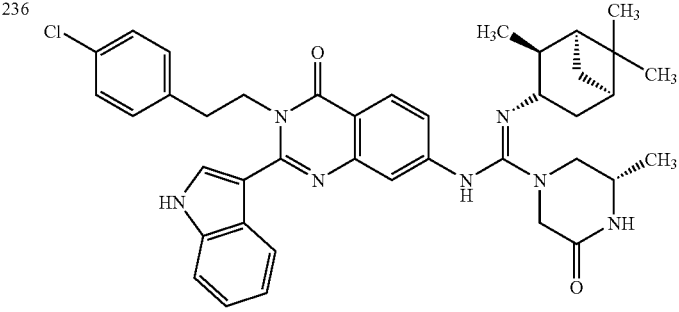 | (3S)-N-[3-[2-(4-chlorophenyl)ethyl]-2-(1H-indol-3-yl)-4-oxo-3,4-dihydroquinazolin-7-yl]-3-methyl-5-oxo-N'-[(1S, 2S, 3S, 5R)-2,6,6-trimethylbicyclo[3.1.1]hept-3-yl]piperazine-1-carboximidamide | 690.4 |
| 237 | 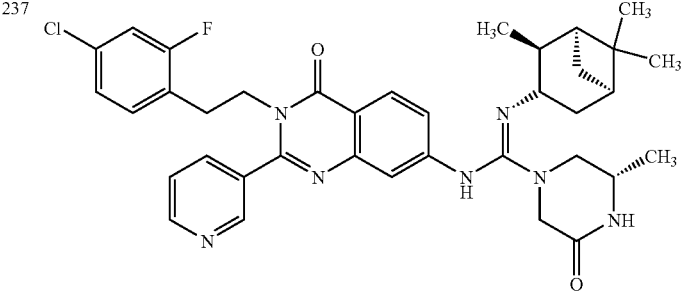 | (3S)-N-{3-[2-(4-chloro-2-fluorophenyl)ethyl]-4-oxo-2-pyridin-3-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 670.4 |
| 238 | 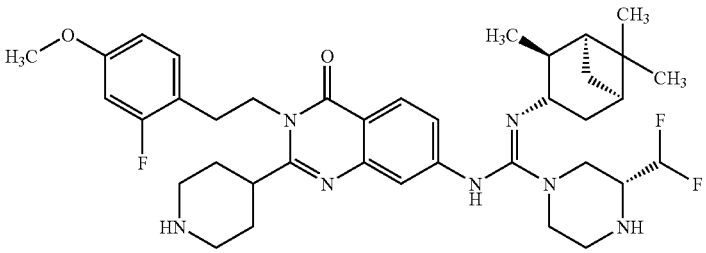 | (3R)-3-(difluoromethyl)-N-{3-[2-(2-fluoro-4-methoxyphenyl)ethyl]-4-oxo-2-piperidin-4-yl-3,4-dihydroquinazolin-7-yl}-N'-[(1S, 2S, 3S, 5R)-2,6,6-trimethylbicyclo[3.1.1]hept-3-yl]piperazine-1-carboximidamide | 694.6 |
| 239 | 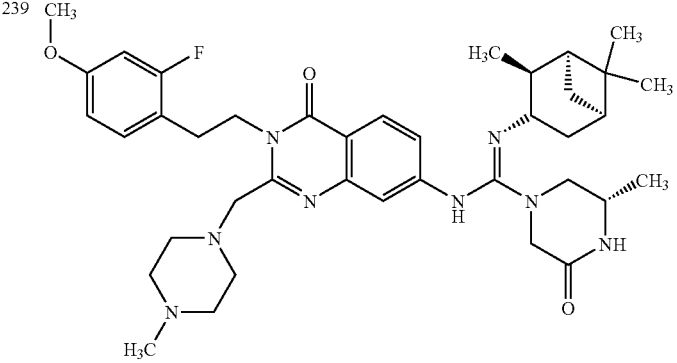 | (3S)-N-{3-[2-(2-fluoro-4-methoxyphenyl)ethyl]-2-[(4-methylpiperazin-1-yl)methyl]-4-oxo-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 701.6 |

-continued

| Ex. | Structure | Name | MH+ |
|---|---|---|---|
| 240 | 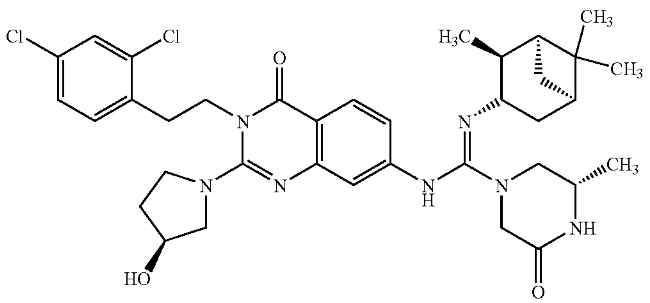 | (3S)-N-{3-[2-(4-dichlorophenyl)ethyl]-2-[(3S)-3-hydroxypyrrolidin-1-yl]-4-oxo-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 694.3 |
| 241 | 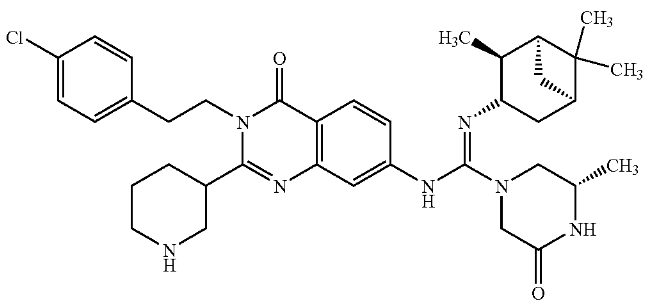 | (3S)-N-{3-[2-(4-chlorophenyl)ethyl]-4-oxo-2-piperidin-3-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 676.5 |
| 242 | 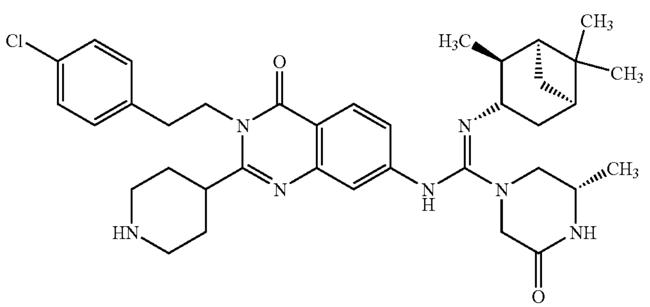 | (3S)-N-{3-[2-(4-chlorophenyl)ethyl]-4-oxo-2-piperidin-4-yl-3,4-dihydroquinazolin-7-yl}-3-methyl-5-oxo-N'-[(1S, 2S, 3S, 5R)-2,6,6-trimethylbicyclo[3.1.1]hept-3-yl]piperazine-1-carboximidamide | 658.5 |
| 243 | 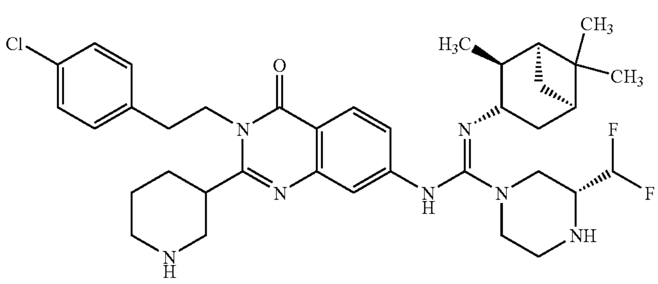 | (3R)-N-{3-[2-(4-chlorophenyl)ethyl]-4-oxo-2-piperidin-3-yl-3,4-dihydroquinazolin-7-yl}-3-(difluoromethyl)-N'-[(1S, 2S, 3S, 5R)-2,6,6-trimethylbicyclo[3.1.1]hept-3-yl]piperazine-1-carboximidamide | 680.5 |
| 244 | 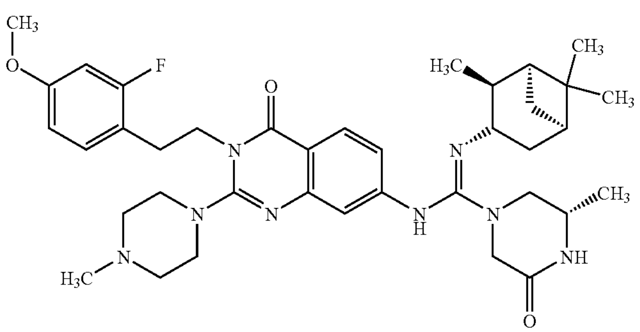 | (3S)-N-[3-[2-(2-fluoro-4-methoxyphenyl)ethyl]-2-(4-methylpiperazin-1-yl)-4-oxo-3,4-dihydroquinazolin-7-yl]-3-methyl-5-oxo-N'-[(1S, 2S, 3S, 5R)-2,6,6-trimethylbicyclo[3.1.1]hept-3-yl]piperazine-1-carboximidamide | 687.4 |

| Ex. | Structure | Name | MH+ |
|---|---|---|---|
| 245 | 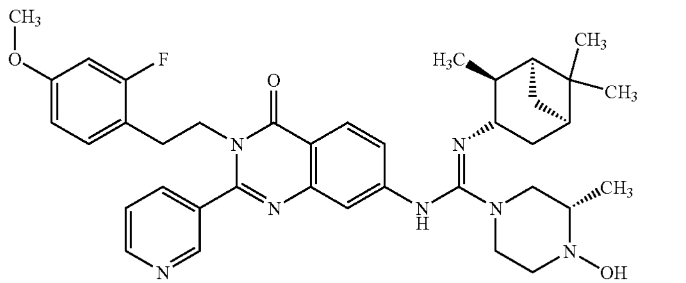 | (3S)-N-{3-[2-(2-fluoro-4-methoxyphenyl)ethyl]-4-oxo-2-pyridin-3-yl-3,4-dihydroquinazolin-7-yl}-4-hydroxy-3-methyl-N'-[(1S, 2S, 3S, 5R)-2,6,6-trimethylbicyclo[3.1.1]hept-3-yl]piperazine-1-carboximidamide | 668.5 |
| 246 | 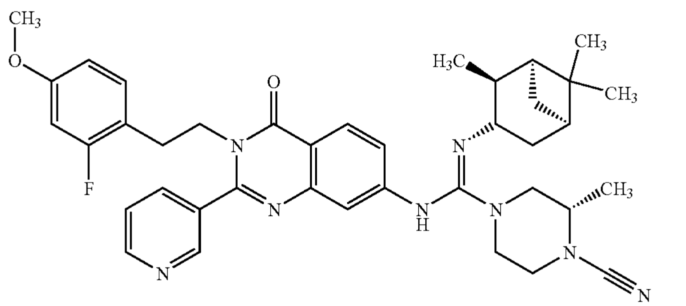 | (3S)-4-cyano-N-{3-[2-(2-fluoro-4-methoxyphenyl)ethyl]-4-oxo-2-pyridin-3-yl-3,4-dihydroquinazolin-7-yl}-3-methyl-N'-[(1S, 2S, 3S, 5R)-2,6,6-trimethylbicyclo[3.1.1]hept-3-yl]piperazine-1-carboximidamide | 677.5 |
| 247 | 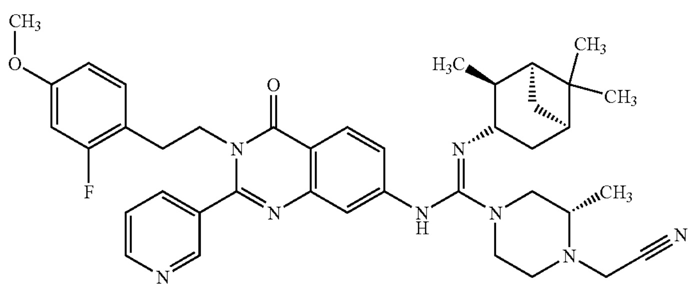 | (3S)-4-(cyanomethyl)-N-{3-[2-(2-fluoro-4-methoxyphenyl)ethyl]-4-oxo-2-pyridin-3-yl-3,4-dihydroquinazolin-7-yl}-3-methyl-N'-[(1S, 2S, 3S, 5R)-2,6,6-trimethylbicyclo[3.1.1]hept-3-yl]piperazine-1-carboximidamide | 691.5 |
| 248 | 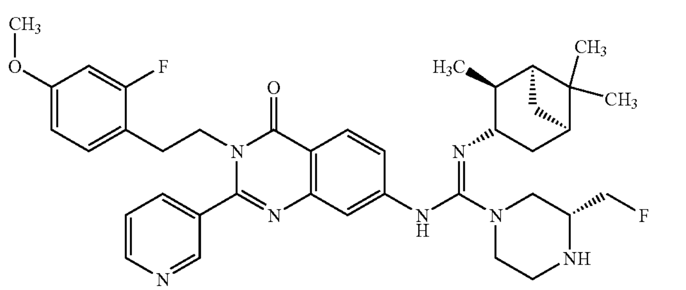 | (3R)-N-{3-[2-(2-fluoro-4-methoxyphenyl)ethyl]-4-oxo-2-pyridin-3-yl-3,4-dihydroquinazolin-7-yl}-3-(fluoromethyl)-N'-[(1S, 2S, 3S, 5R)-2,6,6-trimethylbicyclo[3.1.1]hept-3-yl]piperazine-1-carboximidamide | 670.6 |
| 249 | 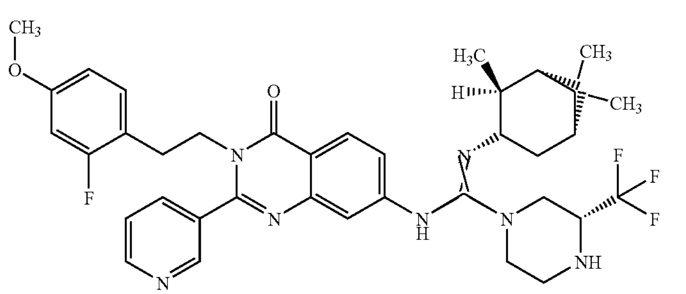 | (3R)-N-{3-[2-(2-fluoro-4-methoxyphenyl)ethyl]-4-oxo-2-pyridin-3-yl-3,4-dihydroquinazolin-7-yl}-3-(trifluoromethyl)-N'-[(1S, 2S, 3S, 5R)-2,6,6-trimethylbicyclo[3.1.1]hept-3-yl]piperazine-1-carboximidamide | 706.5 |

-continued

| Ex. | Structure | Name | MH+ |
| --- | --- | --- | --- |
| 250 | 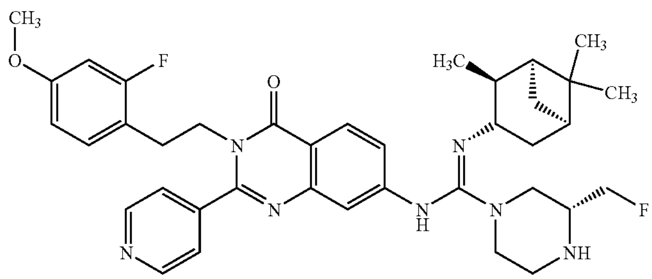 | (3R)-N-{3-[2-(2-fluoro-4-methoxyphenyl)ethyl]-4-oxo-2-pyridin-4-yl-3,4-dihydroquinazolin-7-yl}-3-(fluoromethyl)-N'-[(1S, 2S, 3S, 5R)-2,6,6-trimethylbicyclo[3.1.1]hept-3-yl]piperazine-1-carboximidamide | 670.5 |
| 251 | 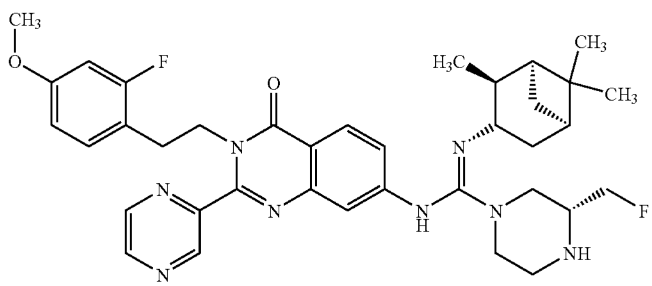 | (3R)-N-{3-[2-(2-fluoro-4-methoxyphenyl)ethyl]-4-oxo-2-pyrazin-2-yl-3,4-dihydroquinazolin-7-yl}-3-(fluoromethyl)-N'-[(1S, 2S, 3S, 5R)-2,6,6-trimethylbicyclo[3.1.1]hept-3-yl]piperazine-1-carboximidamide | 671.4 |
| 252 | 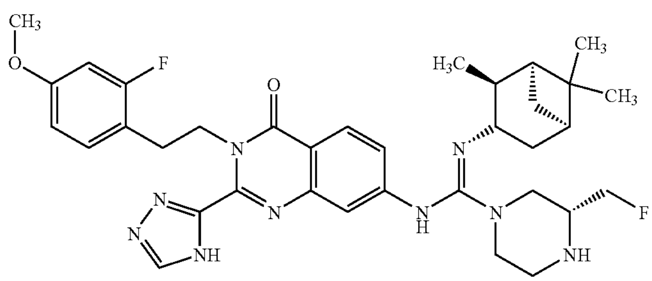 | (3R)-N-[3-[2-(2-fluoro-4-methoxyphenyl)ethyl]-4-oxo-2-(4H-1,2,4-triazol-3-yl)-3,4-dihydroquinazolin-7-yl]-3-(fluoromethyl)-N'-[(1S, 2S, 3S, 5R)-2,6,6-trimethylbicyclo[3.1.1]hept-3-yl]piperazine-1-carboximidamide | 660.5 |
| 253 | 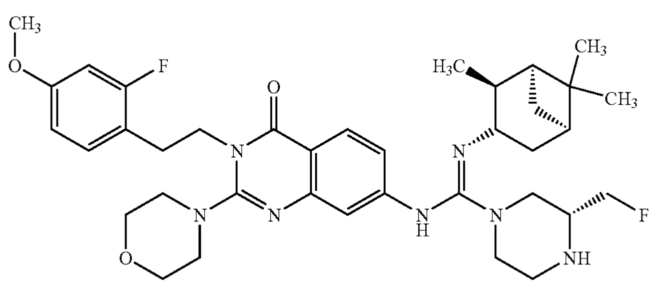 | (3R)-N-{3-[2-(2-fluoro-4-methoxyphenyl)ethyl]-2-morpholin-4-yl-4-oxo-3,4-dihydroquinazolin-7-yl}-3-(fluoromethyl)-N'-[(1S, 2S, 3S, 5R)-2,6,6-trimethylbicyclo[3.1.1]hept-3-yl]piperazine-1-carboximidamide | 678.5 |
| 254 | 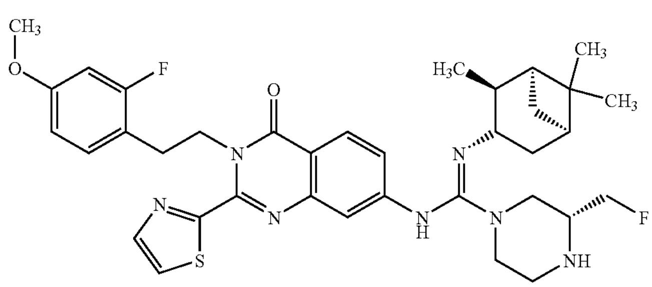 | (3R)-N-[3-[2-(2-fluoro-4-methoxyphenyl)ethyl]-4-oxo-2-(1,3-thiazol-2-yl)-3,4-dihydroquinazolin-7-yl]-3-(fluoromethyl)-N'-[(1S, 2S, 3S, 5R)-2,6,6-trimethylbicyclo[3.1.1]hept-3-yl]piperazine-1-carboximidamide | 676.4 |

-continued

| Ex. | Structure | Name | MH+ |
|---|---|---|---|
| 255 | 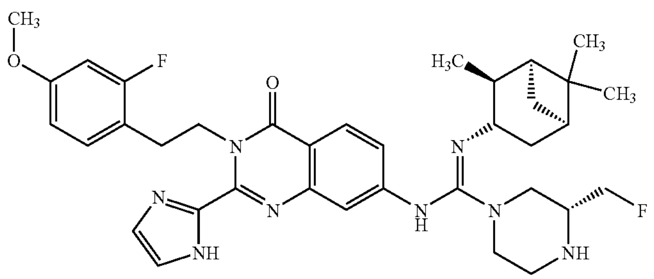 | (3R)-N-[3-[2-(2-fluoro-4-methoxyphenyl)ethyl]-2-(1H-imidazol-2-yl)-4-oxo-3,4-dihydroquinazolin-7-yl]-3-(fluoromethyl)-N'-[(1S, 2S, 3S, 5R)-2,6,6-trimethylbicyclo[3.1.1]hept-3-yl]piperazine-1-carboximidamide | 659.5 |
| 256 | 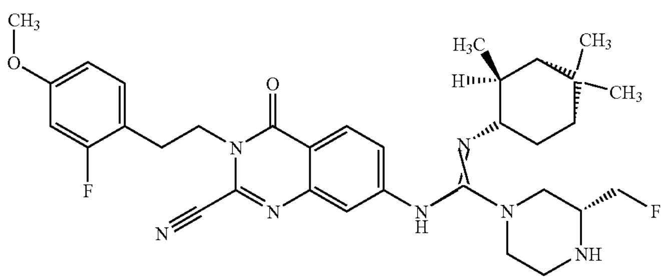 | (3R)-N-{2-cyano-3-[2-(2-fluoro-4-methoxyphenyl)ethyl]-4-oxo-3,4-dihydroquinazolin-7-yl}-3-(fluoromethyl)-N'-[(1S, 2S, 5R)-2,6,6-trimethylbicyclo[3.1.1]hept-3-yl]piperazine-1-carboximidamide | 618.4 |
| 257 | Chiral | (3R)-3-(fluoromethyl)-N-{2-(fluoromethyl)-3-[2-(4-fluorophenyl)ethyl]-4-oxo-3,4-dihydroquinazolin-7-yl}-N'-[(1S, 2S, 3S, 5R)-2,6,6-trimethylbicyclo[3.1.1]hept-3-yl]piperazine-1-carboximidamide | 595.5 |
| 258 | Chiral | (3R)-N-{2-(cyclopropylamino)-3-[2-(2-fluoro-4-methoxyphenyl)ethyl]-4-oxo-3,4-dihydroquinazolin-7-yl}-3-(fluoromethyl)-N'-[(1S, 2S, 3S, 5R)-2,6,6-trimethylbicyclo[3.1.1]hept-3-yl]piperazine-1-carboximidamide | 648.5 |

Chiral

Table of Examples 259-343

| Ex. | Structure | Name | LC Method | Ret. Time (min) | Ion |
|---|---|---|---|---|---|
| 259 | 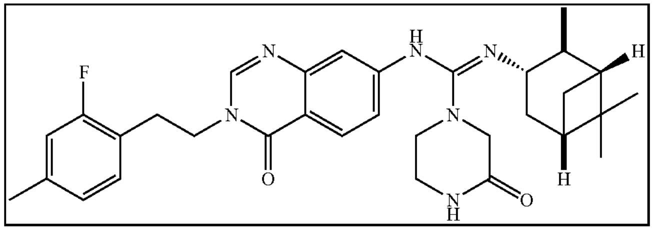 | N-{3-[2-(2-fluoro-4-methylphenyl)ethyl]-4-oxo-3,4-dihydroquinazolin-7-yl}-3-oxo-N'-[(1R, 2S, 3S, 5S)-2,6,6-trimethylbicyclo[3.1.1]hept-3-yl]piperazine-1-carboximidamide | B | 3.35 | M + H 559.3 |
| 260 | 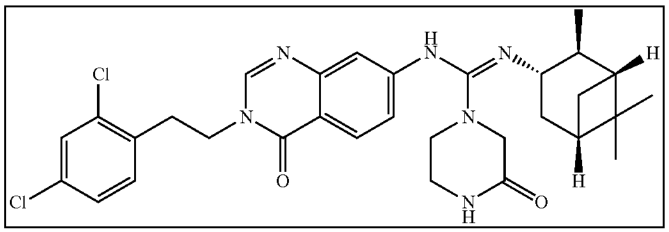 | N-{3-[2-(2,4-dichlorophenyl)ethyl]-4-oxo-3,4-dihydroquinazolin-7-yl}-3-oxo-N'-[(1R, 2S, 3S, 5S)-2,6,6-trimethylbicyclo[3.1.1]hept-3-yl]piperazine-1-carboximidamide | B | 3.44 | M + H 595.2 |
| 261 | 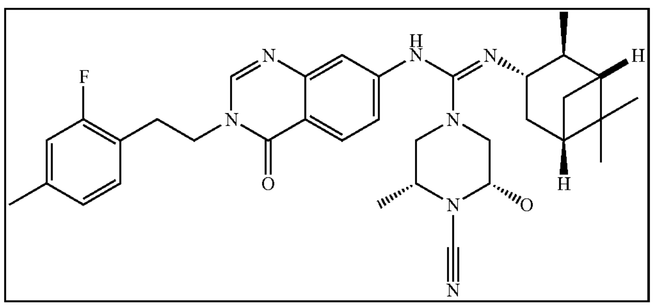 | (3R, 5S)-4-cyano-N-{3-[2-(2-fluoro-4-methylphenyl)ethyl]-4-oxo-3,4-dihydroquinazolin-7-yl}-3,5-dimethyl-N'-[(1R, 2S, 3S, 5S)-2,6,6-trimethylbicyclo[3.1.1]hept-3-yl]piperazine-1-carboximidamide | B | 2.71 | M − H 596.4 |

| Ex. | Structure | Name | LC Method | Ret. Time (min) | Ion |
|---|---|---|---|---|---|
| 262 | 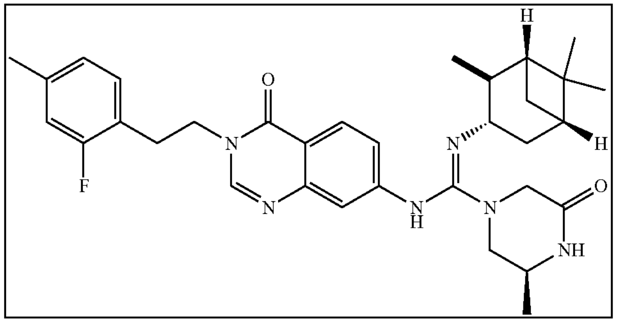 | (3S)-N-[3-[2-(2-fluoro-4-methylphenyl)ethyl]-4-oxo-3,4-dihydroquinazolin-7-yl]-3-methyl-5-oxo-N'-[(1R, 2S, 3S, 5S)-2,6,6-trimethylbicyclo[3.1.1]hept-3-yl]piperazine-1-carboximidamide | A | 2.74 | M + H 574.8 |
| 263 | 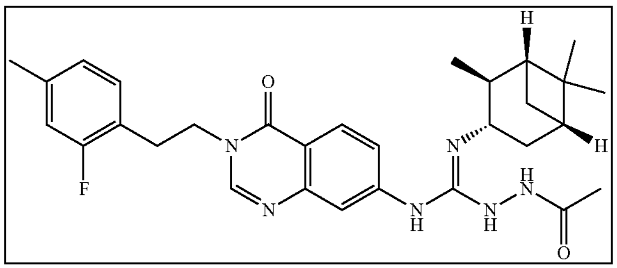 | 2-acetyl-N-[3-[2-(2-fluoro-4-methylphenyl)ethyl]-4-oxo-3,4-dihydroquinazolin-7-yl]-N'-[(1R, 2S, 3S, 5S)-2,6,6-trimethylbicyclo[3.1.1]hept-3-yl]hydrazinecarboximidamide | A | 2.64 | M + H 534.3 |
| 264 | 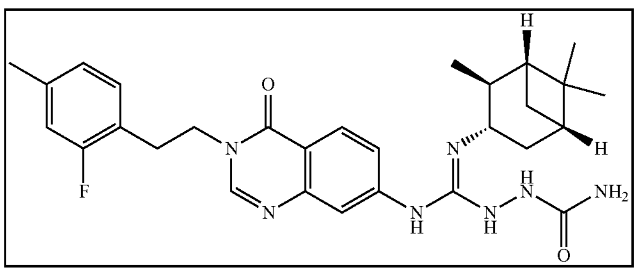 | -((Z)-{3-[2-(2-fluoro-4-methylphenyl)ethyl]-4-oxo-3,4-dihydroquinazolin-7-yl]amino}[((1R, 2S, 3S, 5S)-2,6,6-trimethylbicyclo[3.1.1]hept-3-yl]imino}methyl)hydrazinecarboximidamide | A | 2.61 | M + H 534.4 |

-continued

| Ex. | Structure | Name | LC Method | Ret. Time (min) | Ion |
|---|---|---|---|---|---|
| 265 | 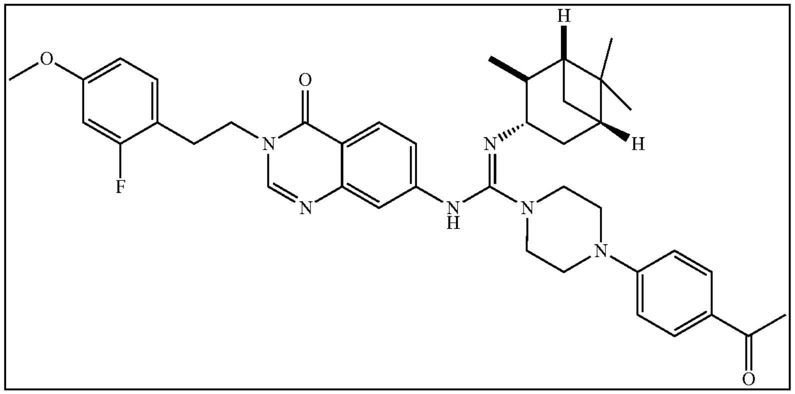 | 4-(4-acetylphenyl)-N-(3-{2-[2-fluoro-4-(methyloxy)phenyl]ethyl}-4-oxo-3,4-dihydro-7-quinazolinyl)-N'-[(1R,2S,3S,5S)-2,6,6-trimethylbicyclo[3.1.1]hept-3-yl]-1-piperazinecarboximidamide | B | 3.53 | M − H 677.32 |
| 266 | 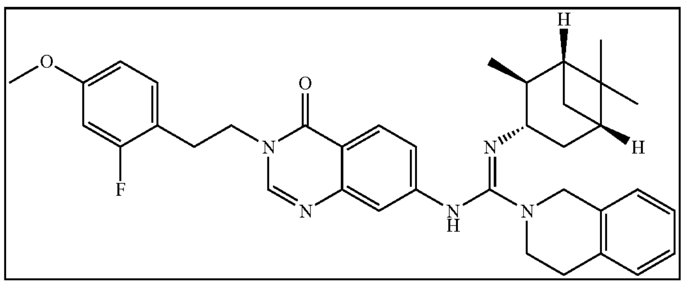 | N-(3-{2-[2-fluoro-4-(methyloxy)phenyl]ethyl}-4-oxo-3,4-dihydro-7-quinazolinyl)-N'-[(1R,2S,3S,5S)-2,6,6-trimethylbicyclo[3.1.1]hept-3-yl]-3,4-dihydro-2(1H)-isoquinolinecarboximidamide | B | 3.62 | M − H 606.29 |
| 267 | 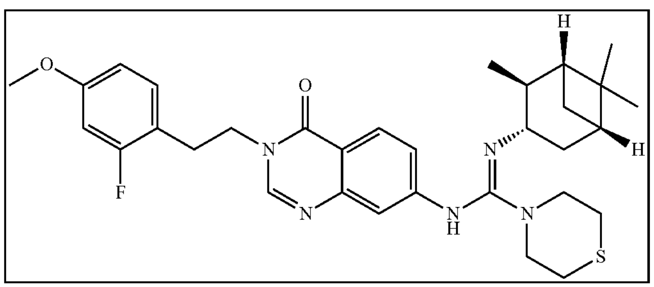 | N-(3-{2-[2-fluoro-4-(methyloxy)phenyl]ethyl}-4-oxo-3,4-dihydro-7-quinazolinyl)-N'-[(1R,2S,3S,5S)-2,6,6-trimethylbicyclo[3.1.1]hept-3-yl]-4-thiomorpholinecarboximidamide | B | 3.49 | M − H 576.25 |

-continued

| Ex. | Structure | Name | LC Method | Ret. Time (min) | Ion |
|---|---|---|---|---|---|
| 268 | 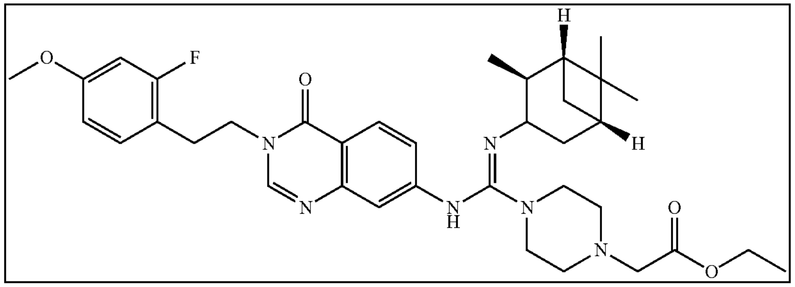 | ethyl [4-((Z)-[(3-{2-[2-fluoro-4-(methyloxy)phenyl]ethyl}-4-oxo-3,4-dihydro-7-quinazolinyl)amino]{[(1R, 2S, 5S)-2,6,6-trimethylbicyclo[3.1.1]hept-3-yl]imino}methyl)-1-piperazinyl]acetate | B | 3.58 | M + H 647.29 |
| 269 | 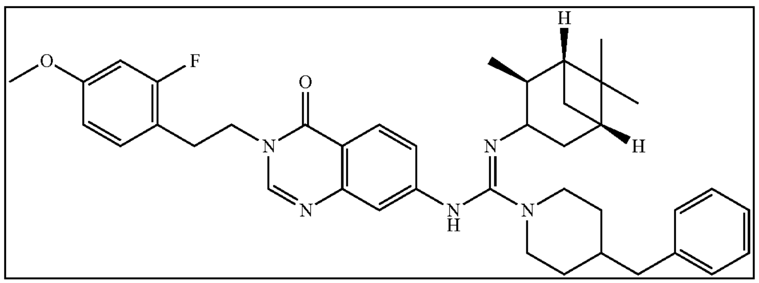 | N-(3-{2-[2-fluoro-4-(methyloxy)phenyl]ethyl}-4-oxo-3,4-dihydro-7-quinazolin-4-(phenylmethyl)-N'-[(1R, 2S, 5S)-2,6,6-trimethylbicyclo[3.1.1]hept-3-yl]-1-piperidinecarboximidamide | B | 3.88 | M + H 650.40 |
| 270 | 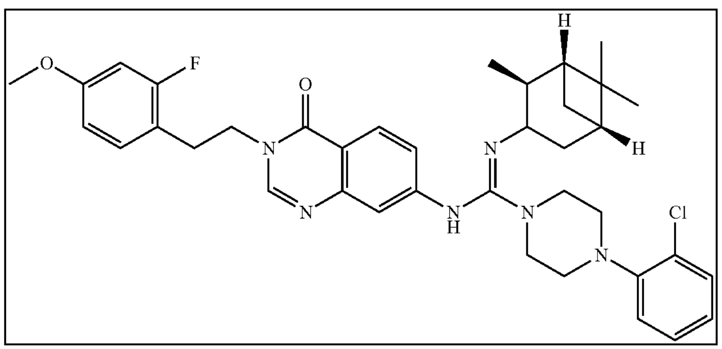 | 4-(2-chlorophenyl)-N-(3-{2-[2-fluoro-4-(methyloxy)phenyl]ethyl}-4-oxo-3,4-dihydro-7-quinazolinyl)-N'-[(1R, 2S, 5S)-2,6,6-trimethylbicyclo[3.1.1]hept-3-yl]-1-piperazinecarboximidamide | B | 3.83 | M + H 671.29 |

-continued

| Ex. | Structure | Name | LC Method | Ret. Time (min) | Ion |
|---|---|---|---|---|---|
| 271 | 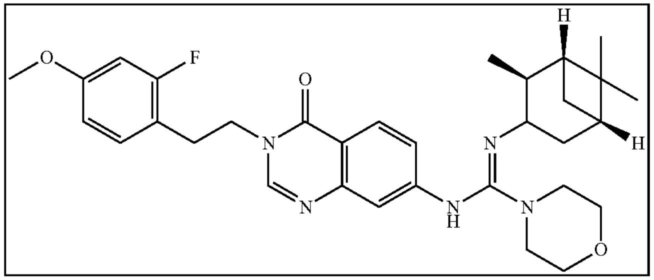 | N-(3-{2-[2-fluoro-4-(methyloxy)phenyl]ethyl}-4-oxo-3,4-dihydro-7-quinazolinyl)-N'-[(1R,2S,5S)-2,6,6-trimethylbicyclo[3.1.1]hept-3-yl]-4-morpholinecarboximidamide | B | 3.54 | M + H 562.25 |
| 272 | 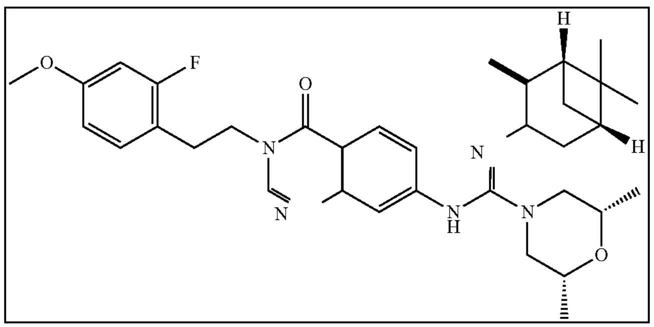 | (2R,6S)-N-(3-{2-[2-fluoro-4-(methyloxy)phenyl]ethyl}-4-oxo-3,4-dihydro-7-quinazolinyl)-N'-[(1R,2S,5S)-2,6,6-trimethylbicyclo[3.1.1]hept-3-yl]-2,6-dimethyl-4-morpholinecarboximidamide | B | 3.59 | M + H 590.29 |
| 273 | 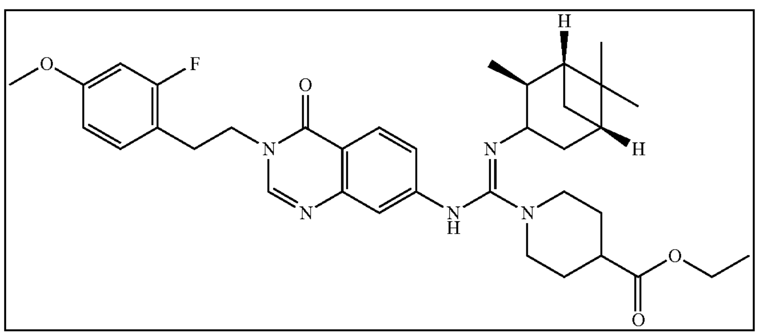 | ethyl 1-((Z)-[(3-{2-[2-fluoro-4-(methyloxy)phenyl]ethyl}-4-oxo-3,4-dihydro-7-quinazolinyl)amino]{[(1R,2S,5S)-2,6,6-trimethylbicyclo[3.1.1]hept-3-yl]imino}methyl)-4-piperidinecarboxylate | B | 3.67 | M + H 590.29 |

| Ex. | Structure | Name | LC Method | Ret. Time (min) | Ion |
|---|---|---|---|---|---|
| 274 | 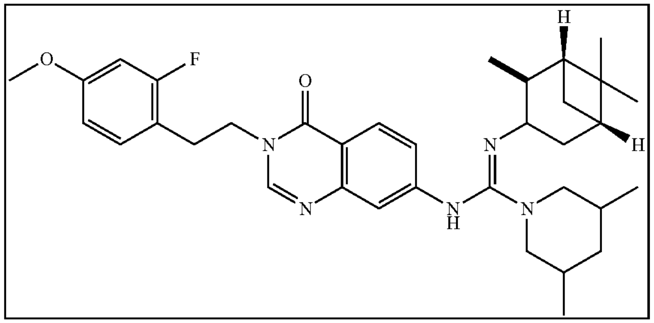 | N-(3-{2-[2-fluoro-4-(methyloxy)phenyl]ethyl}-4-oxo-3,4-dihydro-7-quinazolinyl)-3,5-dimethyl-N'-[(1R, 2S, 5S)-2,6,6-trimethylbicyclo[3.1.1]hept-3-yl]-1-piperidinecarboximidamide | B | 3.75 | M + H 588.31 |
| 275 | 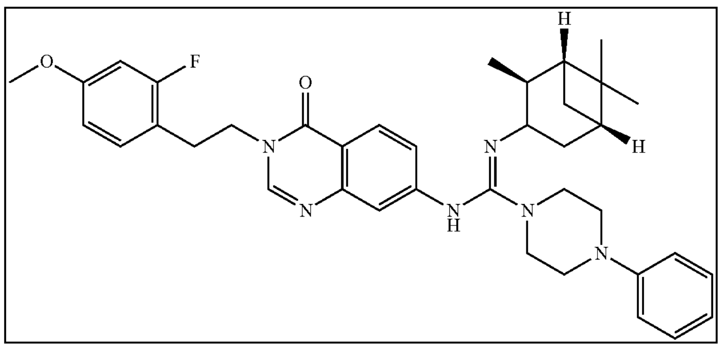 | N-(3-{2-[2-fluoro-4-(methyloxy)phenyl]ethyl}-4-oxo-3,4-dihydro-7-quinazolinyl)-4-phenyl-N'-[(1R, 2S, 5S)-2,6,6-trimethylbicyclo[3.1.1]hept-3-yl]-1-piperazinecarboximidamide | B | 3.75 | M + H 637.34 |
| 276 | 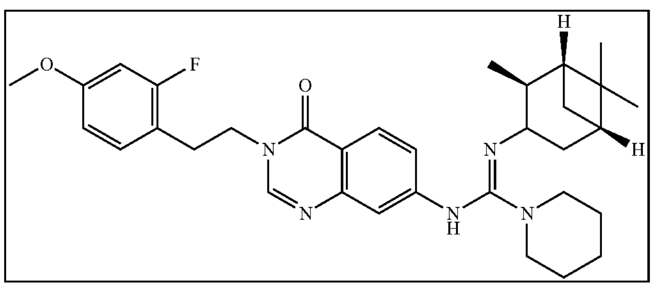 | N-(3-{2-[2-fluoro-4-(methyloxy)phenyl]ethyl}-4-oxo-3,4-dihydro-7-quinazolinyl)-N'-[(1R, 2S, 5S)-2,6,6-trimethylbicyclo[3.1.1]hept-3-yl]-1-piperidinecarboximidamide | B | 3.62 | M + H 560.25 |

-continued

| Ex. | Structure | Name | LC Method | Ret. Time (min) | Ion |
|---|---|---|---|---|---|
| 277 | 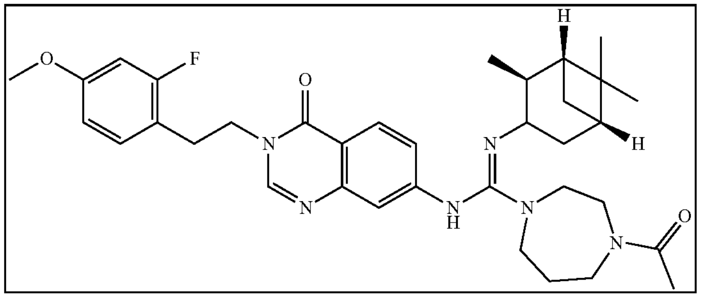 | 4-acetyl-N-(3-{2-[2-fluoro-4-(methyloxy)phenyl]ethyl}-4-oxo-3,4-dihydro-7-quinazolinyl)-N'-[(1R, 2S, 5S)-2,6,6-trimethylbicyclo[3.1.1]hept-3-yl]hexahydro-1H-1,4-diazepine-1-carboximidamide | B | 3.47 | M + H 617.25 |
| 278 | 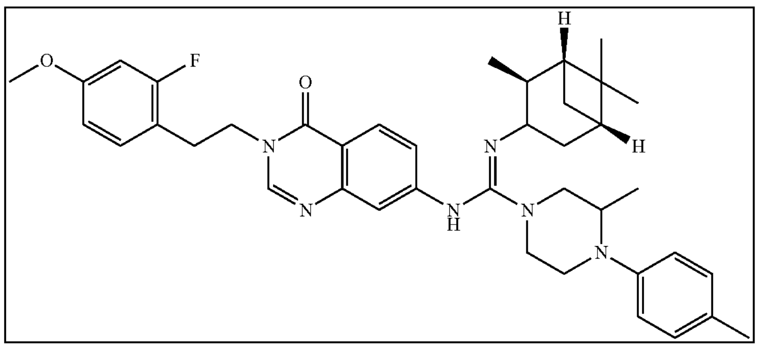 | N-(3-{2-[2-fluoro-4-(methyloxy)phenyl]ethyl}-4-oxo-3,4-dihydro-7-quinazolinyl)-N'-methyl-4-(4-methylphenyl)-N'-[(1R, 2S, 5S)-2,6,6-trimethylbicyclo[3.1.1]hept-3-yl]-1-piperazinecarboximidamide | B | 3.81 | M + H 665.39 |
| 279 | 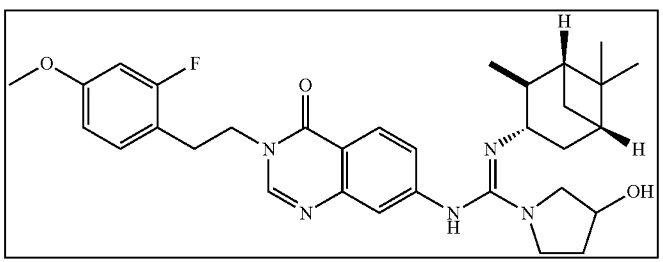 | N-(3-{2-[2-fluoro-4-(methyloxy)phenyl]ethyl}-4-oxo-3,4-dihydro-7-quinazolinyl)-3-hydroxy-N'-[(1R, 2S, 3S, 5S)-2,6,6-trimethylbicyclo[3.1.1]hept-3-yl]-1-pyrrolidinecarboximidamide | B | 3.34 | M + H 562.28 |

| Ex. | Structure | Name | LC Method | Ret. Time (min) | Ion |
|---|---|---|---|---|---|
| 280 | 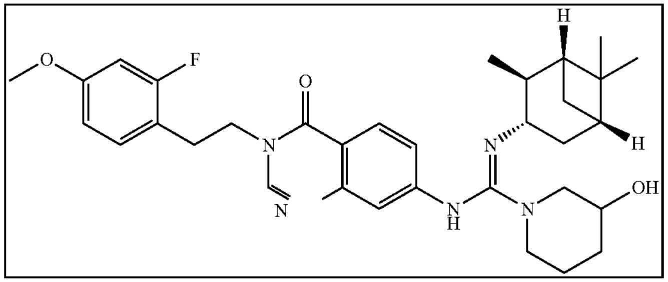 | N-(3-{2-[2-fluoro-4-(methyloxy)phenyl]ethyl}-4-oxo-3,4-dihydro-7-quinazolinyl)-N'-[(1R, 2S, 3S, 5S)-2,6,6-trimethylbicyclo[3.1.1]hept-3-yl]-1-piperidinecarboximidamide | B | 3.27 | M + H 576.30 |
| 281 | 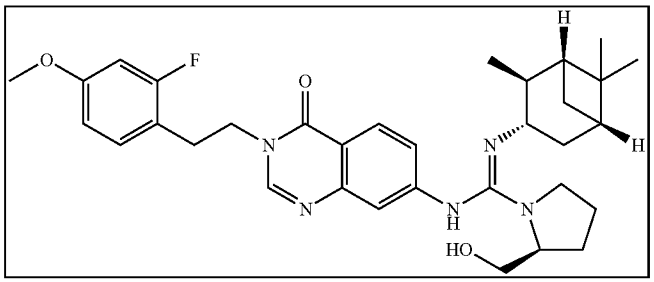 | (2S)-N-(3-{2-[2-fluoro-4-(methyloxy)phenyl]ethyl}-4-oxo-3,4-dihydro-7-quinazolinyl)-2-(hydroxymethyl)-N'-[(1R, 2S, 3S, 5S)-2,6,6-trimethylbicyclo[3.1.1]hept-3-yl]-1-pyrrolidinecarboximidamide | B | 3.31 | M + H 576.35 |
| 282 | 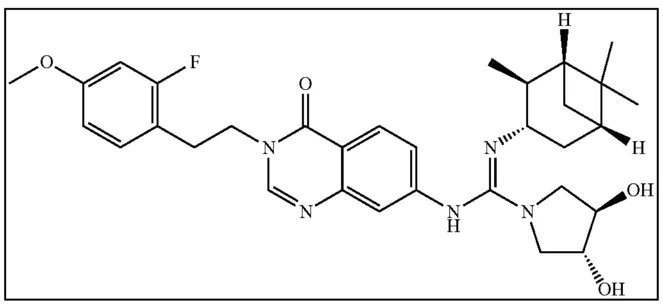 | (3R, 4R)-N-(3-{2-(2-fluoro-4-(methyloxy)phenyl]ethyl}-4-oxo-3,4-dihydro-7-quinazolinyl)-3,4-dihydroxy-N'-[(1R, 2S, 3S, 5S)-2,6,6-trimethylbicyclo[3.1.1]hept-3-yl]-1-pyrrolidinecarboximidamide | B | 3.33 | M + H 577.82 |

-continued

| Ex. | Structure | Name | LC Method | Ret. Time (min) | Ion |
|---|---|---|---|---|---|
| 283 | 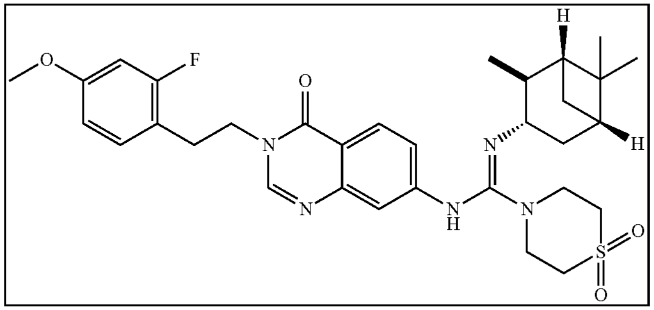 | N-(3-{2-[2-fluoro-4-(methyloxy)phenyl]ethyl}-4-oxo-3,4-dihydro-7-quinazolinyl)-N'-[(1R, 2S, 3S, 5S)-2,6,6-trimethylbicyclo[3.1.1]hept-3-yl]-4-thiomorpholinecarboximidamide 1,1-dioxide | B | 3.62 | M + H 608.20 |
| 284 | 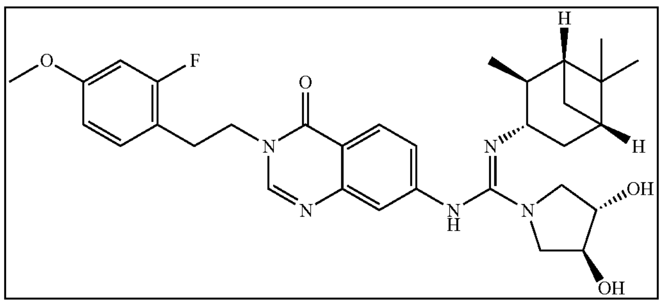 | (3S, 4S)-N-(3-{2-[2-fluoro-4-(methyloxy)phenyl]ethyl}-4-oxo-3,4-dihydro-7-quinazolinyl)-3,4-dihydroxy-N'-[(1R, 2S, 3S, 5S)-2,6,6-trimethylbicyclo[3.1.1]hept-3-yl]-1-pyrrolidinecarboximidamide | B | 3.74 | M + H 578.21 |
| 285 | 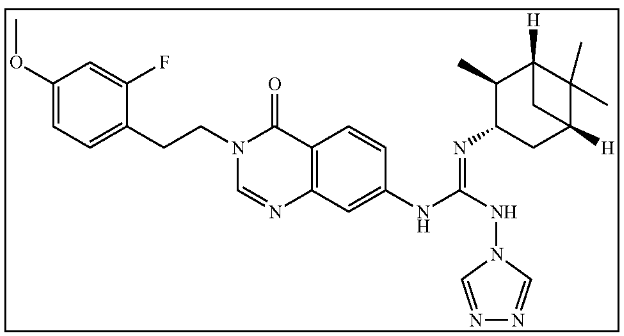 | N-(3-{2-[2-fluoro-4-(methyloxy)phenyl]ethyl}-4-oxo-3,4-dihydro-7-quinazolinyl)-N'-4H-1,2,4-triazol-4-yl-N''-[(1R, 2S, 3S, 5S)-2,6,6-trimethylbicyclo[3.1.1]hept-3-yl]guanidine | B | 3.87 | M + H 559.27 |

| Ex. | Structure | Name | LC Method | Ret. Time (min) | Ion |
|---|---|---|---|---|---|
| 286 | 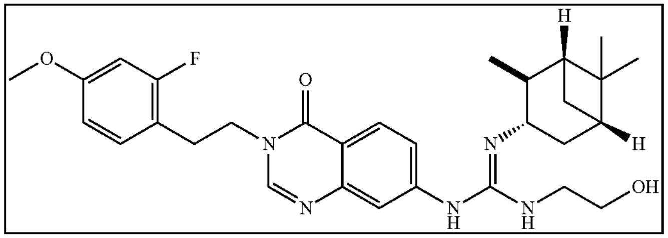 | N-(3-{2-[2-fluoro-4-(methyloxy)phenyl]ethyl}-4-oxo-3,4-dihydro-7-quinazolinyl)-N'-(2-hydroxyethyl)-N''-[(1R, 2S, 3S, 5S)-2,6,6-trimethylbicyclo[3.1.1]hept-3-yl]guanidine | A | 2.72 | M + H 536.23 |
| 287 | 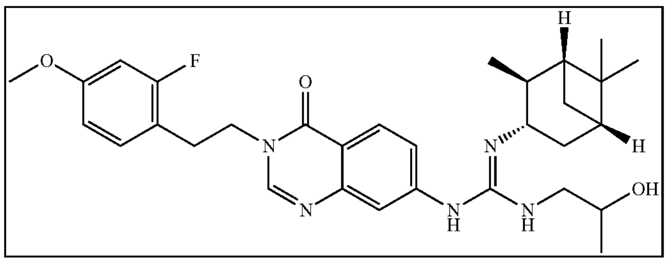 | N-(3-{2-[2-fluoro-4-(methyloxy)phenyl]ethyl}-4-oxo-3,4-dihydro-7-quinazolinyl)-N'-((1R, 2S, 3S, 5S)-2,6,6-trimethylbicyclo[3.1.1]hept-3-yl]guanidine | A | 2.68 | M + H 549.97 |
| 288 | 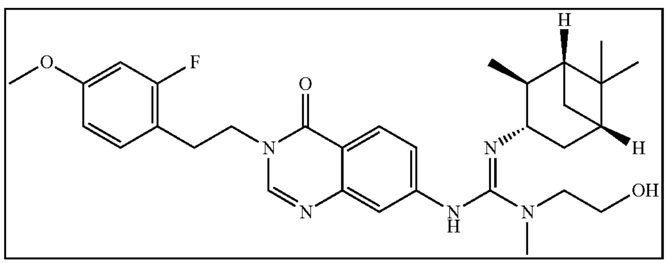 | N'-(3-{2-[2-fluoro-4-(methyloxy)phenyl]ethyl}-4-oxo-3,4-dihydro-7-quinazolinyl)-N'-(2-hydroxyethyl)-N''-methyl-N''-[(1R, 2S, 3S, 5S)-2,6,6-trimethylbicyclo[3.1.1]hept-3-yl]guanidine | A | 2.71 | M − H 548.41 |
| 289 | 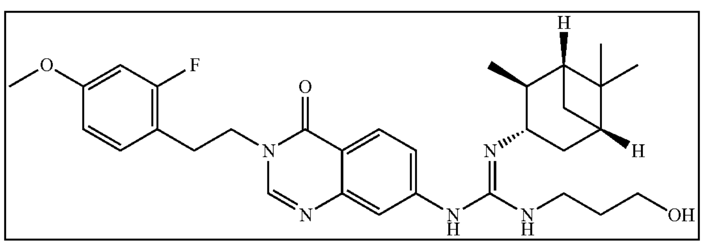 | N-(3-{2-[2-fluoro-4-(methyloxy)phenyl]ethyl}-4-oxo-3,4-dihydro-7-quinazolinyl)-N'-(3-hydroxypropyl)-N''-[(1R, 2S, 3S, 5S)-2,6,6-trimethylbicyclo[3.1.1]hept-3-yl]guanidine | A | 2.72 | M − H 548.35 |

| Ex. | Structure | Name | LC Method | Ret. Time (min) | Ion |
|---|---|---|---|---|---|
| 290 | 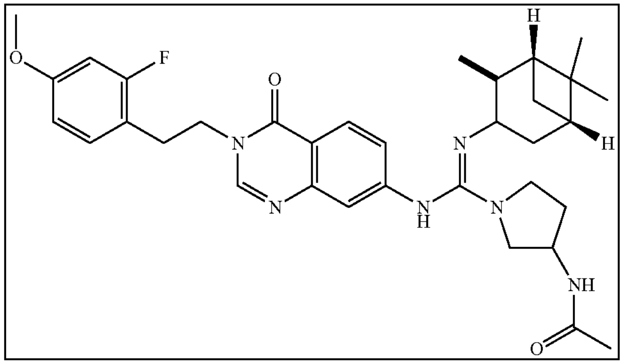 | N-[1-((Z)-[(3-{2-[2-fluoro-4-(methyloxy)phenyl]ethyl]-4-oxo-3,4-dihydro-7-quinazolinyl)amino]{[(1R, 2S, 5S)-2,6,6-trimethylbicyclo[3.1.1]hept-3-yl]imino}methyl)-3-pyrrolidinyl]acetamide | A | 2.6 | M − H 601.27 |
| 291 | 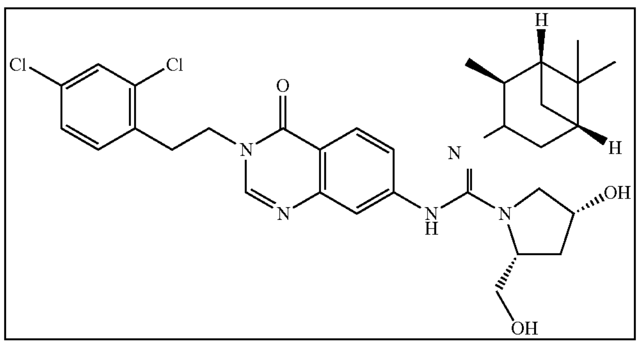 | (2R, 4R)-N-{3-[2-(2,4-dichlorophenyl)ethyl]-4-oxo-3,4-dihydro-7-quinazolinyl}-4-hydroxy-2-(hydroxymethyl)-N'0-[(1R, 2S,5S)-2,6,6-trimethylbicyclo[3.1.1]hept-3-yl]-1-pyrrolidinecarboximidamide | A | 2.68 | M + H 612.21 |

| Ex. | Structure | Name | LC Method | Ret. Time (min) | Ion |
|---|---|---|---|---|---|
| 292 | 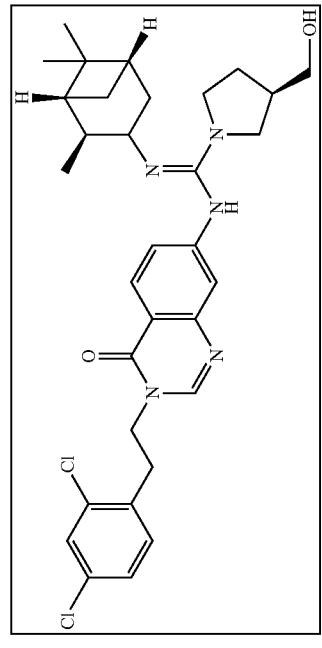 | (3R)-N-{3-[2-(2,4-dichlorophenyl)ethyl]-4-oxo-3,4-dihydro-7-quinazolinyl}-3-(hydroxymethyl)-N'-[(1R, 2S, 5S)-2,6,6-trimethylbicyclo[3.1.1]hept-3-yl]-1-pyrrolidinecarboximidamide | A | 2.66 | M + H 596.22 |
| 293 | 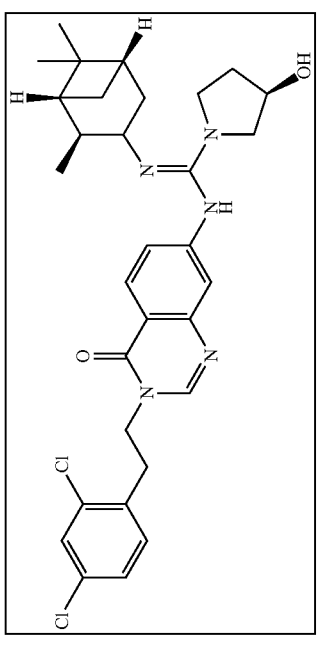 | (3R)-N-{3-[2-(2,4-dichlorophenyl)ethyl]-4-oxo-3,4-dihydro-7-quinazolinyl}-3-hydroxy-N'-[(1R, 2S, 5S)-2,6,6-trimethylbicyclo[3.1.1]hept-3-yl]-1-pyrrolidinecarboximidamide | A | 2.66 | M + H 582.22 |
| 294 | 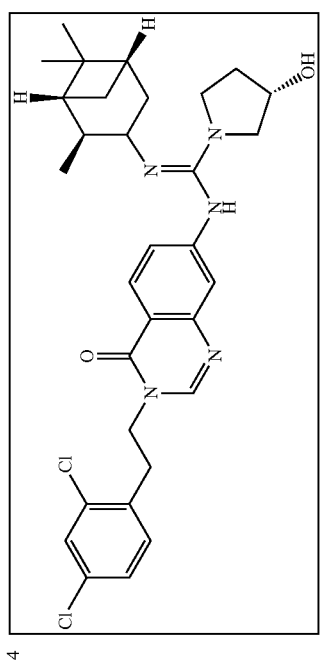 | (3S)-N-{3-[2-(2,4-dichlorophenyl)ethyl]-4-oxo-3,4-dihydro-7-quinazolinyl}-3-hydroxy-N'-[(1R, 2S, 5S)-2,6,6-trimethylbicyclo[3.1.1]hept-3-yl]-1-pyrrolidinecarboximidamide | A | 2.76 | M + H 582.25 |

-continued

| Ex. | Structure | Name | LC Method | Ret. Time (min) | Ion |
|---|---|---|---|---|---|
| 295 | 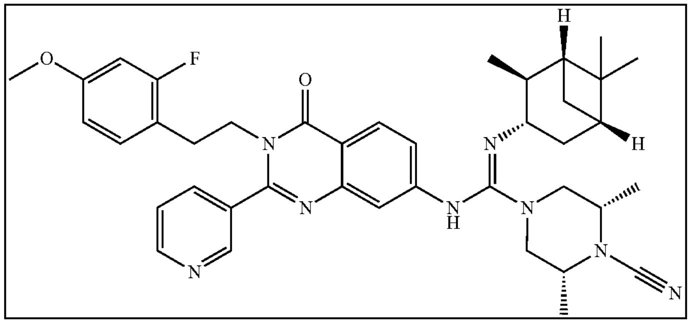 | (3R,5S)-4-cyano-N-[3-{2-[2-fluoro-4-(methyloxy)phenyl]ethyl]-4-oxo-2-(3-pyridinyl)-3,4-dihydro-7-quinazolinyl]-N'-[(1R,2S,3S,5S)-2,6,6-trimethylbicyclo[3.1.1]hept-3-yl]-1-piperazinecarboximidamide | A | 2.71 | M − H 689.38 |
| 296 | 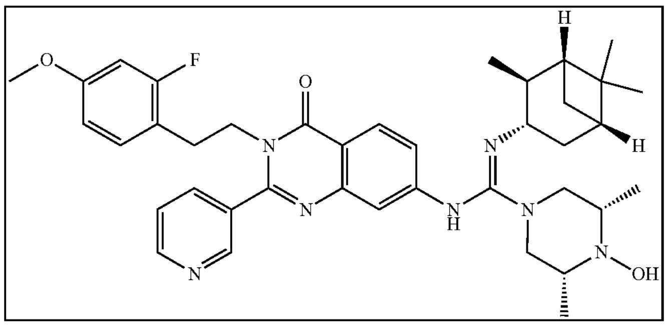 | (3R,5S)-N-[3-{2-[2-fluoro-4-(methyloxy)phenyl]ethyl]-4-oxo-2-(3-pyridinyl)-3,4-dihydro-7-quinazolinyl]-4-hydroxy-3,5-dimethyl-N'-[(1R,2S,3S,5S)-2,6,6-trimethylbicyclo[3.1.1]hept-3-yl]-1-piperazinecarboximidamide | A | 2.73 | M − H 680.39 |
| 297 | 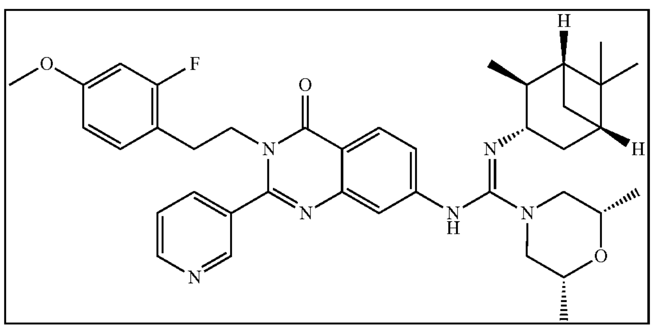 | (2R,6S)-N-[3-{2-[2-fluoro-4-(methyloxy)phenyl]ethyl]-4-oxo-2-(3-pyridinyl)-3,4-dihydro-7-quinazolinyl]-2,6-dimethyl-N'-[(1R,2S,3S,5S)-2,6,6-trimethylbicyclo[3.1.1]hept-3-yl]-4-morpholinecarboximidamide | A | 2.76 | M − H 665.41 |

| Ex. | Structure | Name | LC Method | Ret. Time (min) | Ion |
|---|---|---|---|---|---|
| 298 | 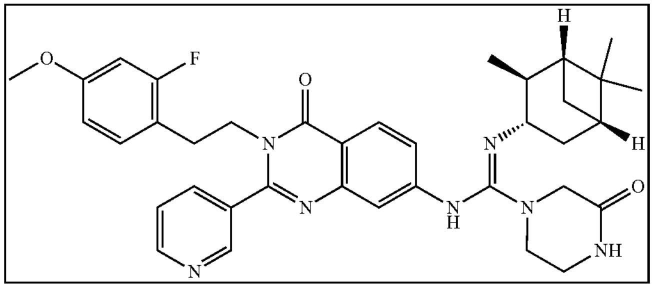 | N-[3-{2-[2-fluoro-4-(methyloxy)phenyl]ethyl}-4-oxo-2-(3-pyridinyl)-3,4-dihydro-7-quinazolinyl]-3-oxo-N'-[(1R,2S,3S,5S)-2,6,6-trimethylbicyclo[3.1.1]hept-3-yl]-1-piperazinecarboximidamide | A | 2.64 | M − H 650.38 |
| 299 | 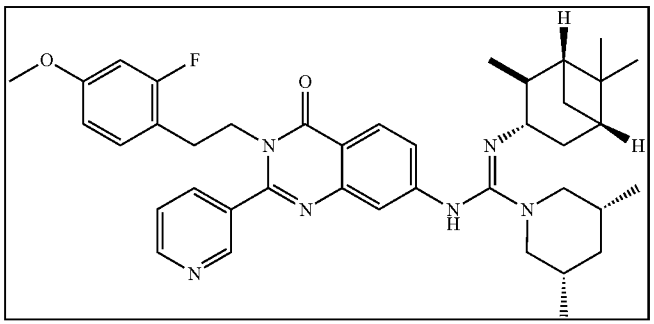 | (3R,5S)-N-[3-{2-[2-fluoro-4-(methyloxy)phenyl]ethyl}-4-oxo-2-(3-pyridinyl)-3,4-dihydro-7-quinazolinyl]-3,5-dimethyl-N'-[(1R,2S,3S,5S)-2,6,6-trimethylbicyclo[3.1.1]hept-3-yl]-1-piperidinecarboximidamide | A | 2.9 | M − H 663.57 |
| 300 | 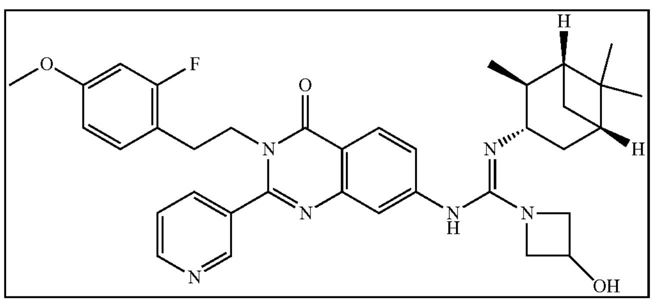 | N-[3-{2-[2-fluoro-4-(methyloxy)phenyl]ethyl}-4-oxo-2-(3-pyridinyl)-3,4-dihydro-7-quinazolinyl]-3-hydroxy-N'-[(1R,2S,3S,5S)-2,6,6-trimethylbicyclo[3.1.1]hept-3-yl]-1-azetidinecarboximidamide | A | 2.71 | M − H 623.33 |

| Ex. | Structure | Name | LC Method | Ret. Time (min) | Ion |
|---|---|---|---|---|---|
| 301 | 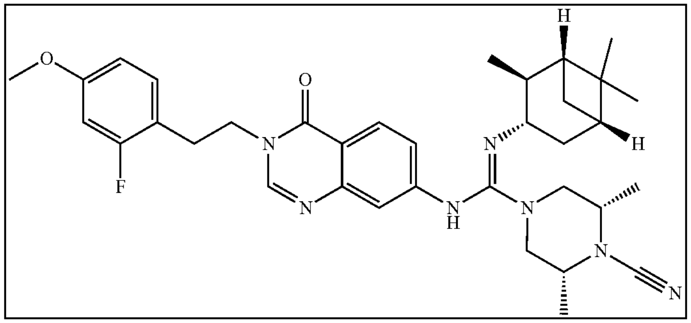 | (3R, 5S)-4-cyano-N-(3-{2-[2-fluoro-4-(methyloxy)phenyl]ethyl}-4-oxo-3,4-dihydro-7-quinazolinyl)-N'-[(1R, 2S, 3S, 5S)-2,6,6-trimethylbicyclo[3.1.1]hept-3-yl]-3,5-dimethyl-N'-[(1R, 2S, 3S, 5S)-2,6,6-trimethylbicyclo[3.1.1]hept-3-yl]-1-piperazinecarboximidamide | B | 3.3 | M − H 612.41 |
| 302 | 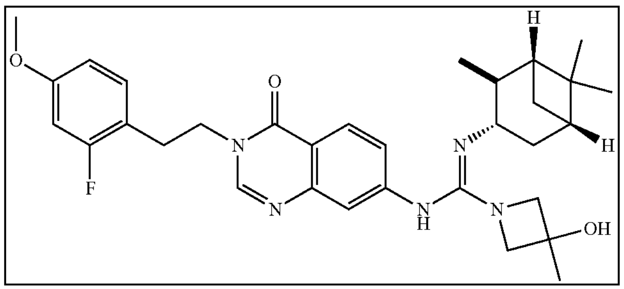 | N-(3-{2-[2-fluoro-4-(methyloxy)phenyl]ethyl}-4-oxo-3,4-dihydro-7-quinazolinyl)-3-hydroxy-3-methyl-N'-[(1R, 2S, 3S, 5S)-2,6,6-trimethylbicyclo[3.1.1]hept-3-yl]-1-azetidinecarboximidamide | A | 2.55 | M − H 560.58 |
| 303 | 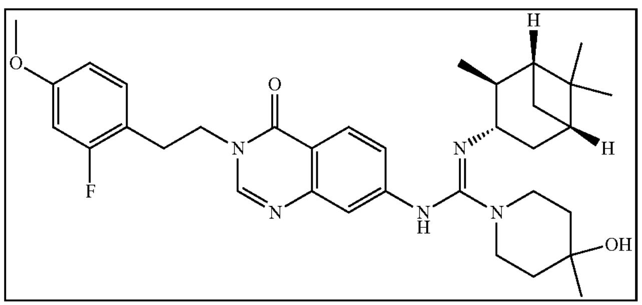 | N-(3-{2-[2-fluoro-4-(methyloxy)phenyl]ethyl}-4-oxo-3,4-dihydro-7-quinazolinyl)-4-hydroxy-4-methyl-N'-[(1R, 2S, 3S, 5S)-2,6,6-trimethylbicyclo[3.1.1]hept-3-yl]-1-piperidinecarboximidamide | A | 2.56 | M − H 588.45 |

-continued

| Ex. | Structure | Name | LC Method | Ret. Time (min) | Ion |
|---|---|---|---|---|---|
| 304 | 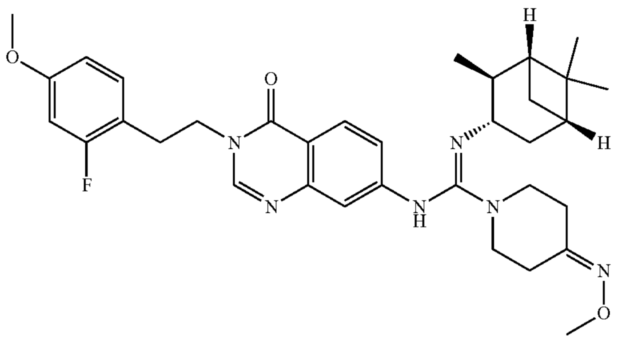 | N-(3-{2-[2-fluoro-4-(methyloxy)phenyl]ethyl}-4-oxo-3,4-dihydro-7-quinazolinyl)-4-[(methyloxy)imino]-N'-[(1R, 2S, 3S, 5S)-2,6,6-trimethylbicyclo[3.1.1]hept-3-yl]-1-piperidinecarboximidamide | A | 2.58 | M − H 601.42 |
| 305 | 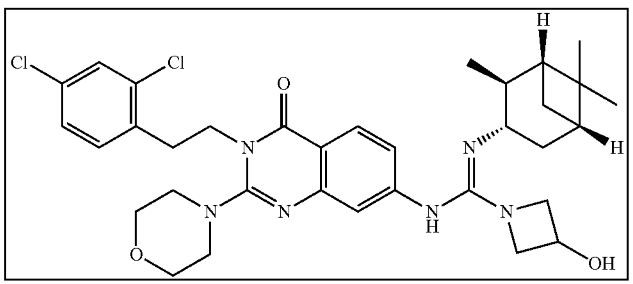 | N-[3-[2-(2,4-dichlorophenyl)ethyl]-2-(4-morpholinyl)-4-oxo-3,4-dihydro-7-quinazolinyl]-3-hydroxy-N'-[(1R, 2S, 3S, 5S)-2,6,6-trimethylbicyclo[3.1.1]hept-3-yl]-1-azetidinecarboximidamide | E | 5.03 | M + H 653 |
| 306 | 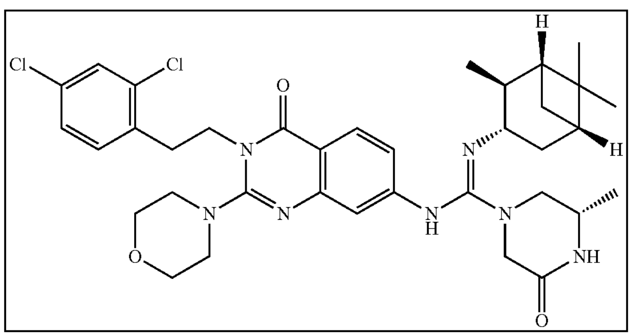 | (3S)-N-[3-[2-(2,4-dichlorophenyl)ethyl]-2-(4-morpholinyl)-4-oxo-3,4-dihydro-7-quinazolinyl]-3-methyl-5-oxo-N'-[(1R, 2S, 3S, 5S)-2,6,6-trimethylbicyclo[3.1.1]hept-3-yl]-1-piperazinecarboximidamide | C | 3.59 | M + H 694 |

| Ex. | Structure | Name | LC Method | Ret. Time (min) | Ion |
|---|---|---|---|---|---|
| 307 | 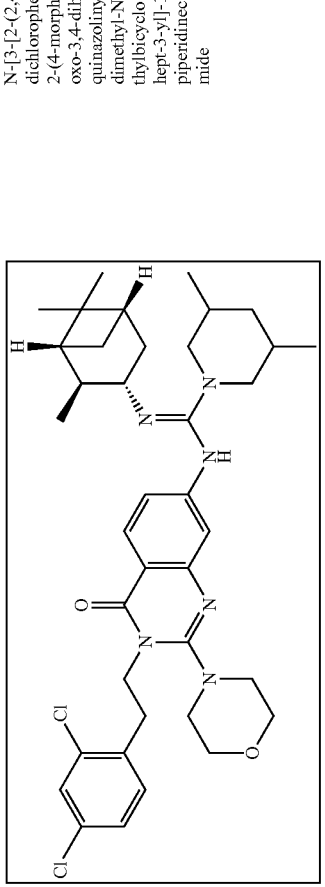 | N-[3-[2-(2,4-dichlorophenyl)ethyl]-2-(4-morpholinyl)-4-oxo-3,4-dihydro-7-quinazolinyl]-3,5-dimethyl-N'-[(1R, 2S, 3S, 5S)-2,6,6-trimethylbicyclo[3.1.1]hept-3-yl]-1-piperidinecarboximidamide | C | 3.73 | M + H 693 |
| 308 | 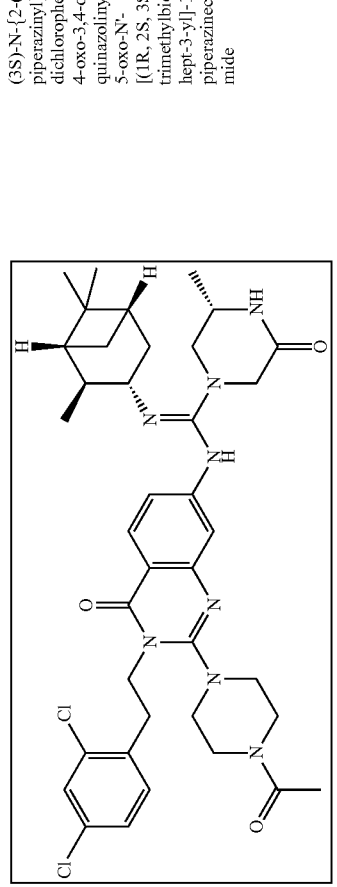 | (3S)-N-{2-(4-acetyl-1-piperazinyl)-3-[2-(2,4-dichlorophenyl)ethyl]-4-oxo-3,4-dihydro-7-quinazolinyl}-3-methyl-N'-[(1R, 2S, 3S, 5S)-2,6,6-trimethylbicyclo[3.1.1]hept-3-yl]-5-oxo-1-piperazinecarboximidamide | C | 3.59 | M + H 735 |
| 309 | 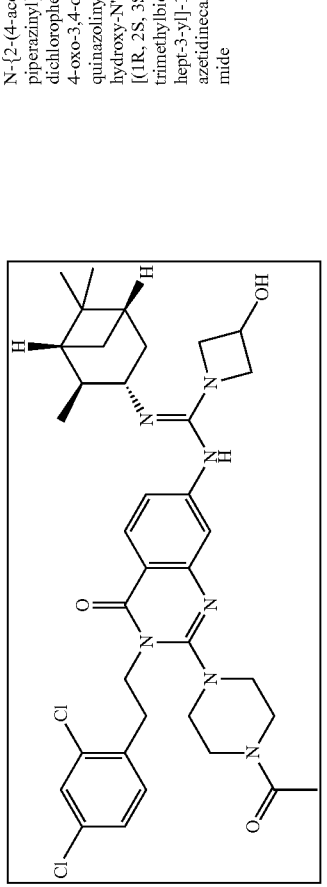 | N-{2-(4-acetyl-1-piperazinyl)-3-[2-(2,4-dichlorophenyl)ethyl]-4-oxo-3,4-dihydro-7-quinazolinyl}-3-hydroxy-N'-[(1R, 2S, 3S, 5S)-2,6,6-trimethylbicyclo[3.1.1]hept-3-yl]-1-azetidinecarboximidamide | C | 3.65 | M + H 694 |

| Ex. | Structure | Name | LC Method | Ret. Time (min) | Ion |
|---|---|---|---|---|---|
| 310 | 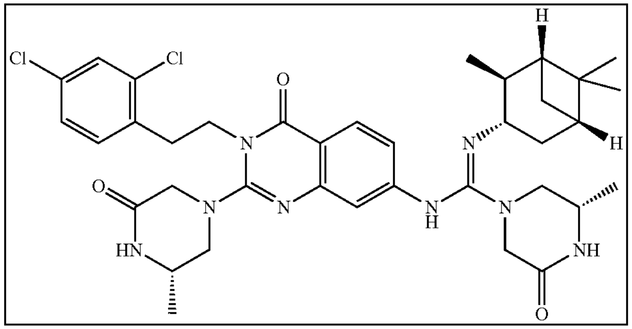 | (3S)-N-[3-[2-(2,4-dichlorophenyl)ethyl]-2-[(3S)-3-methyl-5-oxo-1-piperazinyl]-4-oxo-3,4-dihydro-7-quinazolinyl]-3-methyl-N'-5-oxo-N'-[(1R, 2S, 3S, 5S)-2,6,6-trimethylbicyclo[3.1.1]hept-3-yl]-1-piperazinecarboximidamide | C | 3.6 | M + H 721 |
| 311 | 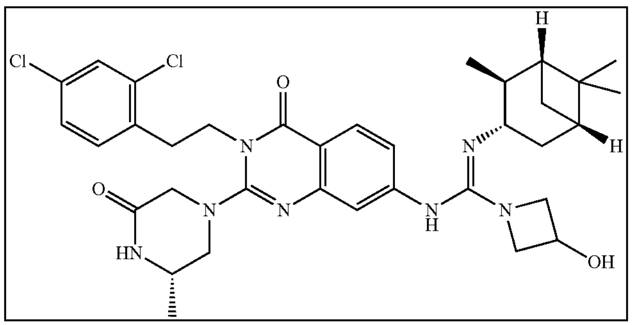 | N-[3-[2-(2,4-dichlorophenyl)ethyl]-2-[(3S)-3-methyl-5-oxo-1-piperazinyl]-4-oxo-3,4-dihydro-7-quinazolinyl]-3-hydroxy-N'-[(1S, 2S, 3S, 5R)-2,6,6-trimethylbicyclo[3.1.1]hept-3-yl]-1-azetidinecarboximidamide | C | 3.61 | M + H 680 |
| 312 | 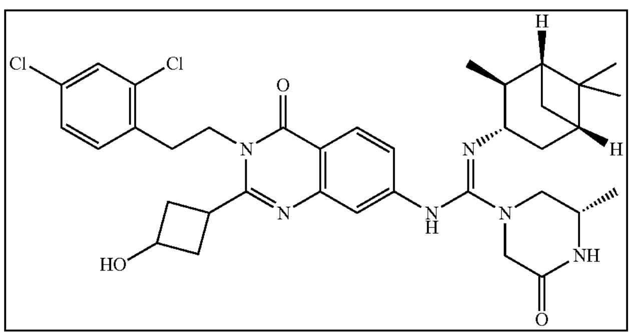 | (3S)-N-[3-[2-(2,4-dichlorophenyl)ethyl]-2-(3-hydroxy-1-azetidinyl)-4-oxo-3,4-dihydro-7-quinazolinyl]-3-methyl-N'-5-oxo-N'-[(1S, 2S, 3S, 5R)-2,6,6-trimethylbicyclo[3.1.1]hept-3-yl]-1-piperazinecarboximidamide | C | 3.59 | M + H 680 |

| Ex. | Structure | Name | LC Method | Ret. Time (min) | Ion |
|---|---|---|---|---|---|
| 313 | 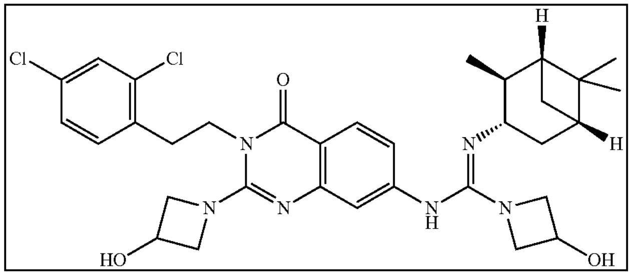 | N-[3-[2-(2,4-dichlorophenyl)ethyl]-4-oxo-3,4-dihydro-7-quinazolinyl]-3-hydroxy-N'-[(1S, 2S, 3S, 5R)-2,6,6-trimethylbicyclo[3.1.1]hept-3-yl]-1-azetidinecarboximidamide | C | 3.62 | M + H 639 |
| 314 | 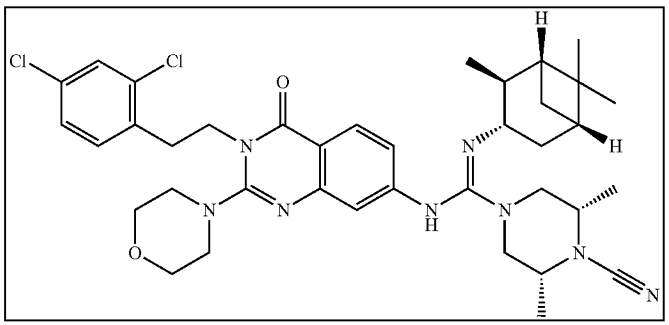 | (3R, 5S)-4-cyano-N-[3-[2-(2,4-dichlorophenyl)ethyl]-4-(4-morpholinyl)-2-oxo-3,4-dihydro-7-quinazolinyl]-3,5-dimethyl-N'-[(1R, 2S, 3S, 5S)-2,6,6-trimethylbicyclo[3.1.1]hept-3-yl]-1-piperazinecarboximidamide | A | 2.81 | M + H 719 |
| 315 | 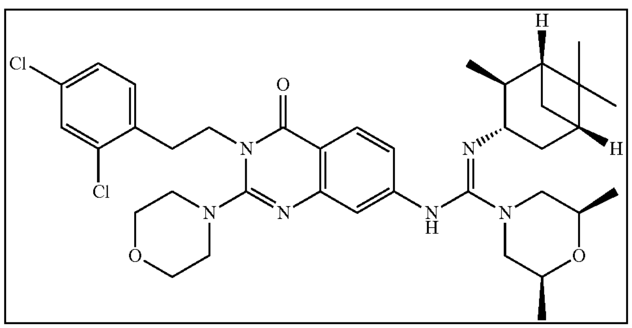 | (2R, 6S)-N-[3-[2-(2,4-dichlorophenyl)ethyl]-4-(4-morpholinyl)-2-oxo-3,4-dihydro-7-quinazolinyl]-2,6-dimethyl-N'-[(1R, 2S, 3S, 5S)-2,6,6-trimethylbicyclo[3.1.1]hept-3-yl]-4-morpholinecarboximidamide | A | 2.84 | M + H 695 |

-continued

| Ex. | Structure | Name | LC Method | Ret. Time (min) | Ion |
|---|---|---|---|---|---|
| 316 | 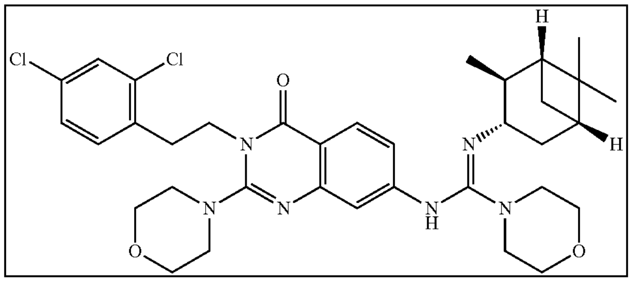 | N-[3-[2-(2,4-dichlorophenyl)ethyl]-2-(4-morpholinyl)-4-oxo-3,4-dihydro-7-quinazolinyl]-N'-[(1S, 2R, 3R, 5R)-2,6,6-trimethylbicyclo[3.1.1]hept-3-yl]-4-morpholinecarboximid-amide | A | 2.78 | M + H 667 |
| 317 | 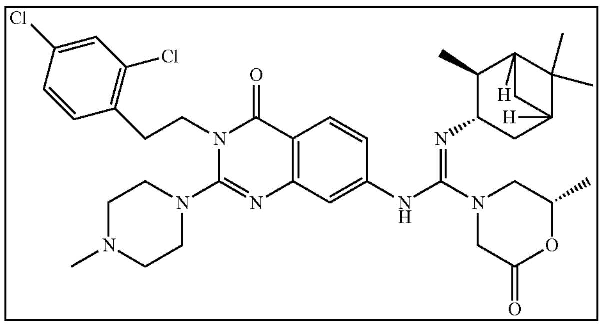 | (3S)-N-[3-[2-(2,4-dichlorophenyl)ethyl]-2-(4-methyl-1-piperazinyl)-4-oxo-3,4-dihydro-7-quinazolinyl]-N'-[(1R, 2S, 3S, 5S)-2,6,6-trimethylbicyclo[3.1.1]hept-3-yl]-1-piperazinecarboximida-mide 5-oxo-N'- | A | 2.31 | M + H 707 |
| 318 | 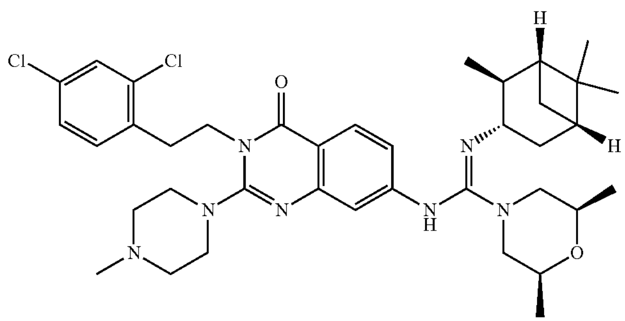 | (2R, 6S)-N-[3-[2-(2,4-dichlorophenyl)ethyl]-2-(4-methyl-1-piperazinyl)-4-oxo-3,4-dihydro-7-quinazolinyl]-2,6-dimethyl-N'-[(1R, 2S, 3S, 5S)-2,6,6-trimethylbicyclo[3.1.1]hept-3-yl]-4-morpholinecarboximid-amide | A | 2.28 | M + H 708 |

| Ex. | Structure | Name | LC Method | Ret. Time (min) | Ion |
|---|---|---|---|---|---|
| 319 | 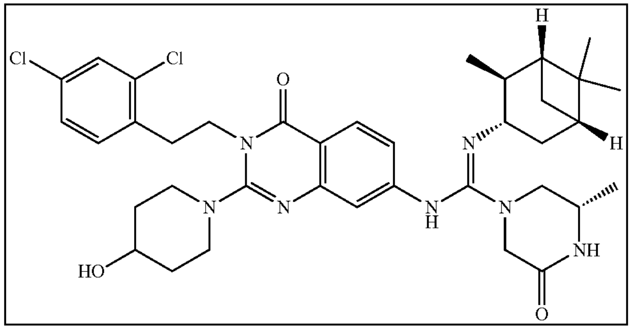 | (3S)-N-[3-[2-(2,4-dichlorophenyl)ethyl]-2-(4-hydroxy-1-piperidinyl)-4-oxo-3,4-dihydro-7-quinazolinyl]-3-methyl-5-oxo-N'-[(1R, 2S, 3S, 5S)-2,6,6-trimethylbicyclo[3.1.1]hept-3-yl]-1-piperazinecarboximidamide | A | 2.74 | M + H 708 |
| 320 | 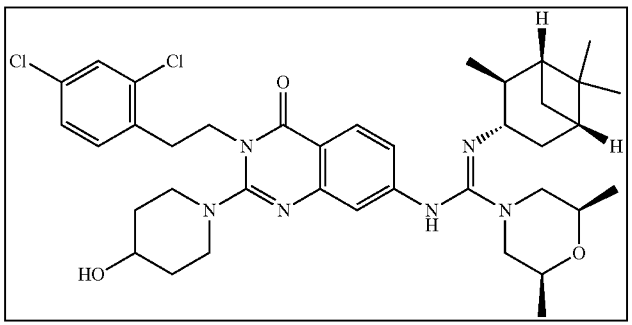 | (2R, 6S)-N-[3-[2-(2,4-dichlorophenyl)ethyl]-2-(4-hydroxy-1-piperidinyl)-4-oxo-3,4-dihydro-7-quinazolinyl]-2,6-dimethyl-N'-[(1R, 2S, 3S, 5S)-2,6,6-trimethylbicyclo[3.1.1]hept-3-yl]-4-morpholinecarboximidamide | A | 2.78 | M + H 709 |
| 321 | 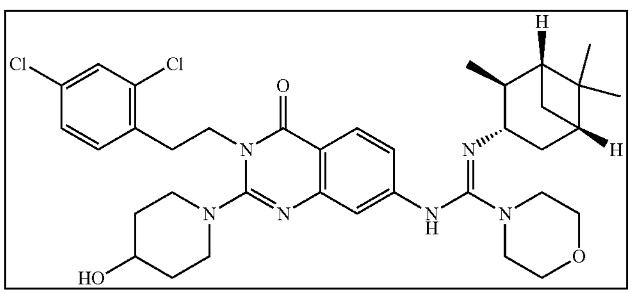 | N-(3-[2-(2,4-dichlorophenyl)ethyl]-2-(4-hydroxy-1-piperidinyl)-4-oxo-3,4-dihydro-7-quinazolinyl]-N'-[(1R, 2S, 3S, 5S)-2,6,6-trimethylbicyclo[3.1.1]hept-3-yl]-4-morpholinecarboximidamide | A | 2.78 | M + H 681 |

| Ex. | Structure | Name | LC Method | Ret. Time (min) | Ion |
|---|---|---|---|---|---|
| 322 | 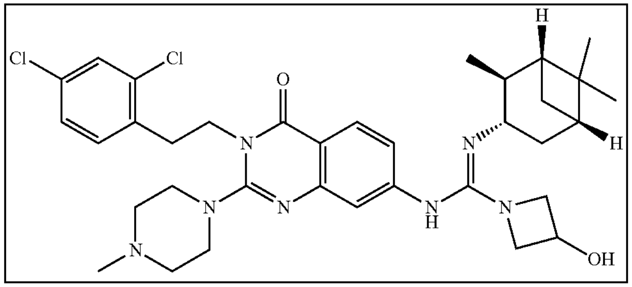 | N-[3-[2-(2,4-dichlorophenyl)ethyl]-2-(4-methyl-1-piperazinyl)-4-oxo-3,4-dihydro-7-quinazolinyl]-3-hydroxy-N'-[(1R, 2S, 3S, 5S)-2,6,6-trimethylbicyclo[3.1.1]hept-3-yl]-1-azetidinecarboximidamide | A | 2.18 | M + H 666 |
| 323 | 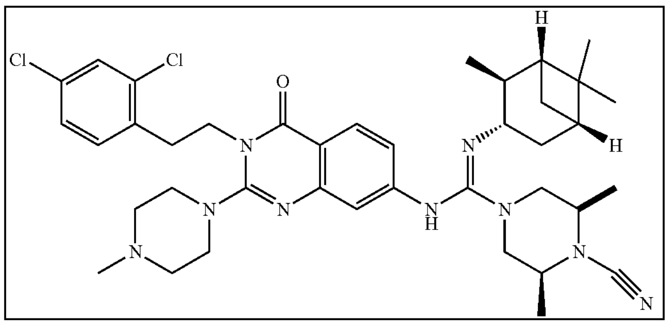 | (3R, 5S)-4-cyano-N-[3-[2-(2,4-dichlorophenyl)ethyl]-2-(4-methyl-1-piperazinyl)-4-oxo-3,4-dihydro-7-quinazolinyl]-3,5-dimethyl-N'-[(1R, 2S, 3S, 5S)-2,6,6-trimethylbicyclo[3.1.1]hept-3-yl]-1-piperazinecarboximidamide | A | 2.14 | M + H 732 |
| 324 | 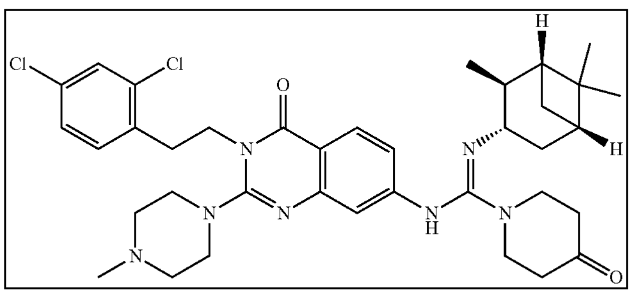 | N-[3-[2-(2,4-dichlorophenyl)ethyl]-2-(4-methyl-1-piperazinyl)-4-oxo-3,4-dihydro-7-quinazolinyl]-4-oxo-N'-[(1R, 2S, 3S, 5S)-2,6,6-trimethylbicyclo[3.1.1]hept-3-yl]-1-piperidinecarboximidamide | A | 2.11 | M + H 692 |

-continued

| Ex. | Structure | Name | LC Method | Ret. Time (min) | Ion |
|---|---|---|---|---|---|
| 325 | 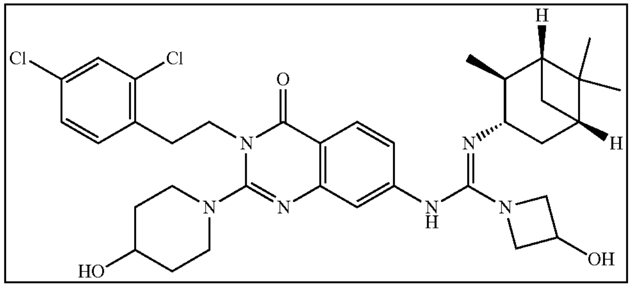 | N-[3-[2-(2,4-dichlorophenyl)ethyl]-2-(4-hydroxy-1-piperidinyl)-4-oxo-3,4-dihydro-7-quinazolinyl]-3-hydroxy-N'-[(1R, 2S, 3S, 5S)-2,6,6-trimethylbicyclo[3.1.1]hept-3-yl]-1-azetidinecarboximidamide | A | 2.63 | M + H 667 |
| 326 | 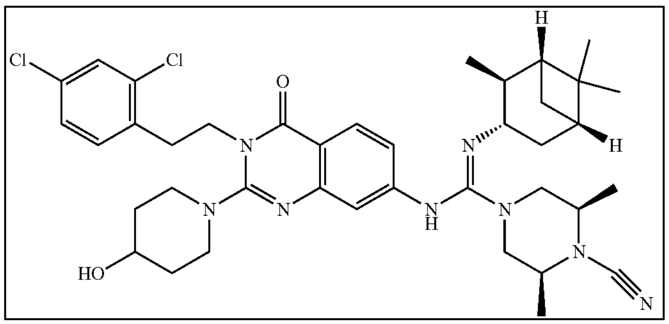 | (3R, 5S)-4-cyano-N-[3-[2-(2,4-dichlorophenyl)ethyl]-2-(4-hydroxy-1-piperidinyl)-4-oxo-3,4-dihydro-7-quinazolinyl]-3,5-dimethyl-N'-[(1R, 2S, 3S, 5S)-2,6,6-trimethylbicyclo[3.1.1]hept-3-yl]-1-piperazinecarboximidamide | A | 2.63 | M + H 733 |
| 327 | 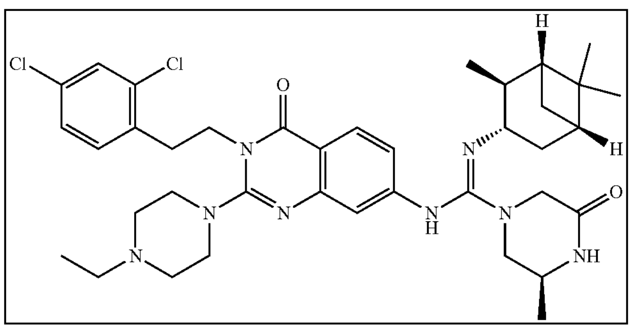 | (3S)-N-[3-[2-(2,4-dichlorophenyl)ethyl]-2-(4-ethyl-1-piperazinyl)-4-oxo-3,4-dihydro-7-quinazolinyl]-3-methyl-5-oxo-N'-[(1R, 2S, 3S, 5S)-2,6,6-trimethylbicyclo[3.1.1]hept-3-yl]-1-piperazinecarboximidamide | A | 1.88 | M + H 721 |

| Ex. | Structure | Name | LC Method | Ret. Time (min) | Ion |
|---|---|---|---|---|---|
| 328 | 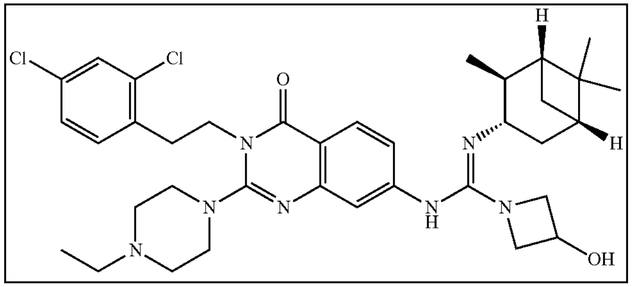 | N-(3-[2-(2,4-dichlorophenyl)ethyl]-2-(4-ethyl-1-piperazinyl)-4-oxo-3,4-dihydro-7-quinazolinyl]-3-hydroxy-N'-[(1R, 2S, 3S, 5S)-2,6,6-trimethylbicyclo[3.1.1]hept-3-yl]-1-azetidinecarboximidamide | A | 2.17 | M + H 680 |
| 329 | 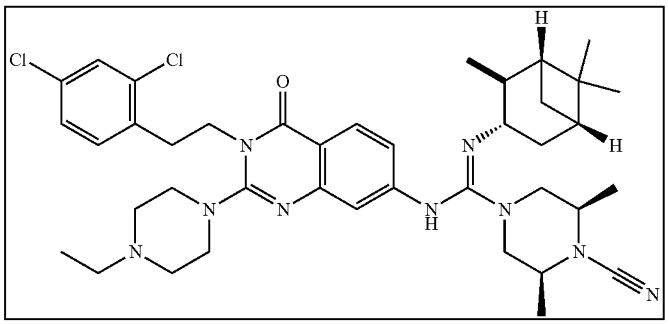 | (3R, 5S)-4-cyano-N-[3-[2-(2,4-dichlorophenyl)ethyl]-2-(4-ethyl-1-piperazinyl)-4-oxo-3,4-dihydro-7-quinazolinyl]-3,5-dimethyl-N'-[(1R, 2S, 3S, 5S)-2,6,6-trimethylbicyclo[3.1.1]hept-3-yl]-1-piperazinecarboximidamide | A | 1.99 | M + H 746 |
| 330 | 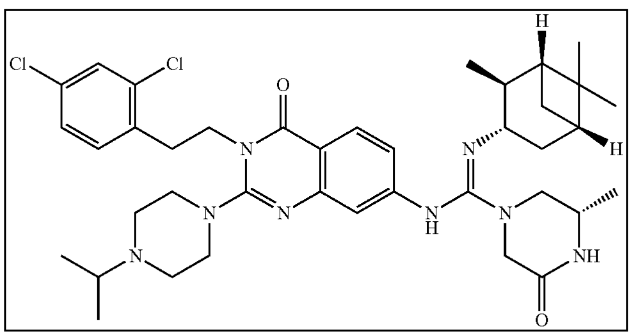 | (3S)-N-[3-[2-(2,4-dichlorophenyl)ethyl]-2-[4-(1-methylethyl)-1-piperazinyl]-4-oxo-3,4-dihydro-7-quinazolinyl]-3-methyl-N'-[(1R, 2S, 3S, 5R)-2-methylbicyclo[3.1.1]hept-3-yl]-5-oxo-1-piperazinecarboximidamide | A | 2.14 | M − H 733 |

| Ex. | Structure | Name | LC Method | Ret. Time (min) | Ion |
|---|---|---|---|---|---|
| 331 | 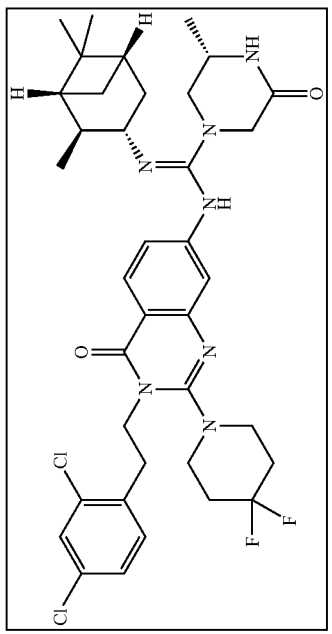 | (3S)-N-[3-[2-(2,4-dichlorophenyl)ethyl]-2-(4,4-difluoro-1-piperidinyl)-4-oxo-3,4-dihydro-7-quinazolinyl]-3-methyl-N'-[(1R,2S,3S,5S)-2,6,6-trimethylbicyclo[3.1.1]hept-3-yl]-1-piperazinecarboximidamide | A | 2.8 | M+H 728 |
| 332 | 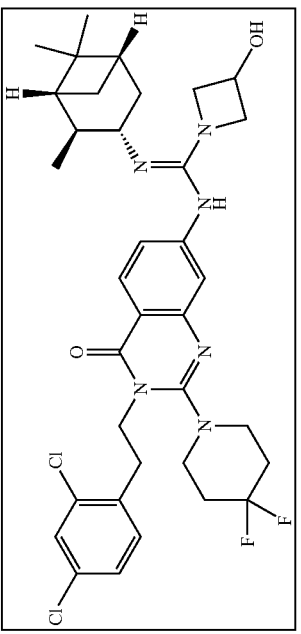 | N-[3-(2-(2,4-dichlorophenyl)ethyl]-2-(4,4-difluoro-1-piperidinyl)-4-oxo-3,4-dihydro-7-quinazolinyl]-3-hydroxy-N'-[(1R,2S,3S,5S)-2,6,6-trimethylbicyclo[3.1.1]hept-3-yl]-1-azetidinecarboximidamide | A | 2.85 | M+H 687 |
| 333 | 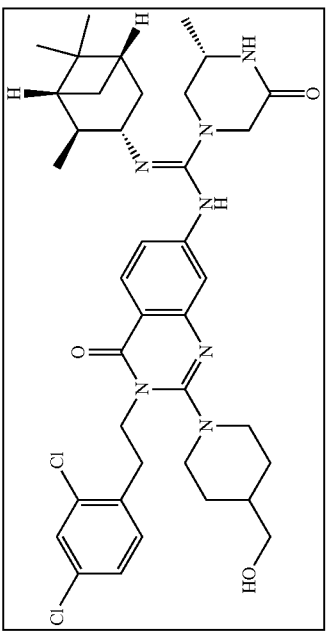 | (3S)-N-[3-[2-(2,4-dichlorophenyl)ethyl]-2-[4-(hydroxymethyl)piperidinyl]-4-oxo-3,4-dihydro-7-quinazolinyl]-3-methyl-N'-[(1S,2S,3S,5R)-2,6,6-trimethylbicyclo[3.1.1]hept-3-yl]-1-piperazinecarboximidamide | A | 2.72 | M+H 722 |

| Ex. | Structure | Name | LC Method | Ret. Time (min) | Ion |
|---|---|---|---|---|---|
| 334 | 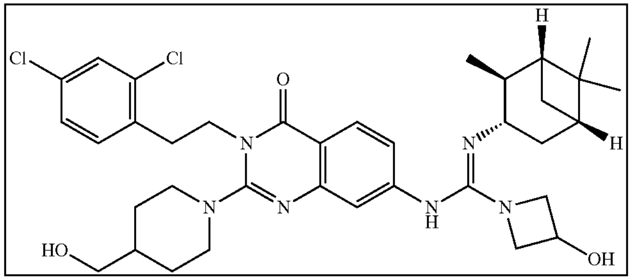 | N-{3-[2-(2,4-dichlorophenyl)ethyl]-2-[4-(hydroxymethyl)-1-piperidinyl]-4-oxo-3,4-dihydro-7-quinazolinyl}-N'-[(1S, 2S, 3S, 5R)-2,6,6-trimethylbicyclo[3.1.1]hept-3-yl]-1-azetidinecarboximidamide | A | 2.68 | M + H 681 |
| 335 | 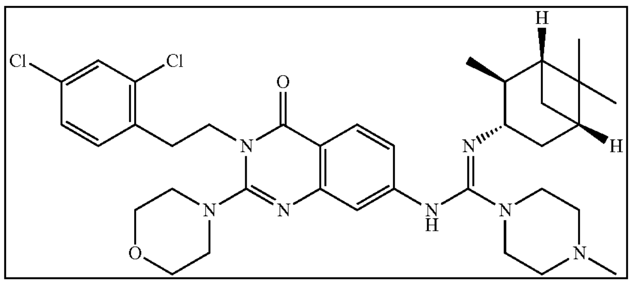 | N-{3-[2-(2,4-dichlorophenyl)ethyl]-2-(4-morpholinyl)-4-oxo-3,4-dihydro-7-quinazolinyl}-N'-[(1R, 2S, 3S, 5S)-2,6,6-trimethylbicyclo[3.1.1]hept-3-yl]-1-piperazinecarboximidamide | A | 2.41 | M + H 680 |
| 336 | 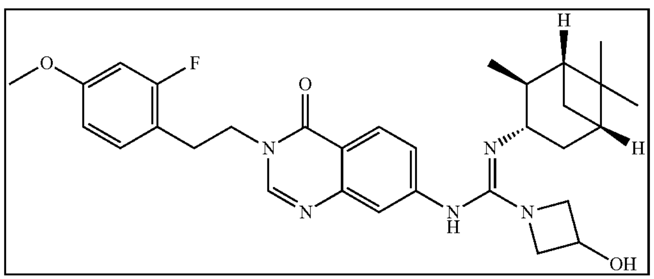 | N-(3-{2-[2-fluoro-4-(methyloxy)phenyl]ethyl}-4-oxo-3,4-dihydro-7-quinazolinyl)-N'-[(1R, 2S, 3S, 5S)-2,6,6-trimethylbicyclo[3.1.1]hept-3-yl]-3-hydroxy-1-azetidinecarboximidamide | A | 3.51 | M + H 548 |

-continued

| Ex. | Structure | Name | LC Method | Ret. Time (min) | Ion |
|---|---|---|---|---|---|
| 337 | 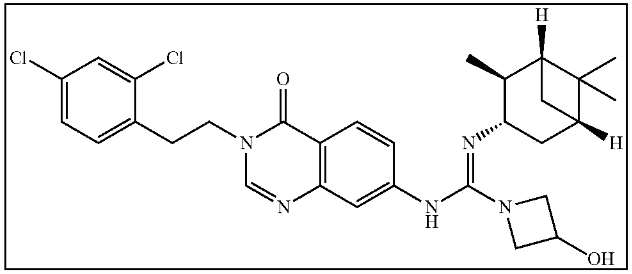 | N-{3-[2-(2,4-dichlorophenyl)ethyl]-4-oxo-3,4-dihydro-7-quinazolinyl}-3-hydroxy-N'-[(1R, 2S, 3S, 5S)-2,6,6-trimethylbicyclo[3.1.1]hept-3-yl]-1-azetidinecarboximidamide | A | 2.7 | M + H 568 |
| 338 | 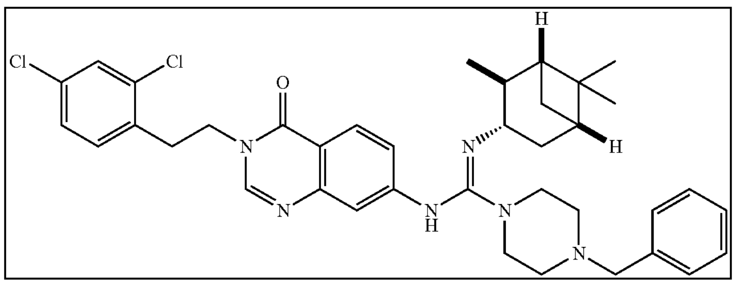 | N-{3-[2-(2,4-dichlorophenyl)ethyl]-4-oxo-3,4-dihydro-7-quinazolinyl}-4-(phenylmethyl)-N'-[(1R, 2S, 3S, 5S)-2,6,6-trimethylbicyclo[3.1.1]hept-3-yl]-1-piperidinecarboximidamide | A | 3.41 | M + H 670 |
| 339 | 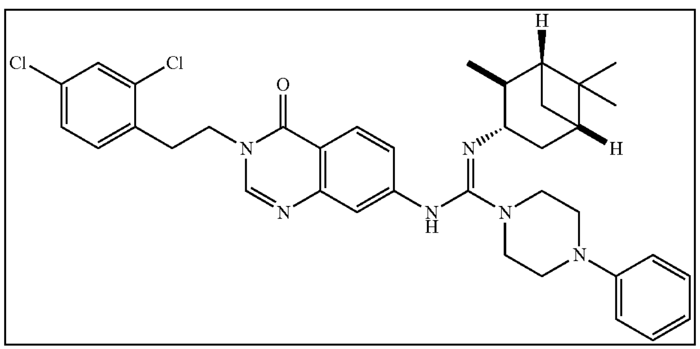 | N-{3-[2-(2,4-dichlorophenyl)ethyl]-4-oxo-3,4-dihydro-7-quinazolinyl}-4-phenyl-N'-[(1R, 2S, 3S, 5S)-2,6,6-trimethylbicyclo[3.1.1]hept-3-yl]-1-piperazinecarboximidamide | A | 3.06 | M + H 657 |

-continued

| Ex. | Structure | Name | LC Method | Ret. Time (min) | Ion |
|---|---|---|---|---|---|
| 340 | 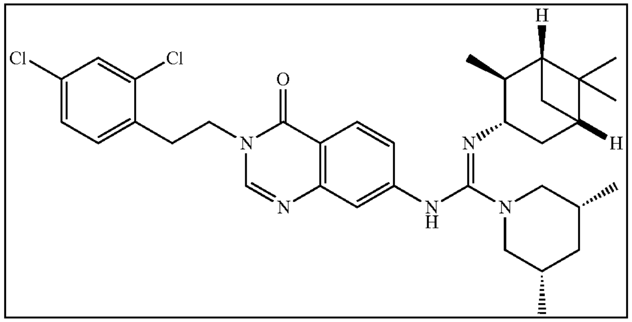 | (3R, 5S)-N-{3-[2-(2,4-dichlorophenyl)ethyl]-4-oxo-3,4-dihydro-7-quinazolinyl}-3,5-dimethyl-N'-[(1R, 2S, 3S, 5S)-2,6,6-trimethylbicyclo[3.1.1]hept-3-yl]-1-piperidinecarboximidamide | A | 3.16 | M + H 608 |
| 341 | 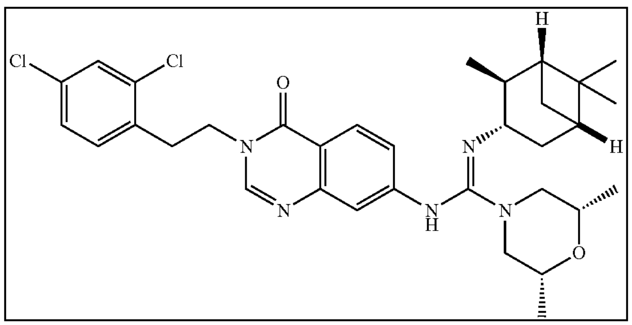 | (2R, 6S)-N-{3-[2-(2,4-dichlorophenyl)ethyl]-4-oxo-3,4-dihydro-7-quinazolinyl}-2,6-dimethyl-N'-[(1R, 2S, 3S, 5S)-2,6,6-trimethylbicyclo[3.1.1]hept-3-yl]-4-morpholinecarboximidamide | A | 2.74 | M + H 610 |
| 342 | 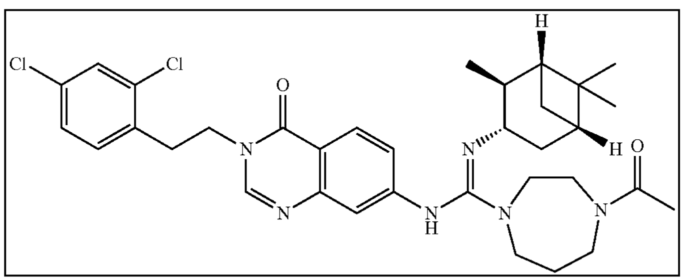 | 4-acetyl-N-{3-[2-(2,4-dichlorophenyl)ethyl]-4-oxo-3,4-dihydro-7-quinazolinyl}-N'-[(1R, 2S, 3S, 5S)-2,6,6-trimethylbicyclo[3.1.1]hept-3-yl]hexahydro-1H-1,4-diazepine-1-carboximidamide | A | 2.54 | M + H 637 |

| Ex. | Structure | Name | LC Method | Ret. Time (min) | Ion |
|---|---|---|---|---|---|
| 343 | 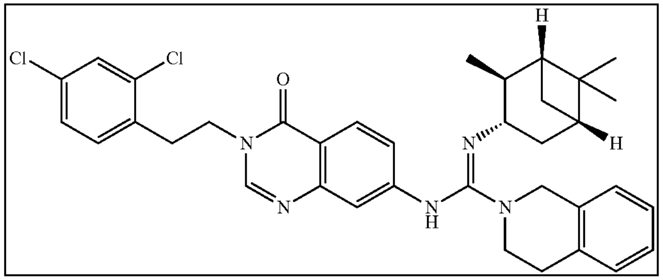 | N-{3-[2-(2,4-dichlorophenyl)ethyl]-4-oxo-3,4-dihydro-7-quinazolinyl}-N'-[(1R, 2S, 3S, 5S)-2,6,6-trimethylbicyclo[3.1.1]hept-3-yl]-3,4-dihydro-2(1H)-isoquinolinecarboximidamide | A | 3.01 | M + H 628 |

Table of Examples 344-390

| Ex. | Structure | Name | LC Method | Ret. Time (min) | Ion |
|---|---|---|---|---|---|
| 344 | 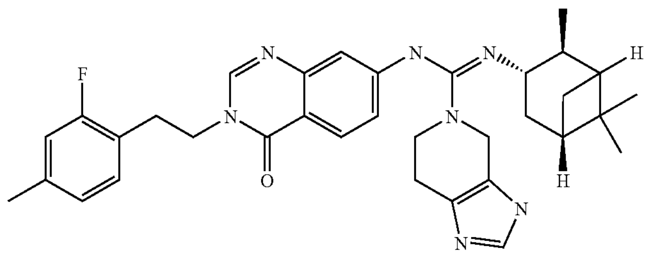 | N-{3-[2-(2-fluoro-4-methylphenyl)ethyl]-4-oxo-3,4-dihydroquinazolin-7-yl}-3-oxo-N'-[(1R,2S,3S,5S)-2,6,6-trimethylbicyclo[3.1.1]hept-3-yl]-3,4,6,7-tetrahydro-5H-imidazo[4,5-c]pyridine-5-carboximidamide | A | 2.32 | M + H 582.3 |
| 345 | 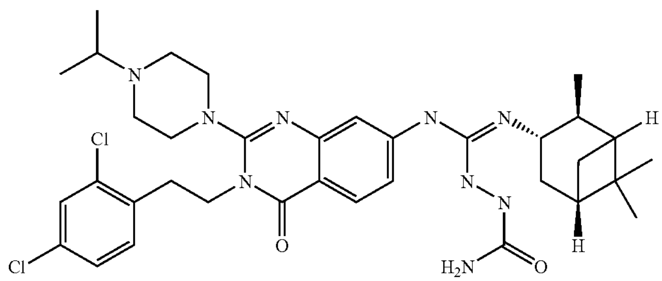 | 2-((Z-{[3-[2-(2,4-dichlorophenyl)ethyl]-2-(4-isopropylpiperazin-1-yl)-4-oxo-3,4-dihydroquinazolin-7-yl]amino}{[(1R,2S,3S,5S)-2,6,6-trimethylbicyclo[3.1.1]hept-3-yl]imino}methyl)hydrazine carboximidamide | A | 2.18 | M + H 696.3 |
| 346 | 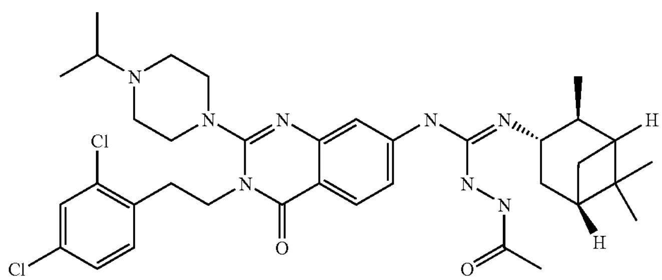 | 2-acetyl-N-[3-[2-(2,4-dichlorophenyl)-ethyl]-2-(4-isopropyl-piperazin-1-yl)-4-oxo-3,4-dihydro-quinazolin-7-yl}-N'-[(1R,2S,3S,5S)-2,6,6-trimethyl-bicyclo[3.1.1]hept-3-yl]hydrazine carboximidamide | A | 2.26 | M + H 695.4 |
| 347 | 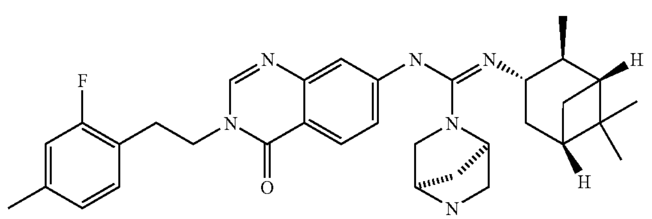 | (1R,4S)-N-{3-[2-(2-fluoro-4-methylphenyl)ethyl]-4-oxo-3,4-dihydroquinazolin-7-yl}-N'-[(1R,2S,3S,5S)-2,6,6-trimethylbicyclo[3.1.1]hept-3-yl]-2,5-diazabicyclo{2.2.1}heptane-2-carboximidamide | A | 2.13 | M + H 555.4 |
| 348 | 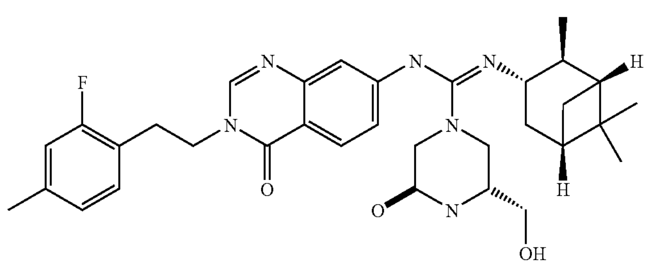 | (3R)-N-{3-[2-(2-fluoro-4-methylphenyl)ethyl]-4-oxo-3,4-dihydroquinazolin-7-yl}-3-(hydroxymethyl)-5-oxo-N'-1(1R,2S,3S,5S)-2,6,6-trimethylbicyclo[3.1.1]hept-3-yl]piperazine-1-carboximidamide | A | 2.6 | M + H 589.6 |

-continued

| Ex. | Structure | Name | LC Method | Ret. Time (min) | Ion |
|---|---|---|---|---|---|
| 349 | 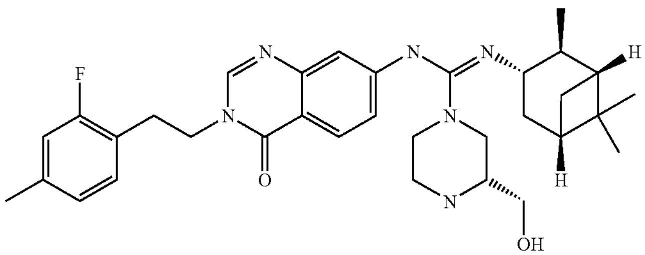 | (3R)-N-{3-[2-(2-fluoro-4-methylphenyl)ethyl]-4-oxo-3,4-dihydroquinazolin-7-yl}-3-(hydroxymethyl)-N'-[(1R,2S,3S,5S)-2,6,6-trimethylbicyclo[3.1.1]hept-3-yl]piperazine-1-carboximidamide | A | 2.48 | M + H 575.8 |
| 350 | 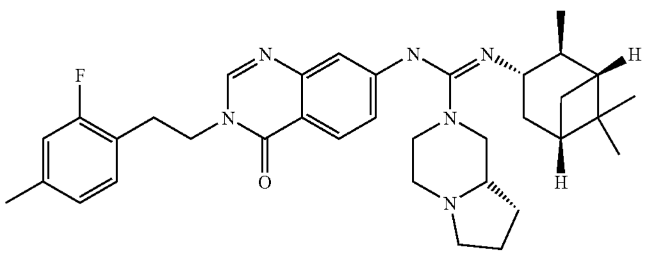 | (8aR)-N-{3-[2-(2-fluoro-4-methylphenyl)ethyl]-4-oxo-3,4-dihydroquinazolin-7-yl}-N'-[(1R,2S,3S,5S)-2,6,6-trimethylbicyclo[3.1.1]hept-3-yl]hexahydropyrrolo[1,2-a]pyrazine-2(1H)-carboximidamide | B | 4.22 | M + H 585.3 |
| 351 | 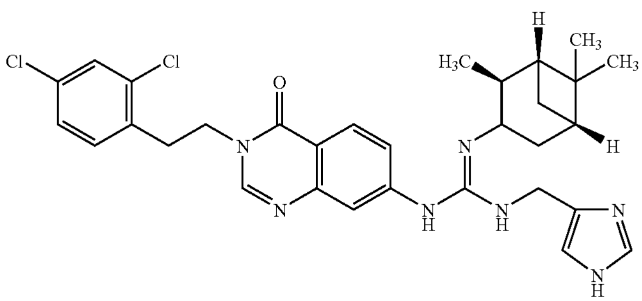 | N-}3-[2-(2,4-dichlorophenyl)ethyl]-4-oxo3,4.dihydro-7-quinazolinyl}-N-(1H-imidazol-4-ylmethyl)-N'-[(1R,2S,5S)-2,6,6-trimethylbicyclo[3.1.1]hept-3-yl]guanidine trifluoroacetate | A | 2.54 | M + H 592.1 |
| 352 | 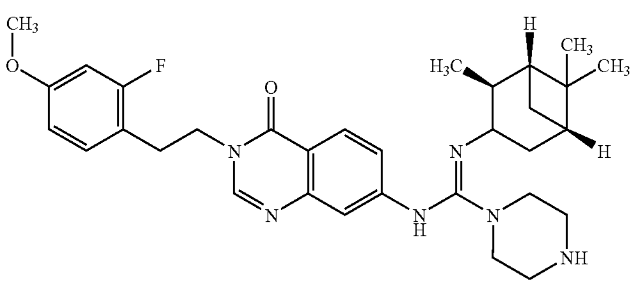 | N-(3-{2-[2-fluoro-4-(methyloxy)phenyl]ethyl]-4-oxo-3,4-dihydro-7-quinazolinyl)-N'-[(1R,2S,5S)-2,6,6-trimethylbicyclo[3.1.1]hept-3-yl]-1-piperazine carboximidamide trifluoroacetate | A | 2.12 | M + H 561.3 |
| 353 | 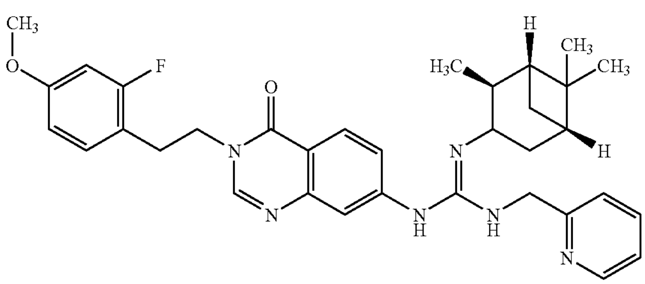 | N-(3-{2-[2-fluoro-4-(methyloxy)phenyl]ethyl}-4-oxo-3,4-dihydro-7-quinazolinyl)-N'-(2-pyridinylmethyl)-N''-[(1R,2S,5S)-2,6,6-trimethylbicyclo[3.1.1]hept-3-yl]guanidine trifluoroacetate | A | 2.73 | M + H 583.2 |

-continued

| Ex. | Structure | Name | LC Method | Ret. Time (min) | Ion |
|---|---|---|---|---|---|
| 354 | 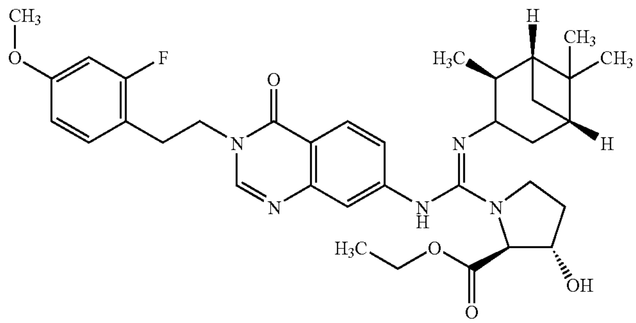 | ethyl(3S)-1-((Z)-[(3-{2-[2-fluoro-4-(methyloxy)phenyl]ethyl}-4-oxo-3,4-dihydro-7-quinazolinyl)amino]{[(1R,2S,5S)-2,6,6-trimethylbicyclo[3.1.1]hept-3-yl]imino}methyl)-3-hydroxy-L-prolinate trifluoroacetate (salt) | A | 2.60 | M + H 634.4 |
| 355 | 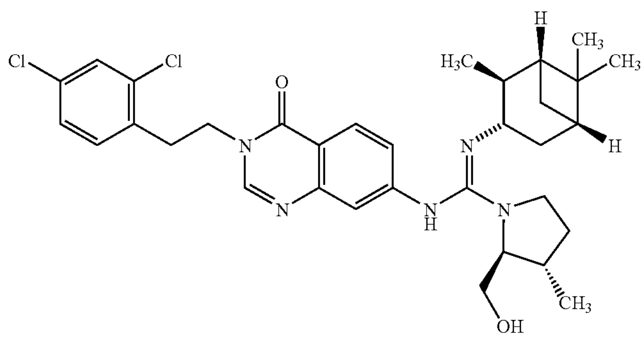 | (2S,3S)-N-{3-[2-(2,4-dichlorophenyl)ethyl]-4-oxo-3,4-dihydro-7-quinazolinyl}-2-(hydroxymethyl)-3-methyl-N'-[(1R,2S,3S,5S)-2,6,6-trimethylbicyclo[3.1.1]hept-3-yl]-1-pyrrolidine carboximidamide trifluoroacetate (salt) | A | 2.70 | M + H 610.3 |
| 356 | 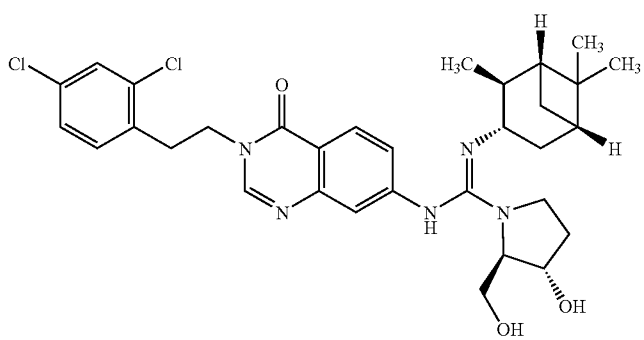 | (2R,3S)-N-{3-[2-(2,4-dichlorophenyl)ethyl]-4-oxo-3,4-dihydro-7-quinazolinyl}-3-hydroxy-2-(hydroxymethyl)-N'-[(1R,2S,3S,5S)-2,6,6-trimethylbicyclo[3.1.1]hept-3-yl]-1-pyrrolidine carboximidamide trifluoroacetate (salt) | A | 2.73 | M + H 612.2 |
| 357 | 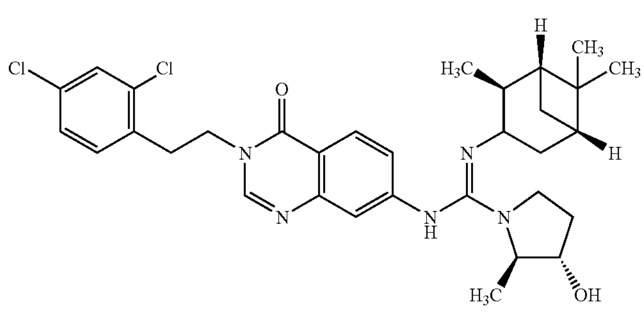 | (2R,3S)-N-{3-[2-(2,4-dichlorophenyl)ethyl]-4-oxo-3,4-dihydro-7-quinazolinyl}-3-hydroxy-2-methyl-N'-[(1R,2S,5S)-2,6,6-trimethylbicyclo[3.1.1]hept-3-yl]-1-pyrrolidine carboximidamide trifluoroacetate (salt) | A | 2.78 | M + H 596.2 |

| Ex. | Structure | Name | LC Method | Ret. Time (min) | Ion |
|---|---|---|---|---|---|
| 358 | 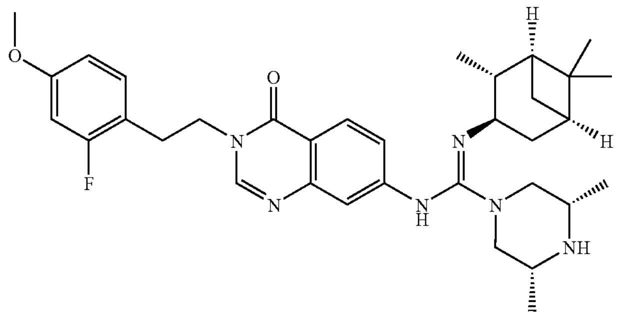 | (3R,5S)-N-(3-{2-[2-fluoro-4-(methyloxy)phenyl]ethyl}-4-oxo-3,4-dihydro-7-quinazolinyl)-3,5-dimethyl-N'-[(1S,2R,3R,5R)-2,6,6-trimethylbicyclo[3.1.1]hept-3-yl]-1-piperazine carboximidamide | B | 3.01 | M + H 589.23 |
| 359 | 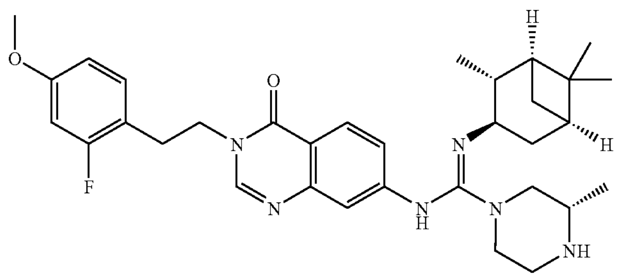 | (3S)-N-(3-{2-[2-fluoro-4-(methyloxy)phenyl]ethyl}-4-oxo-3,4-dihydro-7-quinazolinyl)-3-methyl-N'-[(1S,2R,3R,5R)-2,6,6-trimethylbicyclo[3.1.1]hept-3-yl]-1-piperazine carboximidamide | B | 3.02 | M + H 575.21 |
| 360 | 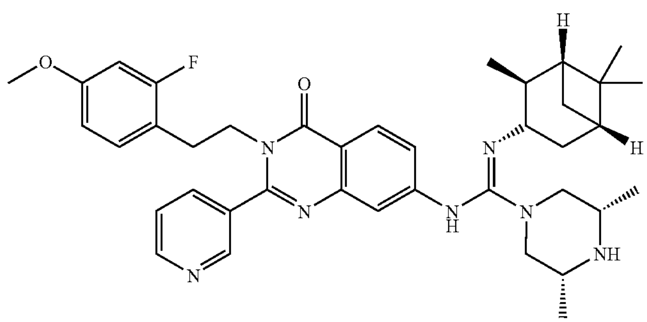 | (3R,5S)-N-[3-{2-[2-fluoro-4-(methyloxy)phenyl]ethyl}-4-oxo-2-(3-pyridinyl)-3,4-dihydro-7-quinazolinyl]-3,5-dimethyl-N-[(1R,2S,3S,5S)-2,6,6-trimethylbicyclo[3.1.1]hept-3-yl]-1-piperazine carboximidamide | D | 2.23 | M + H 666.33 |
| 361 | 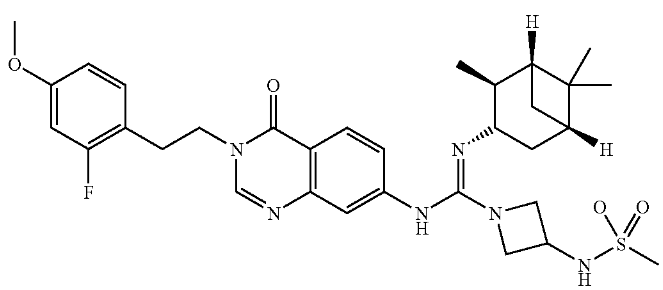 | N-(3-{2-[2-fluoro-4-(methyloxy)phenyl]ethyl}-4-oxo-3,4-dihydro-7-quinazoiinyl)-3-[(methylsulfonyl)amino]-N'-[(1R,2S,3S,5S)-2,6,6-trimethylbicyclo[3.1.1]hept-3-yl]-1-azetidine carboximidamide | D | 2.2 | M + H 625.30 |
| 362 | 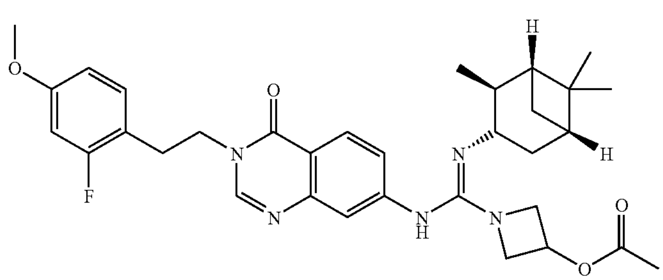 | 1-((Z)-[(3-{2-[2-fluoro-4-(methyloxy)phenyl]ethyl}-4-oxo-3,4-dihydro-7-quinazolinyl)amino]}[(1R,2S,3S,5S)-2,6,6-trimethylbicyclo[3.1.1]hept-3-yl]imino}methyl)-3-azetidinyl acetate | D | 2.57 | M + H 590.33 |

-continued

| Ex. | Structure | Name | LC Method | Ret. Time (min) | Ion |
|---|---|---|---|---|---|
| 363 | 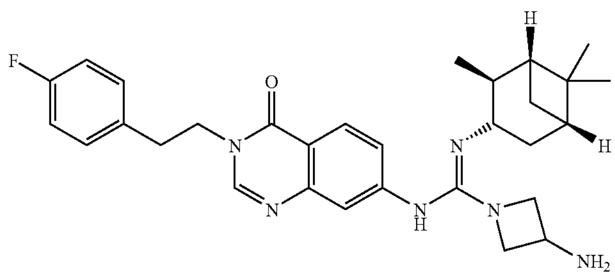 | 3-amino-N-{3-[2-(4-fluorophenyl)ethyl]-4-oxo-3,4-dihydro-7-quinazolinyl}-N'-[(1R,2S,3S,5S)-2,6,6-trimethylbicyclo[3.1.1]hept-3-yl]-1-azetidine carboximidamide | D | 2.19 | M + H 517.20 |
| 364 | 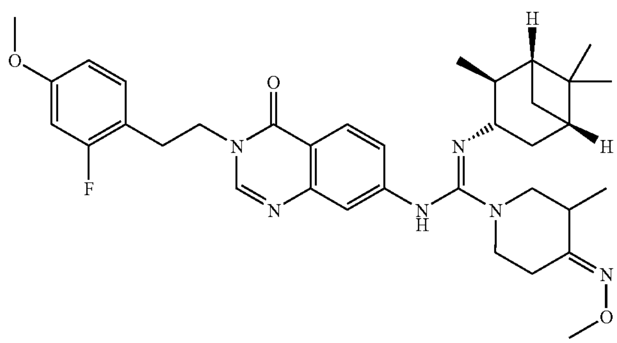 | (4E)-N-(3-{2-(2-fluoro-4-(methyloxy)phenyl]ethyl}-4-oxo-3,4-dihydro-7-quinazolinyl)-3-methyl-4-[(methyloxy)imino]-N'-[(1R,2S,3S,5S)-2,6,6-trimethylbicyclo[3.1.1]hept-3-yl]-1-piperidine carboximidamide | F | 1.07 | M + H 617.21 |
| 365 | 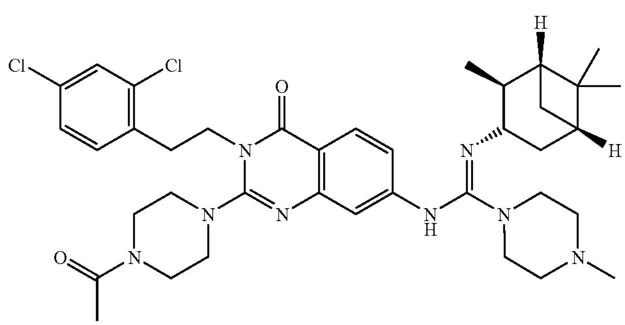 | N-{2-(4-acetyl-1-piperazinyl)-3-(2-(2,4-dichlorophenyl)ethyl]-4-oxo-3,4-dihydro-7-quinazolinyl}-4-methyl-N'-[(1R,2S,3S,5S)-2,6,6-trimethylbicyclo[3.1.1]hept-3-yl]-1-piperazine carboximidamide | C | 3.4 | M + H 721 |
| 366 | 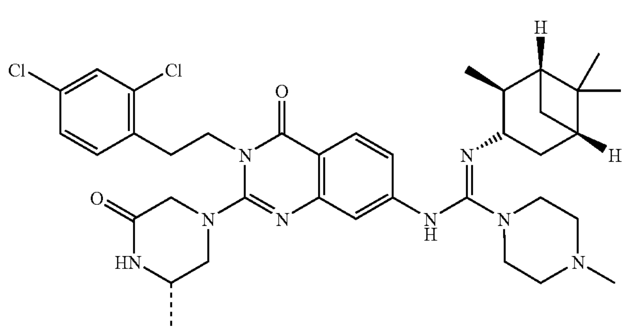 | N{3[2(2,4-dichlorophenyl)ethyl]-2-[(3S)-3-methyl-5-oxo-1-piperazinyl]-4-oxo-3,4-dihydro-7-quinazolinyl}-4-methyl-N'-[(1R,2S,3S,5S)-2,6,6-trimethylbicyclo[3.1.1]hept-3-yl]-1-piperazine carboximidamide | C | 3.49 | M + H 707 |
| 367 | 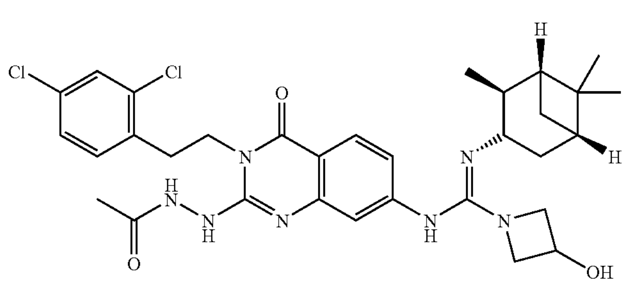 | N-{2-(2-acetylhydrazino)-3-[2-(2,4-dichlorophenyl)ethyl]-4-oxo-3,4-dihydro-7-quinazolinyl}-3-hydroxy-N'-[(1R,2S,3S,5S)-2,6,6-trimethylbicyclo[3.1.1]hept-3-yl]-1-azetidine carboximidamide | A | 2.76 | M + H 640 |

-continued

| Ex. | Structure | Name | LC Method | Ret. Time (min) | Ion |
|---|---|---|---|---|---|
| 368 | 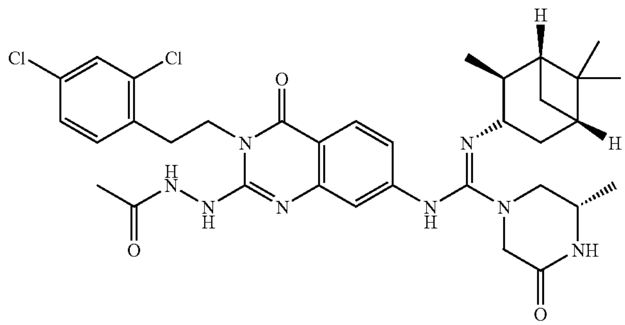 | (3S)-N-{2-(2-acetylhydrazino)-3-[2-(2,4-dichlorophenyl)ethyl]-4-oxo-34-dihydro-7-quinazolinyl}-3-methyl-5-oxo-N'-[(1R,2S,3S,5S)-2,6,6-trimethylbicyclo[3.1.1]hept-3-yl]-1-piperazine carboximidamide | A | 2.84 | M + H 681 |
| 369 | 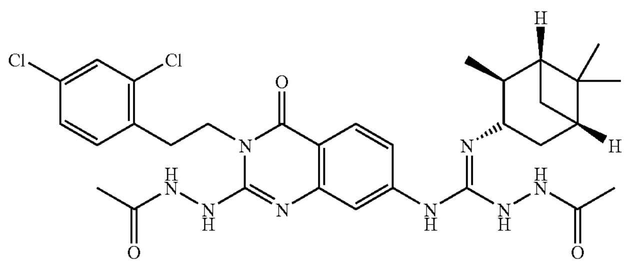 | 2-acetyl-N-{2-(2-acetylhydrazino)-3-[2-(2,4-dichlorophenyl)ethyl]-4-oxo-34-dihydro-7-quinazolinyl}-N'-[(1R,2S,3S,5S)-2,6,6-trimethylbicyclo[3.1.1]hept-3-yl]hydrazine carboximidamide | A | 2.87 | M + H 641 |
| 370 | 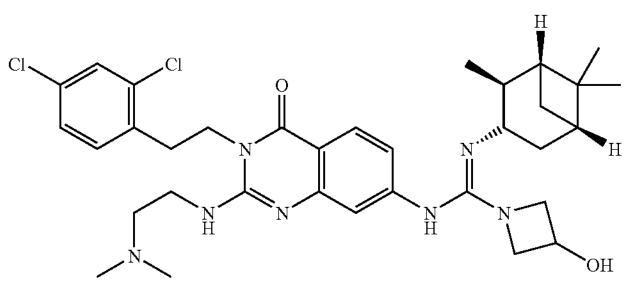 | N-(3-[2-(2,4-dichlorophenyl)-ethyl]-2-{[2-(dimethylamino)ethyl]amino}-4-oxo-3,4-dihydro-7-quinazolinyl)-3-hydroxy-N'-[(1R,2S,3S,5S)-2,6,6-trimethyl-bicyclo[3.1.1]hept-3-yl]-1-azetidine-carboximidamide | A | 2.2 | M + H 654 |
| 371 | 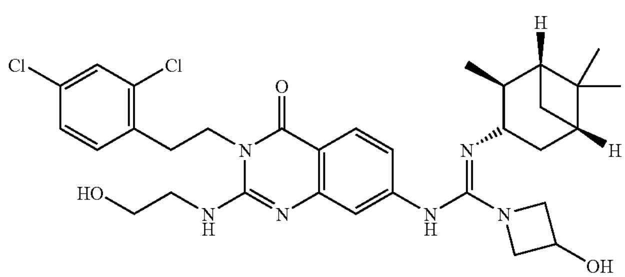 | N-{3-[2-(2,4-dichlorophenyl)ethyl] hydroxyethyl)amino]-4-oxo-3,4-dihydro-7-quinazolinyl}-3-hydroxy-N'-[(1R,2S,3S,5S)-2,6,6-trimethylbicyclo[3.1.1]hept-3-yl]-1-azetidine carboximidamide | A | 2.73 | M + H 627 |
| 372 | 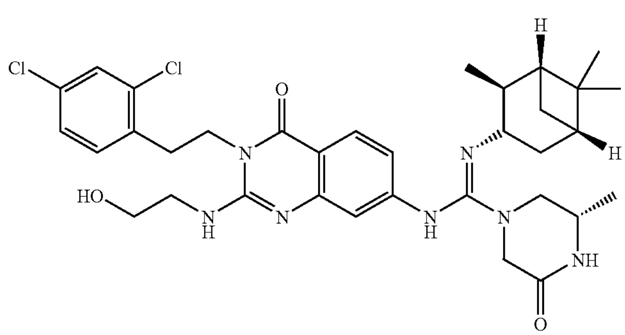 | (3S)-N-{3-[2-(2,4-dichlorophenyl)ethyl]-2-[(2-hydroxyethyl)amino]-4-oxo-3,4-dihydro-7-quinazolinyl}-3-methyl-5-oxo-N'-[(1R,2S,3S,5S)-2,6,6-trimethylbicyclo[3.1.1]hept-3-yl]-1-piperazine carboximidamide | A | 2.68 | M + H 668 |

-continued

| Ex. | Structure | Name | LC Method | Ret. Time (min) | Ion |
|---|---|---|---|---|---|
| 373 | 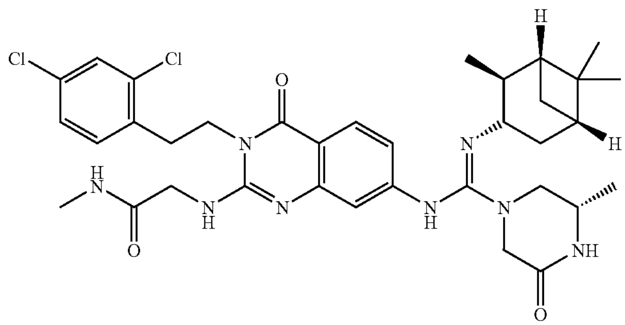 | N2-{3-[2-(2,4-dichlorophenyl)ethyl]-7-[((3S)-3-methyl-5-oxo-1-piperazinyl]{[(1R,2S,3S,5S)-2,6,6-trimethylbicyclo[3.1.1]hept-3-yl]amino}methylidene)amino]-4-oxo-3,4-dihydro-2-quinazolinyl}-NP¹-methylglycinamide | A | 2.31 | M + H 695 |
| 374 | 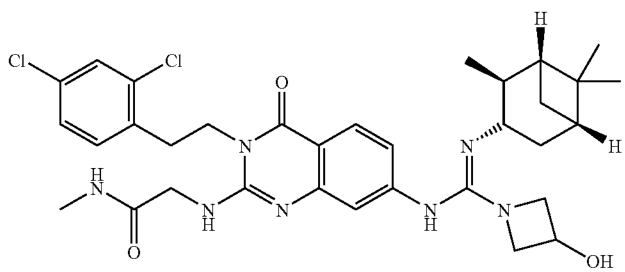 | N²-{3-[2-(2,4-dichlorophenyl)ethyl]-7-[((3-hydroxy-1-azetidinyl){[(1R,2S,3S,5S)-2,6,6-trimethylbicyclo[3.1.1]hept-3-yl]amino}methylidene)amino]-4-oxo-3,4-dihydro-2-quinazolinyl}-N¹-methylglycinamide | A | 2.35 | M + H 654 |
| 375 | 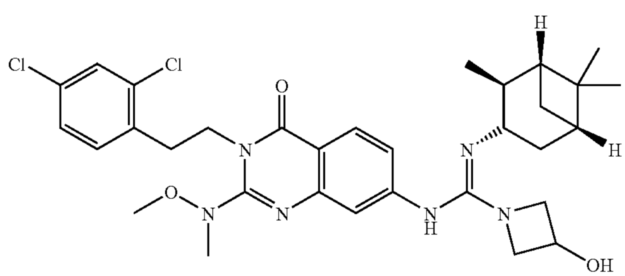 | N-{3-[2-(2,4-dichlorophenyl)ethyl]-2-[methyl(methyloxy)amino]-4-oxo-3,4-dihydro-7-quinazolinyl}-3-hydroxy-N'-[(1R,2S,3S,5S)-2,6,6-trimethyl-bicyclo[3.1.1]hept-3-yl]-1-azetidine-carboximidamide | A | 0.93 | M + H 627 |
| 376 | 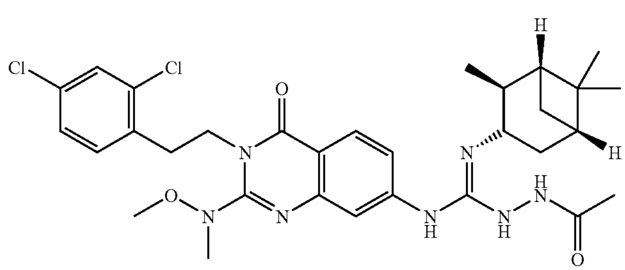 | 2-acetyl-N-{3-[2-(2,4-dichloro-phenyl)ethyl]-2-[methyl(methyloxy)amino]-4-oxo-3,4-dihydro-7-quinazolinyl}-N'-[(1R,2S,3S,5S)-2,6,6-trimethyl-bicyclo[3.1.1]hept-3-yl]hydrazine carboximidamide | A | 2.31 | M + H 628 |
| 377 | 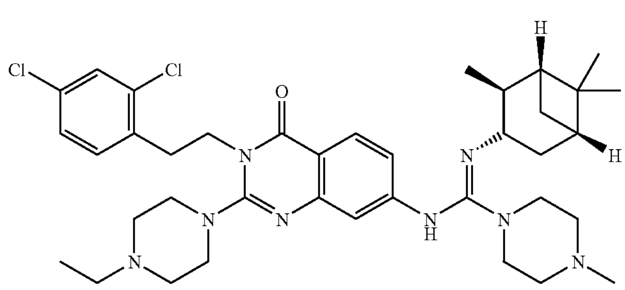 | N-[3-[2-(2,4-dichlorophenyl)ethyl]-2-(4-ethyl-1-piperazinyl)-4-oxo-3,4-dihydro-7-quinazolinyl]-4-methyl-N'-[(1R,2S,3S,5S)-2,6,6-trimethylbicyclo[3.1.1]hept-3-yl]-1-piperazine carboximidamide trifluoroacetate. | A | 1.75 | M + H 707 |

-continued

| Ex. | Structure | Name | LC Method | Ret. Time (min) | Ion |
|---|---|---|---|---|---|
| 378 | 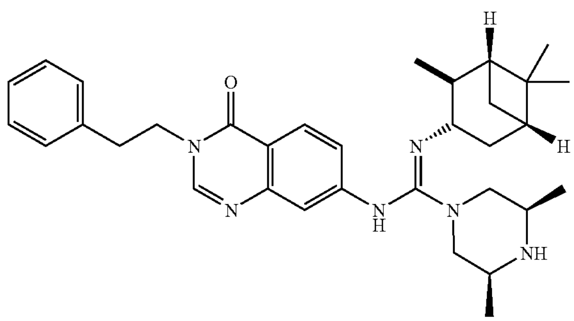 | (3R,5S)-3,5-dimethyl-N-[4-oxo-3-(2-phenylethyl)-3,4-dihydroquinazolin-7-yl]-N'-[(1R,2S,3S,5S)-2,6,6-trimethylbicyclo[3.1.1]hept-3-yl]piperazine-1-carboximidamide | A | 2.09 | M + H 541.26 |
| 379 | 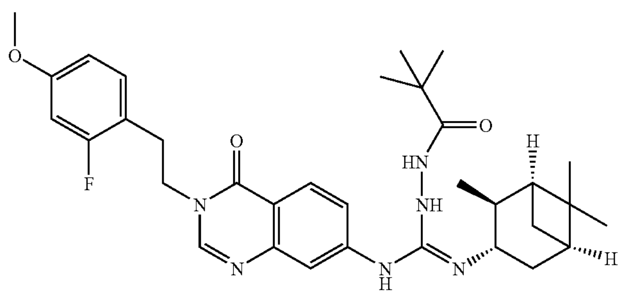 | 2-(2,2-dimethylpropanoyl)-N-{3-[2-(2-fluoro-4-methoxyphenyl)ethyl]-4-oxo-3,4-dihydroquinazolin-7-yl)-N'-[(1S,2S,3S,5R)-2,6,6-trimethylbicyclo[3.1.1]hept-3-yl]hydrazinecarboximidamide | A | 2.34 | M + H 591.00 |
| 380 | 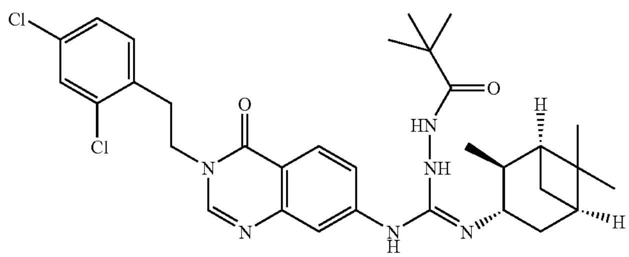 | N-{3-[2-(2,4-dichlorophenyl)ethyl]-4-oxo-3,4-dihydroquinazolin-7-yl}-2,2-dimethylpropanoyl)-N'-[(1S,2S,3S,5R)-2,6,6-trimethylbicyclo[3.1.1]hept-3-yl]hydrazinecarboximidamide | A | 2.51 | M + H 611.00 |
| 381 | 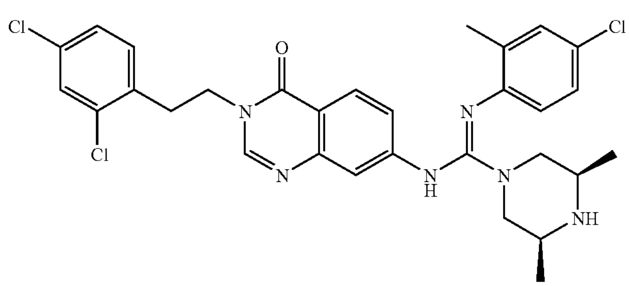 | (3R,5S)-N'-(4-chloro-2-methylphenyl)-N-{3-[2-(2,4-dichlorophenyl)ethyl]-4-oxo-3,4-dihydroquinazolin-7-yl}-3,5-dimethylpiperazine-1-carboximidamide | C | 3.27 | M + H 599.1 |
| 382 | 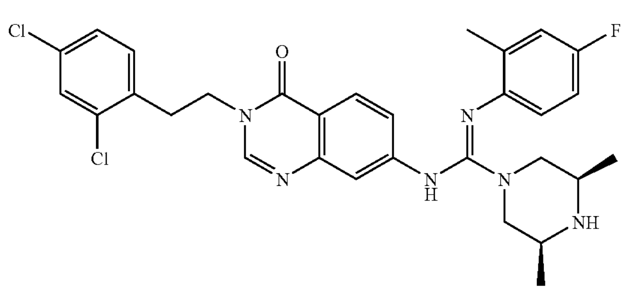 | (3R,5S)-N-{3-[2-(2,4-dichlorophenyl)ethyl]-4-oxo-3,4-dihydroquinazolin-7-yl}-N'-(4-fluoro-2-methylphenyl)-3,5-dimethylpiperazine-1-carboximidamide | C | 3.02 | M + H 583.3 |

-continued

| Ex. | Structure | Name | LC Method | Ret. Time (min) | Ion |
|---|---|---|---|---|---|
| 383 | 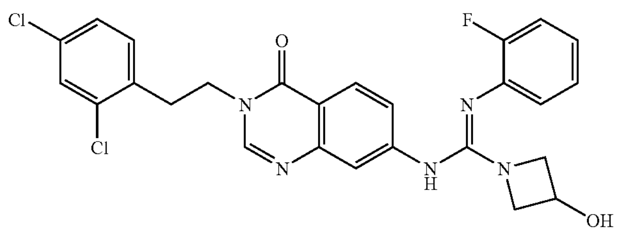 | N-{3-[2-(2,4-dichlorophenyl)ethyl]-4-oxo-3,4-dihydroquinazolin-7-yl}-N'-(2-fluorophenyl)-3-hydroxyazetidine-1 carboximidamide | C | 3.29 | M + H 530.0 |
| 384 | 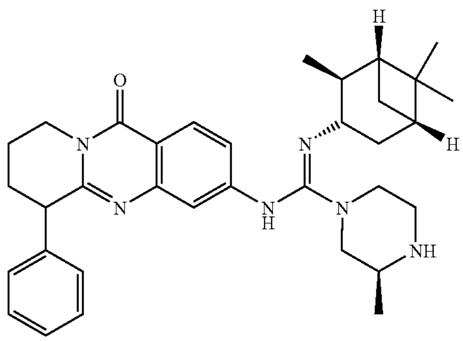 | (3S)-3-methyl-N-(11-oxo-6-phenyl-6,8,9,11-tetrahydro-7H-pyrido[2,1-b]quinazolin-3-yl)-n'-[(1R,2S,3S,5S)-2,6,6-trimethylbicyclo[3.1.1]hept-3-yl]piperazine-1-carboximidamide | A | 1.72 | M + H 553.3 |
| 385 | 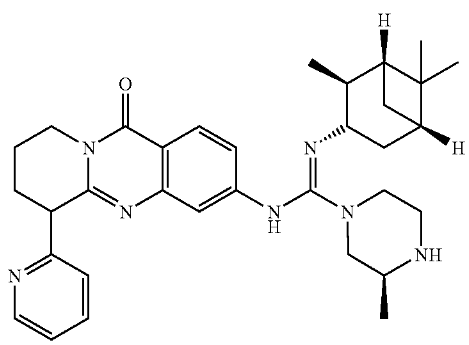 | (3S)-3-methyl-N-(11-oxo-6-pyridin-2-yl-6,8,9,11-tetrahydro-7H-pyrido[2,1-b]quinazolin-3-yl)-N'-{(1R,2S,3S,5S)-2,6,6-trimethylbicyclo[3.1.1]hept-3-yl]piperazine-1-carboximidamide | A | 1.33 | M + H 554.3 |
| 386 | 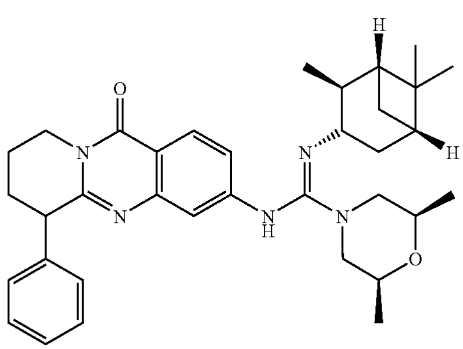 | (2R,6S)-2,6-dimethyl-N-(11-oxo-6-phenyl-6,8,9,11-tetrahydro-7H-pyrido[2,1-[(1R,2S,3S,5S)-2,6,6-trimethylbicyclo[3.1.1]hept-3-yl]morpholine-4-carboximidamide | A | 2.22 | M + H 568.3 |

-continued

| Ex. | Structure | Name | LC Method | Ret. Time (min) | Ion |
|---|---|---|---|---|---|
| 387 | 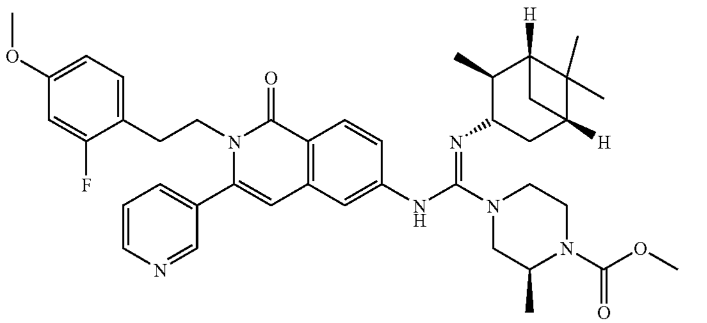 | methyl (2S)-4-((Z)-({2-[2-(2-fluoro-4-methoxyphenyl)ethyl]-1-oxo-3-pyridin-3-yl-1,2-dihydroisoquinolin-6-yl}amino){[(1R,2S,3S,5S)-2 6,6-trimethylbicyclo[3.1.1]hept-3-yl]imino}methyl)-2-methylpiperazine-1-carboxylate | A | 2.24 | M + H 710.4 |
| 388 | 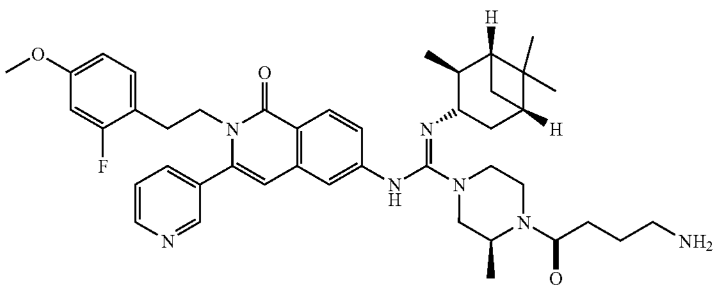 | (3S)-4-(4-aminobutanoyl)-N-{3-[2-(2-fluoro-4-methoxyphenyl)ethyl]-4-oxo-2-pyridin-3-yl-3,4-dihydroquinazolin-7-yl}-3-methyl-N'-[(1R,2S,3S,5S)-2,6,6-trimethylbicyclo[3.1.1]hept-3-yl]piperazine-1-carboximidamide | A | 1.78 | M + H 737.5 |
| 389 | 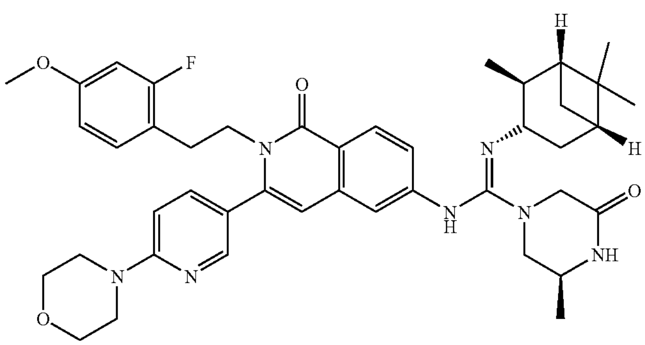 | (3S)-N-[3-[2-(2-fluoro-4-methoxyphenyl)ethyl]-2-(6-morpholin-4-ylpyridin-3-yl)-4-oxo-3,4-dihydroquinazolin-7-yl]-3-methyl-5-oxo-N'-[(1R,2S,3S,5S)-2,6,6-trimethylbicyclo[3.1.1]hept-3-yl]piperazine-1-carboximidamide | A | 2.33 | M + H 751.4 |
| 390 | 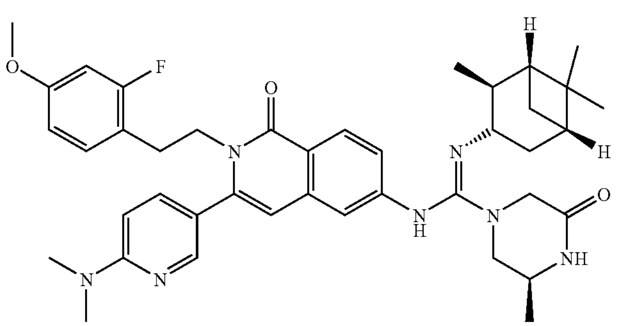 | (3S)-N-{2-[6-(dimethylamino)pyridin-3-yL]-3-[2-(2-fluoro-4-methoxyphenyl)ethyl]-4-oxo-3,4-dihydroquinazolin-7-yl}-3-methyl-5-oxo-N'-[(1R,2S,3S,5S)-2,6,6-trimethylbicyclo[3.1.1]hept-3-yl]piperazine-1-carboximidamide | A | 2.31 | M + H 709.4 |

HPLC Methods

HPLC Method A Semi-Polar Method

This method was accomplished by injection of 3 μL of sample onto a SynergiMax-RP (50×2.0 mm) column (4 μm particle size). Elution was with 15% methanol to 100% methanol over 3.5 minutes, then 1 minute at 100% methanol. Column was heated at 50° C. and the flow rate was 1.5 mL/minute. The water contained 0.1% formic acid, and the methanol contained 0.075% formic acid by volume. DAD scans were collected from 220 to 400 nm.

HPLC Method B Semi-Polar Method

This method was accomplished by injection of 3 μL of sample onto a SynergiMax-RP (50×2.0 mm) column (4 μm particle size). Elution was with 15% methanol to 100% methanol over 5 minutes, then 1 minute at 100% methanol. Column was at room temperature and the flow rate was 1 mL/minute. The water contained 0.1% formic acid, and the methanol contained 0.075% formic acid by volume. DAD scans were collected from 220 to 400 nm.

HPLC Method C Polar Method

This method was accomplished by injection of 3 μL of sample onto a SynergiHydro-RP (50×2.0 mm) column (4 μm particle size). Elution was with 2% methanol to 100% methanol over 5 minutes, then 1 minute at 100% methanol. Column was at room temperature and the flow rate was 1 mL/minute. The water contained 0.1% formic acid, and the methanol contained 0.075% formic acid by volume. DAD scans were collected from 220 to 400 nm.

HPLC Method D Polar Method

This method was accomplished by injection of 3 μL of sample onto a SynergiHydro-RP (50×2.0 mm) column (4 μm particle size). Elution was with 2% methanol to 100% methanol over 3.5 minutes, then 0.5 minutes at 100% methanol. Column was at room temperature and the flow rate was 1.5 mL/minute. The water contained 0.1% formic acid, and the methanol contained 0.075% formic acid by volume. DAD scans were collected from 220 to 400 nm.

HPLC Method E Polar Method

This method was accomplished by injection of 3 μL of sample onto a SynergiHydro-RP (50×2.0 mm) column (4 μm particle size). Elution was with 2% methanol to 100% methanol over 5 minutes, then 1 minute at 100% methanol. Column was at room temperature and the flow rate was 0.8 mL/minute. The water contained 0.1% formic acid, and the methanol contained 0.075% formic acid by volume. DAD scans were collected from 220 to 400 nm.

HPLC Method F Standard Method

This method was accomplished by injection of 3 μL of sample onto a SynergiHydro-RP (50×2.0 mm) column (4 μm particle size). Elution was with 10% methanol to 100% methanol over 3 minutes, then 1 minute at 100% methanol. Column was at room temperature and the flow rate was 2.0 mL/minute. The water contained 0.1% formic acid, and the methanol contained 0.075% formic acid by volume. DAD scans were collected from 220 to 400 nm.

$EC_{50}$ values of test compounds were determined by treating cells expressing MC4-R with test compound and lysing the cells and measuring intercellular cAMP concentration with an Amersham-Pharmacia RPA-559 cAMP Scintillation Proximity Assay (SPA) kit. $EC_{50}$ values of test compounds were also determined using the following method reported by Goetz, et al. which is hereby incorporated by reference in its entirety and for all purposes as if fully set forth herein. Goetz, A. G.; Andrews J. L.; Littleton, T. R.; Ignar, D. M. DEVELOPMENT OF A FACILE METHOD FOR HIGH THROUGHPUT SCREENING WITH REPORTER GENE ASSAYS *J. Biomolec. Screening*, 5, pp 377-384 (2000). CHO-6×CRE-luc+ reporter cell lines expressing human MC1R, MC3R, MC4R, and MC5R (GenBank accession numbers X65634, LO6155, S77415 and U08353) and the CHO host reporter gene cell line were propagated in complete medium in T225 flasks. Forty-eight hours prior to assay, cells were harvested with 2 mL of 0.05% trypsin, washed with complete medium and plated at a concentration of 4000 cells/well in complete medium. Sixteen hours prior to the assay, the medium was removed from the cells and replaced with 90 μL/well of serum-free DMEM/F12. At the time of the assay, agonists were added in a 10 μL volume and plates were incubated for 4 hours at 37° C. in a cell culture incubator. The medium was aspirated followed by the addition of 50 μL of a 1:1 mixture of LucLite™ and dPBS containing 1 mM $CaCl_2$ and 1 mM $MgCl_2$. The plates were then sealed and subjected to dark adaptation at room temperature for 10 minutes before luciferase activity was quantitated using a TopCount™ microplate scintillation counter (Packard) using 3 second/well count time. The NDP-αMSH concentration-response curve data were expressed as a percentage of the fold stimulation in the NDP-αMSH control for each receptor subtype. The control value is the average of duplicate wells treated with $1\times10^{-7}$ M NDP-αMSH.

The compounds described above were synthesized and tested according to the assay procedures described above. Each of the Examples exhibited -log $EC_{50}$ values above about 3. For this reason, each of the exemplary compounds is individually preferred and is preferred as a group. Nomenclature for these compounds was provided using ACD Name version 5.07 software (Nov. 14, 2001) available from Advanced Chemistry Development, Inc and ChemInnovation NamExpert+Nomenclator™ brand software available from ChemInnovation Software, Inc. Some of the starting materials were named using standard IUPAC nomenclature. The Example compounds are illustrative and should not be construed as limiting the instant invention in any manner.

In Vivo Studies of MC4-R Agonists on Energy Intake, Body Weight, Hyperinsulinemia, and Glucose Levels In vivo studies are conducted to observe the effect of MCR-4 agonists on energy intake, body weight, hyperinsulinemia, and glucose levels. All studies are conducted with male 9-10 week old ob/ob mice which display early onset of obesity, insulin resistance and diabetes due to leptin deficiency. Mice are acclimated in the facility for 1 week before studies and are caged individually. Vehicle-treated (control) and drug treated mice studies are always run in parallel. In multi-day studies, mice (8-15 per group) are monitored for baseline body weight, fasting levels of glucose, insulin, blood lipids and energy expenditure and then injected twice daily (9 a.m. and 5 p.m.) with 3 mg/kg of a MC4-R agonist of the present invention for 4 weeks. Body weight as well as food and water intake are monitored daily. Animals are fasted overnight for measurements of fasting levels of glucose, insulin, and lipids once a week until the end of the study. Energy expenditure (resting metabolic rate, i.e., $O_2$ consumption and $CO_2$ production) are monitored in air tight chambers at the end of the study on fed animals. $O_2$ consumption and $CO_2$ production are measured using Oxymax systems (Columbus Instruments). Oral glucose tolerance test (OGTT—a routine test for diabetes and glucose intolerance) is performed on overnight fasted mice at the end of the study. Blood glucose and oral glucose tolerance are measured using a glucose monitor (Onetouch sold by Lifescan). Free fatty acids are measured using an non-esterified free fatty acids enzymatic assay (Waco Chemicals). Serum insulin levels are measured by immunoassay (Alpco).

Results

The effect of the compounds of the present invention on food intake is determined by measuring grams/mouse/day throughout a 4 week study. Food is monitored every morning. Cumulative food intake represents the total amount of grams the mice consume during the study. A significant reduction in food intake is demonstrated in those mice treated IP with the compounds of the present invention.

The effect of the compounds of the present invention on body weight is determined by measuring grams/mouse throughout a 4 week study. Mice are weighed every morning. A significant body weight reduction is demonstrated in those mice treated IP with the compounds of the present invention.

The effect of the compounds of the present invention on blood glucose levels is determined by measuring blood glucose levels as represented as mg of glucose/dL of blood. Mice are fasted overnight and glucose levels are measured the following morning. Vehicle treated mice show an increase in blood glucose consistent with the rapid progression of diabetes in this mouse strain whereas, diabetes is slowed down considerably in drug treated mice. A significant reduction in fasting glucose levels is demonstrated in those mice treated IP with the compounds of this invention.

The effect of the compounds of the present invention on glucose levels during oral glucose tolerance test (OGTT) is determined by measuring blood glucose in overnight fasted mice. Blood glucose is represented as mg of glucose/dL of blood. Glucose levels are measured the following morning. Orally administered glucose quickly elevates blood glucose, similar to a meal, and the response to this exogenous glucose gives a measure of how well the body regulated glucose homeostasis. Vehicle treated mice show an elevated response to glucose consistent with their diabetic state, whereas drug treated mice show a very much improved glucose disposal.

The effect of the compounds of the present invention on free fatty acid (FFA) levels is determined by measuring mmoles of FFA/L of serum. Mice are fasted overnight and free fatty acid levels are measured the following morning. Vehicle treated mice show elevated levels of FFA throughout the study consistent with their obese state, whereas the drug treated mice diabetes show a dramatic decrease.

The effect of the compounds of the present invention on serum insulin levels is determined by measuring serum insulin levels one hour after single IP dosing of 1 and 3 mg/kg in overnight fasted ob/ob mice. Serum insulin levels are represented as ng of insulin/mL of serum. Drug treated mice show a dose dependent decrease relative to vehicle.

Determination of $t_{1/2}$, $C_{max}$, FI, Bioavailability, CI, $V_{ss}$, and Nocturnal Efficacy In vivo studies were conducted to observe the effect of the compounds of formula IA, IB, IIA, and IIIB in the subject animal. Male CD-1 mice, body weight of 20 grams at arrival, were used in these studies. Mice were given 30 mg/kg of compound in HPMC/Tween solution or suspension via oral gavage. Plasma, brain, and liver samples were collected at time periods of 1, 2, 4, 8, and 24 hours post dosing. One mouse was used per time point. Thus, a total of 5 mice were used for each compound tested. For sample collection, mice were euthanized with $CO_2$. Blood samples were taken by cardiac puncture and kept on ice. Brain and liver samples were collected immediately after bleeding and the samples were kept on dry ice. For calculation of tissue half-lives ($t_{1/2}s$), the terminal rate constant k was estimated by the absolute value of the slope of a log-linear regression of the terminal phase of the tissue concentration-time profile. The tissue half-life $t_{1/2}$ is ln(2)/k.

Male C57BL/6J mice of 6-9 weeks age were used in these studies. The mice were singly housed at least 5 days prior to the study. Two and a half hours before the onset of the dark cycle, food was removed from the cage top. Mice were dosed with a compound of the invention (in HPMC/Tween, as vehicle) or vehicle via oral gavage two hours before the onset of the dark cycle. Immediately before the onset of the dark cycle, pre-weighed food was given to each mouse. Food was weighed at 16 and 24 hours after the introduction of food to obtain cumulative food intake values. Mice were then euthanized with $CO_2$ followed by cervical dislocation.

The following table includes $t_{1/2}$ data for plasma, brain, kidney, and liver obtained after oral administration.

Tissue Half-Life Data for Various Quinazolinone Compounds (PO)

| Example | Half-Lives (h) | | | |
| --- | --- | --- | --- | --- |
| | Plasma | Brain | Liver | Kidney |
| 216 | 1.9 | 14 | 2.1 | 2.7 |
| 218 | 2.2 | — | 3.9 | — |
| 220 | 2.1 | 3.1 | 2.5 | — |
| 221 | 2.9 | 6.9 | 2.9 | — |
| 222 | 1.1 | 8.0 | 2.7 | — |
| 224 | 3.0 | 10 | 3.1 | — |
| 227 | 3.9 | — | 9.4 | — |
| 228 | — | — | 9.1 | — |
| 229 | 9.0 | 13 | 16 | — |
| 230 | 3.1 | — | 5.9 | — |
| 231 | 2.6 | 15 | 4.6 | — |
| 233 | 6.4 | 15 | 44 | — |
| 234 | 3.5 | 2.6 | 4.9 | — |
| 235 | 4.7 | 6.1 | 5.6 | — |
| 236 | 7.7 | — | 4.2 | — |
| 239 | 4.5 | 3.6 | — | — |
| 241 | 21 | 51 | 17 | — |
| 245 | 2.2 | 3.1 | 5.2 | 1.7 |
| 246 | 5.7 | 5.8 | 18 | 3.1 |
| 247 | 18 | 12 | 8.0 | 11 |
| 248 | 5.3 | 14 | 6.2 | 11 |
| 250 | 26 | 3.0 | 8.8 | 5.7 |
| 251 | 4.0 | 5.4 | 6.8 | 8.6 |
| 252 | — | — | 16 | 8.4 |
| 253 | 7.3 | 27 | 6.9 | 14 |
| 254 | 15 | 11 | 20 | 9.6 |
| 255 | 5.6 | 25 | 7.3 | — |
| 256 | 5.4 | 15 | 4.3 | — |
| 257 | 20 | 12 | 3.0 | — |
| 258 | 5.3 | — | 2.9 | — |
| 260 | 7.2 | — | — | 7.3 |
| 274 | 2.1 | — | 2.3 | 2.7 |
| 281 | 5.3 | — | — | 6.5 |
| 288 | 1.1 | — | 1.2 | — |
| 295 | 3.3 | 4.9 | 9.5 | — |
| 296 | 4.9 | — | 3.2 | 3.3 |
| 301 | 2.5 | — | 3.6 | 9.4 |
| 337 | 18.9 | — | 4.6 | 5.1 |

All references cited herein are hereby incorporated by reference in their entirety and for all purposes as if fully set forth herein.

It is understood that the invention is not limited to the embodiments set forth herein for illustration, but embraces all such forms thereof as come within the scope of the following claims.

What is claimed is:

1. A compound of formula IA, IB, or IC

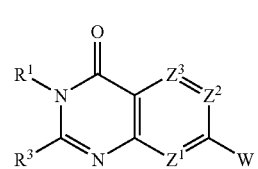

IA

-continued

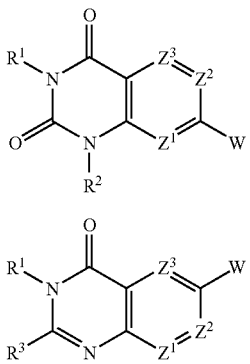

wherein
- $Z^1$ is selected from $CR^4$ or N;
- $Z^2$ is selected from $CR^5$ or N;
- $Z^3$ is selected from $CR^6$ or N;
- $R^1$ is selected from substituted or unsubstituted arylalkyl, heteroarylalkyl, aryl, heteroaryl, heterocyclyl, cycloalkyl, heterocyclylalkyl, cycloalkylalkyl, alkenyl, alkynyl, or alkylgroups;
- $R^2$ is selected from H, or substituted or unsubstituted alkyl, alkenyl, alkynyl, cycloalkyl, aryl, heteroaryl, heterocyclyl, arylalkyl, heteroarylalkyl, cycloalkylalkyl, alkylcarbonyl, or arylcarbonyl groups;
- $R^3$ is selected from H, or substituted or unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, or alkyl groups;
- $R^4$, $R^5$, and $R^6$ are independently selected from H, Cl, I, F, Br, OH, $NH_2$, CN, $NO_2$, or substituted or unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, or heteroarylaminocarbonyl groups;
- W is a group of formula IIA;

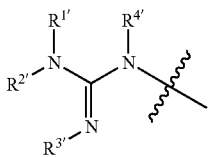

- $R^{1'}$ is selected from H, or substituted or unsubstituted alkyl, alkenyl, alkynyl, cycloalkyl, aryl, heteroaryl, heterocyclyl, arylalkyl, heteroarylalkyl, cycloalkylalkyl groups, or heterocyclylalkyl groups;
- $R^{2'}$ is selected from H, or substituted or unsubstituted alkyl, alkenyl, alkynyl, cycloalkyl, aryl, heteroaryl, heterocyclyl, arylalkyl, heteroarylalkyl, cycloalkylalkyl groups, or heterocyclylalkyl groups;
- wherein at least one of $R^{1'}$ and $R^{2'}$ is a substituted or unsubstituted nonaromatic heterocyclylalkyl group;
- $R^{3'}$ is selected from H, or substituted or unsubstituted aryl, alkyl, alkenyl, alkynyl, cycloalkyl, heteroaryl, heterocyclyl, heterocyclylalkyl, arylalkyl, heteroarylalkyl, or cycloalkylalkyl groups;
- $R^{4'}$ is selected from H, or substituted or unsubstituted alkyl, alkenyl, alkynyl, cycloalkyl, heterocyclyl, heterocyclylalkyl, cycloalkylalkyl, aryl, heteroaryl, heterocyclyl, arylalkyl, or heteroarylalkyl groups; or pharmaceutically acceptable salts thereof, stereoisomers thereof, or tautomers thereof.

2. The compound of claim 1, wherein one of $R^{1'}$ or $R^{2'}$ is a substituted or unsubstituted pyrrolidinylalkyl group.

3. The compound of claim 2, wherein one of $R^{1'}$ or $R^{2'}$ is a substituted or unsubstituted pyrrolidinylmethyl group or is a substituted or unsubstituted pyrrolidinylethyl group.

4. The compound of claim 1, wherein $R^3$ is H.

5. The compound of claim 1, wherein $Z^1$ is a $CR^4$ group, $Z^2$ is a $CR^5$ group, and $Z^3$ is a $CR^6$ group.

6. The compound of claim 1, wherein $R^{3'}$ is selected from substituted or unsubstituted cycloalkyl, polycyclic cycloalkyl, alkenyl, alkyl, or aryl groups.

7. The compound of claim 1, wherein $R^1$ is a 2,4-disubstituted phenylethyl group.

8. The compound of claim 1, wherein $R^1$ is selected from a phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, 2-methoxyphenylethyl, 2-chlorophenylethyl, 2-fluorophenylethyl, 3-methoxyphenylethyl, 3-fluorophenylethyl, thienylethyl, indolylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl) ethyl, or (phenyl)(hydroxymethyl)ethyl group.

9. A composition comprising the compound of claim 1 and a pharmaceutically acceptable carrier.

10. A compound of formula IA, IB, or IC

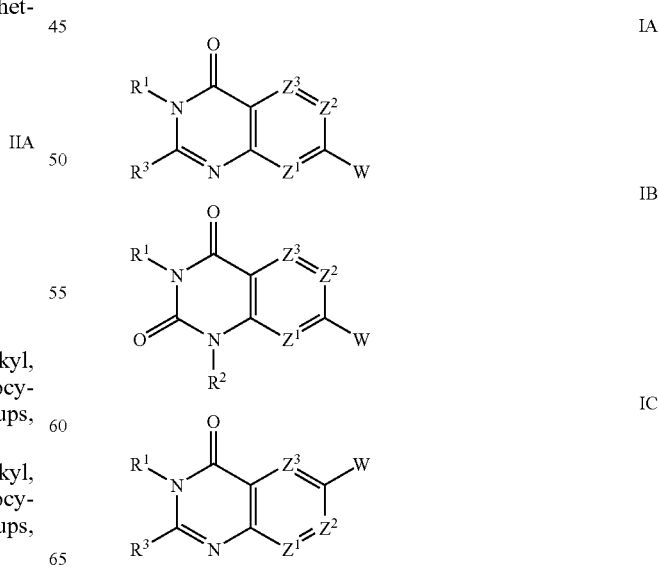

wherein
Z¹ is CR⁴;
Z² is selected from CR⁵ or N;
Z³ is selected from of CR⁶ or N;
R¹ is selected from substituted or unsubstituted arylalkyl, heteroarylalkyl, aryl, heteroaryl, heterocyclyl, cycloalkyl, heterocyclylalkyl, cycloalkylalkyl, alkenyl, alkynyl, or alkyl groups;
R² is selected from H, or substituted or unsubstituted alkyl, alkenyl, alkynyl, cycloalkyl, aryl, heteroaryl, heterocyclyl, arylalkyl, heteroarylalkyl, cycloalkylalkyl, alkylcarbonyl, or arylcarbonyl groups;
R³ is selected from H, or substituted or unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, or alkyl groups;
R⁴, R⁵, and R⁶ are independently selected from H, Cl, I, F, Br, OH, NH₂, CN, NO₂, or substituted or unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, or heteroarylaminocarbonyl groups;
W is a group of formula IIA or IIB;

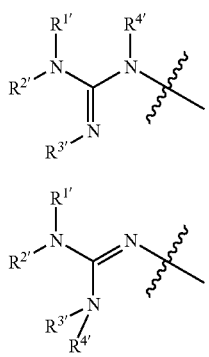

wherein R¹' and R²', together with the nitrogen to which they are bound, join together to form a heterocyclic ring substituted with at least one group selected from substituted or unsubstituted arylalkyl, —C(═O)-alkyl, -alkyl-C(═O)—O-alkyl, —C(═O)—O-alkyl, —C(═O)—NH₂, —C(═O)—NH(alkyl), —C(═O)—N(alkyl)₂, dialkylaminoalkyl, alkylaminoalkyl, aminoalkyl, aryl, heteroaryl, heterocyclyl, heteroarylalkyl, heterocyclylalkyl, or alkylthioalkyl groups;
R³' is selected from substituted or unsubstituted cycloalkyl, polycyclic cycloalkyl, alkenyl, alkyl, or aryl groups;
R⁴' is selected from H, or substituted or unsubstituted alkyl, alkenyl, alkynyl, cycloalkyl, heterocyclylalkyl, cycloalkylalkyl, aryl, heteroaryl, heterocyclyl, arylalkyl, or heteroarylalkyl groups; or
pharmaceutically acceptable salts thereof, stereoisomers thereof, or tautomers thereof.

11. The compound of claim 10, wherein the heterocyclic ring formed by R¹' and R²' and the nitrogen to which they are bound is a substituted piperazine.

12. The compound of claim 11, wherein the piperazine is substituted with a group selected from a phenylalkyl group, a substituted or unsubstituted phenyl group, an -alkyl-SCH₃ group, an indolylalkyl group, a morpholinylalkyl group, a pyridyl group, a piperidinyl group, or a tetrahydrofuranylalkyl group.

13. The compound of claim 10, wherein the heterocyclic ring formed by R¹' and R²' and the nitrogen to which they are bound is a substituted piperidine.

14. The compound of claim 13, wherein the piperidine is substituted with a group selected from a phenylalkyl group, a substituted or unsubstituted phenyl group, an -alkyl-SCH₃ group, an indolylalkyl group, a morpholinylalkyl group, a pyridyl group, a piperidinyl group, or a tetrahydrofuranylalkyl group.

15. The compound of claim 10, wherein R³ is H.

16. The compound of claim 10, wherein Z¹ is a CR⁴ group, Z² is a CR⁵ group, and Z³ is a CR⁶ group.

17. The compound of claim 10, wherein R¹ is a 2,4-disubstituted phenylethyl group.

18. The compound of claim 10, wherein R¹ is selected from a phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, 2-methoxyphenylethyl, 2-chlorophenylethyl, 2-fluorophenylethyl, 3-methoxyphenylethyl, 3-fluorophenylethyl, thienylethyl, indolylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl) ethyl, or (phenyl)(hydroxymethyl)ethyl group.

19. A composition comprising the compound of claim 10 and a pharmaceutically acceptable carrier.

20. A method of treating an MC4-R mediated disease, comprising administering to a subject in need thereof, the compound according to claim 1, wherein the disease is obesity or type II diabetes.

21. A method of treating an MC4-R mediated disease, comprising administering to a subject in need thereof, the compound according to claim 10, wherein the disease is obesity or type II diabetes.

* * * * *